US010988772B2

(12) United States Patent
Ulmasov et al.

(10) Patent No.: US 10,988,772 B2
(45) Date of Patent: Apr. 27, 2021

(54) LOW GLUCOSINOLATE PENNYCRESS MEAL AND METHODS OF MAKING

(71) Applicants: CoverCress Inc., St. Louis, MO (US); Board of Trustees of Illinois State University, Normal, IL (US); Regents of the University of Minnesota, Minneapolis, MN (US)

(72) Inventors: Tim Ulmasov, Chesterfield, MO (US); John C. Sedbrook, Bloomington, IL (US); Michael David Marks, Roseville, MN (US); Michaela G. McGinn, Normal, IL (US); Ratan Chopra, St. Paul, MN (US); Brice Allen Jarvis, Riverwoods, IL (US)

(73) Assignees: CoverCress Inc., St. Louis, MO (US); Board of Trustees of Illinois State University, Normal, IL (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/251,247

(22) Filed: Jan. 18, 2019

(65) Prior Publication Data

US 2019/0225977 A1 Jul. 25, 2019

Related U.S. Application Data

(60) Provisional application No. 62/619,360, filed on Jan. 19, 2018.

(51) Int. Cl.

| | |
|---|---|
| ***A01H 5/10*** | (2018.01) |
| ***A01H 6/20*** | (2018.01) |
| ***C12N 15/82*** | (2006.01) |
| ***A23K 10/30*** | (2016.01) |

(52) U.S. Cl.
CPC .......... *C12N 15/8245* (2013.01); *A01H 5/10* (2013.01); *A01H 6/20* (2018.05); *A23K 10/30* (2016.05)

(58) Field of Classification Search
None
See application file for complete search history.

(56) References Cited

U.S. PATENT DOCUMENTS

| | | | |
|---|---|---|---|
| 7,250,559 | B2 | 7/2007 | Quiros et al. |
| 2009/0306060 | A1 | 12/2009 | Watrin |
| 2015/0005172 | A1 | 1/2015 | Robinson |

FOREIGN PATENT DOCUMENTS

| | | | |
|---|---|---|---|
| IN | 363/DEL/2012 | | 4/2015 |
| WO | 2017091891 | A1 | 6/2017 |
| WO | 2018140782 | A1 | 8/2018 |

OTHER PUBLICATIONS

"Opinion of the Scientific Panel on Contaminants in the Food Chain on a Request form the European Commission on Glucosinolates as Undesirable Substances in Animal Feed", The EFSA Journal, 2008, pp. 1-76, vol. 590.

Chopra et al., "The Adaptable use of *Brassica* NIRS Calibration Equations to Identify Pennycress Variants to Facilitate the Rapid Domestication of a New Winter Oilseed Crop", Industrial Crops and Products, 2019, pp. 55-61, vol. 128.

Dehaan et al., "A Pipeline Strategy for Grain Crop Domestication", Crop Science, 2016, pp. 917-930, vol. 56.

Dorn et al, "A Draft Genome of Field Pennycress (*Thlaspi arvense*) Provides Tools for the Domestication of a New Winter Biofuel Crop", DNA Research, 2015, pp. 121-131, vol. 22, No. 2.

Dorn et al, "De Novo Assembly of the Pennycress (*Thlaspi arvense*) Transcriptome Provides Tools for the Development of a Winter Cover Crop and Biodiesel Feedstock", The Plant Journal, 2013, pp. 1028-1038, vol. 75.

Harper et al., "Associative Transcriptomics of Traits in the Polyploid Crop Species *Brassica napus*", Nature Biotechnology, Aug. 2012, pp. 798-804, vol. 30 No. 8.

International Search Report and Written Opinion for PCT/US2019/014178 dated May 17, 2019.

Jordan et al., "Sustainable Commercialization of New Crops for the Agricultural Bioeconomy", Elementa: Science of the Anthropocene, Jan. 8, 2016, Vo. 4, No. 81.

Kantar et al., "Perennial Grain and Oilseed Crops", Plant Biology, 2016, pp. 703-729, vol. 67.

Kliebensteine et al., "Gene Duplication in the Diversification of Secondary Metabolism: Tandem 2-Oxoglutarate-Dependent Dioxygenases Control Glucosinolate Biosynthesis in *Arabidopsis*", The Plant Cell, 2001, pp. 681-693, vol. 13.

Sedbrook et al., "New Approaches to Facilitate Rapid Domestication of a Wild Plant to an Oilseed Crop: Example Pennycress (*Thlaspi arvense* L.)", Plant Science, 2014, pp. 122-132, vol. 227.

Tripathi et al., "Glucosinolates in Animal Nutrition: A Review", Animal Feed Science and Technology, 2007, pp. 1-27, vol. 132, No. 1-2.

United States Department of Agriculture, "Advancing Field Pennycress as a New Oilseed Biodiesel Feedstock that does not Require New Land Commitments Annual Progress Report", Accession No. 1004021, Date Submitted to NIFA Dec. 6, 2016, 9 pages.

United States Department of Agriculture, "Advancing Field Pennycress as a New Oilseed Biodiesel Feedstock that does not Require New Land Commitments Annual Progress Report", Accession No. 1004021, Date Submitted to NIFA Jan. 9, 2018, 7 pages.

United States Department of Agriculture, "Advancing Field Pennycress as a New Oilseed Biodiesel Feedstock that does not Require New Land Commitments Annual Progress Report", Accession No. 1004021, Date Submitted to NIFA Nov. 30, 2015, 7 pages.

University of Minnesota, "Advancing Field Pennycress as a New Oilseed Biodiesel Feedstock That Does Not Require New Land Commitments", National Institute of Food and Agriculture, 10 pages, retrieved Nov. 26, 2018.

Zhang et al., "Three Genes Encoding AOP2, a Protein Involvied in Aliphatic Glucosinolate Biosynthesis, are Differentially Expressed in *Brassica rapa*", Journal of Experimental Botany, Jul. 17, 2015, pp. 6205-6218, vol. 66, No. 20.

*Primary Examiner* — Phuong T Bui
(74) *Attorney, Agent, or Firm* — McKee, Voorhees & Sease, PLC; Charles P. Romano

(57) ABSTRACT

Pennycress (*Thlaspi arvense*) seed, seed lots, seed meal, and compositions with reduced glucosinolate content as well as plants that yield such seed, seed lots, seed meal, and compositions are provided. Methods of making and using the pennycress plants and/or seed that provide such seed, seed lots, seed meal, and compositions are also provided.

7 Claims, 8 Drawing Sheets

Specification includes a Sequence Listing.

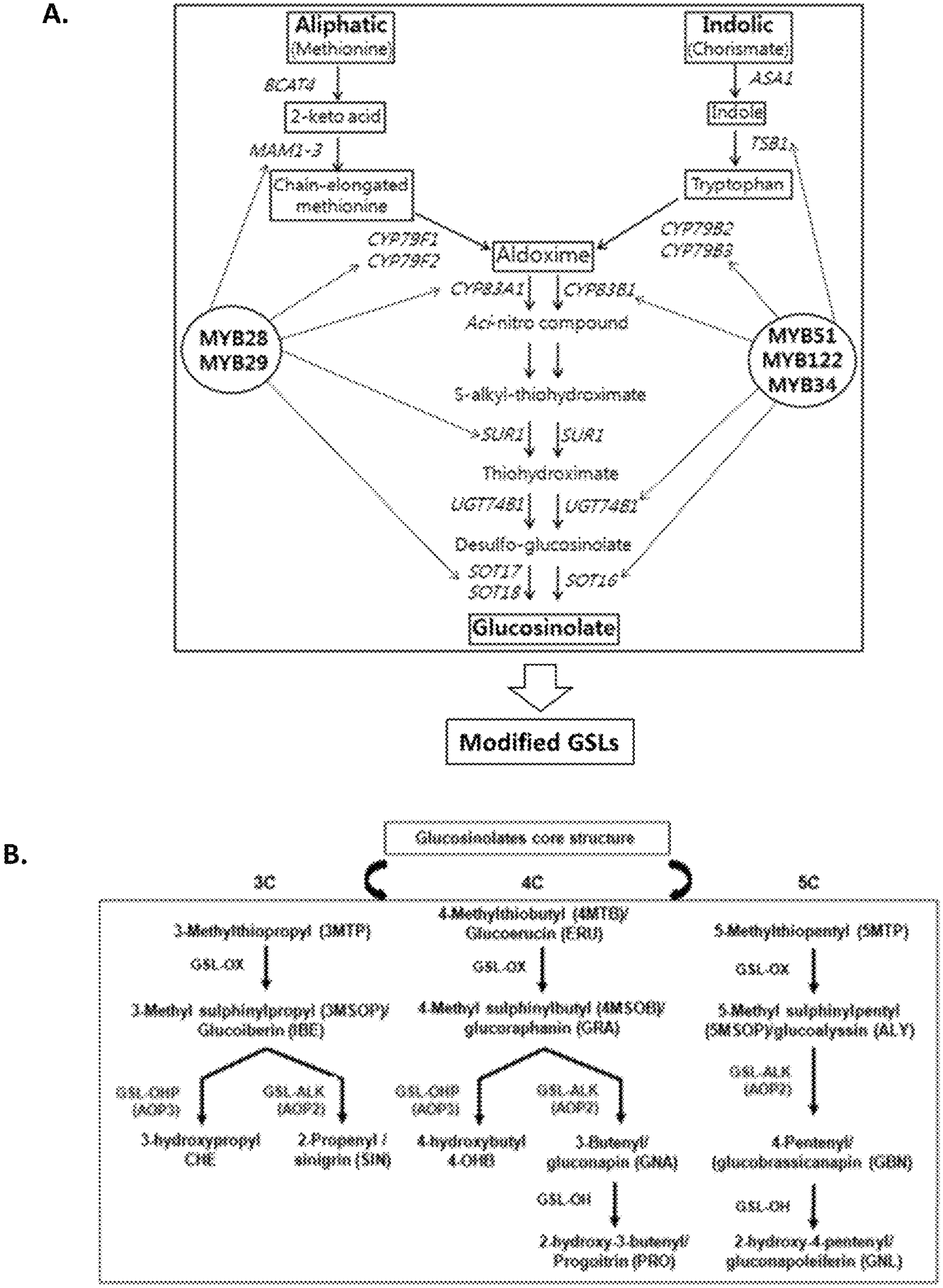
FIGURE 1A, B

A.
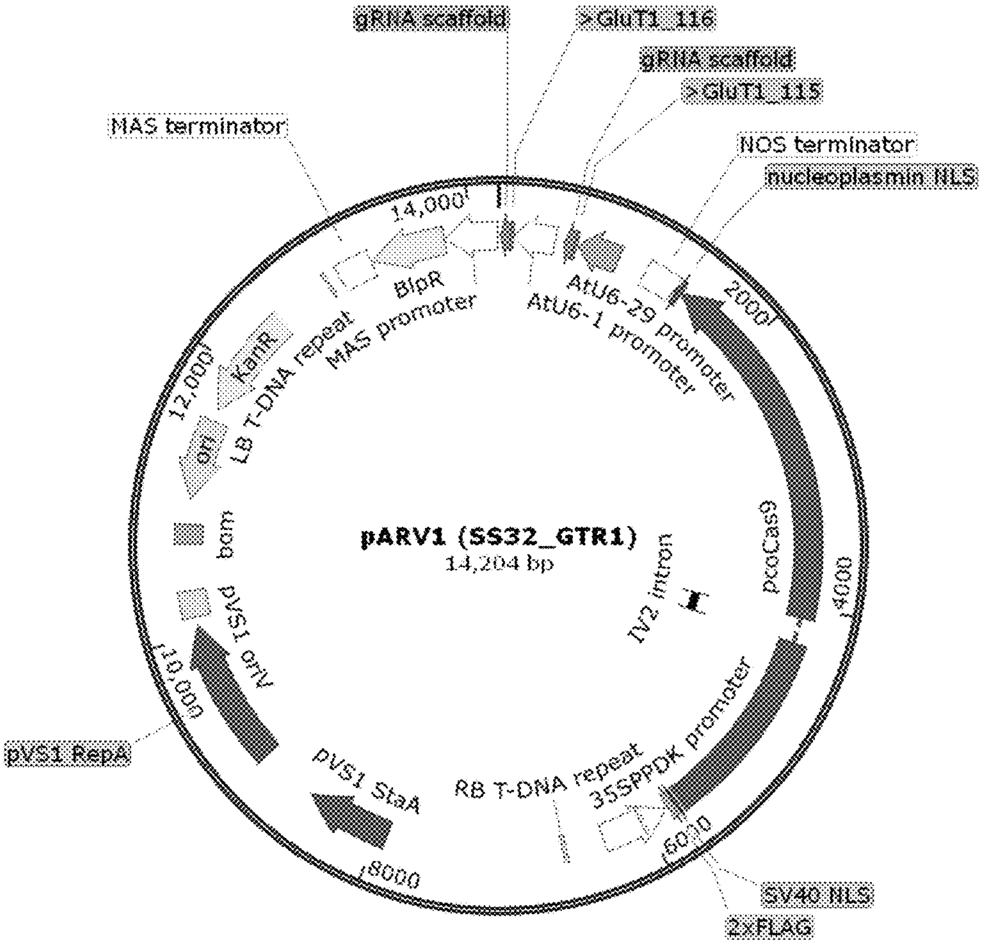
B.
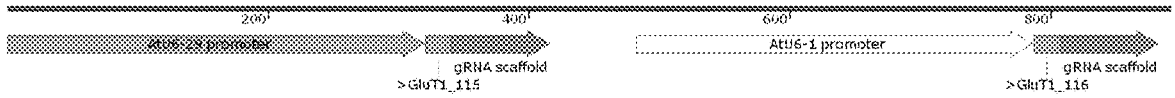
C.
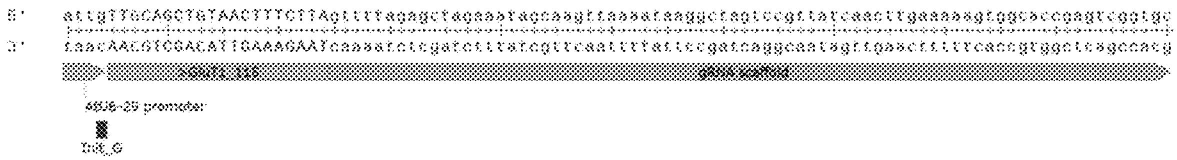
FIGURE 2A, B, C

A.
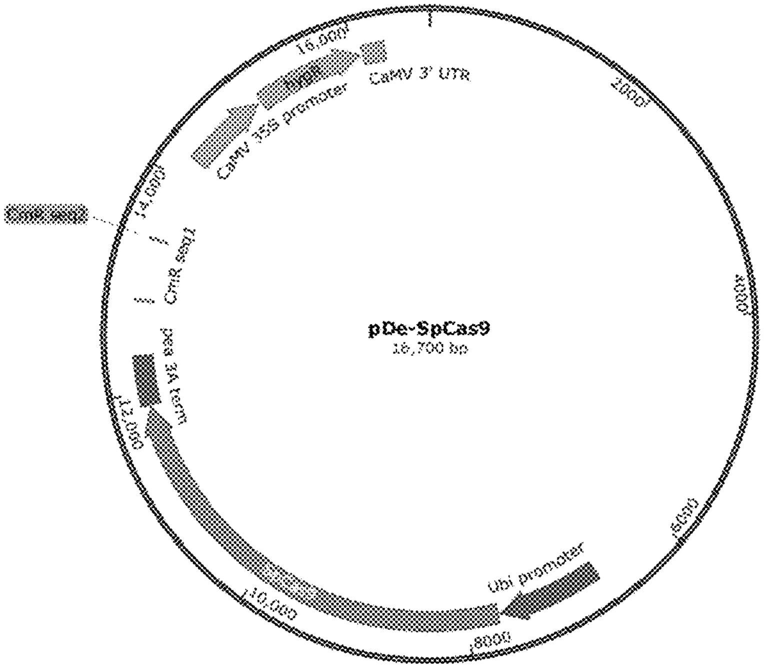
B.
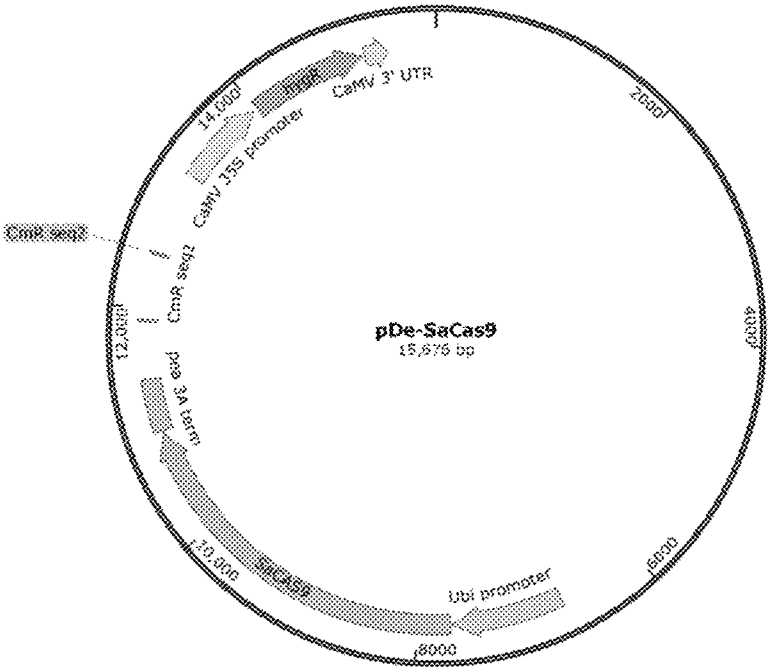
FIGURE 3A,B

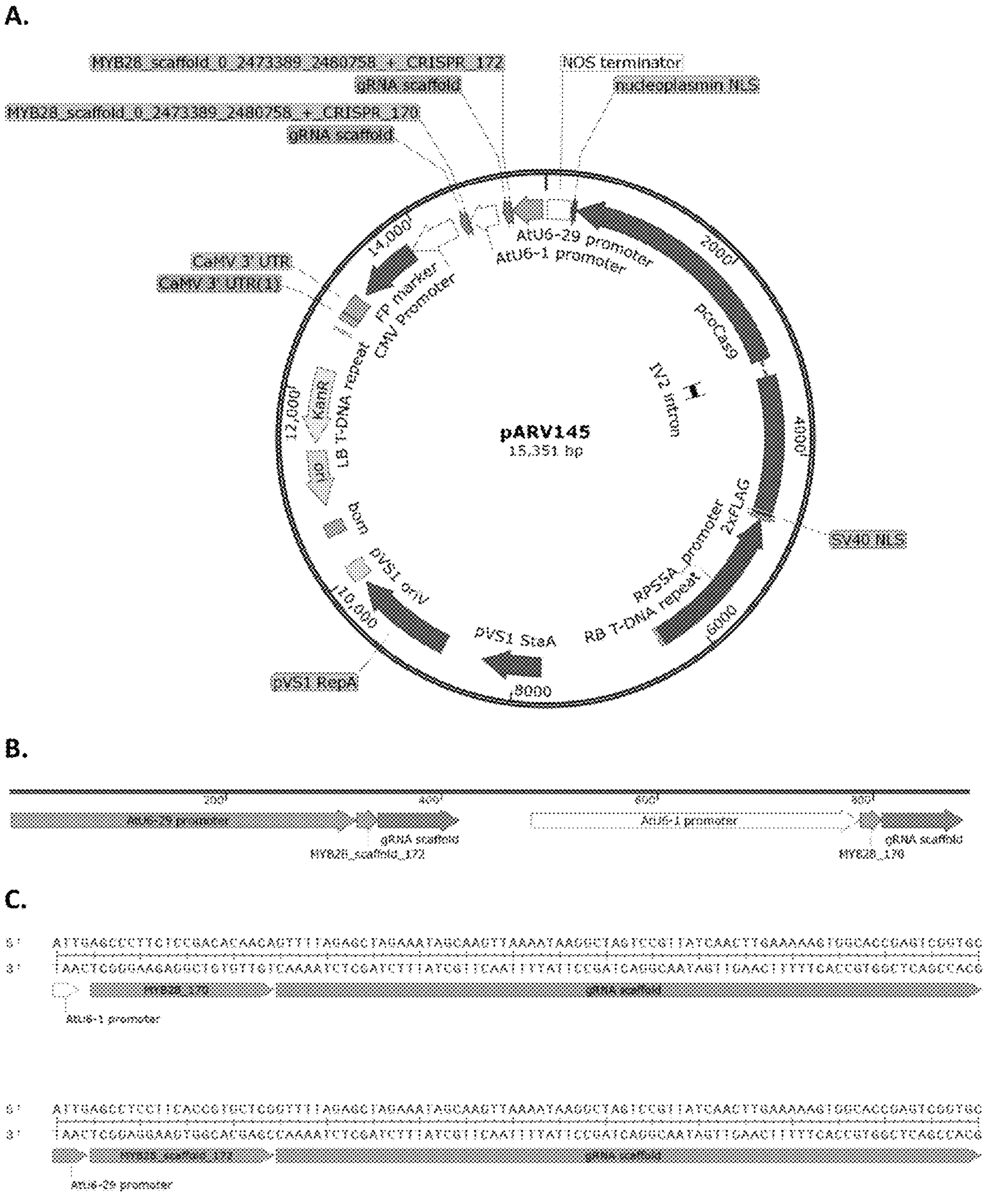
FIGURE 4A, B, C

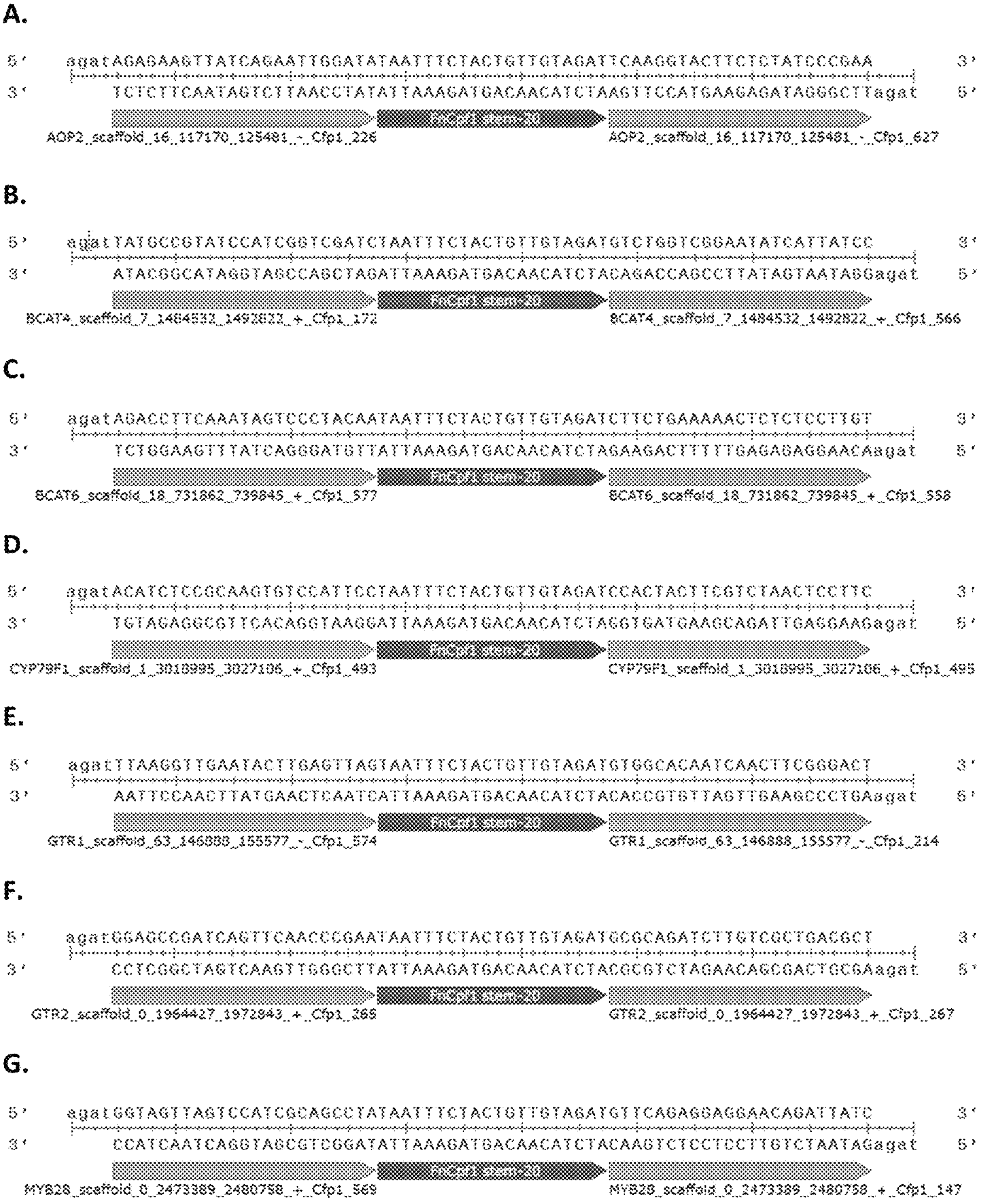

5' agatAGAGAAGTTATCAGAATTGGATATAATTTCTACTGTTGTAGATTCAAGGTACTTCTCTATCCCGAA 3'
3'     TCTCTTCAATAGTCTTAACCTATATTAAAGATGACAACATCTAAGTTCCATGAAGAGATAGGGCTTagat 5'

AOP2_scaffold_16_117170_125481_-_Cfp1_226     AOP2_scaffold_16_117170_125481_-_Cfp1_627

B.

5' agatTATGCCGTATCCATCGGTCGATCTAATTTCTACTGTTGTAGATGTCTGGTCGGAATATCATTATCC 3'
3'     ATACGGCATAGGTAGCCAGCTAGATTAAAGATGACAACATCTACAGACCAGCCTTATAGTAATAGGagat 5'

BCAT4_scaffold_7_1484532_1492822_+_Cfp1_172     BCAT4_scaffold_7_1484532_1492822_+_Cfp1_566

C.

5' agatAGACCTTCAAATAGTCCCTACAATAATTTCTACTGTTGTAGATCTTCTGAAAAACTCTCTCCTTGT 3'
3'     TCTGGAAGTTTATCAGGGATGTTATTAAAGATGACAACATCTAGAAGACTTTTTGAGAGAGGAACAagat 5'

BCAT6_scaffold_18_731862_739845_+_Cfp1_577     BCAT6_scaffold_18_731862_739845_+_Cfp1_558

D.

5' agatACATCTCCGCAAGTGTCCATTCCTAATTTCTACTGTTGTAGATCCACTACTTCGTCTAACTCCTTC 3'
3'     TGTAGAGGCGTTCACAGGTAAGGATTAAAGATGACAACATCTAGGTGATGAAGCAGATTGAGGAAGagat 5'

CYP79F1_scaffold_1_3018995_3027106_+_Cfp1_493     CYP79F1_scaffold_1_3018995_3027106_+_Cfp1_495

E.

5' agatTTAAGGTTGAATACTTGAGTTAGTAATTTCTACTGTTGTAGATGTGGCACAATCAACTTCGGGACT 3'
3'     AATTCCAACTTATGAACTCAATCATTAAAGATGACAACATCTACACCGTGTTAGTTGAAGCCCTGAagat 5'

GTR1_scaffold_63_146888_155577_-_Cfp1_574     GTR1_scaffold_63_146888_155577_-_Cfp1_214

F.

5' agatGGAGCCGATCAGTTCAACCCGAATAATTTCTACTGTTGTAGATGCGCAGATCTTGTCGCTGACGCT 3'
3'     CCTCGGCTAGTCAAGTTGGGCTTATTAAAGATGACAACATCTACGCGTCTAGAACAGCGACTGCGAagat 5'

GTR2_scaffold_0_1964427_1972843_+_Cfp1_265     GTR2_scaffold_0_1964427_1972843_+_Cfp1_267

G.

5' agatGGTAGTTAGTCCATCGCAGCCTATAATTTCTACTGTTGTAGATGTTCAGAGGAGGAACAGATTATC 3'
3'     CCATCAATCAGGTAGCGTCGGATATTAAAGATGACAACATCTACAAGTCTCCTCCTTGTCTAATAGagat 5'

MYB28_scaffold_0_2473389_2480758_+_Cfp1_569     MYB28_scaffold_0_2473389_2480758_+_Cfp1_147

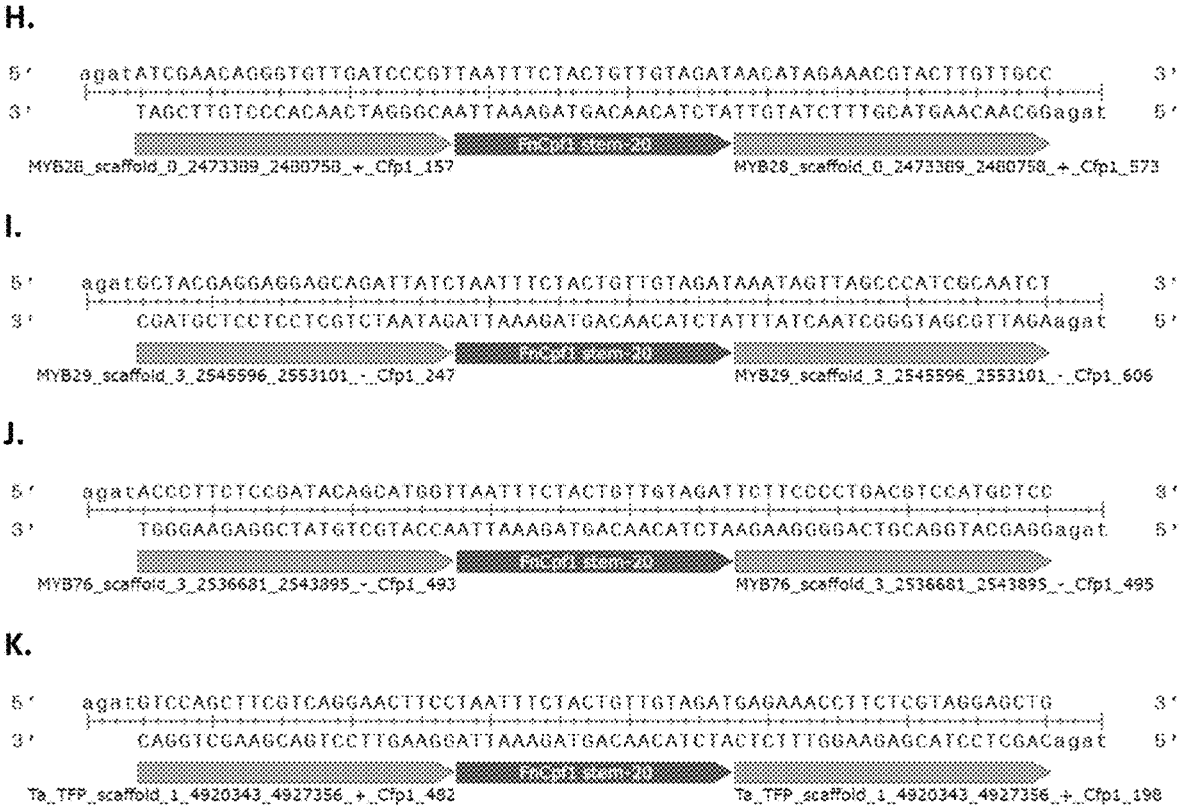
FIGURE 7H, I, J, K

SEQUENCE LISTING

```
<160> NUMBER OF SEQ ID NOS: 261

<210> SEQ ID NO 1
<211> LENGTH: 1365
<212> TYPE: DNA
<213> ORGANISM: Thlaspi arvense

<400> SEQUENCE: 1

atgggttcac tttcaaacac tcctcagctt ccagtcatct acctctcgga ccaaacccta     60

aaaccaggaa gctcaaagtg ggttgaagtc aggagtgatg tccgtaaagc tcttgaagag    120

tacggcggtt tcgaggtgtc gtacgataga gtgtcggagg agcttaagaa gtcggttttg    180

caagccatgg aagagctttt cgcgttacca gttgaggcta aacagagaaa cgtctctcct    240

aaacccttca gcggttattc cactcataac ggtctttccg agagtatggg gatccaggat    300

cctcatgttt tggacaaagt ttacgagttt actcaacttc tacgtcctga tcattgtgac    360

ggtaacaaga gcatcagcga aacgatccag acgttttcag agaagttatc agaattggat    420

ataatggtga gaagaatggt aatggaaagc ttcgggatag agaagtacct tgacaaacac    480

ctgaactcaa cgaattaccg tctgcggctg atgaagtata tagcaccgcc tgatgctgat    540
```

```
gctactaatg ttgcggctga tgccaaagat gctgatgata atgctaagac gattacaaat    600
gataaagttg atgcggctgg tgctaatgat gtagatgctg gtgatatcgc taatggtatt    660
gctaatcttc atattggtga tgatgctaac gctggtgcta atggtgctgg tgttgatgct    720
aatgatggtg gtgaggatgc taagactggt gaggatgcta agactggtga atgtgctagt    780
gttaagtcta atgccgaaga tggtactgat gttaatgcca gtgctgatgc tggtgttact    840
gttggctcta atgctgatgc taatgctaat gctaatgcta atactagtac tgatgctggt    900
gttggcgata gtgttaaagc taatggtggt gctgatgatg ttgagaagaa attgggtcta    960
ccttctcaca ctgataagaa ccttataacg gtgctttatc aatacgagat tgaaggcttg   1020
gaggttctaa ccaaagatga caagtggatc agactcaaac catctcataa ttctttcgtt   1080
gttatggctg gagattctct atacgcactt atgaatggta gactaactcg tccctttcat   1140
cgagtaagag taacggagaa aaagaagaca agatattcaa tagcattgtt ctcggctcca   1200
accgcagatt acatcataga cacaccaaaa gaacttgtgg acgagaagca tccacgtatc   1260
ttcgaaccat ttaactataa cgacttgatg agtttctatc atagtgaagc tggtcgtaaa   1320
gctcgatcta ctcttgatgc tttctgtgcc gtctctcgag cataa                   1365
```

<210> SEQ ID NO 2
<211> LENGTH: 5220
<212> TYPE: DNA
<213> ORGANISM: Thlaspi arvense

<400> SEQUENCE: 2

```
gaacactcgt gaagtaaaac ggctcacggg ccgcatcgcc gcccttaaca gattcatttt     60
tcgatcaacc gacaagtgtc tcccctteta ccaacttctc tgtggtaaaa agcacttcaa    120
gtgggacaaa aaggctttcg gccaactcaa ggagtatcta tcaacgccac cagtcctagc    180
gaagcccgag ctcggcaaaa tgctttacct ctacgtcgcc gtatctcact cggccgtcag    240
cggcgtactc gtcaaagaaa accggggcga gcagaagccg atcttttatg tgagcaagtc    300
attggacgga cctgagagta gatattctac gatggaaaag ctcgcactcg cagtagtaat    360
ctcagcccgg aagttgcgtc cctatttcca atcacactca atcacggttc tcacaaatca    420
accgctgcga acagtcctgc acagcccaag tcaatcgggg caaatgacga tgtgggccgt    480
tgagttaagc gaatacgaca tcaactacaa gaacaggacg tgcgccaagt ctcaggtctt    540
tgccgatttc ctcatagagc taccactcga ctctactccc gtggactctc ccaccgtcgt    600
gcaatggtcg ctatatgtcg acggctcgtc atctcgaaat ggatcgggta tcggagtcag    660
attaatatcg ccaattggaa aaatcctcga gcagtcattt tgccttgagt ttgcggcgtc    720
caacaacgaa gcagaatacg aagctcttat cgccggcctg tgcctggcaa aagcaatagg    780
attaaggcaa atccaagcat tctgtgattc ccagctagta gctagtcaat tcaatggtga    840
ctacgaagca aaaaatgaac gaatggatgc ctacttaaaa gtaatccaaa acctttcaaa    900
ggacttcgac gatctcaccc tcaccaaaat cctgcacagt gataattctc cagtcgatgc    960
gctggccgcc ctcgcgtcaa tctccgaccc aaacctttac cgtatgatac ctgtaaagag   1020
catcaaaact ccgaatggga gacttggtaa aaagtaaaga taaccacgaa aaaagaaagg   1080
ataattatga ataataatat tcataattca tttaggaaaa tgttcattaa tattacatta   1140
aaaatataat atttatctaa actaaaaatt aattatttct cgaaagaaaa ataaaatatc   1200
gagagataga aaatagattt aaaccatctt agttagaatt aaattttcca aacaggctta   1260
```

gtttgtaaaa atcgagtcgt tataataata atcaaaatct aatacaccaa aaaacaaagg 1320
aagaaaacaa ctgactcgtc atagcctata gccaatttga ttttggcatt ttgcgaccca 1380
acaaatccaa aggtaagtgg gtttacctct atatataaat ttgcatgaaa gtaattactg 1440
aaaatagtta ttatataatt ggtgccgaca acgtcaacaa acacaattat tcattacatt 1500
attgtacacg ttcatgctca tgcacatgta ctttattgat tttcacacaa tacataaact 1560
taattacttc ttctcccctc cgaagttatt aatattacaa tatcaaatac ttatcacaca 1620
aattaaacag aagtcaacta atccaaaacc ctttatttga tactacatag ttttgcaaat 1680
tagttgactc ttttgaaaac caccaaaact cgtaacgtaa cgcacacgta tgggttcact 1740
ttcaaacact cctcagcttc cagtcatcta cctctcggac caaaccctaa aaccaggaag 1800
ctcaaagtgg gttgaagtca ggagtgatgt ccgtaaagct cttgaagagt acggcggttt 1860
cgaggtgtcg tacgatagag tgtcggagga gcttaagaag tcggttttgc aagccatgga 1920
agagcttttc gcgttaccag ttgaggctaa acagagaaac gtctctccta aacccttcag 1980
cggttattcc actcataacg gtctttccga gagtatgggg atccaggatc ctcatgtttt 2040
ggacaaagtt tacgagttta ctcaacttct acgtcctgat cattgtgacg gtaacaagag 2100
catcaggtaa tttgtgaaaa atactcaata ttgcttcata atataaaaat actcaatatt 2160
gcttcctaat ctttttggca gtttatttca ctacataaaa taaacccgct tttacatttt 2220
tattgtttgt ggtataagaa tattagttca ctcaaacagc atgaaactaa taattgaaat 2280
tttgtatttg tgtgaaaaac tttagttcac ttaaataaca tttttgttgt ttgtgttgta 2340
aacagcgaaa cgatccagac gttttcagag aagttatcag aattggatat aatggtgaga 2400
agaatggtaa tggaaagctt cgggatagag aagtaccttg acaaacacct gaactcaacg 2460
aattaccgtc tgcggctgat gaagtatata gcaccgcctg atgctgatgc tactaatgtt 2520
gcggctgatg ccaaagatgc tgatgataat gctaagacga ttacaaatga taaagttgat 2580
gcggctggtg ctaatgatgt agatgctggt gatatcgcta atggtattgc taatcttcat 2640
attggtgatg atgctaacgc tggtgctaat ggtgctggtg ttgatgctaa tgatggtggt 2700
gaggatgcta agactggtga ggatgctaag actggtgaat gtgctagtgt taagtctaat 2760
gccgaagatg gtactgatgt taatgccagt gctgatgctg gtgttactgt tggctctaat 2820
gctgatgcta atgctaatgc taatgctaat actagtactg atgctggtgt tggcgatagt 2880
gttaaagcta atggtggtgc tgatgatgtt gagaagaaat tgggtctacc ttctcacact 2940
gataagaacc ttataacggt gctttatcaa tacgagattg aaggcttgga ggttctaacc 3000
aaagatgaca agtggatcag actcaaacca tctcataatt ctttcgttgt tatggctgga 3060
gattctctat acgtaagttt ccaacttctt cttcttcttc tttttctttt tttaagttga 3120
cactcacacg tactgacgta cacgttggtg gatttaaaag taaccctagt ggagaagaag 3180
atgaattttc atttacatta tatcataaac ctacttttta aattagaata agaataatta 3240
aaactaaacc catttttttat tggctcacta tggcctaaag aatataatta aaatattata 3300
taggctcaat aagtcataat attctttagc ctatagaata tttttaaagt attcaataat 3360
taaaattatt ttatagcata tagaatattt tatgggctca ataattacaa gtattctaca 3420
ggatcaccat ggcctaaaga ataatcaaaa gtaaaccgaa ttttaaaatt acaggtatag 3480
agaaagaaaa aagaaagcta aaattaaaac caagaataag ttaaaaatgt atgagaagta 3540
acaaacttag tggcgaaaaa gagaaaaaga ttattattca gtcacgttca cgctcactat 3600
ggaccaactt atcctataga aactattaat attttcttga ttttattcgc tcttatcact 3660

```
ttcacaagtg catgtttgac taaaagcgtt ataacatgat gttttgtttt cttctgatca   3720

tgatctcttg ctgttactta caaacaaaac aaatggtgat tttgtttttg tttttttttg   3780

caggcactta tgaatggtag actaactcgt ccctttcatc gagtaagagt aacggagaaa   3840

aagaagacaa gatattcaat agcattgttc tcggctccaa ccgcagatta catcatagac   3900

acaccaaaag aacttgtgga cgagaagcat ccacgtatct tcgaaccatt taactataac   3960

gacttgatga gtttctatca tagtgaagct ggtcgtaaag ctcgatctac tcttgatgct   4020

ttctgtgccg tctctcgagc ataagttctt atttcctttg ctgtgcaaat ccgaaacacg   4080

tttacaaaat ttacatcagt tctttagtta ttataccaac gacaaaaaaa aaagaaaaca   4140

ttcaaaaatc ataaggagag taccgatgga gtttctcgtg atccaaagac accaacttgg   4200

tttttgcttc cgtacgtgct gactgctgag aaagtaagtg ttggagtgtc ccatttatac   4260

aaaaatttca taatactttc aacacatgtt gcttttcagt tcttttggct ttttctgtag   4320

agaaacacat ataatgaata tacaaaggga ggaaagttgg tgaatttatc acacacaaaa   4380

taaaaacatt aagttggtga atcgtttcct tccttttatt gagtctcaat acattgtatt   4440

attaccttta gagtataaga tgaacaccaa cttaacgact aacctaacct tccttttttt   4500

ttttttgaa aaacaaactt aggctatgaa tatcaatagt ttttaatatg agtttaatag   4560

tttttggtta aaaattttaa agttgaaaaa gaagttttga ggaagaaacc taatatgagt   4620

tttatagttt ttgtttttgt ttttaaagaa ctctatatag agaagttttc gaagatcgta   4680

gtggccaata aaatagtttt ctcaaaaact aaaacaaaaa gtacattata aactacaaaa   4740

tattctcagt cttatcctta attagctaac taactaaaca ctataaccct agttacattc   4800

taaccattgt ataaccattg tataagatat acatttagaa ttctcagcta gtgaaatgat   4860

ttttgtaaag taaagcaata atgaagagaa aaaggagaac agcacatctt taaagtaatc   4920

tctttttgat tgatctcggt tggatccaac tgtgcatttg agtactatgg agcaaaaagc   4980

tgacgtttta actgcatcca cacatcacct cgggaatgtt tctggaaaac cttctcgaga   5040

taagattgaa agtagaagat gatcattgat gaataatctt caacattgtt acaaaatata   5100

agtaaagtat ttacgaggtg aaattttgag tgataactag ttctagtttc tctttaacta   5160

gagctttatc tcatgcataa taccaaataa cttctttttt ttttataaga tccgtatgcc   5220
```

<210> SEQ ID NO 3
<211> LENGTH: 454
<212> TYPE: PRT
<213> ORGANISM: Thlaspi arvense

<400> SEQUENCE: 3

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95
```

```
Gly Ile Gln Asp Pro His Val Leu Asp Lys Val Tyr Glu Phe Thr Gln
            100                 105                 110

Leu Leu Arg Pro Asp His Cys Asp Gly Asn Lys Ser Ile Ser Glu Thr
        115                 120                 125

Ile Gln Thr Phe Ser Glu Lys Leu Ser Glu Leu Asp Ile Met Val Arg
    130                 135                 140

Arg Met Val Met Glu Ser Phe Gly Ile Glu Lys Tyr Leu Asp Lys His
145                 150                 155                 160

Leu Asn Ser Thr Asn Tyr Arg Leu Arg Leu Met Lys Tyr Ile Ala Pro
                165                 170                 175

Pro Asp Ala Asp Ala Thr Asn Val Ala Ala Asp Ala Lys Asp Ala Asp
            180                 185                 190

Asp Asn Ala Lys Thr Ile Thr Asn Asp Lys Val Asp Ala Ala Gly Ala
        195                 200                 205

Asn Asp Val Asp Ala Gly Asp Ile Ala Asn Gly Ile Ala Asn Leu His
    210                 215                 220

Ile Gly Asp Asp Ala Asn Ala Gly Ala Asn Gly Ala Gly Val Asp Ala
225                 230                 235                 240

Asn Asp Gly Gly Glu Asp Ala Lys Thr Gly Glu Asp Ala Lys Thr Gly
                245                 250                 255

Glu Cys Ala Ser Val Lys Ser Asn Ala Glu Asp Gly Thr Asp Val Asn
            260                 265                 270

Ala Ser Ala Asp Ala Gly Val Thr Val Gly Ser Asn Ala Asp Ala Asn
        275                 280                 285

Ala Asn Ala Asn Ala Asn Thr Ser Thr Asp Ala Gly Val Gly Asp Ser
    290                 295                 300

Val Lys Ala Asn Gly Gly Ala Asp Asp Val Glu Lys Lys Leu Gly Leu
305                 310                 315                 320

Pro Ser His Thr Asp Lys Asn Leu Ile Thr Val Leu Tyr Gln Tyr Glu
                325                 330                 335

Ile Glu Gly Leu Glu Val Leu Thr Lys Asp Asp Lys Trp Ile Arg Leu
            340                 345                 350

Lys Pro Ser His Asn Ser Phe Val Val Met Ala Gly Asp Ser Leu Tyr
        355                 360                 365

Ala Leu Met Asn Gly Arg Leu Thr Arg Pro Phe His Arg Val Arg Val
    370                 375                 380

Thr Glu Lys Lys Lys Thr Arg Tyr Ser Ile Ala Leu Phe Ser Ala Pro
385                 390                 395                 400

Thr Ala Asp Tyr Ile Ile Asp Thr Pro Lys Glu Leu Val Asp Glu Lys
                405                 410                 415

His Pro Arg Ile Phe Glu Pro Phe Asn Tyr Asn Asp Leu Met Ser Phe
            420                 425                 430

Tyr His Ser Glu Ala Gly Arg Lys Ala Arg Ser Thr Leu Asp Ala Phe
        435                 440                 445

Cys Ala Val Ser Arg Ala
    450
```

<210> SEQ ID NO 4
<211> LENGTH: 1071
<212> TYPE: DNA
<213> ORGANISM: Thlaspi arvense

<400> SEQUENCE: 4
atggctcctt ctgcgcaacc agttcctaca agtgtttcgg atgagaaata cgcaaatgtg     60

-continued

```
aagtgggaag agttagggtt cgggtttgtt cgtacggaca atatgtatgt tgccaagtgc    120
aaacatggag agagtttcca agagggaact gttgttcctt atgctgattt ccaaatcagc    180
ccttgctctg cagttcttaa ttatggccag ggtttatatg aagggctgaa ggcttacagg    240
acagaagatg gccggataat gatattccga ccagaccaaa acggtctccg ccttcaagcc    300
ggagccaaga gactttgtat gccgtatcca tcggtcgatc aatttgtctc cgccgtcaaa    360
caagttgttc ttgccaacaa gaaatggatt cctcctccgg ggaaaggaac attgtatatc    420
agacctattt tgttcggaag tggtcctata cttggctcac ttccggtccc tgagtacacc    480
ttctcagtat ttgcttgtcc cgttggacgt tttcacaagg ataactctgg cttgaacctg    540
aaaattgaag ataagtttcg ccgcgctttt cctagtggaa ccggtggtgt gaagagtatc    600
acaaactatt ctcctgtttg gataacattg gcagaggcga aagctcaggg tttctctgat    660
gttttgtttt tggatgctgc aactggcaaa aacgtcgaag agcttttcgc ttccaacatt    720
ttcatagtca agggaaatgt tgtgtcgact ccagaaattt caggaactat tttgcccgga    780
gtcacacgaa aaagtatcat tgaattaact cgtgatttcg gctacaaggt tgaggaacgt    840
gttgttcccc ttgaggatct tctcgactcg gaagaagttt tctgcactgg cactgctgcg    900
attgtgacaa ctattgcgtc cgtaaccttc aaagacaaaa agaccggatt caaaacagga    960
gaaaaaacat tggccgcgaa gctctttgcg acgttaatgg atatccagat gggtcgggtc   1020
gaggataaga agggatggac ggtggaggtt gaccggtgcc accagggttg a            1071
```

<210> SEQ ID NO 5
<211> LENGTH: 6184
<212> TYPE: DNA
<213> ORGANISM: Thlaspi arvense

<400> SEQUENCE: 5

```
ggaagttgca acgaaagctt cagaagctca acgggaatgt taagtgacag agacaacaac     60
agcaacaaca ataaccgaga gttcgaggcg gaagttgcaa cattaagcaa tgtaaaacac    120
ataaacgttg tgaagttgtt gtgtagcata acgagtgaag acagcaagtt gcttgtgtat    180
gagtttatgc ctaatggaag cttgtgggaa cagttgcacg agcgtcgtgg tgagcaagag    240
attggatggc gtgtgagaca aacgatagct ttaggagctg ctaaagggct ggagtatctg    300
caccatgggt tagatcggcc tgtgattcat cgtgacgtca agtccagcaa tatcttgctt    360
gatgaggagt ggagaccaag gattgctgat tttggattgg ctaaaatcat tcagtctgat    420
tcggttcaac gagatttctc tgctcctctc gttgaaggaa ctctcggtta cattgcccct    480
ggtacgtcgt cttttctttg gtttaatgaa actatataaa ccctaaacca gaacatgaac    540
tatccgaatt ttacaacctt ataaaattat ctccaagttt cttgcttctc aagcttcaaa    600
ttccttgcgt ttctatatac agtttcttaa cttctctcag ttgcaaataa tttctatgac    660
gtacacagaa tacgcctaca ctacgagcgt gaacgagaag agcgacgtat acagctttgg    720
ggtggttcta atggagttgg tgacggggaa gaagccggtg gaggcagagt tcggagagga    780
cagagacatc gtcatgtggg tttggaacag gagcaaggag atgaacagag agaagatgat    840
ggagatcatc gatccgatta tacaaaatga atacaaagag gatgctctta aagtgttgac    900
aattgctttg ttatgtactg ccaagtctcc tcaggttaga ccgtttatga aatcagtggt    960
ttgtatgctg gagaaaacag agccttcttg caacaacaaa agtggagaag caagttacgt   1020
tgtgagtgat gatgaggaga ttactgatgt ttaatagctc atagattgaa caaactcaca   1080
gaagggttac ttgtcaatct agctcatgtc taaggaccaa gaatataatt tttttccaa    1140
```

-continued atagttataa aattatacag aacttttagg aattgttcta agattataca agagtttttt 1200
ttttttttt tttgccagcg gaaagtttca atatttccaa gttcttagaa atataatcca 1260
gttatccaaa taattagtat ctatataaaa caaatttgag ttgttcacaa agatagtttg 1320
gccgagtggt ctaaggcgcc agatttaggc tctggtccga aagggcgtgg gttcaaatcc 1380
cacagctgtc agaattttat ttcatttgac ttataaattt ttcgggtgct cttccttcaa 1440
cttttcaatg ttcacgtagt tcgtcatttt cctcatcggc ggtatggatg ctggacggtg 1500
gagattcgtc ttcctcctat aattagttgc ctgtatttgg aaactaattg aaagaaataa 1560
catgaagaag aaaaaaagaa agaaagagtg gtggatatac atgtacatga gaaagaaata 1620
gaaagtcaat gaaaaatcga ggaccgaagg ggaataatat aattcgaaaa aagtatatgt 1680
attatgtata gacatgtaag gtgtaacgta ctaacatgtt ggtgcatgaa taaaatttta 1740
tttagtaaaa atggatacaa cttaaaaaaa acagaaattt gggggaaaaa gttatcacaa 1800
ttatgaagaa caagttacta gtatatatat attaatgttt ttcttttaga aaacaaaagt 1860
attcttattt ttaagacttt taatttagaa aaatgattac cttaatacaa ctggatgaat 1920
tcgtattatt tattcaaatg gaaaactaca caagaacaaa tactatagtt ttgaggaaga 1980
ataaaagaaa actgaaaagg catgaatgtt tatttatatt attattacca acaacttttt 2040
aaaattatta catcacaagg gcatgacata atatgataaa cacagagatc cagagacatc 2100
ttcagatgtt ttcttagcta tactatagta tgaaaacaca gagatccaga gacatcttca 2160
gatgttttct tagctatagt atttatataa ttgtcaagtt atacggcttc aagttatggc 2220
tccttctgcg caaccagttc ctacaaggta aaatatatca ttgcaaatat tataatagtc 2280
tcgcatttgc atgtttaaat ctgttactat gatctatgat ttgctgatga tagtttcttt 2340
tacagtgttt cggatgagaa atacgcaaat gtgaagtggg aagagttagg gttcgggttt 2400
gttcgtacgg acaatatgta tgttgccaag tgcaaacatg gagagagttt ccaagaggga 2460
actgttgttc cttatgctga tttccaaatc agcccttgct ctgcagttct taattatggc 2520
caggtttgtt attaatcaat agagatcaaa cttattaaga aaaatttata tcatcagaaa 2580
gaagatataa ccatcaccat atatagaact aatatcgttt tagcattgca tgcatatttg 2640
agctattaga catttaaaat tttgaaaaga taatagaata taaatcaaac gaaatgattt 2700
aaaagtgtta atatgatgat attcttatca agtaaattgt ttcatcaaat aattactata 2760
atatgtttca attcaaagaa aatctagata tgtataacaa cataagtagt ctaactgccc 2820
ccattaaaat gaactaatga gctttcttaa aatatttatg aagaattaaa ttattagatg 2880
ctagattgag tgatgcggaa gcaaagtagt ctgaaatatt tgtaatttgg aaataaatag 2940
ggtttatatg aagggctgaa ggcttacagg acagaagatg gccggataat gatattccga 3000
ccagaccaaa acggtctccg ccttcaagcc ggagccaaga gactttgtat gccgtatcca 3060
tcggtcgatc aatttgtctc cgccgtcaaa caagttgttc ttgccaacaa gaaatgggta 3120
tgtacaggct cggttccaaa agaaaaaaat ctggaccgct caaaaaaacc aaactgtgtt 3180
ctacataaat tctaaatttt gaaattatgg tcgtgttagg cataattgta aaagaaaaaa 3240
aaatgcttta gaatgcttca aaaggcaaat aaatgtaatt tctatgcatt tttcaagata 3300
ttaaatctta acaaatgtat atattttaaa aattatatta atgttcttct ttgaatttta 3360
tatatataca gattcctcct ccggggaaag gaacattgta tatcagacct attttgttcg 3420
gaagtggtcc tatacttggc tcacttccgg tccctgagta caccttctca gtatttgctt 3480

-continued

```
gtcccgttgg acgttttcac aaggtgagtg ttcttgtcaa tatatattat ttttatttta   3540
gtttaaacag taatagacta gagcaatttt ttggaatgat tttgattata atatgttttc   3600
tggtatagga taactctggc ttgaacctga aaattgaaga taagtttcgc cgcgcttttc   3660
ctagtggaac cggtggtgtg aagagtatca caaactattc tcctgtaagt ttgaaaacgt   3720
acatcaaatt tgatattaac atgattagct gtgttttaga tttttgtatg aacgattaat   3780
agttaattaa tataacggat aattttttct taatgaaggt ttggataaca ttggcagagg   3840
cgaaagctca gggtttctct gatgttttgt ttttggatgc tgcaactggc aaaaacgtcg   3900
aagagctttt cgcttccaac attttcatag tcaaggtaat tatatatata aatatatata   3960
tatataatac gttttgaaag agttttaaag aatattaaga tcgatgtgat atggtctgta   4020
tagggaaatg ttgtgtcgac tccagaaatt tcaggaacta ttttgcccgg agtcacacga   4080
aaaagtatca ttgaattaac tcgtgatttc ggctacaagg tttgaatatt tcaataccat   4140
gatattataa tttttttttt ttttgaaaaa gggtttcatg atattataat tttatccatg   4200
ttgattttgt aaataatcta gttttttttc cttggattct tattataata ggttgaggaa   4260
cgtgttgttc cccttgagga tcttctcgac tcggaagaag ttttctgcac tggcactgct   4320
gcgattgtga caactattgc gtccgtaacc ttcaaagaca aaaagtaatg ttttattcca   4380
catctaatca tttttctcaa caaaataaga agaaaaataa aacaaataca gaataactat   4440
accatgattt aaatctggat tttgctttat tctcatatat aagtttgact aaaaattggg   4500
tgtacatatt caatgcgtac aggaccggat tcaaaacagg agaaaaaaca ttggccgcga   4560
agctctttgc gacgttaatg gatatccaga tgggtcgggt cgaggataag aagggatgga   4620
cggtggaggt tgaccggtgc caccagggtt gaggatttgc ggtttgagta gagttgcttt   4680
ttgtgtaaga aactttgagt tgtctataaa gctttggact gcttctcttt atatattcgt   4740
tcacaacaat gtttattata ttaaaaatag taataattta ggcgaaaata ataaggatat   4800
tttctatcca tctttttttg ttgttaaagc tttttttatcc attgttttaa gcaattaact   4860
tttattctat tctattatat cagttcaaag aataggcttt ttcttggcac aaaataatag   4920
gtttcaaatg tacatatata caacatatat ttgttaattg ataatcaaat gtatctcagt   4980
gatccgatta agtttatata tgcctaatgt ttttttatct atacgtttat ttaatattaa   5040
ccttatagct ctgtattttt ttttttgatg tatttatata tgactaactt ttggttggtt   5100
atttcaccaa cttatttgtt tagagaaaaa taaattggga actctagtta gatcacagaa   5160
taatcatcac gtggagaaac ccatttgttt ctcgtcacgt ggagaaaacg ttaagcttta   5220
aaattttctt tttaattatt attatctcgc gggtatggct ggaagaaaga gagtgtttaa   5280
aatgtgaatg cgctcttagt taggtgaagg ttaataggta ggagggtagg tcaaatgtgt   5340
atcagtagtg atggataaaa aatttaaact gtagataatt tctaacaaaa aaacatataa   5400
taaattacat tttcactttt cagtatgcca caaacctata tatgattcaa aaagcatttt   5460
tctactcaga aagctgagag aagtaacaat tttggttatt agcaaaaaaa ttcgttcatg   5520
tttttctttt tcttctgtca gtgtatttgt atgctcaact tctagtcttg attataccgt   5580
agtatgccac tactaattgt tgttttcttc atattgcaaa aacacttaaa attgcaaata   5640
tcggaccaat aagcaaaccc caaagtactt taaacgacca ctttctttgt tttttttatta   5700
ttagacattc aaagttgatt gtttcttact taacctaaac ttaggcagat aaaatattct   5760
tgaatataga tccatgactt gagtcactac tgcaacgaag gcgtctttag tttttgagcg   5820
aagtcgtgag agtttagctt ctcattcatc actctgaatt tctcttttat cctctttatc   5880
```

```
tgttcaaaac attaaaaaca aaagtatgtt attagcataa agctgtctca tacttggtta   5940

tacgtagacc atatttagtt tttcaatagc aaatacaaaa gtaaagcatg atcataagat   6000

tcagggtcaa ggtttggttt acccttctca gctcgatctc cgtgcttcgt ttcttttgat   6060

caagtgattg ccggagattc gtgatgtcga aaatactatc aaggtcgtct tcaaatgcgt   6120

tttccaactc ttcccggaga agagcaggta acttatcgac aataggcatc aggagaaaac   6180

agtt                                                                6184
```

<210> SEQ ID NO 6
<211> LENGTH: 356
<212> TYPE: PRT
<213> ORGANISM: Thlaspi arvense

<400> SEQUENCE: 6

```
Met Ala Pro Ser Ala Gln Pro Val Pro Thr Ser Val Ser Asp Glu Lys
1               5                   10                  15

Tyr Ala Asn Val Lys Trp Glu Glu Leu Gly Phe Gly Phe Val Arg Thr
            20                  25                  30

Asp Asn Met Tyr Val Ala Lys Cys Lys His Gly Glu Ser Phe Gln Glu
        35                  40                  45

Gly Thr Val Val Pro Tyr Ala Asp Phe Gln Ile Ser Pro Cys Ser Ala
    50                  55                  60

Val Leu Asn Tyr Gly Gln Gly Leu Tyr Glu Gly Leu Lys Ala Tyr Arg
65                  70                  75                  80

Thr Glu Asp Gly Arg Ile Met Ile Phe Arg Pro Asp Gln Asn Gly Leu
                85                  90                  95

Arg Leu Gln Ala Gly Ala Lys Arg Leu Cys Met Pro Tyr Pro Ser Val
            100                 105                 110

Asp Gln Phe Val Ser Ala Val Lys Gln Val Val Leu Ala Asn Lys Lys
        115                 120                 125

Trp Ile Pro Pro Pro Gly Lys Gly Thr Leu Tyr Ile Arg Pro Ile Leu
    130                 135                 140

Phe Gly Ser Gly Pro Ile Leu Gly Ser Leu Pro Val Pro Glu Tyr Thr
145                 150                 155                 160

Phe Ser Val Phe Ala Cys Pro Val Gly Arg Phe His Lys Asp Asn Ser
                165                 170                 175

Gly Leu Asn Leu Lys Ile Glu Asp Lys Phe Arg Arg Ala Phe Pro Ser
            180                 185                 190

Gly Thr Gly Gly Val Lys Ser Ile Thr Asn Tyr Ser Pro Val Trp Ile
        195                 200                 205

Thr Leu Ala Glu Ala Lys Ala Gln Gly Phe Ser Asp Val Leu Phe Leu
    210                 215                 220

Asp Ala Ala Thr Gly Lys Asn Val Glu Glu Leu Phe Ala Ser Asn Ile
225                 230                 235                 240

Phe Ile Val Lys Gly Asn Val Val Ser Thr Pro Glu Ile Ser Gly Thr
                245                 250                 255

Ile Leu Pro Gly Val Thr Arg Lys Ser Ile Ile Glu Leu Thr Arg Asp
            260                 265                 270

Phe Gly Tyr Lys Val Glu Glu Arg Val Val Pro Leu Glu Asp Leu Leu
        275                 280                 285

Asp Ser Glu Glu Val Phe Cys Thr Gly Thr Ala Ala Ile Val Thr Thr
    290                 295                 300

Ile Ala Ser Val Thr Phe Lys Asp Lys Lys Thr Gly Phe Lys Thr Gly
```

-continued

```
305                 310                 315                 320

Glu Lys Thr Leu Ala Ala Lys Leu Phe Ala Thr Leu Met Asp Ile Gln
                325                 330                 335

Met Gly Arg Val Glu Asp Lys Lys Gly Trp Thr Val Glu Val Asp Arg
            340                 345                 350

Cys His Gln Gly
        355


<210> SEQ ID NO 7
<211> LENGTH: 1080
<212> TYPE: DNA
<213> ORGANISM: Thlaspi arvense

<400> SEQUENCE: 7

atggctccat ctgtgcagcc ttcttcatca cctcttcgta caagtgaagg agatgaaaaa     60

tacgcgaatg tgaaatggga agagcttgga ttcactctga ctccgacaga ttacatgtat    120

gtggcgaaat gcagacaagg agagagtttt tcagaaggaa agattgttcc ttatggggac    180

atttcaatca gcccttgttc tccgattctc aattatggcc agggactatt tgaaggtctc    240

aaagcttaca ggacagaaga cgaccggatc aggcttttca gacctgaaga aaacgctcgt    300

cgtatgcaaa caggtgcgga taggctttgt atgacaccac cttctctgga gcaattcgtc    360

gactcagtta agcaaaccgt gcttgccaac aagaaatggg ttcctcctcc gggtaaagga    420

gctttgtata taaggccttt gctaataggg agtggcgcta tacttggagt tgctccatca    480

cctgagtaca ctttcctcat ttacgcatct cccgtaggag attaccacaa ggtaagctca    540

ggcttgaacc taaaagttga tcataagtat caccgagccc attcgggtgg aacgggcggt    600

gtcaagagct gcactaacta ttctccagtt gtgaaatcga tggtcgaagc aaagtcgtcg    660

ggtttctctg atgtcttgtt cctggattcg gcaactggta gaaacatcga agaggtttct    720

gcttgtaaca tctttattgt caaggggaac attgtgtcca caccaccaac ttcaggaacc    780

attttaccag gaatcacaag gaaaagcata atcgagctag ctcgtgatct cagctaccag    840

gttcaagaac gtgatgtttc tgtggaggag ctcctagaag cagaggaagc tttctgcacg    900

ggaactgcag tggtcgtgaa agctgttgaa actgtgacct tccatgacaa gaaggtaaag    960

ttcaggacag gagaagcagc gttgtgcacg aagcttcact cgatgctgac gagtattcaa   1020

acaggtcttg ttgaagatac caaaggttgg atggtggaga tcgatccttg tcaaggttga   1080


<210> SEQ ID NO 8
<211> LENGTH: 5021
<212> TYPE: DNA
<213> ORGANISM: Thlaspi arvense

<400> SEQUENCE: 8

atgtccaatt tctctactcc tttcacctca aaactaagct tttcaaccaa aaccgaggga     60

ttagacccgt tcccatgatc atttacagga ggataaccaa cctcaatagt tacaaaaatg    120

gaatctccag gcctgtacac atctttatcc gtttgcacac ttagagtcgg tttgagattg    180

cttccaggaa cacccgaaga gtcattaacg tcgctagtac tgccgatccc caaaaatgaa    240

aaccttgatg ataacatagc ttcaacggct gtgttccttc acagatataa ctagcaaagc    300

agagaagctg actagactaa atccctgaga acagtttgat taggcataaa gcctgcgaaa    360

ttgacgaaag aagagtttag agaacagatg agcaaccctt tgaaggttat agaaaatgcc    420

tcaaacgtag aactgagagc aagtaaaaag agtcataagg tacaaaagaa agactcgcaa    480
```

-continued

```
tccagcgtgt ttcgaaatat cgatcataga tccagagaat gtgcagaggc ccagaaatta    540
gggtttctag ggagaagaag gtgacttaca cgtgatgacg agaatgatca cgtgagttgg    600
aggagcaaga aaaccagatt caaggttcgt caaattggca gcaagtagct taaagaatgg    660
caatcaaatc cagagagaag acgacgcgga tcgctaagat cataaaacca attccgaaca    720
gatgtcgctc acagtcagat tcacagagac tgagcttcta aaaaaaaaca gagacaccgg    780
aaaaaagtct tcaaagccga gagtccggca acagaatcct ccgccgtaag aaacggggaa    840
atgtccagaa aagcttaaag gttaagtttt ctgcagtaaa ccggaaaaga tgaattcagc    900
ttctcgagag caaaataacg aagcagctag tgaggtgatc cagctctata tttcccctct    960
cctaagcttc tctggtgctt caaaattgcc agtggtgtcc ttcttttgga ttttatcagg   1020
ttgaaattag atggatctgg ttgccgttga aggtttctct cgtcgggaaa tctggatcga   1080
agggacgatt gaaacaaaat gcttccccat ctggtttcgg caaatcttcc tcagcttctt   1140
cttcactcgg caaaaattat ggtcctctta tatgttattg ggcttctact tgggttcaat   1200
ggttctgttg ggtcctttga aaatttaatg ttcaaaaaaa aaacacaagt atatataacg   1260
tcgaaaaaaa caaatagagc catggtttag tttcaacaat gtctcataaa ttaaagaccg   1320
gtcacatctt tttttttttt ttgaaaataa gaccggtcac atcttttcaa caaagaacgg   1380
caactttagt ttatttagtc tttagccatc agccttttta tagtttgaag attctacgag   1440
tcatgtgtgt gtaaagggaa tataaacaaa atacgaaaga caaaaggaat caaagggttt   1500
gtttgttgtc gctataaaac gacgcgtgat aagccgctcc taaagcacgt gaccgctcta   1560
agcctctgct tcgcttcact tcacttctct ctctctcttt gtcttcctct ttccatggct   1620
ccatctgtgc agccttcttc atcacctctt cgtacaaggt taataaaatc atcaaccttt   1680
catgaaaatt tattggaaaa aaaagatttc tttttttcat taaagtcgtg aatctcctga   1740
tctgggtatc tcgtgtttgt tcctgtcgtt tatttataac tattttattc atttgtgtga   1800
tttttataac ttttggtggc atgcattgaa atttaaaaca gtgaaggaga tgaaaaatac   1860
gcgaatgtga aatgggaaga gcttggattc actctgactc cgacagatta catgtatgtg   1920
gcgaaatgca gacaaggaga gagtttttca gaaggaaaga ttgttcctta tggggacatt   1980
tcaatcagcc cttgttctcc gattctcaat tatggccagg ttttgttctt acaatcactt   2040
atatggttgt gcaagcttgc tgaatctcac tggattatag gacttttggg tttcattaga   2100
gcatgattca ttaactagtg agggcgcaaa atgatccgca gattgcgtaa agctgtttta   2160
tttgagtgta tgagcgagca aaagtttaga actttagtgt ttatgtacat gcatgtgagg   2220
atttgagaga agaccttgcg atgattcatt agttagacgc tttcatcaaa aactattgag   2280
gggcgaaaaa tgaagattgt gtaaagttgt ttgctttgag tgtataaaag agcaaaagct   2340
ttgaacttta gtgtttgaga gaaaactttc ctctatgcgt ttggctttgt agggactatt   2400
tgaaggtctc aaagcttaca ggacagaaga cgaccggatc aggcttttca gacctgaaga   2460
aaacgctcgt cgtatgcaaa caggtgcgga taggctttgt atgacaccac cttctctgga   2520
gcaattcgtc gactcagtta agcaaaccgt gcttgccaac aagaaatggg tatggactat   2580
gaactatgga ccaatgtctc tctattcaga tatgattctt gatctctaca agtttctaaa   2640
agtgtgttgt tatgtttttt tggttttttt atttggtttt aggttcctcc tccgggtaaa   2700
ggagctttgt atataaggcc tttgctaata gggagtggcg ctatacttgg agttgctcca   2760
tcacctgagt acactttcct catttacgca tctcccgtag gagattacca caaggttaga   2820
tttttgtgc tgctgtttt gaagcaaact ctgccaaaaa gactcgttaa atggttaagc   2880
```

-continued cggttttttc tcaggtaagc tcaggcttga acctaaaagt tgatcataag tatcaccgag 2940
cccattcggg tggaacgggc ggtgtcaaga gctgcactaa ctattctcca gtaagtaaag 3000
agacaccaga aacatttcat ccatggcaac aggtttaggg aatatatata tgtttttctc 3060
tgatttcttc ttgtataaat tttgaaaagg ttgtgaaatc gatggtcgaa gcaaagtcgt 3120
cgggtttctc tgatgtcttg ttcctggatt cggcaactgg tagaaacatc gaagaggttt 3180
ctgcttgtaa catctttatt gtcaaggtaa ataatgagat tcaaaggctt atcacatcta 3240
atactgaaga tttttataca cttcgtagta atcattcaaa tttttagggg aacattgtgt 3300
ccacaccacc aacttcagga accattttac caggaatcac aaggaaaagc ataatcgagc 3360
tagctcgtga tctcagctac caggttgcaa caatttttaa ttcactctat atagttatac 3420
cctttcatat atatatatat atatagactc tgaggaggta gttcacaatg tgatcacagg 3480
ttcaagaacg tgatgtttct gtggaggagc tcctagaagc agaggaagct ttctgcacgg 3540
gaactgcagt ggtcgtgaaa gctgttgaaa ctgtgacctt ccatgacaag aagtaattag 3600
tttcttctat tttgcagata taaagaccct aacaatcaaa tctttcttgg gttacatagt 3660
gctgatacct cgggtcatgt ctgcctttga ccacagggta aagttcagga caggagaagc 3720
agcgttgtgc acgaagcttc actcgatgct gacgagtatt caaacaggtc ttgttgaaga 3780
taccaaaggt tggatggtgg agatcgatcc ttgtcaaggt tgaaaagctg ttgcaaaatt 3840
cgcttactcg ttctgtatcg tttcttttct cttagtgttt tcttttatga gacttgtaat 3900
gaagaactct taaaagataa ggtacaacaa ggtcgttcaa taagtgacta ggattcgtcc 3960
cggtccatat catttgcttt gttgttctcc actgtagcct agtagttaaa atgcataaaa 4020
cccatgatcc aaaaaatgat tcaatgaacc aatctaaatt tgtaagtttc atatattggt 4080
tgagtgatgt agcagaaatc tacaaagttt cattcgtaca aatacaaact taaaggacgg 4140
gagaatgaaa gatgtttggg caccgaccaa tcggttcaat tactgttttg actcgaatga 4200
aaaaagatat atttttaat ttttcacttt tttagaaatc gaaaactaaa aaaaaaaaaa 4260
tcattgacag ctgtgggatt tgaacccacg ccctttcgga ccagagccta aatctggcgc 4320
cttagaccac tcggccaaac tatcattgtt gacaagtttt tagtaatgtt taacttaact 4380
aaacatgtac tatcttcggt atttttgctt ttattattat tagggaagat tacacatata 4440
gcacaaattt attattttat tactagatta gcttttaatt tttttttac tgactaaatt 4500 tttgtgtccg taatatccat taatcatttg ttatgaaaaa tcatatttac aagaatgcca 4560
ttattatttt tttctaactc agcaaaaaat agttaataat tacgaaaaat gccattatat 4620
tcgaaaaaat ctattgtacc agaactgcta atgtatgatg acatacttaa ttttataaac 4680
atacttattt ttagcagtac acttttgtca cagatttatt cagaataata gacttatatc 4740
aataagtctc tcatatgaag caatatactt ttttcagaga aaaggtattt ttgctgataa 4800
acttatttct tagacttgtt atgttttgac catagattta cttattttta ataaactaat 4860
tttttgtaat agacttattt cacatactta tattttgcac gatagactaa tatgtatatg 4920
agtgataact gataacagat ttaaatttta cgttctgaat gatgatagac ttatcgttag 4980
ttttgtatta gtctgctatc attaaaagac ttattttatt t 5021

<210> SEQ ID NO 9
<211> LENGTH: 359
<212> TYPE: PRT
<213> ORGANISM: Thlaspi arvense

<400> SEQUENCE: 9

Met Ala Pro Ser Val Gln Pro Ser Ser Ser Pro Leu Arg Thr Ser Glu
1 5 10 15

Gly Asp Glu Lys Tyr Ala Asn Val Lys Trp Glu Glu Leu Gly Phe Thr
20 25 30

Leu Thr Pro Thr Asp Tyr Met Tyr Val Ala Lys Cys Arg Gln Gly Glu
35 40 45

Ser Phe Ser Glu Gly Lys Ile Val Pro Tyr Gly Asp Ile Ser Ile Ser
50 55 60

Pro Cys Ser Pro Ile Leu Asn Tyr Gly Gln Gly Leu Phe Glu Gly Leu
65 70 75 80

Lys Ala Tyr Arg Thr Glu Asp Asp Arg Ile Arg Leu Phe Arg Pro Glu
85 90 95

Glu Asn Ala Arg Arg Met Gln Thr Gly Ala Asp Arg Leu Cys Met Thr
100 105 110

Pro Pro Ser Leu Glu Gln Phe Val Asp Ser Val Lys Gln Thr Val Leu
115 120 125

Ala Asn Lys Lys Trp Val Pro Pro Pro Gly Lys Gly Ala Leu Tyr Ile
130 135 140

Arg Pro Leu Leu Ile Gly Ser Gly Ala Ile Leu Gly Val Ala Pro Ser
145 150 155 160

Pro Glu Tyr Thr Phe Leu Ile Tyr Ala Ser Pro Val Gly Asp Tyr His
165 170 175

Lys Val Ser Ser Gly Leu Asn Leu Lys Val Asp His Lys Tyr His Arg
180 185 190

Ala His Ser Gly Gly Thr Gly Gly Val Lys Ser Cys Thr Asn Tyr Ser
195 200 205

Pro Val Val Lys Ser Met Val Glu Ala Lys Ser Ser Gly Phe Ser Asp
210 215 220

Val Leu Phe Leu Asp Ser Ala Thr Gly Arg Asn Ile Glu Glu Val Ser
225 230 235 240

Ala Cys Asn Ile Phe Ile Val Lys Gly Asn Ile Val Ser Thr Pro Pro
245 250 255

Thr Ser Gly Thr Ile Leu Pro Gly Ile Thr Arg Lys Ser Ile Ile Glu
260 265 270

Leu Ala Arg Asp Leu Ser Tyr Gln Val Gln Glu Arg Asp Val Ser Val
275 280 285

Glu Glu Leu Leu Glu Ala Glu Glu Ala Phe Cys Thr Gly Thr Ala Val
290 295 300

Val Val Lys Ala Val Glu Thr Val Thr Phe His Asp Lys Lys Val Lys
305 310 315 320

Phe Arg Thr Gly Glu Ala Ala Leu Cys Thr Lys Leu His Ser Met Leu
325 330 335

Thr Ser Ile Gln Thr Gly Leu Val Glu Asp Thr Lys Gly Trp Met Val
340 345 350

Glu Ile Asp Pro Cys Gln Gly
355

<210> SEQ ID NO 10
<211> LENGTH: 1551
<212> TYPE: DNA
<213> ORGANISM: Thlaspi arvense

<400> SEQUENCE: 10

-continued

```
atggcatcaa tcactttact gggccgaata ctagcaagac ccatcaaaac caaagaccgg      60

tctcgccagc ttcctcctgg tccacgagga tggcccatcc tcggcaatct acccgaactc     120

atcatgactc gtcctaggca caagtatttc gcccttgcca tgaaagagct caaatccgag     180

atcggatgtt tcaacttagc cggagtccac gccatcatca taaactccga cgagatcgct     240

agagaagcgt ttagagagcg agacgccgac ttcgcggaca ggcctgatct tttcaacatg     300

aggaccatcg gagacaatca caaatcaatg ggatttcac cttacggtga acaattcatg      360

aagatgaaaa gagtgatcac aacggagatt atgtccgtta aaacattgaa catgttgatg     420

gctgcgagaa ccatcgaagc ggataatctc attgcttacc ttctatcgat gtatcaacga     480

ggcgagacct gcgacgttag agaattctcg agggtttatg gttacacggt gaccatgaga     540

atgttgtttg gaagaagaca tgtcacgaga gaaaacattt tttccgatga aggaagacta     600

ggaaaagctg aaaaacatca tcttgaggcg attttcgaaa ccctaaactg tttgccgagc     660

ttttctcctg cggattacgt agaaaaatgg ttgcaaggat ggaacgtcga tggtcaagag     720

gagagggtga tagtgaatag taatattgtt cgtagttaca acaatccgat aatcgacgag     780

agggtcgcgt tatggaggga gaaaggtggt aaggctgctg ttgaagattg gattgatacg     840

ttcattacgc taaaagatga aaacggaaag tacttggtca cgccagacga aatcaaagct     900

caatgcgttg aattttgtat agcagcgatc gataatccgg caaataacat ggaatggaca     960

cttgcggaga tgttaaagaa cccggagatt ctgaggaaag ctgtgaagga gttagacgaa    1020

gtagtgggaa aagagaggct tgttcaagaa tcagacatac cgaatctaaa ctacttaaaa    1080

gcttgttgcc gagaaacatt caggattcac ccaagtgctc attatgtccc ttctcatgcg    1140

gctcgtcaag ataccactct cggggatat ttcattccca aaggtagcca cattcatgta     1200

agccgtccgg gactaggccg gaaccctaaa atatggaaag atccattggt attcaaaccg    1260

gagcgccacc tcgaaggaga cggaatcaca aaagaggttt ctctggtcga gacagagttg    1320

cgtttcatct cgtttggcac cggtcgacgt ggctgcatcg gtgttaaagt cgggacgatc    1380

atgatggtta taatgttggc taggtttctt caagggttta actggaaact ccatcctgct    1440

tatggaccgt taagtctaga ggaagatgat gcattgctta tggctaagcc tctgctcttg    1500

tccattgagc cacgcttggc accaaacctt tacccaaaat tccgcccttg a             1551
```

<210> SEQ ID NO 11
<211> LENGTH: 4847
<212> TYPE: DNA
<213> ORGANISM: Thlaspi arvense

<400> SEQUENCE: 11

```
gatattatcc ctaatataaa ttgcttcccg ctttcctgaa atatgttgat attcgattgc      60

aaacgtttgt tgtcgattat ccatatatag cgtaattgct ttatcgttgt actaatagtt     120

atttttgagt atttggtata taaaaaaaaa aattgtgtaa gaaaataata aaaatggttt     180

cttatagccg cttcggattt ccaaaaaggc aagaagggct ctttgtatgt atcatatatg     240

caaagatggt tacaacctaa atcagtgtaa gttaggtgga tattgattta ctgcatgtga     300

tgcactaatt ctatctgtta attgttcaga ataagatgtg tttttaacgt atactatata     360

gttggacttg gatcgaatct tcttttttt ttttcctttt tggatttctt gttgttcagt      420

tttggtttgt ttagaatcgt aaatttgact cagtttgact tttgattttc tcaaaccacg     480

gacacagcca caggacgaaa aacagaaaga aataaaacta catcatgaat ccaaatgatg     540

aaagtaattt ccattgaagc tgacgacact catggaaatt cgatagagaa catctaaacg     600
```

```
tggttaccta cccaagagct cccatctagt ttctattcca aaaattcctt tattctgaat    660
cactttttgc tttctctctc tctttcaagt gttgcacatt ttacatttat tcttttttttt    720
tcattttctt ttaataagaa actactacta taatattaat gtagacaaat tcttaactaa    780
tatcatttat ttatcttttt ttcctttcaa aacaaacata tatcatttag tacatttatg    840
aaaacaccat tagattgatg tactttatga aaatatatta aactatcata ttaaaacata    900
tcctacttaa gagttttagg aatgattttc aatcatcagt ctcaccaaca taatttgcga    960
gtagggatcg gattaaccta tgggacctcc tcgatccacc tcatatggga atgggagagc   1020
ctccagtctc cacccaagga ctcaagtagc tagatagtaa gttagatagt gtgatacaag   1080
actgtagtac tgtacgctag gcacgtttgt tacgtgtgag tctgtgacag tgctctagtt   1140
ttgctaccca ttctacgtac ctcctacgta atggcgctaa gtggcagaac tatctgcctc   1200
agaaactagt tatcattatt tttcttctat tttgctaaac atgcttagaa attttgattt   1260
tatttagtta acaaatgtac aaattgaaat gaaacaataa agcttttcct attaaacatg   1320
attagccgct gaaaattaga tacaaaatat ataaacgtga tttccttaca gctagtacct   1380
acccataagc ccaaacccca cacgtgagca tcgcatgcgc atgaaatcga atctataaat   1440
acttgaaaca caagacaatt ccccaatatc aaattatcgc tagtgttcat tgctaacgag   1500
cacacagctc tctctacaca gacacacaaa catgatgacg atgctgagga gccttaccac   1560
atcattacca taccctttc aaatcctact agtctttatc atctccatgg catcaatcac   1620
tttactgggc cgaatactag caagacccat caaaaccaaa gaccggtctc gccagcttcc   1680
tcctggtcca cgaggatggc ccatcctcgg caatctaccc gaactcatca tgactcgtcc   1740
taggcacaag tatttcgccc ttgccatgaa agagctcaaa tccgagatcg gatgtttcaa   1800
cttagccgga gtccacgcca tcatcataaa ctccgacgag atcgctagag aagcgtttag   1860
agagcgagac gccgacttcg cggacaggcc tgatcttttc aacatgagga ccatcggaga   1920
caatcacaaa tcaatgggga tttcacctta cggtgaacaa ttcatgaaga tgaaaagagt   1980
gatcacaacg gagattatgt ccgttaaaac attgaacatg ttgatggctg cgagaaccat   2040
cgaagcggat aatctcattg cttaccttct atcgatgtat caacgaggcg agacctgcga   2100
cgttagagaa ttctcgaggg tttatggtta cacggtgacc atgagaatgt tgtttggaag   2160
aagacatgtc acgagagaaa acatttttc cgatgaagga agactaggaa aagctgaaaa   2220
acatcatctt gaggcgattt tcgaaaccct aaactgtttg ccgagctttt ctcctgcgga   2280
ttacgtagaa aaatggttgc aaggatggaa cgtcgatggt caagaggaga gggtgatagt   2340
gaatagtaat attgttcgta gttacaacaa tccgataatc gacgagaggg tcgcgttatg   2400
gagggagaaa ggtggtaagg ctgctgttga agattggatt gatacgttca ttacgctaaa   2460
agatgaaaac ggaaagtact tggtcacgcc agacgaaatc aaagctcaat gcgttgtaag   2520
taaaaaaaaa atttatttat tgttgatcat catcactaat tagatctata tttactgaat   2580
aattaataat ttaatatgac gatcatcgaa atatatatta ctgatgattc tactgaaaat   2640
ggttatgact tatgagtcat gagaacttta aaagatctgt tgcagccata tttttacaga   2700
tgattgtttg gatactactt acaaagttat aattaagtaa cttaaaaatc attttaaaag   2760
tacaaatatt tagtaataca aaaaatggat tagaaacaaa aaaaatggca tctattttga   2820
tatttttacg tgacgaatca acttttgatc attgtttggt gttttgttac aggaattttg   2880
tatagcagcg atcgataatc cggcaaataa catggaatgg acacttgcgg agatgttaaa   2940
```

```
gaacccggag attctgagga aagctgtgaa ggagttagac gaagtagtgg gaaaagagag   3000

gcttgttcaa gaatcagaca taccgaatct aaactactta aaagcttgtt gccgagaaac   3060

attcaggatt cacccaagtg ctcattatgt cccttctcat gcggctcgtc aagataccac   3120

tctcggggga tatttcattc ccaaaggtaa aacaaactgt gttttttcgt aggattttgc   3180

atttttatca ctagcaagtc aatacatgca tagtttagct taacatgtag ttgagccacc   3240

aataattcga tatgatactt atattaaaaa agtatcggtt ttggacaggt agccacattc   3300

atgtaagccg tccgggacta ggccggaacc ctaaaatatg gaaagatcca ttggtattca   3360

aaccggagcg ccacctcgaa ggagacggaa tcacaaaaga ggtttctctg gtcgagacag   3420

agttgcgttt catctcgttt ggcaccggtc gacgtggctg catcggtgtt aaagtcggga   3480

cgatcatgat ggttataatg ttggctaggt ttcttcaagg gtttaactgg aaactccatc   3540

ctgcttatgg accgttaagt ctagaggaag atgatgcatt gcttatggct aagcctctgc   3600

tcttgtccat tgagccacgc ttggcaccaa acctttaccc aaaattccgc ccttgagaaa   3660

agaacaagac tccttgttgt ttctctgttc tgttctacaa cgctttgtca ttactatgtt   3720

atgttacttt acttggcacc cagtcgtttg ttgttgtttt agactatcct tggctaaata   3780

tcgccatcgt ttcatttgtg tatttttttt ttctttttct atcactgtaa cttaataaca   3840

atcaaacatt ccgagtcatt atacttatag ccaataagtg aggatcagtt taataaagtt   3900

gagattgtta tagattataa tattaaatgg tgaatcctta cgtagacaat attaaaagtc   3960

gatggctcgt gccatggtta taaatattaa caatacttta agctattaaa tcagttagta   4020

cgtagacaaa taaaaattaa accgtttaat agagaaggtc ggtgcatggc cggatgtgat   4080

ggtgcggctc attttcttat aaatatcatt aatattattc tgttcatccc gcatttgttt   4140

tacccgtttt acaccatctt cattcgaaac ctcaactctt cagtcttcaa tatggagtat   4200

aatataacgt aaaactatct accataatta ttttcaaaaa aaaaaaaaac tatctaccat   4260

aatcatccta tattaaattt ttatatgtta acattatata ataatgcatt aaaccattaa   4320

ctctctaata tgtgtttgcc aaattaagtt cactttcgaa cagattaaat tatcttttca   4380

tttgaccctc ttatactgaa aattaattat tttggttata tttctgtaaa ttttgtaaga   4440

cgttaatgca ccgtaagtct ctcaaggaga atgaaggata tgcaatgtat attttattaa   4500

tataaagata ttgaactaat cacataatga tacatggtca aatacgtttt tttaagattt   4560

cttaaacaag aattttgtct ctcttctcct tttttattaa tttatatttt taattgttag   4620

aaattacgtt agatgcaact gatggaaata ttcttagatt ctagagatga atttgcttct   4680

gactaccgaa atggaaagat agaggcagga aagccagtaa gaaaatttca ttggaattgg   4740

tctgtcagat gagttaataa agcaatattg ttgacttttt tttttttttt tgaaagggta   4800

tagttctgag ttgtaaaatg gattgaatca aaagtttgat gatagac                 4847
```

<210> SEQ ID NO 12
<211> LENGTH: 516
<212> TYPE: PRT
<213> ORGANISM: Thlaspi arvense

<400> SEQUENCE: 12

```
Met Ala Ser Ile Thr Leu Leu Gly Arg Ile Leu Ala Arg Pro Ile Lys
1               5                   10                  15

Thr Lys Asp Arg Ser Arg Gln Leu Pro Pro Gly Pro Arg Gly Trp Pro
            20                  25                  30

Ile Leu Gly Asn Leu Pro Glu Leu Ile Met Thr Arg Pro Arg His Lys
```

```
        35                  40                  45

Tyr Phe Ala Leu Ala Met Lys Glu Leu Lys Ser Glu Ile Gly Cys Phe
    50                  55                  60

Asn Leu Ala Gly Val His Ala Ile Ile Ile Asn Ser Asp Glu Ile Ala
65                  70                  75                  80

Arg Glu Ala Phe Arg Glu Arg Asp Ala Asp Phe Ala Asp Arg Pro Asp
                85                  90                  95

Leu Phe Asn Met Arg Thr Ile Gly Asp Asn His Lys Ser Met Gly Ile
            100                 105                 110

Ser Pro Tyr Gly Glu Gln Phe Met Lys Met Lys Arg Val Ile Thr Thr
        115                 120                 125

Glu Ile Met Ser Val Lys Thr Leu Asn Met Leu Met Ala Ala Arg Thr
    130                 135                 140

Ile Glu Ala Asp Asn Leu Ile Ala Tyr Leu Leu Ser Met Tyr Gln Arg
145                 150                 155                 160

Gly Glu Thr Cys Asp Val Arg Glu Phe Ser Arg Val Tyr Gly Tyr Thr
                165                 170                 175

Val Thr Met Arg Met Leu Phe Gly Arg Arg His Val Thr Arg Glu Asn
            180                 185                 190

Ile Phe Ser Asp Glu Gly Arg Leu Gly Lys Ala Glu Lys His His Leu
        195                 200                 205

Glu Ala Ile Phe Glu Thr Leu Asn Cys Leu Pro Ser Phe Ser Pro Ala
    210                 215                 220

Asp Tyr Val Glu Lys Trp Leu Gln Gly Trp Asn Val Asp Gly Gln Glu
225                 230                 235                 240

Glu Arg Val Ile Val Asn Ser Asn Ile Val Arg Ser Tyr Asn Asn Pro
                245                 250                 255

Ile Ile Asp Glu Arg Val Ala Leu Trp Arg Glu Lys Gly Gly Lys Ala
            260                 265                 270

Ala Val Glu Asp Trp Ile Asp Thr Phe Ile Thr Leu Lys Asp Glu Asn
        275                 280                 285

Gly Lys Tyr Leu Val Thr Pro Asp Glu Ile Lys Ala Gln Cys Val Glu
    290                 295                 300

Phe Cys Ile Ala Ala Ile Asp Asn Pro Ala Asn Asn Met Glu Trp Thr
305                 310                 315                 320

Leu Ala Glu Met Leu Lys Asn Pro Glu Ile Leu Arg Lys Ala Val Lys
                325                 330                 335

Glu Leu Asp Glu Val Val Gly Lys Glu Arg Leu Val Gln Glu Ser Asp
            340                 345                 350

Ile Pro Asn Leu Asn Tyr Leu Lys Ala Cys Cys Arg Glu Thr Phe Arg
        355                 360                 365

Ile His Pro Ser Ala His Tyr Val Pro Ser His Ala Ala Arg Gln Asp
    370                 375                 380

Thr Thr Leu Gly Gly Tyr Phe Ile Pro Lys Gly Ser His Ile His Val
385                 390                 395                 400

Ser Arg Pro Gly Leu Gly Arg Asn Pro Lys Ile Trp Lys Asp Pro Leu
                405                 410                 415

Val Phe Lys Pro Glu Arg His Leu Glu Gly Asp Gly Ile Thr Lys Glu
            420                 425                 430

Val Ser Leu Val Glu Thr Glu Leu Arg Phe Ile Ser Phe Gly Thr Gly
        435                 440                 445

Arg Arg Gly Cys Ile Gly Val Lys Val Gly Thr Ile Met Met Val Ile
    450                 455                 460
```

Met Leu Ala Arg Phe Leu Gln Gly Phe Asn Trp Lys Leu His Pro Ala
465 470 475 480

Tyr Gly Pro Leu Ser Leu Glu Glu Asp Asp Ala Leu Leu Met Ala Lys
485 490 495

Pro Leu Leu Leu Ser Ile Glu Pro Arg Leu Ala Pro Asn Leu Tyr Pro
500 505 510

Lys Phe Arg Pro
515

<210> SEQ ID NO 13
<211> LENGTH: 1854
<212> TYPE: DNA
<213> ORGANISM: Thlaspi arvense

<400> SEQUENCE: 13
atggagagaa agccctttga ggttgagacg acggagaatc acaaacccta ctccaccgtc 60
gatggcggtg gcgttggttc tgatttgaga tcgccggtcg attcatttga tgacgagcag 120
aaaaagctcg tttacagagg ctggaaagtc atgcctttta tcattggtaa tgagacattt 180
gagaagattg ggatcatagg gacattatca aaccttcttt tgtacctaac tcaagtattc 240
aaccttaaga aagttacagc tgcaacaatc atcaatgcct ttagtggcac aatcaacttc 300
gggactttca tcgctgcttt cctctgcgac acttactttg gtcgctacaa gactctcagt 360
gtagctgtca tcgcttgttt cctgggatcg cttgtgatat tactgacggc tgcagttcct 420
gcattgcacc cgactccatg tggaacacat agctggtgcc aagggccaag cccgggccag 480
atcgcgttct tgctgctggg tttagcgttt cttgtggtcg gtgcgggtgg gatcaggccg 540
tgtaacttgg cttttggagc tgatcagttc aaccccaaat ccgaatccgg gaagaaagga 600
atcaacagct tctttaactg gtatttcttc accttcacgt ttgcgcagat cgtctcgctc 660
acgctggtcg tgtatatcca gtcgaacgtg agctggacga tcggtttgct catccctgtg 720
gctctgatgt tcttggcctg cgtcatcttc tttgctggac ataaactgta tgtgaaagtg 780
aaagcctcgg gtagtccctt ggctagtatc ggtcacgtta tcacggcagc gatcaagaaa 840
cgagggttga agcaagttaa gcagccttgg ctcgatcttt acaaccacat tccaactaac 900
tatccaaact ccaccttgaa atacaccgac cagtttaggt ttcttgacaa agcagcgatt 960
atgacccctg aggacaagct gaattccgat ggagctgctt tcgatccatg gaccctatgt 1020
acattgcaga aagtggaaga agtgaaatgc attgtgagag tgattccgat ctggtttgct 1080
tgcgcgattt actacctcac tgtaactata cagatgactt atccggtctt ccaagcgcag 1140
cagagcgacc ggagattggg ttctggtggc ttcaagatcc ccgcagccac ctatgtggtg 1200
ttcttgatgt cgggtatgac tgttttcatc gtgttctacg accgtgtcct tgtcccgttg 1260
ctcagaagag tgaccgggtt agaaaccggt ttgaccctct tgcagagagt cggatcaggg 1320
atcttctttg ccatgttgag tttgttggtc tccgggttcg tagaggaacg gagaagaacc 1380
ttcgccctga cgaaaccgac tctcgggatg gagccacgag cgggagagat ctcctccatg 1440
tcggccatgt ggctgattcc gcagctcttg cttgcaggcg taggagaggc ttttacagcc 1500
attggacaga tggagtttta ttacaagcag ttccctgaga acatgaagag cttcgctggc 1560
tctatcttct atgtcggtgc aggtgtttcg agctatcttg ctagcttctt gatctcgact 1620
gttcatcgaa gaactgaaca ttcaccctcc gggaactggt tagctgagga tctgaacaaa 1680
gggagactcg attacttcta cttcatgctc accggaatca tggtcgttaa catggtttac 1740
ttcttgataa tgtctaaatg gtatagatac aaaggcatta acgatgaagc gaattctttg 1800
gtcgagacca atgaagaaga gaccaagcag aaacaagtca agaattctgt ctga 1854

<210> SEQ ID NO 14
<211> LENGTH: 5463
<212> TYPE: DNA
<213> ORGANISM: Thlaspi arvense

<400> SEQUENCE: 14
actccgggcg cgcatccgga ctctggagat tatggcggca ccacgagtaa gaccggatct 60
gctatcgtgc tagggttcgt gatctcgtgg tttccgagtc ccaagagaca gaggaggtgg 120
ctgagattgg attctctccc ataatctttc tccttagcgg ctcatttcct gtgtcccaga 180
cgcctttgcg atcctccgtg cgatggctct tcttctgatg cgcctatttg gtcaaactca 240
tggtttttgc ccttttctta ttttttacac tcgcagtttg tggtgggtgc atgctttcaa 300
acctacttgt agagaccttg ttgtacccct tgttctttca ggatttatta tataaataaa 360
caatgacttt ttcatgtttt atttttattt tttagtccta gaactttgac atgcacctta 420
atcgtacata tacgactaaa ctcgtgcttc aatcgaacag actttctaat ctggagtgag 480
caccataaat ctttgctata ccttatgaat gaactgaact tctgtgcgta tttttagtgt 540
gctgcggttt tccagaaaat gggtcaatgt atgactcgac tactgggatc cgcatgctct 600
tgttgtctgt tttatctgca ggaaacaagc gtttggcctg acacatacgt tcctgtgaca 660
gcgataatcg ttgctctgaa taacaggcac acagtatgag tgctcttgac tgggtggagc 720
tttggatgtc ttcaagggct ggctttgctt cgcttaagtc cctcgaaatg tgcatcttcg 780
ggatggcgac cttctaggga aagttgcttc tgagcctggt ggccgagccc atctccggga 840
gcgaggtttc ctctccgctc tactgctcct ttgttcttct gccatgtggc accccagaac 900
gactgttgtt gcctctgacc gccgtggatt ttaacatttt cggcgattaa ttgcttgact 960
acttcttttg tggtgttgta tatcaatatt tctcttttct tcttctaacg ataattatta 1020
agacataaat tataaaatcc gtacagaagt atgtgtttgt ctaaatgtta gaaattacgt 1080
tgttttcaag tttcatcttc tctaacttct catatctaaa caaatatata tctatatata 1140
ttctgttatg ccaaataaat atatatttag tttgtaataa aattatattt atttatatta 1200
tttattcata cggtatatat gataattatg ttaaaatatt atatcatatt ataaaaagtt 1260
ttaaaataat attaaaatta aattgactta cattatttta atattatata tgatttatta 1320
atattatctg ttaataaatt catataattt aatttatttt tttaaaaata aatttagtaa 1380
tatatttaat aaacatcatg gtagatttta gacattttat aaagtagggt ttgtctttta 1440
atagtaaaaa tcagttaaac agatcggaaa aatgagtcat tcacacatgt ctctatcctc 1500
cacagccaaa ttgaccattg tttgattttc cccttttgtc cagattcgga caattcccac 1560
tggatccatc cactatataa caagacgata gagcgaagct tgagatgaag agtagagtca 1620
tcctcagcca tagagagaga agagataaga agaataataa cattaacaac aaagacatct 1680
cctgtaattt cacacagatt gaaaccatgg agagaaagcc ctttgaggtt gagacgacgg 1740
agaatcacaa accctactcc accgtcgatg gcggtggcgt tggttctgat ttgagatcgc 1800
cggtcgattc atttgatgac gagcagaaaa agctcgttta cagaggctgg aaagtcatgc 1860
cttttatcat tggtaacgct ttttttctct cttcagacat cgtgtttttt tttttttttt 1920
tttttaatta cactctgttt tgtgtccctt tgtcggattt taaacacctc ccggagaaaa 1980
agaaatgaga aagtaaaatt caacattttg tccgtgattt gtttaatttc attctctttt 2040

```
tctcttctct ttgatttgac ctgactgtgt caaaaatcgt cgtgctttga gatttagaaa   2100
tgaaattgtt tctaaaaaaa cgagatttga ttgaaaccta gatcaaaacc agaggaaatt   2160
tcactagatc tagagaaaga aatattacaa ttgtttttct tttcaaatat ttttaatttt   2220
ccgccgaaag agactccgaa tcatgcaaga taagtggata agatttgaga attttgtacg   2280
gttgaagaca aagtttctgg gagttagatc agttattaga tgaattgtgt gtttccgttt   2340
caaagctgtg aattaaattt taaaagtttt attaccttat ttttggttta actaatcatt   2400
tatttttgtt tttttcttga caggtaatga gacatttgag aagattggga tcatagggac   2460
attatcaaac cttcttttgt acctaactca agtattcaac cttaagaaag ttacagctgc   2520
aacaatcatc aatgccttta gtggcacaat caacttcggg actttcatcg ctgctttcct   2580
ctgcgacact tactttggtc gctacaagac tctcagtgta gctgtcatcg cttgtttcct   2640
ggtactaaca attgatcttg aaatggaata ttataaacgt caagattcag tctttttctt   2700
tactaaaaaa ccattttttt acgtctttgt agggatcgct tgtgatatta ctgacggctg   2760
cagttcctgc attgcacccg actccatgtg gaacacatag ctggtgccaa gggccaagcc   2820
cgggccagat cgcgttcttg ctgctgggtt tagcgtttct tgtggtcggt gcgggtggga   2880
tcaggccgtg taacttggct tttggagctg atcagttcaa ccccaaatcc gaatccggga   2940
agaaaggaat caacagcttc tttaactggt atttcttcac cttcacgttt gcgcagatcg   3000
tctcgctcac gctggtcgtg tatatccagt cgaacgtgag ctggacgatc ggtttgctca   3060
tccctgtggc tctgatgttc ttggcctgcg tcatcttctt tgctggacat aaactgtatg   3120
tgaaagtgaa agcctcgggt agtcccttgg ctagtatcgg tcacgttatc acggcagcga   3180
tcaagaaacg agggttgaag caagttaagc agccttggct cgatctttac aaccacattc   3240
caactaacta tccaaactcc accttgaaat acaccgacca gtttaggtaa acccaacatt   3300
tctctctctc tctgtttcta tgttcccttt gcttttatat taatctcttg ctgagcaata   3360
ctggtttgtt atgtttgcta ggtttcttga caaagcagcg attatgaccc ctgaggacaa   3420
gctgaattcc gatggagctg ctttcgatcc atggacccta tgtacattgc agaaagtgga   3480
agaagtgaaa tgcattgtga gagtgattcc gatctggttt gcttgcgcga tttactacct   3540
cactgtaact atacagatga cttatccggt cttccaagcg cagcagagcg accggagatt   3600
gggttctggt ggcttcaaga tccccgcagc cacctatgtg gtgttcttga tgtcgggtat   3660
gactgttttc atcgtgttct acgaccgtgt ccttgtcccg ttgctcagaa gagtgaccgg   3720
gttagaaacc ggtttgaccc tcttgcagag agtcggatca gggatcttct ttgccatgtt   3780
gagtttgttg gtctccgggt tcgtagagga acggagaaga accttcgccc tgacgaaacc   3840
gactctcggg atggagccac gagcgggaga gatctcctcc atgtcggcca tgtggctgat   3900
tccgcagctc ttgcttgcag gcgtaggaga ggcttttaca gccattggac agatggagtt   3960
ttattacaag cagttccctg agaacatgaa gagcttcgct ggctctatct tctatgtcgg   4020
tgcaggtgtt tcgagctatc ttgctagctt cttgatctcg actgttcatc gaagaactga   4080
acattcaccc tccgggaact ggttagctga ggatctgaac aaagggagac tcgattactt   4140
ctacttcatg ctcaccggaa tcatggtcgt taacatggtt tacttcttga taatgtctaa   4200
atggtataga tacaaaggca ttaacgatga agcgaattct ttggtcgaga ccaatgaaga   4260
agagaccaag cagaaacaag tcaagaattc tgtctgatct gtaaaacttt tattattttt   4320
ggtcttctaa ttcagtctct actctttgtt gtttgtactc cattagagaa aatgaatgaa   4380
```

```
ggagaaatat aataatacct tagcgttttt gtcgaataag atttttctgc taaattcaaa   4440

ctgtgtatga agtttgttgt ttcgtcacga accactaaaa gaagactaca aggattgtga   4500

ttttttttat gtattaaagc caaaaagaga ggttctttta tgtatctttg tccaagaatg   4560

taaaagaaag aagaagaaaa aaaatggcca aatagttcgg aggacctctg caaaggtgtg   4620

aagaagaaga tgaggttatc cagaaatgtt ttcttcttct cttctccgtc tttataaatt   4680

acattggaaa attattcagg acgaatcgag aggtagaagc tttccttcag gcattgctat   4740

atacaaaata tttgggttat tttcgtgtgg gagattgatt tagctgagga aagctttata   4800

cttttattat cttctggtct ctaaagttgc ttagaaggtc ttagagattg gggaaatcac   4860

aattaccaat caagtgccaa gctcgaaagt agcaaggatt gtgataaagt cgttggataa   4920

tagaccgttg cttctgtatt gcctagtgga tatttcctga gttaaagatg ggtacacaat   4980

aaagggtgga caaaaagtag gcggggtctt agacttgatt tggcaaatga caatcactta   5040

tataagctaa tggcaacata accgtctctc tcaccaatac atgccgaatt tgaagcactc   5100

tgatttgagc cagtactaaa aacatggagc ttgaacctga gcttgaaact gatggaaaag   5160

agcttatagc cgatgttgga cagtttaaag ccgaggtaaa acagtttgag gccgaggtga   5220

aagagttagt agccgaggta agacagctgg aggccgagct gacgcaactt gaagccgagg   5280

tgaagcaaga tacttcggat gagcttgtag cagaggataa gcttgtagct gaggaagcag   5340

ttcgtcttgg agttaatcgt gagacaaaat agagaagaca tgatcctaaa cctccctggt   5400

ttttgatcca aagaatatca acaaatggac aagtggttca taagcactct tttcccctta   5460

ctt                                                                 5463
```

```
<210> SEQ ID NO 15
<211> LENGTH: 617
<212> TYPE: PRT
<213> ORGANISM: Thlaspi arvense

<400> SEQUENCE: 15

Met Glu Arg Lys Pro Phe Glu Val Glu Thr Thr Glu Asn His Lys Pro
1               5                   10                  15

Tyr Ser Thr Val Asp Gly Gly Gly Val Gly Ser Asp Leu Arg Ser Pro
            20                  25                  30

Val Asp Ser Phe Asp Asp Glu Gln Lys Lys Leu Val Tyr Arg Gly Trp
        35                  40                  45

Lys Val Met Pro Phe Ile Ile Gly Asn Glu Thr Phe Glu Lys Ile Gly
    50                  55                  60

Ile Ile Gly Thr Leu Ser Asn Leu Leu Leu Tyr Leu Thr Gln Val Phe
65                  70                  75                  80

Asn Leu Lys Lys Val Thr Ala Ala Thr Ile Ile Asn Ala Phe Ser Gly
                85                  90                  95

Thr Ile Asn Phe Gly Thr Phe Ile Ala Ala Phe Leu Cys Asp Thr Tyr
            100                 105                 110

Phe Gly Arg Tyr Lys Thr Leu Ser Val Ala Val Ile Ala Cys Phe Leu
        115                 120                 125

Gly Ser Leu Val Ile Leu Leu Thr Ala Ala Val Pro Ala Leu His Pro
    130                 135                 140

Thr Pro Cys Gly Thr His Ser Trp Cys Gln Gly Pro Ser Pro Gly Gln
145                 150                 155                 160

Ile Ala Phe Leu Leu Leu Gly Leu Ala Phe Leu Val Val Gly Ala Gly
                165                 170                 175
```

-continued

```
Gly Ile Arg Pro Cys Asn Leu Ala Phe Gly Ala Asp Gln Phe Asn Pro
            180                 185                 190

Lys Ser Glu Ser Gly Lys Lys Gly Ile Asn Ser Phe Phe Asn Trp Tyr
        195                 200                 205

Phe Phe Thr Phe Thr Phe Ala Gln Ile Val Ser Leu Thr Leu Val Val
    210                 215                 220

Tyr Ile Gln Ser Asn Val Ser Trp Thr Ile Gly Leu Leu Ile Pro Val
225                 230                 235                 240

Ala Leu Met Phe Leu Ala Cys Val Ile Phe Phe Ala Gly His Lys Leu
                245                 250                 255

Tyr Val Lys Val Lys Ala Ser Gly Ser Pro Leu Ala Ser Ile Gly His
            260                 265                 270

Val Ile Thr Ala Ala Ile Lys Lys Arg Gly Leu Lys Gln Val Lys Gln
        275                 280                 285

Pro Trp Leu Asp Leu Tyr Asn His Ile Pro Thr Asn Tyr Pro Asn Ser
    290                 295                 300

Thr Leu Lys Tyr Thr Asp Gln Phe Arg Phe Leu Asp Lys Ala Ala Ile
305                 310                 315                 320

Met Thr Pro Glu Asp Lys Leu Asn Ser Asp Gly Ala Ala Phe Asp Pro
                325                 330                 335

Trp Thr Leu Cys Thr Leu Gln Lys Val Glu Glu Val Lys Cys Ile Val
            340                 345                 350

Arg Val Ile Pro Ile Trp Phe Ala Cys Ala Ile Tyr Tyr Leu Thr Val
        355                 360                 365

Thr Ile Gln Met Thr Tyr Pro Val Phe Gln Ala Gln Gln Ser Asp Arg
    370                 375                 380

Arg Leu Gly Ser Gly Gly Phe Lys Ile Pro Ala Ala Thr Tyr Val Val
385                 390                 395                 400

Phe Leu Met Ser Gly Met Thr Val Phe Ile Val Phe Tyr Asp Arg Val
                405                 410                 415

Leu Val Pro Leu Leu Arg Arg Val Thr Gly Leu Glu Thr Gly Leu Thr
            420                 425                 430

Leu Leu Gln Arg Val Gly Ser Gly Ile Phe Phe Ala Met Leu Ser Leu
        435                 440                 445

Leu Val Ser Gly Phe Val Glu Glu Arg Arg Arg Thr Phe Ala Leu Thr
    450                 455                 460

Lys Pro Thr Leu Gly Met Glu Pro Arg Ala Gly Glu Ile Ser Ser Met
465                 470                 475                 480

Ser Ala Met Trp Leu Ile Pro Gln Leu Leu Leu Ala Gly Val Gly Glu
                485                 490                 495

Ala Phe Thr Ala Ile Gly Gln Met Glu Phe Tyr Tyr Lys Gln Phe Pro
            500                 505                 510

Glu Asn Met Lys Ser Phe Ala Gly Ser Ile Phe Tyr Val Gly Ala Gly
        515                 520                 525

Val Ser Ser Tyr Leu Ala Ser Phe Leu Ile Ser Thr Val His Arg Arg
    530                 535                 540

Thr Glu His Ser Pro Ser Gly Asn Trp Leu Ala Glu Asp Leu Asn Lys
545                 550                 555                 560

Gly Arg Leu Asp Tyr Phe Tyr Phe Met Leu Thr Gly Ile Met Val Val
                565                 570                 575

Asn Met Val Tyr Phe Leu Ile Met Ser Lys Trp Tyr Arg Tyr Lys Gly
            580                 585                 590

Ile Asn Asp Glu Ala Asn Ser Leu Val Glu Thr Asn Glu Glu Glu Thr
```

595 600 605

Lys Gln Lys Gln Val Lys Asn Ser Val
610 615

<210> SEQ ID NO 16
<211> LENGTH: 1842
<212> TYPE: DNA
<213> ORGANISM: Thlaspi arvense

<400> SEQUENCE: 16
atggagagac agcctctcga actcgagtct acggatcacc aaaaaccttc cccgccgtc 60 tacggtggct ctgttacgac ggttgattct gttgaggaag aagttcagga gaaaaaagtc 120
gtatatagag gctggaaagt catgcccttt atcattggaa atgagacatt cgagaagctt 180
gggatcattg gaacactatc aaaccttctg gtttttttaa cagctgtctt caacatgaag 240
agtatcacag ctgcaacaat cattaacgca ttcagtggca caataaattt cggaactttc 300
gttgctgctt tcctctgcga cacttacttc ggtcgataca agacactaac cgtcgcggtc 360
atcgcctgtt ttcttggatc acttgtgata ctattgacag ctgcagtgcc acaactgcac 420
ccagctccat gtggaacagc gagctcgtgc agcggtccaa gcggtgggca aatcgcgttt 480
cttctgatgg gtctcgggtt tcttgtagtt ggagcgggcg ggatcagacc gtgcaatcta 540
gctttcggag ccgatcagtt caacccgaag agcgagtcag ggagaagagg gactgatagt 600
ttcttcaatt ggtacttctt cagcttcact ttcgcgcaga tcttgtcgct gacgctagtg 660
gtctacatcc agtctaacgt cagctggacg atcggtctaa ccataccggt ggttctaatg 720
ttcttggcct ccgtgatctt ctttgcggga gataagctgt atgtgaaagt caaggcctcg 780
ggtagtccat tggctggtat agctcaagtg atcattgttg caatcaagaa acgcggatta 840
aagcccgtga aacagccttg gcttaacctc tacaattact gccctccaaa acacgcaaac 900
tccattctca aatacaccga ccaattcaga tttcttgata aggcggcgat cttggctccc 960
gaggacaagt tggaggcgga tggtaagcct gcggatccat ggaagctgtg tacgatgcaa 1020
caggtggaag aagtgaagtg cattgtgaga gtgcttccta tatggttcgc tgcatcaatc 1080
tactacgtaa ccataaccca gcaaatgaca tatccggtct tccaagccct gcagagcgat 1140
cgtcgcttag gctcgggagg gttcgtgatc cccgcagcca cctacgtggt cttcttgatg 1200
acagggatga cggttttcat catcatctac gaccgtctcc tcgtgcctac cttgagaaga 1260
ataaccggtc tagacaccgg gatcacgctc ctgcagagaa tcggaaccgg gatcttcttc 1320
gcctttgcaa gcttagtagt ctccggtttc gtcgaggagc ggaggagaca cattgcgctg 1380
actaaaccaa ctcttggcat ggcgccaaga aaaggagaaa tctcctcaat gtcagctatg 1440
tggctcatcc cgcagctcac tctctcgggt gtagccgagg cgtttggagc catcggacag 1500
atggagtttt actacaagca gttcccagaa aacatgagga gtttcgcggg ttccatcttt 1560
tatgtaggaa taggggtttc gagttacctc ggcagcttct tgattgcaac ggttcaccgg 1620
acgacgcaga actcggcggg tggtaactgg ttggctgagg atttgaacaa aggcagattg 1680
gattacttct atttcatgat cgctggaatc ttggctgtta atttcgccta cttcttggtc 1740
gtgtcaagat ggtataggta caaagaaagt gatgatgatc aaaagacagc ttctgaaacc 1800
aatggagatg tcatcaaaca acaagacaag aacactgcct ga 1842

<210> SEQ ID NO 17
<211> LENGTH: 613
<212> TYPE: PRT

<213> ORGANISM: Thlaspi arvense

<400> SEQUENCE: 17

Met Glu Arg Gln Pro Leu Glu Leu Glu Ser Thr Asp His Gln Lys Pro
1 5 10 15

Ser Pro Ala Val Tyr Gly Gly Ser Val Thr Thr Val Asp Ser Val Glu
20 25 30

Glu Glu Val Gln Glu Lys Lys Val Val Tyr Arg Gly Trp Lys Val Met
35 40 45

Pro Phe Ile Ile Gly Asn Glu Thr Phe Glu Lys Leu Gly Ile Ile Gly
50 55 60

Thr Leu Ser Asn Leu Leu Val Phe Leu Thr Ala Val Phe Asn Met Lys
65 70 75 80

Ser Ile Thr Ala Ala Thr Ile Ile Asn Ala Phe Ser Gly Thr Ile Asn
85 90 95

Phe Gly Thr Phe Val Ala Ala Phe Leu Cys Asp Thr Tyr Phe Gly Arg
100 105 110

Tyr Lys Thr Leu Thr Val Ala Val Ile Ala Cys Phe Leu Gly Ser Leu
115 120 125

Val Ile Leu Leu Thr Ala Ala Val Pro Gln Leu His Pro Ala Pro Cys
130 135 140

Gly Thr Ala Ser Ser Cys Ser Gly Pro Ser Gly Gly Gln Ile Ala Phe
145 150 155 160

Leu Leu Met Gly Leu Gly Phe Leu Val Val Gly Ala Gly Gly Ile Arg
165 170 175

Pro Cys Asn Leu Ala Phe Gly Ala Asp Gln Phe Asn Pro Lys Ser Glu
180 185 190

Ser Gly Arg Arg Gly Thr Asp Ser Phe Phe Asn Trp Tyr Phe Phe Ser
195 200 205

Phe Thr Phe Ala Gln Ile Leu Ser Leu Thr Leu Val Val Tyr Ile Gln
210 215 220

Ser Asn Val Ser Trp Thr Ile Gly Leu Thr Ile Pro Val Val Leu Met
225 230 235 240

Phe Leu Ala Ser Val Ile Phe Phe Ala Gly Asp Lys Leu Tyr Val Lys
245 250 255

Val Lys Ala Ser Gly Ser Pro Leu Ala Gly Ile Ala Gln Val Ile Ile
260 265 270

Val Ala Ile Lys Lys Arg Gly Leu Lys Pro Val Lys Gln Pro Trp Leu
275 280 285

Asn Leu Tyr Asn Tyr Cys Pro Pro Lys His Ala Asn Ser Ile Leu Lys
290 295 300

Tyr Thr Asp Gln Phe Arg Phe Leu Asp Lys Ala Ala Ile Leu Ala Pro
305 310 315 320

Glu Asp Lys Leu Glu Ala Asp Gly Lys Pro Ala Asp Pro Trp Lys Leu
325 330 335

Cys Thr Met Gln Gln Val Glu Glu Val Lys Cys Ile Val Arg Val Leu
340 345 350

Pro Ile Trp Phe Ala Ala Ser Ile Tyr Tyr Val Thr Ile Thr Gln Gln
355 360 365

Met Thr Tyr Pro Val Phe Gln Ala Leu Gln Ser Asp Arg Arg Leu Gly
370 375 380

Ser Gly Gly Phe Val Ile Pro Ala Ala Thr Tyr Val Val Phe Leu Met
385 390 395 400

```
Thr Gly Met Thr Val Phe Ile Ile Ile Tyr Asp Arg Leu Leu Val Pro
                405                 410                 415

Thr Leu Arg Arg Ile Thr Gly Leu Asp Thr Gly Ile Thr Leu Leu Gln
            420                 425                 430

Arg Ile Gly Thr Gly Ile Phe Phe Ala Phe Ala Ser Leu Val Val Ser
        435                 440                 445

Gly Phe Val Glu Glu Arg Arg Arg His Ile Ala Leu Thr Lys Pro Thr
    450                 455                 460

Leu Gly Met Ala Pro Arg Lys Gly Glu Ile Ser Ser Met Ser Ala Met
465                 470                 475                 480

Trp Leu Ile Pro Gln Leu Thr Leu Ser Gly Val Ala Glu Ala Phe Gly
                485                 490                 495

Ala Ile Gly Gln Met Glu Phe Tyr Tyr Lys Gln Phe Pro Glu Asn Met
            500                 505                 510

Arg Ser Phe Ala Gly Ser Ile Phe Tyr Val Gly Ile Gly Val Ser Ser
        515                 520                 525

Tyr Leu Gly Ser Phe Leu Ile Ala Thr Val His Arg Thr Thr Gln Asn
    530                 535                 540

Ser Ala Gly Gly Asn Trp Leu Ala Glu Asp Leu Asn Lys Gly Arg Leu
545                 550                 555                 560

Asp Tyr Phe Tyr Phe Met Ile Ala Gly Ile Leu Ala Val Asn Phe Ala
                565                 570                 575

Tyr Phe Leu Val Val Ser Arg Trp Tyr Arg Tyr Lys Glu Ser Asp Asp
            580                 585                 590

Asp Gln Lys Thr Ala Ser Glu Thr Asn Gly Asp Val Ile Lys Gln Gln
        595                 600                 605

Asp Lys Asn Thr Ala
    610
```

<210> SEQ ID NO 18
<211> LENGTH: 5002
<212> TYPE: DNA
<213> ORGANISM: Thlaspi arvense

<400> SEQUENCE: 18

```
tgccatgaat ctctgaactg gagtgaacaa aaccttttg tatatcgttg atcgcatttc     60

tttgacaact acaagcaact aaatatgaaa gcatatgctt gaggatttta tttgaggatc    120

aaattggtaa aatgaaagag attaaagttg aattgaagcc caagttgaag agattgaaat    180

aatggcacac atcccttatt ggtgtcatgt ctgactaatt ttaccaacat ggcaacatct    240

cataagtaat attgaatatc aggctttgtg atttctacaa ttaattttaa cagttttaac    300

tgatatggtc caagactcgc tattgaatag aaatcaaaaa gccatatcca acatctctgt    360

taaatgtagt cttaggtcgg ttacttgtat acgttttaaa tgattcaaaa aattggcgcc    420

tcatcattta tccgattgta gagtaaaatt aaaataatat cataagaaat tataattttc    480

tctaatccac aaagattgtc ttacatctta tgtactttat attacaatat agagcaatat    540

atctgaatta gtctttggaa aaaaaatctg aatcaaataa aatcgaacgc aagtaaaatt    600

cttaaaataa cttctagtat gtaaaaaata ttcttatttt ctggttaaag tacacgtaaa    660

aattatataa attactagaa tatatattca tgacaaaaga gtataagtat agtatataac    720

ctcgaaatca taacaagaaa atttaatgaa gatggatata tatatagtat acagtcgaaa    780

aataaagaga agaagaagaa gaagaagata aataaataaa taagaaaatg gatgatggaa    840

aacaatttga agaagaagaa gataaataaa taaataagaa aatggatgat ggaaaacaat    900
```

```
ttgactgaaa gtggacggag agcttaaaga acgtgccgtt attaagaggg agtgttatga    960
tggggccaag ggcacttgaa atggaatcta cattttcatg tatttttttt ctgtttcttt   1020
tgaagagaag tttatttttt ttgtaagaaa aggagaaaag ataattaata aaaaatgtaa   1080
tattttaatc tctaacacag ctctctttca cggccaaatt cacaaattac cactttgtct   1140
agattccggc atctccacca tcctcttcct tcttaccact atatagtcta taaatagaga   1200
cggctctaag ataaagaaca gagtcatcat tagcctttga gacaaataca acagacaaaa   1260
caaggaagta caatttaaaa aaaatggaga gacagcctct cgaactcgag tctacggatc   1320
accaaaaacc ttcccccgcc gtctacggtg gctctgttac gacggttgat tctgttgagg   1380
aagaagttca ggagaaaaaa gtcgtatata gaggctggaa agtcatgccc tttatcattg   1440
gtaaatattt accgttttta acactttttt ttcttggtcc tggaaactat ttttttcagt   1500
tggattcatg tagttaggaa ttacccataa aatcataaga aaaagatcga aaacatcagt   1560
cttgctcgaa gacttgcttg gtttgaattt tttttttttt tttaaatttg aaagattctc   1620
tgtgttgttt gtcttaagct ttgacttagt caaacagtaa cttaagacaa aaagaaggac   1680
atcttgaaat tgaggagatt ttataacata actaatcaag aattaatttt aaaacacaga   1740
tttcatctaa ctgtttgatt cttggtttgg tttctgatac aatcaaatgc aaagcttgaa   1800
acttaatctt cattttttgtt gttgttatca ggaaatgaga cattcgagaa gcttgggatc   1860
attggaacac tatcaaacct tctggttttt ttaacagctg tcttcaacat gaagagtatc   1920
acagctgcaa caatcattaa cgcattcagt ggcacaataa atttcggaac tttcgttgct   1980
gctttcctct gcgacactta cttcggtcga tacaagacac taaccgtcgc ggtcatcgcc   2040
tgttttcttg taaaaaccca tcctttcttg tcttgtcttt cttcctccac aagcatatat   2100
atacaagcgg aaaaaactta tcggtgaaat ggtttctttt tgtagggatc acttgtgata   2160
ctattgacag ctgcagtgcc acaactgcac ccagctccat gtggaacagc gagctcgtgc   2220
agcggtccaa gcggtgggca aatcgcgttt cttctgatgg gtctcgggtt tcttgtagtt   2280
ggagcgggcg ggatcagacc gtgcaatcta gctttcggag ccgatcagtt caacccgaag   2340
agcgagtcag ggagaagagg gactgatagt ttcttcaatt ggtacttctt cagcttcact   2400
ttcgcgcaga tcttgtcgct gacgctagtg gtctacatcc agtctaacgt cagctggacg   2460
atcggtctaa ccataccggt ggttctaatg ttcttggcct ccgtgatctt ctttgcggga   2520
gataagctgt atgtgaaagt caaggcctcg ggtagtccat tggctggtat agctcaagtg   2580
atcattgttg caatcaagaa acgcggatta aagcccgtga aacagccttg gcttaacctc   2640
tacaattact gccctccaaa acacgcaaac tccattctca aatacaccga ccaattcagg   2700
taaccaaaaa acttaaactt gttttccttt aagagtcttt tttattgtca ggatgttctt   2760
tactcagaga aaggttcctg ttttgggcag atttcttgat aaggcggcga tcttggctcc   2820
cgaggacaag ttggaggcgg atggtaagcc tgcggatcca tggaagctgt gtacgatgca   2880
acaggtggaa gaagtgaagt gcattgtgag agtgcttcct atatggttcg ctgcatcaat   2940
ctactacgta accataaccc agcaaatgac atatccggtc ttccaagccc tgcagagcga   3000
tcgtcgctta ggctcgggag ggttcgtgat ccccgcagcc acctacgtgg tcttcttgat   3060
gacagggatg acggttttca tcatcatcta cgaccgtctc ctcgtgccta ccttgagaag   3120
aataaccggt ctagacaccg ggatcacgct cctgcagaga atcggaaccg ggatcttctt   3180
cgcctttgca agcttagtag tctccggttt cgtcgaggag cggaggagac acattgcgct   3240
```

-continued gactaaacca actcttggca tggcgccaag aaaaggagaa atctcctcaa tgtcagctat 3300
gtggctcatc ccgcagctca ctctctcggg tgtagccgag gcgtttggag ccatcggaca 3360
gatggagttt tactacaagc agttcccaga aaacatgagg agtttcgcgg gttccatctt 3420
ttatgtagga ataggggttt cgagttacct cggcagcttc ttgattgcaa cggttcaccg 3480
gacgacgcag aactcggcgg gtggtaactg gttggctgag gatttgaaca aaggcagatt 3540
ggattacttc tatttcatga tcgctggaat cttggctgtt aatttcgcct acttcttggt 3600
cgtgtcaaga tggtataggt acaaagaaag tgatgatgat caaaagacag cttctgaaac 3660
caatggagat gtcatcaaac aacaagacaa gaacactgcc tgatcattat gggtttctca 3720
tcttctcgac ttagtttttg gtcagcttcg atcccctttg gattttcttg gaataagccc 3780
atagagaaac caagtaatca tcatatactt gttctcgctc tttttttttc ttttcctcgt 3840
ttatatttaa atcacttctc tttctttcta tcattgtgga caaaaaggga aattataaca 3900
tcaaatgtaa tgcaaaaata aaaaaaaatt tgtcttacac tttgaggatg ctgtttctat 3960
ttctgccatt cttcatcata caagagaaca aacttacaag aaggaaacaa accgaccaaa 4020
taatactact aaggcctttg atacttatat gcataatttg tatcgaagtt tcaaacagag 4080
atattgagac gagtcgtggg ctttctctct acgattttgt cagactgtgt aagattgttg 4140
aatggtttca atgtcgagac cttttagcct cacgacagat tcaacgtgac ccttgagtgt 4200
gtgaagctcc cgcaacctat caaagtgtaa gagagaatga gacaaatcac aaatgttccg 4260
gttcgaccaa aacaaagcaa aaacaaacgt tccggttttg tgttccttct ctgaccctca 4320
cggctcacag gaagaaacta ggcttaccta gcgatctcgg ctcttctctt tgcttcttca 4380
gccatttggg aaagctcgtt gaaatgggtt cgctctggga acattttagc atctggtgct 4440
tgcaggccat gtagcgttct ctgtgcgtgc gcccattgta gctccctttg ttctttccca 4500
aaatccttct gcctcgtgaa tgcaatctat ggaaacgagt ttacatgaaa gatcaagtac 4560
agataaagaa aatggaaaga ggtgaaatga gaagaaaata tgtttgcttt ttgatactta 4620
ccctttgctc aataacaagg tcccaggctc tgccgctaag ggcgtaccga atcaagaact 4680
tgatgatatc aagaggaata tagaacacaa tgttgtagag ccaaatgacc ccggcccatc 4740
cccacccgat cccttcgatc gcagcaaagc tccaattcgc atagacggca attagagtag 4800
ccacctgttt ggaagaaaat ggtcaagaaa acagtgattt caaaacttct tacttgagtg 4860
ctgaccacag atagtgtgta gtgtcacact aaccaattgt gcgacgataa aggctatcac 4920
aagcaacatc ccaggacgtt ccacataaga ccaactccgt gaccgggtca caaagattag 4980
cgcctgacta ataatgctga ct 5002

<210> SEQ ID NO 19
<211> LENGTH: 1110
<212> TYPE: DNA
<213> ORGANISM: Thlaspi arvense

<400> SEQUENCE: 19
atgtcaagaa agccgtgttg tgtcggagaa gggctgaaga aaggggcatg gaccaccgaa 60
gaagacaaga aactcatctc ttacatccac gagcacggtg aaggaggctg gcgcgacatt 120
ccccaaaaag ctgggttgaa acggtgtgga aagagttgta ggctgcgatg gactaactac 180
ctaaaacctg agatcaaaag aggcgagttt agttcagagg aggaacagat tatcattatg 240
cttcatgctt ctcgtggcaa caagtggtcg gtcatagcga gacatttacc tagaagaaca 300
gacaacgaga tcaagaacta ctggaacacg catctcaaaa aacgtttgat cgaacagggt 360
gttgatcccg tgactcacaa gcctctagct tccaactccg gccctactgc caccacgccg 420
cctgagaatt tgcatttcct agatgaatct agctcagaca agcaatactc tcggtcgagc 480
tcaatgcctt ccctgtctcg tcttccttcc tccggattca acacggtttc cgagatagcc 540
agcaatgttg ggacaccagt tcaggtcggt tccttgagtt gcaagaaacg ttttaagaaa 600
tcgagttcga catcaaggct tctgaacaaa tttgcggcta aggccacttc catcaaagat 660
atattgtcgg cttccatgga aggtagctcg agtgctgcta ctacaatatc acatgcaagc 720
tttttaaatg gcttttctga gcagagtcgc aatgaagagg atagttctaa cgcatccctg 780
acaaatactc tagccgaatt tgatcccttc tctcagtcat cgttgtaccc ggagcatgag 840
atcaatgtta cttctgatat cggcatggac caggtttacg atttctcaca atttctcgaa 900
aagctcggga gtgaaggcca caacgaactg aatgtcgagt atggtcatga tcttcttatg 960
tccgatgttt cgcaagaagt ctcatcacct agcgttgatg atcaagacaa tatgattgga 1020
agcttcgaag gttggtcaaa ttatcttctt gaccatgctg attttatata tgacaccgac 1080
tcagattccc tcgaaaagca tttcatgtga 1110

<210> SEQ ID NO 20
<211> LENGTH: 2745
<212> TYPE: DNA
<213> ORGANISM: Thlaspi arvense

<400> SEQUENCE: 20
ccacattgga tccatgttat ttattgtgtg tgcaaactca ttcaattcca tgtataatac 60
tcataaattc atttaatttg atactccaat ttttttattc tatgaaaatt gaatatttaa 120
taatttaggg ttattaattt aatataattt atctagtaag aaagcgcatt ttcctaacca 180
aaataaatat atatatatat ataccaaaat atagtaatat acaacatcgc tttgcaaaca 240
ttgttcttat aaaaaaagaa taacgaacta gctataacta attaatctat ttaaaataag 300
aataatttac atactctgtg tatatatata gaggagcata gctcgtaagc tcaccaccat 360
cacacaatcc atgcctcttg gtttttcttc ttcagcttct tgattctaat cttagtgtcg 420
taatattata agaataggac aaaaaaaaag atttggggct ctacgtgaaa aacatgaaaa 480
cgcctagcag ctctgtggga aagacccaag agcgtttctc gattagtctc atattcagat 540
gcatcagagt tctcataaac agatctattt cttacttatc tttttagaaa aattcctttc 600
aaattttact ttccttaaga atagtgttct ctacattttt tttcttgggt gttcgtgaga 660
ggttatatga attttttgtc attagtgttc atatcggaag aagatgtcaa gaaagccgtg 720
ttgtgtcgga gaagggctga agaaaggggc atggaccacc gaagaagaca agaaactcat 780
ctcttacatc cacgagcacg gtgaaggagg ctggcgcgac attcccccaaa aagctggtta 840 atatctctat taaaatctat acatgttcaa ttagtatttc ttgtatgaaa tttttataat 900
caatatggtg ttaactaaat agggttgaaa cggtgtggaa agagttgtag gctgcgatgg 960
actaactacc taaaacctga gatcaaaaga ggcgagttta gttcagagga ggaacagatt 1020
atcattatgc ttcatgcttc tcgtggcaac aagtacgttt ctatgtttaa atgtgtgtgt 1080
atatatgtat cctcgaataa acaatgaaat gcatgaaaag gtttcatata tattacttta 1140
attaaagata caattattat tctaatatcg tgtcttccat attatatttt aatcgccttt 1200
gatctttgaa tctctcttct tatcgttagg tggtcggtca tagcgagaca tttacctaga 1260
agaacagaca acgagatcaa gaactactgg aacacgcatc tcaaaaaacg tttgatcgaa 1320

```
cagggtgttg atcccgtgac tcacaagcct ctagcttcca actccggccc tactgccacc   1380

acgccgcctg agaatttgca tttcctagat gaatctagct cagacaagca atactctcgg   1440

tcgagctcaa tgccttccct gtctcgtctt ccttcctccg gattcaacac ggtttccgag   1500

atagccagca atgttgggac accagttcag gtcggttcct tgagttgcaa gaaacgtttt   1560

aagaaatcga gttcgacatc aaggcttctg aacaaatttg cggctaaggc cacttccatc   1620

aaagatatat tgtcggcttc catggaaggt agctcgagtg ctgctactac aatatcacat   1680

gcaagctttt taaatggctt ttctgagcag agtcgcaatg aagaggatag ttctaacgca   1740

tccctgacaa atactctagc cgaatttgat cccttctctc agtcatcgtt gtacccggag   1800

catgagatca atgttacttc tgatatcggc atggaccagg tttacgattt ctcacaattt   1860

ctcgaaaagc tcgggagtga aggccacaac gaactgaatg tcgagtatgg tcatgatctt   1920

cttatgtccg atgtttcgca agaagtctca tcacctagcg ttgatgatca agacaatatg   1980

attggaagct tcgaaggttg gtcaaattat cttcttgacc atgctgattt tatatatgac   2040

accgactcag attccctcga aaagcatttc atgtgaatcc tcgtatccaa acggaaaggt   2100

ttcaaactat ttaaaacttt cctgaaccac aatttatgta tgtctttctt atttggaact   2160

tttagtatat gtccaagtct ccaagatctc atggttattt aatcccaggt ttagggtttg   2220

tgtgatgtta agtaagggtg aatctttata tatgaattag ggtttctctg acattgagaa   2280

ccatgcattg cggatcaatt ggtaattgat tgcacgagcc acgatgtttc ttttataatg   2340

tttattacta ataaagcttg ttttgttatc gtatttcata atagcatcca ttatcatcat   2400

ttttttgggg tttatactta aagtccacat tccatcataa acatcaatca tgcacttttt   2460

tggttttcat actcttcttt atgattaaat aattgtttcc aactttccat ggcatgaagg   2520

tggttgtatc tttcgttgga tctgaaccga ccacaatata ataaataagt aagtttttaa   2580

aataaatgat aaaaaaaggc tcaaacgaca gagacgttcc aagaaaaagt gtaaacgtgt   2640

ggtccataaa caattgagac gaaagctaaa gatcaagagg tgaattaagc agataactgg   2700

aattttgtga cccgacaaat attatcttaa aacgaaatct aatgt                   2745


<210> SEQ ID NO 21
<211> LENGTH: 369
<212> TYPE: PRT
<213> ORGANISM: Thlaspi arvense

<400> SEQUENCE: 21

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Thr Asn Tyr Leu Lys Pro Glu
    50                  55                  60

Ile Lys Arg Gly Glu Phe Ser Ser Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Arg Arg Thr Asp Asn Glu Ile Lys Asn Tyr Trp Asn Thr His Leu
            100                 105                 110

Lys Lys Arg Leu Ile Glu Gln Gly Val Asp Pro Val Thr His Lys Pro
        115                 120                 125
```

Leu Ala Ser Asn Ser Gly Pro Thr Ala Thr Thr Pro Pro Glu Asn Leu
    130                 135                 140

His Phe Leu Asp Glu Ser Ser Ser Asp Lys Gln Tyr Ser Arg Ser Ser
145                 150                 155                 160

Ser Met Pro Ser Leu Ser Arg Leu Pro Ser Ser Gly Phe Asn Thr Val
                165                 170                 175

Ser Glu Ile Ala Ser Asn Val Gly Thr Pro Val Gln Val Gly Ser Leu
            180                 185                 190

Ser Cys Lys Lys Arg Phe Lys Lys Ser Ser Ser Thr Ser Arg Leu Leu
        195                 200                 205

Asn Lys Phe Ala Ala Lys Ala Thr Ser Ile Lys Asp Ile Leu Ser Ala
    210                 215                 220

Ser Met Glu Gly Ser Ser Ser Ala Ala Thr Thr Ile Ser His Ala Ser
225                 230                 235                 240

Phe Leu Asn Gly Phe Ser Glu Gln Ser Arg Asn Glu Glu Asp Ser Ser
                245                 250                 255

Asn Ala Ser Leu Thr Asn Thr Leu Ala Glu Phe Asp Pro Phe Ser Gln
            260                 265                 270

Ser Ser Leu Tyr Pro Glu His Glu Ile Asn Val Thr Ser Asp Ile Gly
        275                 280                 285

Met Asp Gln Val Tyr Asp Phe Ser Gln Phe Leu Glu Lys Leu Gly Ser
    290                 295                 300

Glu Gly His Asn Glu Leu Asn Val Glu Tyr Gly His Asp Leu Leu Met
305                 310                 315                 320

Ser Asp Val Ser Gln Glu Val Ser Ser Pro Ser Val Asp Asp Gln Asp
                325                 330                 335

Asn Met Ile Gly Ser Phe Glu Gly Trp Ser Asn Tyr Leu Leu Asp His
            340                 345                 350

Ala Asp Phe Ile Tyr Asp Thr Asp Ser Asp Ser Leu Glu Lys His Phe
        355                 360                 365

Met

<210> SEQ ID NO 22
<211> LENGTH: 1080
<212> TYPE: DNA
<213> ORGANISM: Thlaspi arvense

<400> SEQUENCE: 22
atgtcaagaa agccatgttg tgtgggagaa gggctgaaga aaggagcatg gaccgccgaa 60
gaagacaaga aactcatctc ttacatccat gaacatggcg aaggaggctg gcgtgacatt 120
ccccaaaaag ctggactaaa acgatgtgga aaaagttgta gattgcgatg ggctaactat 180
ttgaaaccgg atatcaagag aggagaattt agctacgagg aggagcagat tatcatcatg 240
cttcacgctt cccgtggcaa caagtggtcg gtcatagcga gacatttgcc caaaaggaca 300
gacaacgaga tcaagaacta ttggaacaca caccttaaaa aacgccttat cgatcaaggt 360
attgatcccg tgacccacaa gccacttgcc cctagcccta gtccggccac gctcaagcct 420
tctgatttcc aagatgactc atcaaacctg ggaaactcgg atgagcattc acattcgggt 480
tctatgtctc caaaatctct tcctccgtct tcaagctcct gcaatctagc ggagataagc 540
agcagtgatg agacaccgaa aaatgatggt tccttgaaat ccaagaaacg ttcttttaag 600
agatcaagtt ctacatcaaa gctgttaaac aaagttgcat ctagggctgc ttccattgga 660
aatatcttat cagcgtccat ggaaggaacc ttggttagct ctaccgcact gtctccatgt 720
ctcaatgatg acttttccga agctagccaa ttccagatgg acgaatatga tccattccct 780
cagtcgtctg aacacataac tgatcatatg aaggaggaca ccggcatgat ctttgatctc 840
aacaactccg aatatgattt ctcgcagttt ctcgagcaat ttagtaacga aggcgaagaa 900
accgagaaca ttgggggata taatcaagat ctcctttcgt ctgacgtctc atcaccaagc 960
gttgatgaag acaatatgat gggaaacata accggttccg gttggtccag ttatcttgtt 1020
gaccattccg attttgttta tgacaagatc caagataacg acgacaggaa cttcatatga 1080

<210> SEQ ID NO 23
<211> LENGTH: 5588
<212> TYPE: DNA
<213> ORGANISM: Thlaspi arvense

<400> SEQUENCE: 23
aaattcaagt ttgataatat atgttgttaa gttaattttt tactaagtaa gtgtacattc 60
attatgacga ttccaaaatc taatttctc aattaagtcc aaaacaaaac agaaattata 120
aaatttccaa ttcgtttcaa ccctcgtgac caggtccgta tgataacaat taaaaaggat 180
cagtgtcaac atatttgttt ctattcatca caagtctcct ccaaacatat ttgaaacact 240
ggcaagggac attttataat gtttgtgtcc acggtctgaa tatccctttt tattcatttg 300
aatattaccc taattaaaga agccacctcc gagaaaaagt tcaggtgaac tctgctctgg 360
tacatccata taagtgggcg attctaatgc catattaatt aacacttgtc actttttctt 420
ggtgcataga cacaaaattt accaattcag ctagttaagc tataattaac taattcagat 480
tcatactgtc atcataatca gttaaaatcc atgcaaagcg atactaatct tatacagtgc 540
atgatgatag tctatgttgt tttttgtttt ttaattaacg cttaattatc caaagatcaa 600
attaatcagg cgccctttaa atcgtctctc catggcgttc atgttttatt tgtatcagtc 660
atcacagttt attcaagttg catttatgat catgaaagtg acagcctaag caactaacat 720
accaaaaacc atgaatagtt ttgttcaaag tttcgctaaa cgatggttga actgggtcta 780
atgtcctatt ttttcccaaa ttgattatgc cttcttagcc ctttttataa acaaaaactg 840
ggtctaatgt cgggactact atttatatat tttttaaaaa ataattctaa cattttaatg 900
cattataatt tataattata tgttcagtat tgcataaagc atataaaaaa ccaaattaag 960
acataatata tttttattaa aattaataaa ttataaattt aagttgaatg aagtcgtcaa 1020
attttacact taactaatca tttttctttt gagttaactc tgcaagttcc gaagaggcat 1080
aactattaga aacaatagtg aagtccaagt gagatgtgag atgtgagatg agaagaaaca 1140
aacattgata agtaagcaaa attactattt aatattttga atacagctcc tagtgtttca 1200
gggatagcca aagtggcaaa caaataggac cgaggctgaa aacgaacacg tgatgattaa 1260
tcgcatatat atatatatat aataaaatag taataaatac gctaataatt atgaaaaatg 1320
ataatggttt ttatctgtgc aataaaaaag aatttatcaa tatgttttct ttaaacatat 1380
ttattaaaca cgttatagat ggttttatcc gtatcatttt actgctacaa catacatgtt 1440
ttttttttaa tatataaaca tatatatata tatatatttt ctaatatggt cttataattt 1500
gtctattaga aaccatagac gatgttactc tttacctaat aatctctaat gaaaatgata 1560
tgatgataac catatttgtg accttttttcg ggtcggcact gcaattatca attcaattac 1620
tatcagaaaa ctattgcaat tatgaaaacc atattttttta agtctctctc aaactattta 1680
acagttttta aaataaagaa actatttgaa cagttccacg tccaaaagaa gatgatgaac 1740

-continued

```
gctcactacc cttttaatga ggtttttttt ttgttatttc atctgaaatc acaatgtaaa   1800
cctttacaaa agagccatgt agctaccaaa aagagccttg atatgtctag gaaccacaca   1860
ttgatgagtt aatattgtat ttattttttt agatttattt attttatttt attttacgta   1920
ggcttttaaa agtattctga cacgagtgcg cactataagg cttataaata gatgctcata   1980
tacatacata attaactcat tacagagaag tatctcacaa tgtcttagat ctttgataca   2040
tctacaactt tttttttact agcgttttca aatgttactg aaaatgaaaa cacaaaatca   2100
ctcaacgatc taccatagtt tttcagttag tttcatattc agatgcatca gagttctcat   2160
caacagatct attggtctct tgccttaatt tagacgacat ttctgagttc ttttcccctt   2220
tgctactcat cttctttagg ttgcgagatt tttgtgtgtg ttaaacttat aggtcgtatg   2280
taaatctata gatattgtat atatatccga aggaaaaaaa ggagaaaaat gtcaagaaag   2340
ccatgttgtg tgggagaagg gctgaagaaa ggagcatgga ccgccgaaga agacaagaaa   2400
ctcatctctt acatccatga acatggcgaa ggaggctggc gtgacattcc ccaaaaagct   2460
ggtatattac acatatatag cttatagtta aaccaagcat aatctatgat ctaattgatg   2520
tttatatggc tgtggtgttt aattaggact aaaacgatgt ggaaaaagtt gtagattgcg   2580
atgggctaac tatttgaaac cggatatcaa gagaggagaa tttagctacg aggaggagca   2640
gattatcatc atgcttcacg cttcccgtgg caacaagtaa tacatatata cttaagtcaa   2700
aattcatata ttaattctca atcttaaatt aagcattaat aatttgtttt ctcttgtttt   2760
aacgttattt tcattttttt aaaaaccaat gtcctgttga attttattta taaaaataaa   2820
atattcaacc tcaagtcaaa gttgatttaa aaatagttat aagttgggat aaagatacca   2880
ggaacaactt atttttatat aaaaaatgaa ctttctaact tcatcttaat ttgtgtaaaa   2940
actgtcaaaa agtacgtatt atatattgcg aaacagggga gtgcactgaa agttttgata   3000
tattctactt ttctttgacg tccttactat aggtggtcgg tcatagcgag acatttgccc   3060
aaaaggacag acaacgagat caagaactat tggaacacac accttaaaaa acgccttatc   3120
gatcaaggta ttgatcccgt gacccacaag ccacttgccc ctagccctag tccggccacg   3180
ctcaagcctt ctgatttcca agatgactca tcaaacctgg gaaactcgga tgagcattca   3240
cattcgggtt ctatgtctcc aaaatctctt cctccgtctt caagctcctg caatctagcg   3300
gagataagca gcagtgatga gacaccgaaa aatgatggtt ccttgaaatc caagaaacgt   3360
tcttttaaga gatcaagttc tacatcaaag ctgttaaaca aagttgcatc tagggctgct   3420
tccattggaa atatcttatc agcgtccatg gaaggaacct tggttagctc taccgcactg   3480
tctccatgtc tcaatgatga cttttccgaa gctagccaat tccagatgga cgaatatgat   3540
ccattccctc agtcgtctga acacataact gatcatatga aggaggacac cggcatgatc   3600
tttgatctca acaactccga atatgatttc tcgcagtttc tcgagcaatt tagtaacgaa   3660
ggcgaagaaa ccgagaacat tgggggatat aatcaagatc tcctttcgtc tgacgtctca   3720
tcaccaagcg ttgatgaaga caatatgatg ggaaacataa ccggttccgg ttggtccagt   3780
tatcttgttg accattccga ttttgtttat gacaagatcc aagataacga cgacaggaac   3840
ttcatatgac cagttgattg ctacccggac ttgagttgag tggttaatta agggtttcac   3900
tatattaatt tttctaagat gttttcgtaa gttattaatt aagggtcact atagggttat   3960
ccaataaggg attctcttag ttagagaacc atgtgttccc ctggatcaat tagtatttga   4020
tttgcgggag acacgagtta ttttttttttg ctttaagaac tgttaagagt aaatattaaa   4080
taaagcttgc attttcataa ttccattatg tataattatt ctgtatattt aaatatcaat   4140
```

```
catgctaaga gtaattattc tggatagatt tagaggaact tacgaacgta acaaggatta   4200
aaaagtgact atttttagct gacataaact tttaacatgc cttcatgacc caaaatctaa   4260
actacttttt ggagctttcg catgcgttca ctgtactaca atcatttgat ttaaagtttg   4320
agcgttagat tagaacagat gagccgtgtt accaaaaata tatggaagaa aatgtaagac   4380
attttagaat tttggggatg aaactcccat taaaaaaaaa ccccctacct acgaataaag   4440
tcattgaagt ttttttagag atgaattttt ttttgggggt tgcataaaca tgatttttta   4500
cacttgtata ttagaagtat atataactgg aaacattaaa taaatgagat agttaaaatt   4560
aaatgaattg aatactaaac tagtggagca gagttaaaaa agagaataat ttgcttttct   4620
cgtaaactaa tttgcagaga gatatatact tgatatactt taacgttaca gcaaaatatc   4680
ttaagaaaaa gttaagaaaa tttagtcaaa aataaaaaat ttcagtaaat gtatttagta   4740
agacgataca ctctagattt tgttcattta aaactaataa tctggcgatc ataaacaact   4800
tctcggaaaa ccaaaagcaa tatattgata aagtttttttg tgtggtaaat attcataaag   4860
tctgtagata ttgttttttt aatttagata taaagtattt cgatctttcg taatcgaacg   4920
tggggcagaa acgcaccatc ctttttcttt tcgacataac atggaaaata gcaaaaatct   4980
atattagtac gacgaatacc agtaaataaa taaaaacaaa caagaaataa aaatgctgtt   5040
cccaatctgt gtatatatat ggtccacaaa tacataatta ttttcagaag ctaaagaaca   5100
ataagtgagc aaacataatt ggattagtga cccgacatat acagtattgt gtgcaaagtt   5160
aataaacatt caatgatata aatatcatca taattcatag tatgtgtgat acaaggagct   5220
ttggttttta tgtggctaca cgtcaacgac tcaattcctg tttttatatc ttagaaactt   5280
ggtttgctac cgacaatctg tagctaccgc tgattcctaa tcgatttaga tcttgaacac   5340
acataatcaa ttcacacgca gtatcttgtc ttctaaactt gcagcccata aacctttttg   5400
cctgataaaa ctctcaatat gcagcacaca ggttacaggt attgagtgtc ttgaatcatc   5460
tccaacatct tcagactcga ctgtactttt ctttgactta ggcgatagtt acgtatattg   5520
atacgtaata gtgacttata tatctatctt tcaatctcat ttggattcaa gtgcgtataa   5580
cttaaaca                                                            5588
```

<210> SEQ ID NO 24
<211> LENGTH: 359
<212> TYPE: PRT
<213> ORGANISM: Thlaspi arvense

<400> SEQUENCE: 24

```
Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110
```

```
Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Ser Cys Asn Leu
                165                 170                 175

Ala Glu Ile Ser Ser Ser Asp Glu Thr Pro Lys Asn Asp Gly Ser Leu
            180                 185                 190

Lys Ser Lys Lys Arg Ser Phe Lys Arg Ser Ser Ser Thr Ser Lys Leu
        195                 200                 205

Leu Asn Lys Val Ala Ser Arg Ala Ala Ser Ile Gly Asn Ile Leu Ser
    210                 215                 220

Ala Ser Met Glu Gly Thr Leu Val Ser Ser Thr Ala Leu Ser Pro Cys
225                 230                 235                 240

Leu Asn Asp Asp Phe Ser Glu Ala Ser Gln Phe Gln Met Asp Glu Tyr
                245                 250                 255

Asp Pro Phe Pro Gln Ser Ser Glu His Ile Thr Asp His Met Lys Glu
            260                 265                 270

Asp Thr Gly Met Ile Phe Asp Leu Asn Asn Ser Glu Tyr Asp Phe Ser
        275                 280                 285

Gln Phe Leu Glu Gln Phe Ser Asn Glu Gly Glu Glu Thr Glu Asn Ile
    290                 295                 300

Gly Gly Tyr Asn Gln Asp Leu Leu Ser Ser Asp Val Ser Ser Pro Ser
305                 310                 315                 320

Val Asp Glu Asp Asn Met Met Gly Asn Ile Thr Gly Ser Gly Trp Ser
                325                 330                 335

Ser Tyr Leu Val Asp His Ser Asp Phe Val Tyr Asp Lys Ile Gln Asp
            340                 345                 350

Asn Asp Asp Arg Asn Phe Ile
        355
```

<210> SEQ ID NO 25
<211> LENGTH: 1017
<212> TYPE: DNA
<213> ORGANISM: Thlaspi arvense

<400> SEQUENCE: 25

```
atgtcgaaaa gaccatgctg tatcggagaa gggttaaaga aaggagcatg gacgtcaggg      60

gaagacaaaa aactcatctc ttatatccat gaacatggcg aaggaggttg gcgtgacatt     120

cccgaaaaag ctgggctaaa acggtgtgga aagagttgca gactgcgatg ggcgaactat     180

ttgaaccccg atatcaagag aggaggattt agctacgagg aagaacagat catcatcatg     240

cttcatgctt ctcgtggcaa caagtggtca gtcatagcaa gacatttgcc gcaaagaaca     300

gacaacgaga tcaaaaacta ttggaacaca catctcaaga aacgcctgat caataagagc     360

actgattccg tgacccacaa gcctctagct tcctctaacc ctagtcctac cgagcgtaag     420

aagctcgatt cccaagaaga atccaatccc aaggagcagt cgttacagcc gggttcgaag     480

tctccagtat ctctttccct ttcttcgagt ttcaacgaca ctgtacccga gatcatgacc     540

agtgatgaga cgcctctaga aagtggtttc ttgagttgca aaaaaagtgt cgagagatcg     600

agctcaacat caaggctttt aaacaaagtt gcagctagag cttcttccat cgggagtatc     660
```

-continued ttatcaacct ccatagaagg aactttgaga tctcctgcat cgtcctcatg tctcccaaac 720
tcattgtgtc aatcatctga acacaacaag gatcaagatc tcggtacgag cattgatctt 780
agcatccccg attacgatta ctcccacttt ctcgagcact tcatcaatag cgaagacgaa 840
gccgaaaaca ttggtggctg caatcaagat ctccttatgt ccgatttccc atcaacatta 900
gtggataaag aaaatatgaa ttttgaagac ataaccggtt ggtcaagtta tcttctcgac 960
catcccagtt ttacgtatga atcggaacaa gattccgacg acaacaactt gttatga 1017

<210> SEQ ID NO 26
<211> LENGTH: 3950
<212> TYPE: DNA
<213> ORGANISM: Thlaspi arvense

<400> SEQUENCE: 26
ggtaatccat cggaaagttt atacggatta tcgacgactt gctttcgtcg gaaatttaag 60
acgaattttc gatgacttgc aacattccgt ccatttgtaa tcgacgaatc atttttgtcg 120
aaaatttccg acggattttt gacaaaaatg gccgtcgctt ctttcttgta gtgtataata 180
aatgcgcttt aatttagata tttcggtatt gtgcatttag taggtgaagt atattaatta 240
tatatcctag aaacaaagat tagtagaatt ttgatccagt ggcttgctaa taaataggac 300
tcaagagcgg ttttgataca tcaaatctat gattcaaact tcaaaatatg tgatttcttg 360
catattatga atacaaagat actcagggat ggatacgtac gtgctctgaa ttaatcgaat 420
cttgtgccac aatttatggt gtgcaaattg gattattaat ttgtaataga catgaatatt 480
aaaaataaaa catatttaat ctgaaaaatt tcagaacatc gtagatcaga taacatctgg 540
attcgagatg gagagaaaaa aaaaaaagta gattgtggcc ttgtgggcga ttctagtggg 600
acatctgctg aattagagaa agaaatggtt aaatgttaaa atattttaga ttggatagta 660
tctgaagtag agaccacaga aaaagaaaaa aagtgaattg tgggtgagcc tagaggaaca 720
aggctgtgac atacgtggga agacagacga aagagcccaa aaacgtgcac cgtccaagat 780
tctctatacg tacctaacct ccttccaggg actcttcact tgacacttac acttacactt 840
gcacttgcac tcactcacac tcacactcac actcacactc acacttacac tcaaacttag 900
ccagctaatt ttgttttaat ttgtattggt gatttgactg atgaataata taacaacggc 960
aacatcaacg gttatagagt ggaaaaaaaa aaaaaccgcg aactacacat cttgtaaata 1020
ttagtttaga tgtcattgtc tcccatatcg agacgtagac acgtcgtaag cgatttttat 1080
tttttttgtc actcttcaaa tgatatatag aaaacttggt tttcttcaca tgtttatcaa 1140
cggtaaaatt gtagatgtaa tctaaattaa taaattaata tttacaagat gtgtcattca 1200
ttctaatcac gttcatttta tatttatgta taacactaca gtagcggata agcttagtat 1260
gtgcagaaag aatgggtaga atcgtacgtg ggtttacaag tttattgtca tgagtaatat 1320
atactagatc taagctaaaa aaaaacaaat attagaccct taaaatgaac acatacggta 1380
ttacgatctt atacacataa tctcgcggtt aatctcaacg gaccatgcat catatgtaat 1440
tatattaaat aaacatcagt ctctctatat atccttgatt tacaatatct tttctttctg 1500
cacatttttt cgaaatgcaa agaaggaatg tcgaaaagac catgctgtat cggagaaggg 1560
ttaaagaaag gagcatggac gtcaggggaa gacaaaaaac tcatctctta tatccatgaa 1620
catggcgaag gaggttggcg tgacattccc gaaaaagctg gtacatgcat ttcatttaca 1680
gattttgtaa tatttattta tcgaattgat ctttatatgc ttttcatttt ctgagtttaa 1740
ttagggctaa aacggtgtgg aaagagttgc agactgcgat gggcgaacta tttgaacccc 1800
gatatcaaga gaggaggatt tagctacgag gaagaacaga tcatcatcat gcttcatgct 1860
tctcgtggca acaagtacta caacgtttgc ctatatattt gtttttgtat atgcatgtaa 1920
tacaatcatc aacgtataca taactttacg acacgatcaa tgtaattgga ctgtactata 1980
ttttttatta ggtggtcagt catagcaaga catttgccgc aaagaacaga caacgagatc 2040
aaaaactatt ggaacacaca tctcaagaaa cgcctgatca ataagagcac tgattccgtg 2100
acccacaagc ctctagcttc ctctaaccct agtcctaccg agcgtaagaa gctcgattcc 2160
caagaagaat ccaatcccaa ggagcagtcg ttacagccgg gttcgaagtc tccagtatct 2220
ctttcccttt cttcgagttt caacgacact gtacccgaga tcatgaccag tgatgagacg 2280
cctctagaaa gtggtttctt gagttgcaaa aaaagtgtcg agagatcgag ctcaacatca 2340
aggcttttaa acaaagttgc agctagagct tcttccatcg ggagtatctt atcaacctcc 2400
atagaaggaa ctttgagatc tcctgcatcg tcctcatgtc tcccaaactc attgtgtcaa 2460
tcatctgaac acaacaagga tcaagatctc ggtacgagca ttgatcttag catccccgat 2520
tacgattact cccactttct cgagcacttc atcaatagcg aagacgaagc cgaaaacatt 2580
ggtggctgca atcaagatct ccttatgtcc gatttcccat caacattagt ggataaagaa 2640
aatatgaatt ttgaagacat aaccggttgg tcaagttatc ttctcgacca tcccagtttt 2700
acgtatgaat cggaacaaga ttccgacgac aacaacttgt tatgatctat ctgtctgtgg 2760
ctcgtcacct gctcattgaa ccaggggctg accagttaat ctcatgttgg tatgtccaag 2820
ataaggggtt caatatctta gataaatttc aacttgttaa attgcgttac tagattattt 2880
agtaagaggc acttatgtaa taaaaaaaaa accatgtact cccgtgtatc gaatagtatt 2940
gatttgatct gcgtaagagt ttttcttata actattttgt aaaatatatg ttgaataaat 3000
taagctttat gcatgtgtac cttttttttaa taaaaaaaaa actaagcttt atggtccaca 3060
aacactacca aaaggtaaag agcaatgatt gagcaacaaa attggatggg tgacctggcg 3120
aatctttatt aatgttcaat gaaatgatca tacatttatg ggaagctttt gtttctatgt 3180
gcatggctgt acatgaataa tttaattttt ttattggtcg tgttacatca ttatcaaaaa 3240
cattccatca aattcattta catatatgcg aatatgcgat tatgatgaac aactccacga 3300
tacagttttc cacatgtgac acacacggat ctgtaacaga tagagacata gagttgcaca 3360
tcaaaatctt tcgataagat ttgtatctat caatatacag aaacttgtct gcatttgtta 3420
ggaatcgaac ctcaaatata tggtgtagta ggtcaagggc tttcacaatt ttactgttgt 3480
tgtgtgtaaa actgatcgtg tgaagtgaac gttcagaaaa aagaatactt cctctctatg 3540
tttttctaca cttaatttag ttttgtgcct aaaaatataa tttcaatagt aaataatact 3600
tgacgtggtt tattacagaa aaagttacat acagtataaa tgtaagaatt acatacagaa 3660
agaatcatgt tagcattcat tcaaagaaaa aatggaatta tgttagcaaa tcaagtcgat 3720
ctaagtttta ttacatgttg gcattcatta aacccttgca gtatctgaaa agaattgctc 3780
tccacaccag accaagtccg gttcgataat accatgattg ctattggaaa acgtcgtacc 3840
gagacataag aaccggtagt aagttaatta cgaaagtagc cttacagcta aacaatcggt 3900
agtctaaact ctgaagcgat cgcgattagc cccttgggag tgattgggag 3950

<210> SEQ ID NO 27
<211> LENGTH: 338
<212> TYPE: PRT
<213> ORGANISM: Thlaspi arvense

<400> SEQUENCE: 27

Met Ser Lys Arg Pro Cys Cys Ile Gly Glu Gly Leu Lys Lys Gly Ala
1               5                   10                  15

Trp Thr Ser Gly Glu Asp Lys Lys Leu Ile Ser Tyr Ile His Glu His
            20                  25                  30

Gly Glu Gly Gly Trp Arg Asp Ile Pro Glu Lys Ala Gly Leu Lys Arg
        35                  40                  45

Cys Gly Lys Ser Cys Arg Leu Arg Trp Ala Asn Tyr Leu Asn Pro Asp
    50                  55                  60

Ile Lys Arg Gly Gly Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Gln Arg Thr Asp Asn Glu Ile Lys Asn Tyr Trp Asn Thr His Leu
            100                 105                 110

Lys Lys Arg Leu Ile Asn Lys Ser Thr Asp Ser Val Thr His Lys Pro
        115                 120                 125

Leu Ala Ser Ser Asn Pro Ser Pro Thr Glu Arg Lys Lys Leu Asp Ser
    130                 135                 140

Gln Glu Glu Ser Asn Pro Lys Glu Gln Ser Leu Gln Pro Gly Ser Lys
145                 150                 155                 160

Ser Pro Val Ser Leu Ser Leu Ser Ser Ser Phe Asn Asp Thr Val Pro
                165                 170                 175

Glu Ile Met Thr Ser Asp Glu Thr Pro Leu Glu Ser Gly Phe Leu Ser
            180                 185                 190

Cys Lys Lys Ser Val Glu Arg Ser Ser Ser Thr Ser Arg Leu Leu Asn
        195                 200                 205

Lys Val Ala Ala Arg Ala Ser Ser Ile Gly Ser Ile Leu Ser Thr Ser
    210                 215                 220

Ile Glu Gly Thr Leu Arg Ser Pro Ala Ser Ser Ser Cys Leu Pro Asn
225                 230                 235                 240

Ser Leu Cys Gln Ser Ser Glu His Asn Lys Asp Gln Asp Leu Gly Thr
                245                 250                 255

Ser Ile Asp Leu Ser Ile Pro Asp Tyr Asp Tyr Ser His Phe Leu Glu
            260                 265                 270

His Phe Ile Asn Ser Glu Asp Glu Ala Glu Asn Ile Gly Gly Cys Asn
        275                 280                 285

Gln Asp Leu Leu Met Ser Asp Phe Pro Ser Thr Leu Val Asp Lys Glu
    290                 295                 300

Asn Met Asn Phe Glu Asp Ile Thr Gly Trp Ser Ser Tyr Leu Leu Asp
305                 310                 315                 320

His Pro Ser Phe Thr Tyr Glu Ser Glu Gln Asp Ser Asp Asp Asn Asn
                325                 330                 335

Leu Leu

<210> SEQ ID NO 28
<211> LENGTH: 1047
<212> TYPE: DNA
<213> ORGANISM: Thlaspi arvense

<400> SEQUENCE: 28
atggctcgga ctttgcaagg cgagtggatg aaggtggagc agaaaggagg acaagtacca      60
gcaccgagaa gctcacacgg catagccgtg atcggagaca agctctattg tttcggcggc     120

```
gaggatccgc catatgagtc catcgacaac gacctttatg tctttgactt caacacccac    180
acttggtcaa tcgctccggc caacggagac gttccaaaga ccagagtctt aggcacccgc    240
atggtggccg tgggaacgaa gctctatgtg ttcggaggcc gcaataaaca gttagagttc    300
gaggactttt actcgtacga tacggtgaaa gaggagtgga agttcctgac gaagctggac    360
gaaaagggag gacccgaagc tcgtactttc cattcgatga cttcagatga aaaccacgtg    420
tacgtgttcg gtggggtgag caaaggaggg ctgaatgcaa cccccctttcg gttcaggacg   480
atcgaggcct ataacattgc tgaagggaaa tgggctcagc tccctgaccc tggagaggat    540
ttcgagaaaa gaggaatggc cggattcctt gtggtgcaag gcaagctttg ggtgttttac    600
ggattcgcga ctgcgaatga tcctaagata cccacactct acgggtccca ggactacgag    660
tctaatcgtg tgcactgcta tgatcccgct actcaaaaat ggaccgaagt ggagaccaca    720
ggtttcgaga aaccttctcg taggagctgt tttgcgcatg cggctgtggg gaaatatata    780
ataatattcg gaggtgagat tgagcgggac ccagaagcac atcaaggtcc ggggacgttg    840
tcccgtgagg gttttgcgtt ggacactgag acattggtgt gggagaggta tgaaggagga    900
ccaatcaaac cgagcaaccg cggttgggtg gcctccacga cgaccaccat caacggaaag    960
aaaggtctgc tcgtgcatgg agggaaactt atgaccaacg agcgcaccga tgagatgtac   1020
ttcttcgcag tcaattcctc cacgtaa                                       1047
```

<210> SEQ ID NO 29
<211> LENGTH: 4094
<212> TYPE: DNA
<213> ORGANISM: Thlaspi arvense

<400> SEQUENCE: 29

```
cgaacatttt tttttttgg caaacacact tagaacgtga tcacaatcca aggaaaccca      60
gcactcgatg cctaaatatc tgaagttgat gcaaaaactg aaatataaag tttagtatag    120
atagataact ggttatattt atagaagaca accgaaaggt tctgcaaaag gggtagtttt    180
tatactagtt caatctaaca aatgatcagt tttttttgg gcaaatataa tcagtttgtt     240
tatatatata tatatatatt tttggtcaat tgtttattta tatataacac actattttat    300
atcatatcat tctaaatttc taatgggttt aaattttta ttactatgca attaaaatac     360
acagctcata tattgaacta aatagttgta aataatttta ggtgaattac aaattgttat    420
cacctatatc tatattatta atttcgaatc aggaaagtaa cattttgttc actaaagcta    480
aaagcctaaa agtatgataa aatgttcaaa atggtgaata aagaatgata tggggtttaa    540
gtgtttaact ggtaatatta cagcgataca caaaatagga aaaaaaaaca ataattttg     600
tatctcgtgt taaaagtcaa acaaatgtac aattatgcta agatagtttg ataacgctgc    660
tttagatatt tttgtggtgt ttgctgtttt aaaaattgtt gtatttttga aaattatatg    720
gtagaaaaaa aagaaaagaa atgttccaca acgcaataaa aatcaagttt gaagatatcg    780
atcatgtttt atagtaataa gcaaaaaaaa acaaacacat gcatcatcat catcaagcta    840
tcaagtaaca atcatgtttc atagtaataa gcaatatcat catcatgctg tcaagtatca    900
atcatgtttc atagttttaa gcaatatgaa ttaacacatg catcatcatc ttcatgcttt    960
aatttagact aacatgtggc gcagaaaccg agaagctcac acggcatata tacccgtcgc   1020
ctaacagcta tgttagcttt tgttaatctt catgactgtg gcacatctct ttgagcactg   1080
cgcaccatcc atgcatgttt tctaactgct ccaagacctt ttatcctaaa caaacacaat   1140
tattcattct ccttttctga tttattttct gttttttttt tgccaactga ttttctgatt   1200
```

```
tatcgctcac tcgcgaagat atttttgtaa gggagattta ccaactaagc ttaaagaaat   1260
taatatgctt ctcacatttt ttagataata atttaacact ttcacttcct ttttgggggt   1320
acaaaatacc cacaagttca cagaaattca taagcaccac acagttggaa atatcttctt   1380
cttttttttc ttttcttttt tgtttgttaa acaatcaata attggagata ccttgacacg   1440
cagaattgtt tagcctatat atagaagagc agcgaaagaa gaggagacac acaaacaaat   1500
agaaaagaaa agaaaaaaag agttgaatat tgcagctatg gctcggactt tgcaaggcga   1560
gtggatgaag gtattgccta cttagtcaag gatttttatt taagatatta attttgcacg   1620
agagaagcat aagccatagg ctatgtatta tgtatatatg tataatattg gttattagta   1680
aaaagttatg tatgacaaca cccttaattc ccatgttctc gacacgttat accccattcg   1740
tatccctcct gaaaagaggg gatgttgatg gtttacttgt aattaacctg tcatgtattc   1800
gaatgattaa ccggctcatc agtatccgtt ttaaccatca attcattttg gtcactggtt   1860
gacaggtgga gcagaaagga ggacaagtac cagcaccgag aagctcacac ggcatagccg   1920
tgatcggaga caagctctat tgtttcggcg gcgaggatcc gccatatgag tccatcgaca   1980
acgaccttta tgtctttgac ttcaacaccc acacttggtc aatcgctccg gccaacggag   2040
acgttccaaa gaccagagtc ttaggcaccc gcatggtggc cgtgggaacg aagctctatg   2100
tgttcggagg ccgcaataaa cagttagagt tcgaggactt ttactcgtac gatacggtga   2160
aagaggagtg gaagttcctg acgaagctgg acgaaaaggg aggacccgaa gctcgtactt   2220
tccattcgat gacttcagat gaaaaccacg tgtacgtgtt cggtggggtg agcaaaggag   2280
ggctgaatgc aaccccccttt cggttcagga cgatcgaggc ctataacatt gctgaaggga   2340
aatgggctca gctccctgac cctggagagg atttcgagaa aagaggaatg gccggattcc   2400
ttgtggtgca aggcaagctt tgggtgtttt acggattcgc gactgcgaat gatcctaaga   2460
tacccacact ctacgggtcc caggactacg agtctaatcg tgtgcactgc tatgatcccg   2520
ctactcaaaa atggaccgaa gtggagacca caggtttcga gaaaccttct cgtaggagct   2580
gttttgcgca tgcggctgtg ggaaatata taataatatt cggaggtgag attgagcggg   2640
acccagaagc acatcaaggt ccggggacgt tgtcccgtga gggttttgcg ttggacactg   2700
agacattggt gtgggagagg tatgaaggag gaccaatcaa accgagcaac cgcggttggg   2760
tggcctccac gacgaccacc atcaacggaa agaaaggtct gctcgtgcat ggagggaaac   2820
ttatgaccaa cgagcgcacc gatgagatgt acttcttcgc agtcaattcc tccacgtaat   2880
caatgctctc tcaccctcca aggtctgttt gtgtgtgtgg ggggtcaagg ttttatatga   2940
ttcaataaag gtttgtgaga ccttcagaaa ctcaccctat cgtcgctgtt ttcctttta   3000
aatattatta tcaaataaaa taaatgtgtg tgctgtgtga ctgtgtgtgg ggtttggaaa   3060
ctattatcat tggaataata tgtgtgtttt gtgtacgtgt gagtataata aaatcataaa   3120
ttatactatg aaattatcta cttatttgtc gtatcattta acttccctca atcgccataa   3180
catttattca tgtgtatcca agtggatgac gaaactatat ctaccaattc taatttggaa   3240
gcattatgat tttttttgcg attttgaaat ttaaaagtgg gatagagtaa atatttggaa   3300
agcatgggaa tatttatttt cctaactgga ttataaaaaa aactgtattt atagttattt   3360
catgggtata aaaaaagata tgtttttagt taaataattg atattttata ttatagatta   3420
aatttaagtg tatagtatat acacctttta atattatttg atgtcgggtg ttttatcata   3480
taaatataaa tataaacaat actaataata tgtatactgt atataccttt ttaacacttt   3540
```

-continued

```
tttttaata ctaacatata acacattgaa atagtcatac gcagcgccaa tattttagct   3600

tgaaggttaa taatttgata tgttgagctc ttgcatcatt cgagatccaa aaagcatcca   3660

caaaaataca aaacatcagt aattaattag cttttgcttg gagagtttga gggcagtcat   3720

cattcatttt cagcttaatc tggaaagcat tatagttcaa acattatttt cagattctta   3780

acttcctttt ttagctgact ttactttccc ttgcgtatag ttttggatta aagattatca   3840

gagaaatcca catgagattt cagatttgat gaaaatgaag aaaaactttt taagtttgga   3900

aaatgataaa tgtatcagct ctggtcaaag atgagatcga aataggccca ctggactatc   3960

ttggggaaca agctttaagc cttcgaaaaa aaggctgttt ccgcttgttt tattattacc   4020

aaacagatag aaagatgtct taatagtttc ttgttctata aaagtcttat tacagacact   4080

cttaaaactc tctt                                                     4094
```

<210> SEQ ID NO 30
<211> LENGTH: 348
<212> TYPE: PRT
<213> ORGANISM: Thlaspi arvense

<400> SEQUENCE: 30

```
Met Ala Arg Thr Leu Gln Gly Glu Trp Met Lys Val Glu Gln Lys Gly
1               5                   10                  15

Gly Gln Val Pro Ala Pro Arg Ser Ser His Gly Ile Ala Val Ile Gly
            20                  25                  30

Asp Lys Leu Tyr Cys Phe Gly Gly Glu Asp Pro Pro Tyr Glu Ser Ile
        35                  40                  45

Asp Asn Asp Leu Tyr Val Phe Asp Phe Asn Thr His Thr Trp Ser Ile
    50                  55                  60

Ala Pro Ala Asn Gly Asp Val Pro Lys Thr Arg Val Leu Gly Thr Arg
65                  70                  75                  80

Met Val Ala Val Gly Thr Lys Leu Tyr Val Phe Gly Gly Arg Asn Lys
                85                  90                  95

Gln Leu Glu Phe Glu Asp Phe Tyr Ser Tyr Asp Thr Val Lys Glu Glu
            100                 105                 110

Trp Lys Phe Leu Thr Lys Leu Asp Glu Lys Gly Gly Pro Glu Ala Arg
        115                 120                 125

Thr Phe His Ser Met Thr Ser Asp Glu Asn His Val Tyr Val Phe Gly
    130                 135                 140

Gly Val Ser Lys Gly Gly Leu Asn Ala Thr Pro Phe Arg Phe Arg Thr
145                 150                 155                 160

Ile Glu Ala Tyr Asn Ile Ala Glu Gly Lys Trp Ala Gln Leu Pro Asp
                165                 170                 175

Pro Gly Glu Asp Phe Glu Lys Arg Gly Met Ala Gly Phe Leu Val Val
            180                 185                 190

Gln Gly Lys Leu Trp Val Phe Tyr Gly Phe Ala Thr Ala Asn Asp Pro
        195                 200                 205

Lys Ile Pro Thr Leu Tyr Gly Ser Gln Asp Tyr Glu Ser Asn Arg Val
    210                 215                 220

His Cys Tyr Asp Pro Ala Thr Gln Lys Trp Thr Glu Val Glu Thr Thr
225                 230                 235                 240

Gly Phe Glu Lys Pro Ser Arg Arg Ser Cys Phe Ala His Ala Ala Val
                245                 250                 255

Gly Lys Tyr Ile Ile Ile Phe Gly Gly Glu Ile Glu Arg Asp Pro Glu
            260                 265                 270
```

```
Ala His Gln Gly Pro Gly Thr Leu Ser Arg Glu Gly Phe Ala Leu Asp
        275                 280                 285

Thr Glu Thr Leu Val Trp Glu Arg Tyr Glu Gly Gly Pro Ile Lys Pro
    290                 295                 300

Ser Asn Arg Gly Trp Val Ala Ser Thr Thr Thr Thr Ile Asn Gly Lys
305                 310                 315                 320

Lys Gly Leu Leu Val His Gly Gly Lys Leu Met Thr Asn Glu Arg Thr
                325                 330                 335

Asp Glu Met Tyr Phe Phe Ala Val Asn Ser Ser Thr
            340                 345
```

<210> SEQ ID NO 31
<211> LENGTH: 19
<212> TYPE: DNA
<213> ORGANISM: Thlaspi arvense

<400> SEQUENCE: 31
acgatcttcg aaaacttct 19

<210> SEQ ID NO 32
<211> LENGTH: 22
<212> TYPE: DNA
<213> ORGANISM: Thlaspi arvense

<400> SEQUENCE: 32
atcttcgaaa acttctctat at 22

<210> SEQ ID NO 33
<211> LENGTH: 22
<212> TYPE: DNA
<213> ORGANISM: Thlaspi arvense

<400> SEQUENCE: 33
aagaaaccta atatgagttt ta 22

<210> SEQ ID NO 34
<211> LENGTH: 19
<212> TYPE: DNA
<213> ORGANISM: Thlaspi arvense

<400> SEQUENCE: 34
tttttcaact ttaaaattt 19

<210> SEQ ID NO 35
<211> LENGTH: 22
<212> TYPE: DNA
<213> ORGANISM: Thlaspi arvense

<400> SEQUENCE: 35
aaacactgta aaagaaacta tc 22

<210> SEQ ID NO 36
<211> LENGTH: 19
<212> TYPE: DNA
<213> ORGANISM: Thlaspi arvense

<400> SEQUENCE: 36
acatttgcgt atttctcat 19

<210> SEQ ID NO 37
<211> LENGTH: 19
<212> TYPE: DNA

-continued

<213> ORGANISM: Thlaspi arvense

<400> SEQUENCE: 37
cgaaccctaa ctcttccca 19

<210> SEQ ID NO 38
<211> LENGTH: 22
<212> TYPE: DNA
<213> ORGANISM: Thlaspi arvense

<400> SEQUENCE: 38
tcgggtttgt tcgtacggac aa 22

<210> SEQ ID NO 39
<211> LENGTH: 19
<212> TYPE: DNA
<213> ORGANISM: Thlaspi arvense

<400> SEQUENCE: 39
tcgctaagat cataaaacc 19

<210> SEQ ID NO 40
<211> LENGTH: 19
<212> TYPE: DNA
<213> ORGANISM: Thlaspi arvense

<400> SEQUENCE: 40
agattcacag agactgagc 19

<210> SEQ ID NO 41
<211> LENGTH: 22
<212> TYPE: DNA
<213> ORGANISM: Thlaspi arvense

<400> SEQUENCE: 41
aagacttttt tccggtgtct ct 22

<210> SEQ ID NO 42
<211> LENGTH: 22
<212> TYPE: DNA
<213> ORGANISM: Thlaspi arvense

<400> SEQUENCE: 42
gtgttttttt tttgaacatt aa 22

<210> SEQ ID NO 43
<211> LENGTH: 19
<212> TYPE: DNA
<213> ORGANISM: Thlaspi arvense

<400> SEQUENCE: 43
agacaattcc ccaatatca 19

<210> SEQ ID NO 44
<211> LENGTH: 22
<212> TYPE: DNA
<213> ORGANISM: Thlaspi arvense

<400> SEQUENCE: 44
gtgataattt gatattgggg aa 22

<210> SEQ ID NO 45
<211> LENGTH: 19

<212> TYPE: DNA
<213> ORGANISM: Thlaspi arvense

<400> SEQUENCE: 45
agtgttcatt gctaacgag 19

<210> SEQ ID NO 46
<211> LENGTH: 22
<212> TYPE: DNA
<213> ORGANISM: Thlaspi arvense

<400> SEQUENCE: 46
catgtttgtg tgtctgtgta ga 22

<210> SEQ ID NO 47
<211> LENGTH: 22
<212> TYPE: DNA
<213> ORGANISM: Thlaspi arvense

<400> SEQUENCE: 47
gtttctccgg gactccctta tg 22

<210> SEQ ID NO 48
<211> LENGTH: 22
<212> TYPE: DNA
<213> ORGANISM: Thlaspi arvense

<400> SEQUENCE: 48
ggggttcctc aagcagaggt tc 22

<210> SEQ ID NO 49
<211> LENGTH: 22
<212> TYPE: DNA
<213> ORGANISM: Thlaspi arvense

<400> SEQUENCE: 49
gtgcaagcgc tctacaagga aa 22

<210> SEQ ID NO 50
<211> LENGTH: 22
<212> TYPE: DNA
<213> ORGANISM: Thlaspi arvense

<400> SEQUENCE: 50
gagtccggat gcgcgcccgg ag 22

<210> SEQ ID NO 51
<211> LENGTH: 22
<212> TYPE: DNA
<213> ORGANISM: Thlaspi arvense

<400> SEQUENCE: 51
gaagttagag aagatgaaac tt 22

<210> SEQ ID NO 52
<211> LENGTH: 22
<212> TYPE: DNA
<213> ORGANISM: Thlaspi arvense

<400> SEQUENCE: 52
ttatgccaaa taaatatata tt 22

<210> SEQ ID NO 53

```
<211> LENGTH: 22
<212> TYPE: DNA
<213> ORGANISM: Thlaspi arvense

<400> SEQUENCE: 53

aaacgtgctt ttcgagaaaa aa                                            22


<210> SEQ ID NO 54
<211> LENGTH: 22
<212> TYPE: DNA
<213> ORGANISM: Thlaspi arvense

<400> SEQUENCE: 54

atattaacaa tggaaattta ca                                            22


<210> SEQ ID NO 55
<211> LENGTH: 22
<212> TYPE: DNA
<213> ORGANISM: Thlaspi arvense

<400> SEQUENCE: 55

tttgcttctt attccctttt tc                                            22


<210> SEQ ID NO 56
<211> LENGTH: 22
<212> TYPE: DNA
<213> ORGANISM: Thlaspi arvense

<400> SEQUENCE: 56

aaaaattata taaattacta ga                                            22


<210> SEQ ID NO 57
<211> LENGTH: 22
<212> TYPE: DNA
<213> ORGANISM: Thlaspi arvense

<400> SEQUENCE: 57

aatgaagatg gatatatata ta                                            22


<210> SEQ ID NO 58
<211> LENGTH: 19
<212> TYPE: DNA
<213> ORGANISM: Thlaspi arvense

<400> SEQUENCE: 58

accgattggt gcaagcaga                                                19


<210> SEQ ID NO 59
<211> LENGTH: 19
<212> TYPE: DNA
<213> ORGANISM: Thlaspi arvense

<400> SEQUENCE: 59

tcaactaact tagatggcc                                                19


<210> SEQ ID NO 60
<211> LENGTH: 22
<212> TYPE: DNA
<213> ORGANISM: Thlaspi arvense

<400> SEQUENCE: 60

aataagctgc acacctacag tt                                            22
```

<210> SEQ ID NO 61
<211> LENGTH: 22
<212> TYPE: DNA
<213> ORGANISM: Thlaspi arvense

<400> SEQUENCE: 61
attttaattg aagagtgggg aa 22

<210> SEQ ID NO 62
<211> LENGTH: 22
<212> TYPE: DNA
<213> ORGANISM: Thlaspi arvense

<400> SEQUENCE: 62
tgaaaagaaa tctcaaacca cc 22

<210> SEQ ID NO 63
<211> LENGTH: 22
<212> TYPE: DNA
<213> ORGANISM: Thlaspi arvense

<400> SEQUENCE: 63
ctactcgtta actagcacaa ac 22

<210> SEQ ID NO 64
<211> LENGTH: 19
<212> TYPE: DNA
<213> ORGANISM: Thlaspi arvense

<400> SEQUENCE: 64
agtttcttta ttttaaaaa 19

<210> SEQ ID NO 65
<211> LENGTH: 22
<212> TYPE: DNA
<213> ORGANISM: Thlaspi arvense

<400> SEQUENCE: 65
atacttttaa aagcctacgt aa 22

<210> SEQ ID NO 66
<211> LENGTH: 19
<212> TYPE: DNA
<213> ORGANISM: Thlaspi arvense

<400> SEQUENCE: 66
agccttatag tgcgcactc 19

<210> SEQ ID NO 67
<211> LENGTH: 22
<212> TYPE: DNA
<213> ORGANISM: Thlaspi arvense

<400> SEQUENCE: 67
aaatagatgc tcatatacat ac 22

<210> SEQ ID NO 68
<211> LENGTH: 19
<212> TYPE: DNA
<213> ORGANISM: Thlaspi arvense

<400> SEQUENCE: 68
aagacgaatt ttcaatgac 19

<210> SEQ ID NO 69
<211> LENGTH: 22
<212> TYPE: DNA
<213> ORGANISM: Thlaspi arvense

<400> SEQUENCE: 69
gaatgttgca agtcattgaa aa 22

<210> SEQ ID NO 70
<211> LENGTH: 19
<212> TYPE: DNA
<213> ORGANISM: Thlaspi arvense

<400> SEQUENCE: 70
cattccgtcc atttgtaac 19

<210> SEQ ID NO 71
<211> LENGTH: 22
<212> TYPE: DNA
<213> ORGANISM: Thlaspi arvense

<400> SEQUENCE: 71
acaaaaatga ttcgtcggtt ac 22

<210> SEQ ID NO 72
<211> LENGTH: 19
<212> TYPE: DNA
<213> ORGANISM: Thlaspi arvense

<400> SEQUENCE: 72
aaactatgaa acatgattg 19

<210> SEQ ID NO 73
<211> LENGTH: 22
<212> TYPE: DNA
<213> ORGANISM: Thlaspi arvense

<400> SEQUENCE: 73
tcatgaagat taacaaaagc ta 22

<210> SEQ ID NO 74
<211> LENGTH: 19
<212> TYPE: DNA
<213> ORGANISM: Thlaspi arvense

<400> SEQUENCE: 74
gccacagtca tgaagatta 19

<210> SEQ ID NO 75
<211> LENGTH: 22
<212> TYPE: DNA
<213> ORGANISM: Thlaspi arvense

<400> SEQUENCE: 75
tggagatacc ttgacacgca ga 22

<210> SEQ ID NO 76
<211> LENGTH: 20
<212> TYPE: DNA
<213> ORGANISM: Thlaspi arvense

<400> SEQUENCE: 76
ttgcagctgt aactttctta 20

<210> SEQ ID NO 77
<211> LENGTH: 20
<212> TYPE: DNA
<213> ORGANISM: Thlaspi arvense

<400> SEQUENCE: 77
gaagttgatt gtgccactaa 20

<210> SEQ ID NO 78
<211> LENGTH: 20
<212> TYPE: DNA
<213> ORGANISM: Thlaspi arvense

<400> SEQUENCE: 78
gatcggtcta accataccgg 20

<210> SEQ ID NO 79
<211> LENGTH: 20
<212> TYPE: DNA
<213> ORGANISM: Thlaspi arvense

<400> SEQUENCE: 79
attgttgcaa tcaagaaacg 20

<210> SEQ ID NO 80
<211> LENGTH: 1109
<212> TYPE: DNA
<213> ORGANISM: Thlaspi arvense

<400> SEQUENCE: 80
atgtcaagaa agccgtgttt gtcggagaag ggctgaagaa aggggcatgg accaccgaag 60
aagacaagaa actcatctct tacatccacg agcacggtga aggaggctgg cgcgacattc 120
cccaaaaagc tgggttgaaa cggtgtggaa agagttgtag gctgcgatgg actaactacc 180
taaaacctga gatcaaaaga ggcgagttta gttcagagga ggaacagatt atcattatgc 240
ttcatgcttc tcgtggcaac aagtggtcgg tcatagcgag acatttacct agaagaacag 300
acaacgagat caagaactac tggaacacgc atctcaaaaa acgtttgatc gaacagggtg 360
ttgatcccgt gactcacaag cctctagctt ccaactccgg ccctactgcc accacgccgc 420
ctgagaattt gcatttccta gatgaatcta gctcagacaa gcaatactct cggtcgagct 480
caatgccttc cctgtctcgt cttccttcct ccggattcaa cacggtttcc gagatagcca 540
gcaatgttgg gacaccagtt caggtcggtt ccttgagttg caagaaacgt tttaagaaat 600
cgagttcgac atcaaggctt ctgaacaaat ttgcggctaa ggccacttcc atcaaagata 660
tattgtcggc ttccatggaa ggtagctcga gtgctgctac tacaatatca catgcaagct 720
ttttaaatgg cttttctgag cagagtcgca atgaagagga tagttctaac gcatccctga 780
caaatactct agccgaattt gatcccttct ctcagtcatc gttgtacccg gagcatgaga 840
tcaatgttac ttctgatatc ggcatggacc aggtttacga tttctcacaa tttctcgaaa 900
agctcgggag tgaaggccac aacgaactga atgtcgagta tggtcatgat cttcttatgt 960
ccgatgtttc gcaagaagtc tcatcaccta gcgttgatga tcaagacaat atgattggaa 1020
gcttcgaagg ttggtcaaat tatcttcttg accatgctga ttttatatat gacaccgact 1080
cagattccct cgaaaagcat ttcatgtga 1109

<210> SEQ ID NO 81

<211> LENGTH: 11
<212> TYPE: PRT
<213> ORGANISM: Thlaspi arvense

<400> SEQUENCE: 81

Met Ser Arg Lys Pro Cys Leu Ser Glu Lys Gly
1 5 10

<210> SEQ ID NO 82
<211> LENGTH: 1111
<212> TYPE: DNA
<213> ORGANISM: Thlaspi arvense

<400> SEQUENCE: 82
atgtcaagaa agccgtgttg atgtcggaga agggctgaag aaaggggcat ggaccaccga 60
agaagacaag aaactcatct cttacatcca cgagcacggt gaaggaggct ggcgcgacat 120
tccccaaaaa gctgggttga aacggtgtgg aaagagttgt aggctgcgat ggactaacta 180
cctaaaacct gagatcaaaa gaggcgagtt tagttcagag gaggaacaga ttatcattat 240
gcttcatgct tctcgtggca acaagtggtc ggtcatagcg agacatttac ctagaagaac 300
agacaacgag atcaagaact actggaacac gcatctcaaa aaacgtttga tcgaacaggg 360
tgttgatccc gtgactcaca agcctctagc ttccaactcc ggccctactg ccaccacgcc 420
gcctgagaat ttgcatttcc tagatgaatc tagctcagac aagcaatact ctcggtcgag 480
ctcaatgcct tccctgtctc gtcttccttc ctccggattc aacacggttt ccgagatagc 540
cagcaatgtt gggacaccag ttcaggtcgg ttccttgagt tgcaagaaac gttttaagaa 600
atcgagttcg acatcaaggc ttctgaacaa atttgcggct aaggccactt ccatcaaaga 660
tatattgtcg gcttccatgg aaggtagctc gagtgctgct actacaatat cacatgcaag 720
ctttttaaat ggcttttctg agcagagtcg caatgaagag gatagttcta acgcatccct 780
gacaaatact ctagccgaat ttgatccctt ctctcagtca tcgttgtacc cggagcatga 840
gatcaatgtt acttctgata tcggcatgga ccaggtttac gatttctcac aatttctcga 900
aaagctcggg agtgaaggcc acaacgaact gaatgtcgag tatggtcatg atcttcttat 960
gtccgatgtt tcgcaagaag tctcatcacc tagcgttgat gatcaagaca atatgattgg 1020
aagcttcgaa ggttggtcaa attatcttct tgaccatgct gattttatat atgacaccga 1080
ctcagattcc ctcgaaaagc atttcatgtg a 1111

<210> SEQ ID NO 83
<211> LENGTH: 6
<212> TYPE: PRT
<213> ORGANISM: Thlaspi arvense

<400> SEQUENCE: 83

Met Ser Arg Lys Pro Cys
1 5

<210> SEQ ID NO 84
<211> LENGTH: 1111
<212> TYPE: DNA
<213> ORGANISM: Thlaspi arvense

<400> SEQUENCE: 84
atgtcaagaa agccgtgttg tgtcggagaa gggctgaaga aaggggcatg gaccaccgaa 60
gaagacaaga aactcatctc ttacatccac gaggcacggt gaaggaggct ggcgcgacat 120
tccccaaaaa gctgggttga aacggtgtgg aaagagttgt aggctgcgat ggactaacta 180

```
cctaaaacct gagatcaaaa gaggcgagtt tagttcagag gaggaacaga ttatcattat    240

gcttcatgct tctcgtggca acaagtggtc ggtcatagcg agacatttac ctagaagaac    300

agacaacgag atcaagaact actggaacac gcatctcaaa aaacgtttga tcgaacaggg    360

tgttgatccc gtgactcaca agcctctagc ttccaactcc ggccctactg ccaccacgcc    420

gcctgagaat ttgcatttcc tagatgaatc tagctcagac aagcaatact ctcggtcgag    480

ctcaatgcct tccctgtctc gtcttccttc ctccggattc aacacggttt ccgagatagc    540

cagcaatgtt gggacaccag ttcaggtcgg ttccttgagt tgcaagaaac gttttaagaa    600

atcgagttcg acatcaaggc ttctgaacaa atttgcggct aaggccactt ccatcaaaga    660

tatattgtcg gcttccatgg aaggtagctc gagtgctgct actacaatat cacatgcaag    720

ctttttaaat ggcttttctg agcagagtcg caatgaagag gatagttcta acgcatccct    780

gacaaatact ctagccgaat ttgatccctt ctctcagtca tcgttgtacc cggagcatga    840

gatcaatgtt acttctgata tcggcatgga ccaggtttac gatttctcac aatttctcga    900

aaagctcggg agtgaaggcc acaacgaact gaatgtcgag tatggtcatg atcttcttat    960

gtccgatgtt tcgcaagaag tctcatcacc tagcgttgat gatcaagaca atatgattgg   1020

aagcttcgaa ggttggtcaa attatcttct tgaccatgct gattttatat atgacaccga   1080

ctcagattcc ctcgaaaagc atttcatgtg a                                  1111
```

<210> SEQ ID NO 85
<211> LENGTH: 33
<212> TYPE: PRT
<213> ORGANISM: Thlaspi arvense

<400> SEQUENCE: 85

```
Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Glu Ala
            20                  25                  30

Arg
```

<210> SEQ ID NO 86
<211> LENGTH: 1110
<212> TYPE: DNA
<213> ORGANISM: Thlaspi arvense

<400> SEQUENCE: 86

```
atgtcaagaa agccgtgttg tgtcggagaa gggctgaaga aaggggcatg gaccaccgaa     60

gaagacaaga aactcatctc ttacatccac gggcacggtg aaggaggctg gcgcgacatt    120

ccccaaaaag ctgggttgaa acggtgtgga aagagttgta ggctgcgatg gactaactac    180

ctaaaacctg agatcaaaag aggcgagttt agttcagagg aggaacagat tatcattatg    240

cttcatgctt ctcgtggcaa caagtggtcg gtcatagcga gacatttacc tagaagaaca    300

gacaacgaga tcaagaacta ctggaacacg catctcaaaa aacgtttgat cgaacagggt    360

gttgatcccg tgactcacaa gcctctagct tccaactccg gccctactgc caccacgccg    420

cctgagaatt tgcatttcct agatgaatct agctcagaca agcaatactc tcggtcgagc    480

tcaatgcctt ccctgtctcg tcttccttcc tccggattca acacggtttc cgagatagcc    540

agcaatgttg ggacaccagt tcaggtcggt tccttgagtt gcaagaaacg ttttaagaaa    600

tcgagttcga catcaaggct tctgaacaaa tttgcggcta aggccacttc catcaaagat    660
```

```
atattgtcgg cttccatgga aggtagctcg agtgctgcta ctacaatatc acatgcaagc    720

tttttaaatg gcttttctga gcagagtcgc aatgaagagg atagttctaa cgcatccctg    780

acaaatactc tagccgaatt tgatcccttc tctcagtcat cgttgtaccc ggagcatgag    840

atcaatgtta cttctgatat cggcatggac caggtttacg atttctcaca atttctcgaa    900

aagctcggga gtgaaggcca caacgaactg aatgtcgagt atggtcatga tcttcttatg    960

tccgatgttt cgcaagaagt ctcatcacct agcgttgatg atcaagacaa tatgattgga   1020

agcttcgaag gttggtcaaa ttatcttctt gaccatgctg attttatata tgacaccgac   1080

tcagattccc tcgaaaagca tttcatgtga                                    1110


<210> SEQ ID NO 87
<211> LENGTH: 369
<212> TYPE: PRT
<213> ORGANISM: Thlaspi arvense

<400> SEQUENCE: 87

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Gly His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Thr Asn Tyr Leu Lys Pro Glu
    50                  55                  60

Ile Lys Arg Gly Glu Phe Ser Ser Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Arg Arg Thr Asp Asn Glu Ile Lys Asn Tyr Trp Asn Thr His Leu
            100                 105                 110

Lys Lys Arg Leu Ile Glu Gln Gly Val Asp Pro Val Thr His Lys Pro
        115                 120                 125

Leu Ala Ser Asn Ser Gly Pro Thr Ala Thr Thr Pro Pro Glu Asn Leu
    130                 135                 140

His Phe Leu Asp Glu Ser Ser Ser Asp Lys Gln Tyr Ser Arg Ser Ser
145                 150                 155                 160

Ser Met Pro Ser Leu Ser Arg Leu Pro Ser Ser Gly Phe Asn Thr Val
                165                 170                 175

Ser Glu Ile Ala Ser Asn Val Gly Thr Pro Val Gln Val Gly Ser Leu
            180                 185                 190

Ser Cys Lys Lys Arg Phe Lys Lys Ser Ser Ser Thr Ser Arg Leu Leu
        195                 200                 205

Asn Lys Phe Ala Ala Lys Ala Thr Ser Ile Lys Asp Ile Leu Ser Ala
    210                 215                 220

Ser Met Glu Gly Ser Ser Ser Ala Ala Thr Thr Ile Ser His Ala Ser
225                 230                 235                 240

Phe Leu Asn Gly Phe Ser Glu Gln Ser Arg Asn Glu Glu Asp Ser Ser
                245                 250                 255

Asn Ala Ser Leu Thr Asn Thr Leu Ala Glu Phe Asp Pro Phe Ser Gln
            260                 265                 270

Ser Ser Leu Tyr Pro Glu His Glu Ile Asn Val Thr Ser Asp Ile Gly
        275                 280                 285

Met Asp Gln Val Tyr Asp Phe Ser Gln Phe Leu Glu Lys Leu Gly Ser
```

290 295 300

Glu Gly His Asn Glu Leu Asn Val Glu Tyr Gly His Asp Leu Leu Met
305 310 315 320

Ser Asp Val Ser Gln Glu Val Ser Ser Pro Ser Val Asp Asp Gln Asp
325 330 335

Asn Met Ile Gly Ser Phe Glu Gly Trp Ser Asn Tyr Leu Leu Asp His
340 345 350

Ala Asp Phe Ile Tyr Asp Thr Asp Ser Asp Ser Leu Glu Lys His Phe
355 360 365

Met

<210> SEQ ID NO 88
<211> LENGTH: 1111
<212> TYPE: DNA
<213> ORGANISM: Thlaspi arvense

<400> SEQUENCE: 88
atgtcaagaa agccgtgttg tgtcggagaa gggctgaaga aaggggcatg gaccaccgaa 60
gaagacaaga aactcatctc ttacatccac gaagcacggt gaaggaggct ggcgcgacat 120
tccccaaaaa gctgggttga aacggtgtgg aaagagttgt aggctgcgat ggactaacta 180
cctaaaacct gagatcaaaa gaggcgagtt tagttcagag gaggaacaga ttatcattat 240
gcttcatgct tctcgtggca acaagtggtc ggtcatagcg agacatttac ctagaagaac 300
agacaacgag atcaagaact actggaacac gcatctcaaa aaacgtttga tcgaacaggg 360
tgttgatccc gtgactcaca agcctctagc ttccaactcc ggccctactg ccaccacgcc 420
gcctgagaat ttgcatttcc tagatgaatc tagctcagac aagcaatact ctcggtcgag 480
ctcaatgcct tccctgtctc gtcttccttc ctccggattc aacacggttt ccgagatagc 540
cagcaatgtt gggacaccag ttcaggtcgg ttccttgagt tgcaagaaac gttttaagaa 600
atcgagttcg acatcaaggc ttctgaacaa atttgcggct aaggccactt ccatcaaaga 660
tatattgtcg gcttccatgg aaggtagctc gagtgctgct actacaatat cacatgcaag 720
ctttttaaat ggcttttctg agcagagtcg caatgaagag gatagttcta acgcatccct 780
gacaaatact ctagccgaat ttgatccctt ctctcagtca tcgttgtacc cggagcatga 840
gatcaatgtt acttctgata tcggcatgga ccaggtttac gatttctcac aatttctcga 900
aaagctcggg agtgaaggcc acaacgaact gaatgtcgag tatggtcatg atcttcttat 960
gtccgatgtt tcgcaagaag tctcatcacc tagcgttgat gatcaagaca atatgattgg 1020
aagcttcgaa ggttggtcaa attatcttct tgaccatgct gattttatat atgacaccga 1080
ctcagattcc ctcgaaaagc atttcatgtg a 1111

<210> SEQ ID NO 89
<211> LENGTH: 33
<212> TYPE: PRT
<213> ORGANISM: Thlaspi arvense

<400> SEQUENCE: 89

Met Ser Arg Lys Pro Cys Cys Val Gly Glu Gly Leu Lys Lys Gly Ala
1 5 10 15

Trp Thr Thr Glu Glu Asp Lys Lys Leu Ile Ser Tyr Ile His Glu Ala
20 25 30

Arg

<210> SEQ ID NO 90
<211> LENGTH: 1108
<212> TYPE: DNA
<213> ORGANISM: Thlaspi arvense

<400> SEQUENCE: 90
atgtcaagaa agccgtgttg tgtcggagaa gggctgaaga aaggggcatg gaccaccgaa 60
gaagacaaga aactcatctc ttacatccac gcacggtgaa ggaggctggc gcgacattcc 120
ccaaaaagct gggttgaaac ggtgtggaaa gagttgtagg ctgcgatgga ctaactacct 180
aaaacctgag atcaaaagag gcgagtttag ttcagaggag gaacagatta tcattatgct 240
tcatgcttct cgtggcaaca agtggtcggt catagcgaga catttaccta gaagaacaga 300
caacgagatc aagaactact ggaacacgca tctcaaaaaa cgtttgatcg aacagggtgt 360
tgatcccgtg actcacaagc ctctagcttc caactccggc cctactgcca ccacgccgcc 420
tgagaatttg catttcctag atgaatctag ctcagacaag caatactctc ggtcgagctc 480
aatgccttcc ctgtctcgtc ttccttcctc cggattcaac acggtttccg agatagccag 540
caatgttggg acaccagttc aggtcggttc cttgagttgc aagaaacgtt ttaagaaatc 600
gagttcgaca tcaaggcttc tgaacaaatt tgcggctaag gccacttcca tcaaagatat 660
attgtcggct tccatggaag gtagctcgag tgctgctact acaatatcac atgcaagctt 720
tttaaatggc ttttctgagc agagtcgcaa tgaagaggat agttctaacg catccctgac 780
aaatactcta gccgaatttg atcccttctc tcagtcatcg ttgtacccgg agcatgagat 840
caatgttact tctgatatcg gcatggacca ggtttacgat ttctcacaat ttctcgaaaa 900
gctcgggagt gaaggccaca acgaactgaa tgtcgagtat ggtcatgatc ttcttatgtc 960
cgatgtttcg caagaagtct catcacctag cgttgatgat caagacaata tgattggaag 1020
cttcgaaggt tggtcaaatt atcttcttga ccatgctgat tttatatatg acaccgactc 1080
agattccctc gaaaagcatt tcatgtga 1108

<210> SEQ ID NO 91
<211> LENGTH: 32
<212> TYPE: PRT
<213> ORGANISM: Thlaspi arvense

<400> SEQUENCE: 91

Met Ser Arg Lys Pro Cys Cys Val Gly Glu Gly Leu Lys Lys Gly Ala
1 5 10 15

Trp Thr Thr Glu Glu Asp Lys Lys Leu Ile Ser Tyr Ile His Ala Arg
20 25 30

<210> SEQ ID NO 92
<211> LENGTH: 1509
<212> TYPE: DNA
<213> ORGANISM: Thlaspi arvense

<400> SEQUENCE: 92
atggaagata tcatcatcgg cgttgtggct ctcgccgccg ttctcctctt cttcctctac 60
caaagcccaa aaaccaaacg gtataagctg cctcccggcc cacggccgct tccggtgatc 120
ggaaacctcc accagcttag ccaggttaac ccacaacggt tcttctatgg atgggccaaa 180
aaatatggac caatcttatc atacaagata ggaaacaaaa caatgatggt aatttcttcg 240
gctgagctaa ccaaagagct tctcaagacg caagatgtca acttcgccaa ccggcctcct 300
caccgtggtc acgagctcat gacctacggc cgaagtgaca tggcgatgaa ccactacaca 360

```
ccgttgtacc gggagatgag gaagatgggc atgaaccact tgttctcccc cactcgtgta    420
gccaccttta agcacgtacg ggaggaggag gctaggagga tgatgtttaa gatcgagaag    480
gctgcggaga gatctgaacc ggtcgatata agcgagctta tgttgacctt cacgaactcg    540
gttgtgtgta ggcaagcttt cgggaagaag tacaatgaag atggggaaga gatgaagaga    600
ttcatcagga ttctttatgg gactcagagc gtattgggga agattttttt ctctgatttt    660
ttcccgttta ctcgctacgt tcttgataat tggaccggcc tcacgaaata tatgatggac    720
tgttttgaaa gacaagacac ttacatacaa gagattatcg atgagacact tgatcccaac    780
aaggtaaagc cagaaacgga gagcatgatc gatctcttga tggaggtcta caaagaacaa    840
ccattcgcct ccaagttcac aattgggaat gtcaaaggcg ttatcttgaa tatagtggtt    900
gcgggaaccg acacggcggc tgcggcggtt gtgtggggga tgacgtatct aatgaagtac    960
cctcaagtta tgaagaaagc tcaagcagaa gtgagagagt atgcaaaaga gaaagatcta   1020
acgtttatta ctgaagacga cgtcaagaac cttccttact tcagagcttt agttaaagaa   1080
accttaagga tcgaaccagt gattcctctc cttatccctc gttgttgcat tcaagacacc   1140
aagatcgccg gttacgatgt ccccgcgggg accacggtca acgtaaacgc gtgggcggtg   1200
tcacgcgacg agaaggagtg ggcccaaac cctgatgaat tcaggcccga gaggtttctt   1260
gagaaggacg tggacttcaa aggcacggac tatgagttta taccgtttgg gtcaggccgg   1320
agaatgtgcc ctggaatgcg tcttggcgcg gcgatgatcg aggttccgta tgcgaacctt   1380
ttgctcaact ttgacttcaa acttgctgat ggactgaaac cagaagagat caacatggat   1440
gttatgacag gtcttgctat gcacaaggcg gttcatctca ggcttgttcc cgagaaagtg   1500
aggaagtga                                                           1509
```

<210> SEQ ID NO 93
<211> LENGTH: 4468
<212> TYPE: DNA
<213> ORGANISM: Thlaspi arvense

<400> SEQUENCE: 93

```
atggcaagac ttgatattcg agtcggtaaa atcgtcaagg ctcggaaaca tcctaacgca     60
gattcattgt atttggaaga gatcgatgtt ggaggaggtg aagttcgcac cgttgtgagt    120
ggactggtca aatacatacc tcttgaggag atgcaggttt gttaaatctc cacgaatcaa    180
acctaaccta gtcatctgct ttcatcccaa tatatctgac tgttcttttt ggacagaacc    240
gtatggtttg tgttctttgc aacttgaagc cggcgaaaat gagggatgtt atgtcacaag    300
cgatggttct tgccgcttct agtagtgatg gcagcaaggt aaaagtccac aagaatgagt    360
ctctgacctg ttcatcgtta cgctatatcc atttcgttta tagataattt gtttttgggg    420
aactttcagg ttgagttagt cgagcctcct gaatctgcta agatcggaga gagggttagg    480
tttgccgggt ttgaaggcga gccagacgat gttttaaacc ctaagaagaa aatatgggag    540
acacttgtgg tggatctgca cacaaatgag aatctagttg cttgctacaa agatttgcct    600
ttcactacag attcaggtgt atgcaaggtt tcatccatca gcaatggtac aatccggtaa    660
aaaagcttta agttggtctt tatctttctt catttctctc tctctctttt gaggggaaac    720
acatttttct gagatttcat ttgaagaatt gattctatta acaaaccttg tcttgtaaac    780
tcaaactcgt cactttttttg gttcttaatt tggttttgag aaacaatatg ttaatttttt    840
ctttagacaa acttggtagg ccttttggta tatcaatatc agctttttat actggacccg    900
gacggaaagc aaccacacaa gttgttgagg tttcgatgat agtgtataaa taattatcgt    960
```

```
atttatcaaa aggtcaatca catcatttat ttattttcag taacaacttt gtaataaagt   1020
cttccgcaag caaacttttg tgcaaatttc ttggaaactc agtttgcgac aaactacaaa   1080
gtaaatgttg gctatgtatg acatcgttat gattagttca aagtacctta ggtaaatttg   1140
gttttacttt tgtatttata aaattgagta tgttttagaa ttctagctat atatgtcagc   1200
gtatgttaca tttttctgta taagattgga ttgtactata gtgcataggc ccggggttgg   1260
tttagaccac tcagtgaagc aagttaaata aagatctgtg taaactacaa atagatatgg   1320
acaaatatga ctgcgactgc atgaaagtat ataaccatat atgttaatta aaagcatagg   1380
acattagagg gaccttgggt aggtgaaggt gtttctcaac tctaacacgt gaggttttca   1440
taagtaggta gtaaaaaagg agtaagcgtt ttgattataa aattagattt cggtttaatt   1500
cggttatggt atttggtttg gtaaagaaga aaaggaatgc aattaataat ttctctatat   1560
attaaggagc tgtgtgctgt ttatgtacca ctcaaaagta gtaagtaaac aactaagaat   1620
ggaagatatc atcatcggcg ttgtggctct cgccgccgtt ctcctcttct tcctctacca   1680
aagcccaaaa accaaacggt ataagctgcc tcccggccca cggccgcttc cggtgatcgg   1740
aaacctccac cagcttagcc aggttaaccc acaacggttc ttctatggat gggccaaaaa   1800
atatggacca atcttatcat acaagatagg aaacaaaaca atgatggtaa tttcttcggc   1860
tgagctaacc aaagagcttc tcaagacgca agatgtcaac ttcgccaacc ggcctcctca   1920
ccgtggtcac gagctcatga cctacggccg aagtgacatg gcgatgaacc actacacacc   1980
gttgtaccgg gagatgagga agatgggcat gaaccacttg ttctccccca ctcgtgtagc   2040
cacctttaag cacgtacggg aggaggaggc taggaggatg atgtttaaga tcgagaaggc   2100
tgcggagaga tctgaaccgg tcgatataag cgagcttatg ttgaccttca cgaactcggt   2160
tgtgtgtagg caagctttcg ggaagaagta caatgaagat ggggaagaga tgaagagatt   2220
catcaggatt ctttatggga ctcagagcgt attggggaag attttttttct ctgatttttt   2280
cccgtttact cgctacgttc ttgataattg gaccggcctc acgaaatata tgatggactg   2340
ttttgaaaga caagacactt acatacaaga gattatcgat gagacacttg atcccaacaa   2400
ggtaaagcca gaaacggaga gcatgatcga tctcttgatg gaggtctaca aagaacaacc   2460
attcgcctcc aagttcacaa ttgggaatgt caaaggcgtt atcttggtac gtataaaacc   2520
acttctcaat ttctttttgt tttgaatcgt tgcttgtgct acaagcaccc actcgcttgc   2580
gtttcactct tcttttcgtt gttgtgtttc aaaagaatat agtggttgcg ggaaccgaca   2640
cggcggctgc ggcggttgtg tgggggatga cgtatctaat gaagtaccct caagttatga   2700
agaaagctca agcagaagtg agagagtatg caaaagagaa agatctaacg tttattactg   2760
aagacgacgt caagaacctt ccttacttca gagctttagt taaagaaacc ttaaggatcg   2820
aaccagtgat tcctctcctt atccctcgtt gttgcattca agacaccaag atcgccggtt   2880
acgatgtccc cgcggggacc acggtcaacg taaacgcgtg ggcggtgtca cgcgacgaga   2940
aggagtgggg cccaaaccct gatgaattca ggcccgagag gtttcttgag aaggacgtgg   3000
acttcaaagg cacggactat gagtttatac cgtttgggtc aggccggaga atgtgccctg   3060
gaatgcgtct tggcgcggcg atgatcgagg ttccgtatgc gaaccttttg ctcaactttg   3120
acttcaaact tgctgatgga ctgaaaccag aagagatcaa catggatgtt atgacaggtc   3180
ttgctatgca caaggcggtt catctcaggc ttgttcccga gaaagtgagg aagtgacagt   3240
ttctagtagt aaaataaatc tctcactctt gttatataat atattgttcc ctaaagcgta   3300
```

```
ctatgcttta aggtttggtt tctgtattaa gtggcaatcg tctctcttat aatttttcct   3360

tttacatcaa acgacttacg caaaaaagct agatagccga gccaaaaggt cgtcttggta   3420

cataagaaaa aaaaaccaaa gcaaaagaga acataaatga ttaaattagg cttttttttt   3480

ttcttgtgat tcatttaagt tgattcctcg aaacatgttg accactcatg ggttcatta   3540

ataatttcca aaacaaagct tctaagtcat agtgaagtga caagagccta tcctaagcca   3600

ctaaacgcgg ctcaagtctt ctatgagcca tcacactagt gactggacaa atgttagctg   3660

ttttgatatc cagtggactc gcgggtcttt ggtcctgatg aaccacgtaa tctattagaa   3720

tatatactag ctcaaagggt acttgtgttc aatcaataga tttcctcttt agatagtctt   3780

ttataggtaa tattagatca acgtaatatt agtttaaggg aaattcttat cgaagttcat   3840

tataaaatga aaaaaatatt attagttttt ttttgtaata caaacaaata ttaatttttt   3900

tttctccaaa atatcacttt cagaatatca attttcaaaa tactaatatt tattttaaaa   3960

atatttataa aacttaacaa aggtctctta acaatataat aataataatt ttaatatagt   4020

ataattgtat ggtttaattt taaggtttct taaaaaagtt aaattaaatt atctcaaagt   4080

ttgatttgag agaccctttt cattcttttc ttcccaactt ttattatttt taatattaga   4140

aacttttta aatacttcta atgaagatgt tctaataatt tatacaaaat aataaactat   4200

gcaaacctta taaaatcctt ttgcaagaaa tataatatac atatctacaa aagaattggt   4260

tctgcatctg tattttcctt ctccatgtag acattctttc tagtttttct acccacatga   4320

cttgtatttt cttattctta gcattttgta attatgtata acaatgcctt ctcatatttt   4380

tatgtgtttt ctcatcttgt tatatggacg tcgaattatc attgcccata ttattttatc   4440

catgatttt tgttttatgt tttcagaa                                        4468
```

```
<210> SEQ ID NO 94
<211> LENGTH: 502
<212> TYPE: PRT
<213> ORGANISM: Thlaspi arvense

<400> SEQUENCE: 94

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser
            100                 105                 110

Asp Met Ala Met Asn His Tyr Thr Pro Leu Tyr Arg Glu Met Arg Lys
        115                 120                 125

Met Gly Met Asn His Leu Phe Ser Pro Thr Arg Val Ala Thr Phe Lys
    130                 135                 140

His Val Arg Glu Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr
```

-continued

```
                165                 170                 175

Phe Thr Asn Ser Val Val Cys Arg Gln Ala Phe Gly Lys Lys Tyr Asn
            180                 185                 190

Glu Asp Gly Glu Glu Met Lys Arg Phe Ile Arg Ile Leu Tyr Gly Thr
        195                 200                 205

Gln Ser Val Leu Gly Lys Ile Phe Phe Ser Asp Phe Phe Pro Phe Thr
    210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
            260                 265                 270

Leu Met Glu Val Tyr Lys Glu Gln Pro Phe Ala Ser Lys Phe Thr Ile
        275                 280                 285

Gly Asn Val Lys Gly Val Ile Leu Asn Ile Val Val Ala Gly Thr Asp
    290                 295                 300

Thr Ala Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Asp Val Lys Asn Leu Pro
            340                 345                 350

Tyr Phe Arg Ala Leu Val Lys Glu Thr Leu Arg Ile Glu Pro Val Ile
        355                 360                 365

Pro Leu Leu Ile Pro Arg Cys Cys Ile Gln Asp Thr Lys Ile Ala Gly
    370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Glu Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
        435                 440                 445

Gly Ala Ala Met Ile Glu Val Pro Tyr Ala Asn Leu Leu Leu Asn Phe
    450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500
```

<210> SEQ ID NO 95
<211> LENGTH: 1510
<212> TYPE: DNA
<213> ORGANISM: Thlaspi arvense

<400> SEQUENCE: 95

```
atggaagata tcatcatcgg cgttgtggct ctcgccgccg ttctcctctt cttcctctac      60

caaagcccaa aaaccaaacg gtataagctg cctcccggcc cacggccgct tccggtgatc     120

ggaaacctcc accagcttag ccaggttaac ccacaacggt tcttctatgg atgggccaaa     180
```

-continued

```
aaatatggac caatcttatc ataccaagat aggaaacaaa acaatgatgg taatttcttc    240

ggctgagcta accaaagagc ttctcaagac gcaagatgtc aacttcgcca accggcctcc    300

tcaccgtggt cacgagctca tgacctacgg ccgaagtgac atggcgatga accactacac    360

accgttgtac cgggagatga ggaagatggg catgaaccac ttgttctccc ccactcgtgt    420

agccaccttt aagcacgtac gggaggagga ggctaggagg atgatgttta agatcgagaa    480

ggctgcggag agatctgaac cggtcgatat aagcgagctt atgttgacct tcacgaactc    540

ggttgtgtgt aggcaagctt tcgggaagaa gtacaatgaa gatggggaag agatgaagag    600

attcatcagg attctttatg ggactcagag cgtattgggg aagatttttt tctctgattt    660

tttcccgttt actcgctacg ttcttgataa ttggaccggc ctcacgaaat atatgatgga    720

ctgttttgaa agacaagaca cttacataca agagattatc gatgagacac ttgatcccaa    780

caaggtaaag ccagaaacgg agagcatgat cgatctcttg atggaggtct acaaagaaca    840

accattcgcc tccaagttca caattgggaa tgtcaaaggc gttatcttga atatagtggt    900

tgcgggaacc gacacggcgg ctgcggcggt tgtgtggggg atgacgtatc taatgaagta    960

ccctcaagtt atgaagaaag ctcaagcaga agtgagagag tatgcaaaag agaaagatct   1020

aacgtttatt actgaagacg acgtcaagaa ccttccttac ttcagagctt tagttaaaga   1080

aaccttaagg atcgaaccag tgattcctct ccttatccct cgttgttgca ttcaagacac   1140

caagatcgcc ggttacgatg tccccgcggg gaccacggtc aacgtaaacg cgtgggcggt   1200

gtcacgcgac gagaaggagt ggggcccaaa ccctgatgaa ttcaggcccg agaggtttct   1260

tgagaaggac gtggacttca aaggcacgga ctatgagttt ataccgtttg ggtcaggccg   1320

gagaatgtgc cctggaatgc gtcttggcgc ggcgatgatc gaggttccgt atgcgaacct   1380

tttgctcaac tttgacttca aacttgctga tggactgaaa ccagaagaga tcaacatgga   1440

tgttatgaca ggtcttgcta tgcacaaggc ggttcatctc aggcttgttc ccgagaaagt   1500

gaggaagtga                                                          1510
```

<210> SEQ ID NO 96
<211> LENGTH: 81
<212> TYPE: PRT
<213> ORGANISM: Thlaspi arvense

<400> SEQUENCE: 96

```
Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Gln Asp Arg Lys Gln Asn Asn Asp Gly Asn Phe Phe
65                  70                  75                  80

Gly
```

<210> SEQ ID NO 97
<211> LENGTH: 1509
<212> TYPE: DNA
<213> ORGANISM: Thlaspi arvense

<400> SEQUENCE: 97

-continued

```
atggaagata tcatcatcgg cgttgtggct ctcgccgccg ttctcctctt cttcctctac      60
caaagcccaa aaaccaaacg gtataagctg cctcccggcc cacggccgct tccggtgatc     120
ggaaacctcc accagcttag ccaggttaac ccacaacggt tcttctatgg atgggccaaa     180
aaatatggac caatcttatc atccaagata ggaaacaaaa caatgatggt aatttcttcg     240
gctgagctaa ccaaagagct tctcaagacg caagatgtca acttcgccaa ccggcctcct     300
caccgtggtc acgagctcat gacctacggc cgaagtgaca tggcgatgaa ccactacaca     360
ccgttgtacc gggagatgag gaagatgggc atgaaccact tgttctcccc cactcgtgta     420
gccacccttta agcacgtacg ggaggaggag gctaggagga tgatgtttaa gatcgagaag    480
gctgcggaga gatctgaacc ggtcgatata agcgagctta tgttgacctt cacgaactcg     540
gttgtgtgta ggcaagcttt cgggaagaag tacaatgaag atggggaaga gatgaagaga     600
ttcatcagga ttctttatgg gactcagagc gtattgggga agattttttt ctctgatttt     660
ttcccgttta ctcgctacgt tcttgataat tggaccggcc tcacgaaata tatgatggac     720
tgttttgaaa gacaagacac ttacatacaa gagattatcg atgagacact tgatcccaac     780
aaggtaaagc cagaaacgga gagcatgatc gatctcttga tggaggtcta caaagaacaa     840
ccattcgcct ccaagttcac aattgggaat gtcaaaggcg ttatcttgaa tatagtggtt     900
gcgggaaccg acacggcggc tgcggcggtt gtgtggggga tgacgtatct aatgaagtac     960
cctcaagtta tgaagaaagc tcaagcagaa gtgagagagt atgcaaaaga gaaagatcta    1020
acgtttatta ctgaagacga cgtcaagaac cttccttact tcagagcttt agttaaagaa    1080
accttaagga tcgaaccagt gattcctctc cttatccctc gttgttgcat tcaagacacc    1140
aagatcgccg gttacgatgt ccccgcgggg accacggtca acgtaaacgc gtgggcggtg    1200
tcacgcgacg agaaggagtg gggcccaaac cctgatgaat tcaggcccga gaggtttctt    1260
gagaaggacg tggacttcaa aggcacggac tatgagttta taccgtttgg gtcaggccgg    1320
agaatgtgcc ctggaatgcg tcttggcgcg gcgatgatcg aggttccgta tgcgaacctt    1380
ttgctcaact ttgacttcaa acttgctgat ggactgaaac cagaagagat caacatggat    1440
gttatgacag gtcttgctat gcacaaggcg gttcatctca ggcttgttcc cgagaaagtg    1500
aggaagtga                                                            1509
```

<210> SEQ ID NO 98
<211> LENGTH: 502
<212> TYPE: PRT
<213> ORGANISM: Thlaspi arvense

<400> SEQUENCE: 98

```
Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Ser Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser
```

```
            100                 105                 110

Asp Met Ala Met Asn His Tyr Thr Pro Leu Tyr Arg Glu Met Arg Lys
        115                 120                 125

Met Gly Met Asn His Leu Phe Ser Pro Thr Arg Val Ala Thr Phe Lys
    130                 135                 140

His Val Arg Glu Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr
                165                 170                 175

Phe Thr Asn Ser Val Val Cys Arg Gln Ala Phe Gly Lys Lys Tyr Asn
            180                 185                 190

Glu Asp Gly Glu Glu Met Lys Arg Phe Ile Arg Ile Leu Tyr Gly Thr
        195                 200                 205

Gln Ser Val Leu Gly Lys Ile Phe Phe Ser Asp Phe Phe Pro Phe Thr
    210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
            260                 265                 270

Leu Met Glu Val Tyr Lys Glu Gln Pro Phe Ala Ser Lys Phe Thr Ile
        275                 280                 285

Gly Asn Val Lys Gly Val Ile Leu Asn Ile Val Val Ala Gly Thr Asp
    290                 295                 300

Thr Ala Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Asp Val Lys Asn Leu Pro
            340                 345                 350

Tyr Phe Arg Ala Leu Val Lys Glu Thr Leu Arg Ile Glu Pro Val Ile
        355                 360                 365

Pro Leu Leu Ile Pro Arg Cys Cys Ile Gln Asp Thr Lys Ile Ala Gly
    370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Glu Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
        435                 440                 445

Gly Ala Ala Met Ile Glu Val Pro Tyr Ala Asn Leu Leu Leu Asn Phe
    450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500
```

<210> SEQ ID NO 99

<211> LENGTH: 20
<212> TYPE: DNA
<213> ORGANISM: Thlaspi arvense

<400> SEQUENCE: 99
ggtgtcgtac gatagagtgt 20

<210> SEQ ID NO 100
<211> LENGTH: 20
<212> TYPE: DNA
<213> ORGANISM: Thlaspi arvense

<400> SEQUENCE: 100
acggtctttc cgagagtatg 20

<210> SEQ ID NO 101
<211> LENGTH: 19
<212> TYPE: DNA
<213> ORGANISM: Thlaspi arvense

<400> SEQUENCE: 101
atccaggatc ctcatgttt 19

<210> SEQ ID NO 102
<211> LENGTH: 20
<212> TYPE: DNA
<213> ORGANISM: Thlaspi arvense

<400> SEQUENCE: 102
actcaacgaa ttaccgtctg 20

<210> SEQ ID NO 103
<211> LENGTH: 20
<212> TYPE: DNA
<213> ORGANISM: Thlaspi arvense

<400> SEQUENCE: 103
gttaagtcta atgccgaaga 20

<210> SEQ ID NO 104
<211> LENGTH: 20
<212> TYPE: DNA
<213> ORGANISM: Thlaspi arvense

<400> SEQUENCE: 104
ccactcataa cggtctttcc 20

<210> SEQ ID NO 105
<211> LENGTH: 20
<212> TYPE: DNA
<213> ORGANISM: Thlaspi arvense

<400> SEQUENCE: 105
ccactcataa cggtctttcc 20

<210> SEQ ID NO 106
<211> LENGTH: 20
<212> TYPE: DNA
<213> ORGANISM: Thlaspi arvense

<400> SEQUENCE: 106
agcctccttc accgtgctcg 20

<210> SEQ ID NO 107
<211> LENGTH: 20
<212> TYPE: DNA
<213> ORGANISM: Thlaspi arvense

<400> SEQUENCE: 107
tcaagaaagc cgtgttgtgt 20

<210> SEQ ID NO 108
<211> LENGTH: 20
<212> TYPE: DNA
<213> ORGANISM: Thlaspi arvense

<400> SEQUENCE: 108
aagaagacaa gaaactcatc 20

<210> SEQ ID NO 109
<211> LENGTH: 19
<212> TYPE: DNA
<213> ORGANISM: Thlaspi arvense

<400> SEQUENCE: 109
agggttgaaa cggtgtgga 19

<210> SEQ ID NO 110
<211> LENGTH: 20
<212> TYPE: DNA
<213> ORGANISM: Thlaspi arvense

<400> SEQUENCE: 110
gaccatgctg tatcggagaa 20

<210> SEQ ID NO 111
<211> LENGTH: 20
<212> TYPE: DNA
<213> ORGANISM: Thlaspi arvense

<400> SEQUENCE: 111
aaggagcagt cgttacagcc 20

<210> SEQ ID NO 112
<211> LENGTH: 20
<212> TYPE: DNA
<213> ORGANISM: Thlaspi arvense

<400> SEQUENCE: 112
gacgaagccg aaaacattgg 20

<210> SEQ ID NO 113
<211> LENGTH: 20
<212> TYPE: DNA
<213> ORGANISM: Thlaspi arvense

<400> SEQUENCE: 113
acttgcccct agccctagtc 20

<210> SEQ ID NO 114
<211> LENGTH: 20
<212> TYPE: DNA
<213> ORGANISM: Thlaspi arvense

<400> SEQUENCE: 114
actcggatga gcattcacat 20

<210> SEQ ID NO 115
<211> LENGTH: 20
<212> TYPE: DNA
<213> ORGANISM: thlaspi arvense

<400> SEQUENCE: 115
tgaacatggc gaaggaggct 20

<210> SEQ ID NO 116
<211> LENGTH: 20
<212> TYPE: DNA
<213> ORGANISM: Thlaspi arvense

<400> SEQUENCE: 116
tggaaggaac cttggttagc 20

<210> SEQ ID NO 117
<211> LENGTH: 20
<212> TYPE: DNA
<213> ORGANISM: Thlaspi arvense

<400> SEQUENCE: 117
ccaatcttat catacaagat 20

<210> SEQ ID NO 118
<211> LENGTH: 20
<212> TYPE: DNA
<213> ORGANISM: Thlaspi arvense

<400> SEQUENCE: 118
aaaccctact ccaccgtcga 20

<210> SEQ ID NO 119
<211> LENGTH: 20
<212> TYPE: DNA
<213> ORGANISM: Thlaspi arvense

<400> SEQUENCE: 119
gaagaagtga aatgcattgt 20

<210> SEQ ID NO 120
<211> LENGTH: 20
<212> TYPE: DNA
<213> ORGANISM: Thlaspi arvense

<400> SEQUENCE: 120
ttcctctgcg acacttactt 20

<210> SEQ ID NO 121
<211> LENGTH: 20
<212> TYPE: DNA
<213> ORGANISM: Thlaspi arvense

<400> SEQUENCE: 121
gaagaagtga aatgcattgt 20

<210> SEQ ID NO 122
<211> LENGTH: 20
<212> TYPE: DNA
<213> ORGANISM: Thlaspi arvense

<400> SEQUENCE: 122
tgtatgtgaa agtcaaagcc 20

<210> SEQ ID NO 123
<211> LENGTH: 20
<212> TYPE: DNA
<213> ORGANISM: Thlaspi arvense

<400> SEQUENCE: 123
tccaagcgca gcagagcgac 20

<210> SEQ ID NO 124
<211> LENGTH: 20
<212> TYPE: DNA
<213> ORGANISM: Thlaspi arvense

<400> SEQUENCE: 124
tctcctccat gtcggccatg 20

<210> SEQ ID NO 125
<211> LENGTH: 20
<212> TYPE: DNA
<213> ORGANISM: Thlaspi arvense

<400> SEQUENCE: 125
ccctactcca ccgtcgatgg 20

<210> SEQ ID NO 126
<211> LENGTH: 20
<212> TYPE: DNA
<213> ORGANISM: Thlaspi arvense

<400> SEQUENCE: 126
actctcggga tggagccacg 20

<210> SEQ ID NO 127
<211> LENGTH: 1016
<212> TYPE: DNA
<213> ORGANISM: Thlaspi arvense

<400> SEQUENCE: 127
atgtcgaaaa gaccatgctg tatcggagaa gggttaaaga aagggcatgg acgtcagggg 60
aagacaaaaa actcatctct tatatccatg aacatggcga aggaggttgg cgtgacattc 120
ccgaaaaagc tgggctaaaa cggtgtggaa agagttgcag actgcgatgg gcgaactatt 180
tgaaccccga tatcaagaga ggaggattta gctacgagga agaacagatc atcatcatgc 240
ttcatgcttc tcgtggcaac aagtggtcag tcatagcaag acatttgccg caaagaacag 300
acaacgagat caaaaactat tggaacacac atctcaagaa acgcctgatc aataagagca 360
ctgattccgt gacccacaag cctctagctt cctctaaccc tagtcctacc gagcgtaaga 420
agctcgattc ccaagaagaa tccaatccca aggagcagtc gttacagccg ggttcgaagt 480
ctccagtatc tctttccctt tcttcgagtt tcaacgacac tgtacccgag atcatgacca 540
gtgatgagac gcctctagaa agtggtttct tgagttgcaa aaaaagtgtc gagagatcga 600
gctcaacatc aaggctttta aacaaagttg cagctagagc ttcttccatc gggagtatct 660
tatcaacctc catagaagga actttgagat ctcctgcatc gtcctcatgt ctcccaaact 720
cattgtgtca atcatctgaa cacaacaagg atcaagatct cggtacgagc attgatctta 780
gcatccccga ttacgattac tcccactttc tcgagcactt catcaatagc gaagacgaag 840
ccgaaaacat tggtggctgc aatcaagatc tccttatgtc cgatttccca tcaacattag 900
tggataaaga aaatatgaat tttgaagaca taaccggttg gtcaagttat cttctcgacc 960
atcccagttt tacgtatgaa tcggaacaag attccgacga caacaacttg ttatga 1016

<210> SEQ ID NO 128
<211> LENGTH: 45
<212> TYPE: PRT
<213> ORGANISM: Thlaspi arvense

<400> SEQUENCE: 128

Met Ser Lys Arg Pro Cys Cys Ile Gly Glu Gly Leu Lys Lys Gly His
1               5                   10                  15

Gly Arg Gln Gly Lys Thr Lys Asn Ser Ser Leu Ile Ser Met Asn Met
            20                  25                  30

Ala Lys Glu Val Gly Val Thr Phe Pro Lys Lys Leu Gly
        35                  40                  45

<210> SEQ ID NO 129
<211> LENGTH: 989
<212> TYPE: DNA
<213> ORGANISM: Thlaspi arvense

<400> SEQUENCE: 129
atgtcgaaaa gaccatgcta tggacgtcag gggaagacaa aaaactcatc tcttatatcc 60
atgaacatgg cgaaggaggt tggcgtgaca ttcccgaaaa agctgggcta aaacggtgtg 120
gaaagagttg cagactgcga tgggcgaact atttgaaccc cgatatcaag agaggaggat 180
ttagctacga ggaagaacag atcatcatca tgcttcatgc ttctcgtggc aacaagtggt 240
cagtcatagc aagacatttg ccgcaaagaa cagacaacga gatcaaaaac tattggaaca 300
cacatctcaa gaaacgcctg atcaataaga gcactgattc cgtgacccac aagcctctag 360
cttcctctaa ccctagtcct accgagcgta agaagctcga ttcccaagaa gaatccaatc 420
ccaaggagca gtcgttacag ccgggttcga agtctccagt atctctttcc ctttcttcga 480
gtttcaacga cactgtaccc gagatcatga ccagtgatga gacgcctcta gaaagtggtt 540
tcttgagttg caaaaaaagt gtcgagagat cgagctcaac atcaaggctt ttaaacaaag 600
ttgcagctag agcttcttcc atcgggagta tcttatcaac ctccatagaa ggaactttga 660
gatctcctgc atcgtcctca tgtctcccaa actcattgtg tcaatcatct gaacacaaca 720
aggatcaaga tctcggtacg agcattgatc ttagcatccc cgattacgat tactcccact 780
ttctcgagca cttcatcaat agcgaagacg aagccgaaaa cattggtggc tgcaatcaag 840
atctccttat gtccgatttc ccatcaacat tagtggataa agaaaatatg aattttgaag 900
acataaccgg ttggtcaagt tatcttctcg accatcccag ttttacgtat gaatcggaac 960
aagattccga cgacaacaac ttgttatga 989

<210> SEQ ID NO 130
<211> LENGTH: 36
<212> TYPE: PRT
<213> ORGANISM: Thlaspi arvense

<400> SEQUENCE: 130

Met Ser Lys Arg Pro Cys Tyr Gly Arg Gln Gly Lys Thr Lys Asn Ser
1               5                   10                  15

Ser Leu Ile Ser Met Asn Met Ala Lys Glu Val Gly Val Thr Phe Pro
            20                  25                  30

Lys Lys Leu Gly
        35

<210> SEQ ID NO 131
<211> LENGTH: 491
<212> TYPE: DNA
<213> ORGANISM: Thlaspi arvense

<400> SEQUENCE: 131
atgtcaagaa agccatgttg tgtgggagaa gggctgaaga aaggagcatg gaccgccgaa 60
gaagacaaga aactcatctc ttacatccat gaaaaggaac cttggttagc tctaccgcac 120
tgtctccatg tctcaatgat gacttttccg aagctagcca attccagatg gacgaatatg 180
atccattccc tcagtcgtct gaacacataa ctgatcatat gaaggaggac accggcatga 240
tctttgatct caacaactcc gaatatgatt tctcgcagtt tctcgagcaa tttagtaacg 300
aaggcgaaga aaccgagaac attgggggat ataatcaaga tctcctttcg tctgacgtct 360
catcaccaag cgttgatgaa gacaatatga tgggaaacat aaccggttcc ggttggtcca 420
gttatcttgt tgaccattcc gattttgttt atgacaagat ccaagataac gacgacagga 480
acttcatatg a 491

<210> SEQ ID NO 132
<211> LENGTH: 69
<212> TYPE: PRT
<213> ORGANISM: Thlaspi arvense

<400> SEQUENCE: 132

Met Ser Arg Lys Pro Cys Cys Val Gly Glu Gly Leu Lys Lys Gly Ala
1 5 10 15

Trp Thr Ala Glu Glu Asp Lys Lys Leu Ile Ser Tyr Ile His Glu Lys
20 25 30

Glu Pro Trp Leu Ala Leu Pro His Cys Leu His Val Ser Met Met Thr
35 40 45

Phe Pro Lys Leu Ala Asn Ser Arg Trp Thr Asn Met Ile His Ser Leu
50 55 60

Ser Arg Leu Asn Thr
65

<210> SEQ ID NO 133
<211> LENGTH: 477
<212> TYPE: DNA
<213> ORGANISM: Thlaspi arvense

<400> SEQUENCE: 133
atgtcaagaa agccatgttg tgtgggagaa gggctgaaga aaggagcatg gaccgccgaa 60
gaagacaaga aactcatcta aggaaccttg gttagctcta ccgcactgtc tccatgtctc 120
aatgatgact tttccgaagc tagccaattc cagatggacg aatatgatcc attccctcag 180
tcgtctgaac acataactga tcatatgaag gaggacaccg gcatgatctt tgatctcaac 240
aactccgaat atgatttctc gcagtttctc gagcaattta gtaacgaagg cgaagaaacc 300
gagaacattg ggggatataa tcaagatctc ctttcgtctg acgtctcatc accaagcgtt 360
gatgaagaca atatgatggg aaacataacc ggttccggtt ggtccagtta tcttgttgac 420
cattccgatt ttgtttatga caagatccaa gataacgacg acaggaactt catatga 477

<210> SEQ ID NO 134
<211> LENGTH: 26
<212> TYPE: PRT
<213> ORGANISM: Thlaspi arvense

<400> SEQUENCE: 134

Met Ser Arg Lys Pro Cys Cys Val Gly Glu Gly Leu Lys Lys Gly Ala
1 5 10 15

Trp Thr Ala Glu Glu Asp Lys Lys Leu Ile
20 25

<210> SEQ ID NO 135
<211> LENGTH: 1082
<212> TYPE: DNA
<213> ORGANISM: Thlaspi arvense

<400> SEQUENCE: 135
atgtcaagaa agccatgttg tgtgggagaa gggctgaaga aaggagcatg gaccgccgaa 60
gaagacaaga aactcatctc ttacatccat gaaacatggc gaaggaggct ggcgtgacat 120
tccccaaaaa gctggactaa aacgatgtgg aaaaagttgt agattgcgat gggctaacta 180
tttgaaaccg gatatcaaga gaggagaatt tagctacgag gaggagcaga ttatcatcat 240
gcttcacgct tcccgtggca acaagtggtc ggtcatagcg agacatttgc ccaaaaggac 300
agacaacgag atcaagaact attggaacac acaccttaaa aaacgcctta tcgatcaagg 360
tattgatccc gtgacccaca agccacttgc ccctagccct agtccggcca cgctcaagcc 420
ttctgatttc caagatgact catcaaacct gggaaactcg gatgagcatt cacattcggg 480
ttctatgtct ccaaaatctc ttcctccgtc ttcaagctcc tgcaatctag cggagataag 540
cagcagtgat gagacaccga aaaatgatgg ttccttgaaa tccaagaaac gttcttttaa 600
gagatcaagt tctacatcaa agctgttaaa caaagttgca tctagggctg cttccattgg 660
aaatatctta tcagcgtcca tggaaaggaa ccttggttag ctctaccgca ctgtctccat 720
gtctcaatga tgacttttcc gaagctagcc aattccagat ggacgaatat gatccattcc 780
ctcagtcgtc tgaacacata actgatcata tgaaggagga caccggcatg atctttgatc 840
tcaacaactc cgaatatgat ttctcgcagt ttctcgagca atttagtaac gaaggcgaag 900
aaaccgagaa cattggggga tataatcaag atctcctttc gtctgacgtc tcatcaccaa 960
gcgttgatga agacaatatg atgggaaaca taaccggttc cggttggtcc agttatcttg 1020
ttgaccattc cgattttgtt tatgacaaga tccaagataa cgacgacagg aacttcatat 1080
ga 1082

<210> SEQ ID NO 136
<211> LENGTH: 38
<212> TYPE: PRT
<213> ORGANISM: Thlaspi arvense

<400> SEQUENCE: 136

Met Ser Arg Lys Pro Cys Cys Val Gly Glu Gly Leu Lys Lys Gly Ala
1 5 10 15

Trp Thr Ala Glu Glu Asp Lys Lys Leu Ile Ser Tyr Ile His Glu Thr
20 25 30

Trp Arg Arg Arg Leu Ala
35

<210> SEQ ID NO 137
<211> LENGTH: 1077
<212> TYPE: DNA
<213> ORGANISM: Thlaspi arvense

<400> SEQUENCE: 137

```
atgtcaagaa agccatgttg tgtgggagaa gggctgaaga aaggagcatg gaccgccgaa     60

gaagacaaga aactcatctc ttacatccat gaacatggcg aaggaggctg gcgtgacatt    120

ccccaaaaag ctggactaaa acgatgtgga aaaagttgta gattgcgatg ggctaactat    180

ttgaaaccgg atatcaagag aggagaattt agctacgagg aggagcagat tatcatcatg    240

cttcacgctt cccgtggcaa caagtggtcg gtcatagcga gacatttgcc caaaaggaca    300

gacaacgaga tcaagaacta ttggaacaca caccttaaaa aacgccttat cgatcaaggt    360

attgatcccg tgacccacaa gccacttgcc cctagcccta gtccggccac gctcaagcct    420

tctgatttcc aagatgactc atcaaacctg ggaaactcgg atgagcattc acattcgggt    480

tctatgtctc caaaatctct tcctccgtct tcaagctcct gcaatctagc ggagataagc    540

agcagtgatg agacaccgaa aaatgatggt tccttgaaat ccaagaaacg ttcttttaag    600

agatcaagtt ctacatcaaa gctgttaaac aaagttgcat ctagggctgc ttccattgga    660

aatatcttat cagcgtccaa aggaaccttg gttagctcta ccgcactgtc tccatgtctc    720

aatgatgact tttccgaagc tagccaattc cagatggacg aatatgatcc attccctcag    780

tcgtctgaac acataactga tcatatgaag gaggacaccg gcatgatctt tgatctcaac    840

aactccgaat atgatttctc gcagtttctc gagcaattta gtaacgaagg cgaagaaacc    900

gagaacattg gggatataa tcaagatctc ctttcgtctg acgtctcatc accaagcgtt    960

gatgaagaca atatgatggg aaacataacc ggttccggtt ggtccagtta tcttgttgac   1020

cattccgatt ttgtttatga caagatccaa gataacgacg acaggaactt catatga      1077
```

<210> SEQ ID NO 138
<211> LENGTH: 358
<212> TYPE: PRT
<213> ORGANISM: Thlaspi arvense

<400> SEQUENCE: 138

```
Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Ser Cys Asn Leu
                165                 170                 175

Ala Glu Ile Ser Ser Ser Asp Glu Thr Pro Lys Asn Asp Gly Ser Leu
```

-continued

```
            180                 185                 190

Lys Ser Lys Lys Arg Ser Phe Lys Arg Ser Ser Ser Thr Ser Lys Leu
        195                 200                 205

Leu Asn Lys Val Ala Ser Arg Ala Ala Ser Ile Gly Asn Ile Leu Ser
    210                 215                 220

Ala Ser Lys Gly Thr Leu Val Ser Ser Thr Ala Leu Ser Pro Cys Leu
225                 230                 235                 240

Asn Asp Asp Phe Ser Glu Ala Ser Gln Phe Gln Met Asp Glu Tyr Asp
                245                 250                 255

Pro Phe Pro Gln Ser Ser Glu His Ile Thr Asp His Met Lys Glu Asp
            260                 265                 270

Thr Gly Met Ile Phe Asp Leu Asn Asn Ser Glu Tyr Asp Phe Ser Gln
        275                 280                 285

Phe Leu Glu Gln Phe Ser Asn Glu Gly Glu Glu Thr Glu Asn Ile Gly
    290                 295                 300

Gly Tyr Asn Gln Asp Leu Leu Ser Ser Asp Val Ser Ser Pro Ser Val
305                 310                 315                 320

Asp Glu Asp Asn Met Met Gly Asn Ile Thr Gly Ser Gly Trp Ser Ser
                325                 330                 335

Tyr Leu Val Asp His Ser Asp Phe Val Tyr Asp Lys Ile Gln Asp Asn
            340                 345                 350

Asp Asp Arg Asn Phe Ile
        355


<210> SEQ ID NO 139
<211> LENGTH: 1076
<212> TYPE: DNA
<213> ORGANISM: Thlaspi arvense

<400> SEQUENCE: 139

atgtcaagaa agccatgttg tgtgggagaa gggctgaaga aaggagcatg gaccgccgaa      60

gaagacaaga aactcatctc ttacatccat gaacatggcg aaggaggctg gcgtgacatt     120

ccccaaaaag ctggactaaa acgatgtgga aaaagttgta gattgcgatg ggctaactat     180

ttgaaaccgg atatcaagag aggagaattt agctacgagg aggagcagat tatcatcatg     240

cttcacgctt cccgtggcaa caagtggtcg gtcatagcga gacatttgcc caaaaggaca     300

gacaacgaga tcaagaacta ttggaacaca caccttaaaa aacgccttat cgatcaaggt     360

attgatcccg tgacccacaa gccacttgcc cctagcccta gtccggccac gctcaagcct     420

tctgatttcc aagatgactc atcaaacctg ggaaactcgg atgagcattc acattcgggt     480

tctatgtctc caaaatctct tcctccgtct tcaagctcct gcaatctagc ggagataagc     540

agcagtgatg agacaccgaa aaatgatggt tccttgaaat ccaagaaacg ttcttttaag     600

agatcaagtt ctacatcaaa gctgttaaac aaagttgcat ctagggctgc ttccattgga     660

aatatcttat cagcgtccaa ggaaccttgg ttagctctac cgcactgtct ccatgtctca     720

atgatgactt ttccgaagct agccaattcc agatggacga atatgatcca ttccctcagt     780

cgtctgaaca cataactgat catatgaagg aggacaccgg catgatcttt gatctcaaca     840

actccgaata tgatttctcg cagtttctcg agcaatttag taacgaaggc gaagaaaccg     900

agaacattgg gggatataat caagatctcc tttcgtctga cgtctcatca ccaagcgttg     960

atgaagacaa tatgatggga aacataaccg gttccggttg gtccagttat cttgttgacc    1020

attccgattt tgtttatgac aagatccaag ataacgacga caggaacttc atatga        1076
```

<210> SEQ ID NO 140
<211> LENGTH: 264
<212> TYPE: PRT
<213> ORGANISM: Thlaspi arvense

<400> SEQUENCE: 140

Met Ser Arg Lys Pro Cys Cys Val Gly Glu Gly Leu Lys Lys Gly Ala
1 5 10 15

Trp Thr Ala Glu Glu Asp Lys Lys Leu Ile Ser Tyr Ile His Glu His
20 25 30

Gly Glu Gly Gly Trp Arg Asp Ile Pro Gln Lys Ala Gly Leu Lys Arg
35 40 45

Cys Gly Lys Ser Cys Arg Leu Arg Trp Ala Asn Tyr Leu Lys Pro Asp
50 55 60

Ile Lys Arg Gly Glu Phe Ser Tyr Glu Glu Glu Gln Ile Ile Ile Met
65 70 75 80

Leu His Ala Ser Arg Gly Asn Lys Trp Ser Val Ile Ala Arg His Leu
85 90 95

Pro Lys Arg Thr Asp Asn Glu Ile Lys Asn Tyr Trp Asn Thr His Leu
100 105 110

Lys Lys Arg Leu Ile Asp Gln Gly Ile Asp Pro Val Thr His Lys Pro
115 120 125

Leu Ala Pro Ser Pro Ser Pro Ala Thr Leu Lys Pro Ser Asp Phe Gln
130 135 140

Asp Asp Ser Ser Asn Leu Gly Asn Ser Asp Glu His Ser His Ser Gly
145 150 155 160

Ser Met Ser Pro Lys Ser Leu Pro Pro Ser Ser Ser Ser Cys Asn Leu
165 170 175

Ala Glu Ile Ser Ser Ser Asp Glu Thr Pro Lys Asn Asp Gly Ser Leu
180 185 190

Lys Ser Lys Lys Arg Ser Phe Lys Arg Ser Ser Ser Thr Ser Lys Leu
195 200 205

Leu Asn Lys Val Ala Ser Arg Ala Ala Ser Ile Gly Asn Ile Leu Ser
210 215 220

Ala Ser Lys Glu Pro Trp Leu Ala Leu Pro His Cys Leu His Val Ser
225 230 235 240

Met Met Thr Phe Pro Lys Leu Ala Asn Ser Arg Trp Thr Asn Met Ile
245 250 255

His Ser Leu Ser Arg Leu Asn Thr
260

<210> SEQ ID NO 141
<211> LENGTH: 1079
<212> TYPE: DNA
<213> ORGANISM: Thlaspi arvense

<400> SEQUENCE: 141
atgtcaagaa agccatgttg tgtgggagaa gggctgaaga aaggagcatg gaccgccgaa 60
gaagacaaga aactcatctc ttacatccat gaacatggcg aaggaggctg gcgtgacatt 120
ccccaaaaag ctggactaaa acgatgtgga aaaagttgta gattgcgatg ggctaactat 180
ttgaaaccgg atatcaagag aggagaattt agctacgagg aggagcagat tatcatcatg 240
cttcacgctt cccgtggcaa caagtggtcg gtcatagcga gacatttgcc caaaaggaca 300
gacaacgaga tcaagaacta ttggaacaca caccttaaaa aacgccttat cgatcaaggt 360

```
attgatcccg tgacccacaa gccacttgcc cctagcccta gtccggccac gctcaagcct    420

tctgatttcc aagatgactc atcaaacctg ggaaactcgg atgagcattc acattcgggt    480

tctatgtctc caaaatctct tcctccgtct tcaagctcct gcaatctagc ggagataagc    540

agcagtgatg agacaccgaa aaatgatggt tccttgaaat ccaagaaacg ttcttttaag    600

agatcaagtt ctacatcaaa gctgttaaac aaagttgcat ctagggctgc ttccattgga    660

aatatcttat cagcgtccat ggaggaacct tggttagctc taccgcactg tctccatgtc    720

tcaatgatga cttttccgaa gctagccaat tccagatgga cgaatatgat ccattccctc    780

agtcgtctga acacataact gatcatatga aggaggacac cggcatgatc tttgatctca    840

acaactccga atatgatttc tcgcagtttc tcgagcaatt tagtaacgaa ggcgaagaaa    900

ccgagaacat tgggggatat aatcaagatc tcctttcgtc tgacgtctca tcaccaagcg    960

ttgatgaaga caatatgatg ggaaacataa ccggttccgg ttggtccagt tatcttgttg   1020

accattccga ttttgtttat gacaagatcc aagataacga cgacaggaac ttcatatga    1079


<210> SEQ ID NO 142
<211> LENGTH: 265
<212> TYPE: PRT
<213> ORGANISM: Thlaspi arvense

<400> SEQUENCE: 142

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Ser Pro Ala Thr Leu Lys Pro Ser Asp Phe Gln
    130                 135                 140

Asp Asp Ser Ser Asn Leu Gly Asn Ser Asp Glu His Ser His Ser Gly
145                 150                 155                 160

Ser Met Ser Pro Lys Ser Leu Pro Pro Ser Ser Ser Ser Cys Asn Leu
                165                 170                 175

Ala Glu Ile Ser Ser Ser Asp Glu Thr Pro Lys Asn Asp Gly Ser Leu
            180                 185                 190

Lys Ser Lys Lys Arg Ser Phe Lys Arg Ser Ser Ser Thr Ser Lys Leu
        195                 200                 205

Leu Asn Lys Val Ala Ser Arg Ala Ala Ser Ile Gly Asn Ile Leu Ser
    210                 215                 220

Ala Ser Met Glu Glu Pro Trp Leu Ala Leu Pro His Cys Leu His Val
225                 230                 235                 240

Ser Met Met Thr Phe Pro Lys Leu Ala Asn Ser Arg Trp Thr Asn Met
                245                 250                 255
```

Ile His Ser Leu Ser Arg Leu Asn Thr
260 265

<210> SEQ ID NO 143
<211> LENGTH: 1841
<212> TYPE: DNA
<213> ORGANISM: Thlaspi arvense

<400> SEQUENCE: 143
atggagagaa agccctttga ggttgagacg acggagaatc acaaacccta ctccaccgtc 60
gatggcggtg gcgttggttc tgatttgaga tcgccggtcg attcatttga tgacgagcag 120
aaaaagctcg tttacagagg ctggaaagtc atgcctttta tcattggtaa tgagacattt 180
gagaagattg ggatcatagg gacattatca aaccttcttt tgtacctaac tcaagtattc 240
aaccttaaga aagttacagc tgcaacaatc atcaatgcct ttagtggcac aatcaacttc 300
gggactttca tcgctgcttt ccttttggtc gctacaagac tctcagtgta gctgtcatcg 360
cttgtttcct gggatcgctt gtgatattac tgacggctgc agttcctgca ttgcacccga 420
ctccatgtgg aacacatagc tggtgccaag ggccaagccc gggccagatc gcgttcttgc 480
tgctgggttt agcgtttctt gtggtcggtg cgggtgggat caggccgtgt aacttggctt 540
ttggagctga tcagttcaac cccaaatccg aatccgggaa gaaaggaatc aacagcttct 600
ttaactggta tttcttcacc ttcacgtttg cgcagatcgt ctcgctcacg ctggtcgtgt 660
atatccagtc gaacgtgagc tggacgatcg gtttgctcat ccctgtggct ctgatgttct 720
tggcctgcgt catcttcttt gctggacata aactgtatgt gaaagtgaaa gcctcgggta 780
gtcccttggc tagtatcggt cacgttatca cggcagcgat caagaaacga gggttgaagc 840
aagttaagca gccttggctc gatctttaca accacattcc aactaactat ccaaactcca 900
ccttgaaata caccgaccag tttaggtttc ttgacaaagc agcgattatg acccctgagg 960
acaagctgaa ttccgatgga gctgctttcg atccatggac cctatgtaca ttgcagaaag 1020
tggaagaagt gaaatgcatt gtgagagtga ttccgatctg gtttgcttgc gcgatttact 1080
acctcactgt aactatacag atgacttatc cggtcttcca agcgcagcag agcgaccgga 1140
gattgggttc tggtggcttc aagatccccg cagccaccta tgtggtgttc ttgatgtcgg 1200
gtatgactgt tttcatcgtg ttctacgacc gtgtccttgt cccgttgctc agaagagtga 1260
ccgggttaga aaccggtttg accctcttgc agagagtcgg atcagggatc ttctttgcca 1320
tgttgagttt gttggtctcc gggttcgtag aggaacggag aagaaccttc gccctgacga 1380
aaccgactct cgggatggag ccacgagcgg gagagatctc ctccatgtcg gccatgtggc 1440
tgattccgca gctcttgctt gcaggcgtag gagaggcttt tacagccatt ggacagatgg 1500
agttttatta caagcagttc cctgagaaca tgaagagctt cgctggctct atcttctatg 1560
tcggtgcagg tgtttcgagc tatcttgcta gcttcttgat ctcgactgtt catcgaagaa 1620
ctgaacattc accctccggg aactggttag ctgaggatct gaacaaaggg agactcgatt 1680
acttctactt catgctcacc ggaatcatgg tcgttaacat ggtttacttc ttgataatgt 1740
ctaaatggta tagatacaaa ggcattaacg atgaagcgaa ttctttggtc gagaccaatg 1800
aagaagagac caagcagaaa caagtcaaga attctgtctg a 1841

<210> SEQ ID NO 144
<211> LENGTH: 116
<212> TYPE: PRT
<213> ORGANISM: Thlaspi arvense

<400> SEQUENCE: 144

Met Glu Arg Lys Pro Phe Glu Val Glu Thr Thr Glu Asn His Lys Pro
1 5 10 15

Tyr Ser Thr Val Asp Gly Gly Gly Val Gly Ser Asp Leu Arg Ser Pro
20 25 30

Val Asp Ser Phe Asp Asp Glu Gln Lys Lys Leu Val Tyr Arg Gly Trp
35 40 45

Lys Val Met Pro Phe Ile Ile Gly Asn Glu Thr Phe Glu Lys Ile Gly
50 55 60

Ile Ile Gly Thr Leu Ser Asn Leu Leu Leu Tyr Leu Thr Gln Val Phe
65 70 75 80

Asn Leu Lys Lys Val Thr Ala Ala Thr Ile Ile Asn Ala Phe Ser Gly
85 90 95

Thr Ile Asn Phe Gly Thr Phe Ile Ala Ala Phe Leu Leu Val Ala Thr
100 105 110

Arg Leu Ser Val
115

<210> SEQ ID NO 145
<211> LENGTH: 1843
<212> TYPE: DNA
<213> ORGANISM: Thlaspi arvense

<400> SEQUENCE: 145
atggagagac agcctctcga actcgagtct acggatcacc aaaaaccttc ccccgccgtc 60
tacggtggct ctgttacgac ggttgattct gttgaggaag aagttcagga gaaaaaagtc 120
gtatatagag gctggaaagt catgcccttt atcattggaa atgagacatt cgagaagctt 180
gggatcattg gaacactatc aaaccttctg gttttttaa cagctgtctt caacatgaag 240
agtatcacag ctgcaacaat cattaacgca ttcagtggca caataaattt cggaactttc 300
gttgctgctt tcctctgcga cacttacttc ggtcgataca agacactaac cgtcgcggtc 360
atcgcctgtt ttcttggatc acttgtgata ctattgacag ctgcagtgcc acaactgcac 420
ccagctccat gtggaacagc gagctcgtgc agcggtccaa gcggtgggca aatcgcgttt 480
cttctgatgg gtctcgggtt tcttgtagtt ggagcgggcg ggatcagacc gtgcaatcta 540
gctttcggag ccgatcagtt caacccgaag agcgagtcag ggagaagagg gactgatagt 600
ttcttcaatt ggtacttctt cagcttcact ttcgcgcaga tcttgtcgct gacgctagtg 660
gtctacatcc agtctaacgt cagctggacg atcggtctaa ccataccggt ggttctaatg 720
ttcttggcct ccgtgatctt ctttgcggga gataagctgt atgtgaaagt caaggcctcg 780
ggtagtccat tggctggtat agctcaagtg atcattgttg caatcaagaa acgcggatta 840
aagcccgtga aacagccttg gcttaacctc tacaattact gccctccaaa acacgcaaac 900
tccattctca aatacaccga ccaattcaga tttcttgata aggcggcgat cttggctccc 960
gaggacaagt tggaggcgga tggtaagcct gcggatccat ggaagctgtg tacgatgcaa 1020
caggtggaag aagtgaagtg catttgtgag agtgcttcct atatggttcg ctgcatcaat 1080
ctactacgta accataaccc agcaaatgac atatccggtc ttccaagccc tgcagagcga 1140
tcgtcgctta ggctcgggag ggttcgtgat ccccgcagcc acctacgtgg tcttcttgat 1200
gacagggatg acggttttca tcatcatcta cgaccgtctc ctcgtgccta ccttgagaag 1260
aataaccggt ctagacaccg ggatcacgct cctgcagaga atcggaaccg ggatcttctt 1320

```
cgcctttgca agcttagtag tctccggttt cgtcgaggag cggaggagac acattgcgct   1380

gactaaacca actcttggca tggcgccaag aaaaggagaa atctcctcaa tgtcagctat   1440

gtggctcatc ccgcagctca ctctctcggg tgtagccgag gcgtttggag ccatcggaca   1500

gatggagttt tactacaagc agttcccaga aaacatgagg agtttcgcgg gttccatctt   1560

ttatgtagga ataggggttt cgagttacct cggcagcttc ttgattgcaa cggttcaccg   1620

gacgacgcag aactcggcgg gtggtaactg gttggctgag gatttgaaca aaggcagatt   1680

ggattacttc tatttcatga tcgctggaat cttggctgtt aatttcgcct acttcttggt   1740

cgtgtcaaga tggtataggt acaaagaaag tgatgatgat caaaagacag cttctgaaac   1800

caatggagat gtcatcaaac aacaagacaa gaacactgcc tga                      1843


<210> SEQ ID NO 146
<211> LENGTH: 461
<212> TYPE: PRT
<213> ORGANISM: Thlaspi arvense

<400> SEQUENCE: 146

Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285
```

-continued

```
Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Cys Glu Ser Ala
            340                 345                 350

Ser Tyr Met Val Arg Cys Ile Asn Leu Leu Arg Asn His Asn Pro Ala
        355                 360                 365

Asn Asp Ile Ser Gly Leu Pro Ser Pro Ala Glu Arg Ser Ser Leu Arg
    370                 375                 380

Leu Gly Arg Val Arg Asp Pro Arg Ser His Leu Arg Gly Leu Leu Asp
385                 390                 395                 400

Asp Arg Asp Asp Gly Phe His His His Leu Arg Pro Ser Pro Arg Ala
                405                 410                 415

Tyr Leu Glu Lys Asn Asn Arg Ser Arg His Arg Asp His Ala Pro Ala
            420                 425                 430

Glu Asn Arg Asn Arg Asp Leu Leu Arg Leu Cys Lys Leu Ser Ser Leu
        435                 440                 445

Arg Phe Arg Arg Gly Ala Glu Glu Thr His Cys Ala Asp
    450                 455                 460


<210> SEQ ID NO 147
<211> LENGTH: 1366
<212> TYPE: DNA
<213> ORGANISM: Thlaspi arvense

<400> SEQUENCE: 147

atgggttcac tttcaaacac tcctcagctt ccagtcatct acctctcgga ccaaacccta      60

aaaccaggaa gctcaaagtg ggttgaagtc aggagtgatg tccgtaaagc tcttgaagag     120

tacggcggtt tcgaggtgtc gtacgataga gtgtcggagg agcttaagaa gtcggttttg     180

caagccatgg aagagctttt cgcgttacca gttgaggcta aacagagaaa cgtctctcct     240

aaacccttca gcggttattc cactcataac ggtctttccg agagtaatgg ggatccagga     300

tcctcatgtt ttggacaaag tttacgagtt tactcaactt ctacgtcctg atcattgtga     360

cggtaacaag agcatcagcg aaacgatcca gacgttttca gagaagttat cagaattgga     420

tataatggtg agaagaatgg taatggaaag cttcgggata gagaagtacc ttgacaaaca     480

cctgaactca acgaattacc gtctgcggct gatgaagtat atagcaccgc ctgatgctga     540

tgctactaat gttgcggctg atgccaaaga tgctgatgat aatgctaaga cgattacaaa     600

tgataaagtt gatgcggctg gtgctaatga tgtagatgct ggtgatatcg ctaatggtat     660

tgctaatctt catattggtg atgatgctaa cgctggtgct aatggtgctg gtgttgatgc     720

taatgatggt ggtgaggatg ctaagactgg tgaggatgct aagactggtg aatgtgctag     780

tgttaagtct aatgccgaag atggtactga tgttaatgcc agtgctgatg ctggtgttac     840

tgttggctct aatgctgatg ctaatgctaa tgctaatgct aatactagta ctgatgctgg     900

tgttggcgat agtgttaaag ctaatggtgg tgctgatgat gttgagaaga aattgggtct     960

accttctcac actgataaga accttataac ggtgctttat caatacgaga ttgaaggctt    1020

ggaggttcta accaaagatg acaagtggat cagactcaaa ccatctcata attctttcgt    1080

tgttatggct ggagattctc tatacgcact tatgaatggt agactaactc gtccctttca    1140
```

-continued tcgagtaaga gtaacggaga aaaagaagac aagatattca atagcattgt tctcggctcc 1200
aaccgcagat tacatcatag acacaccaaa agaacttgtg gacgagaagc atccacgtat 1260
cttcgaacca tttaactata acgacttgat gagtttctat catagtgaag ctggtcgtaa 1320
agctcgatct actcttgatg ctttctgtgc cgtctctcga gcataa 1366

<210> SEQ ID NO 148
<211> LENGTH: 116
<212> TYPE: PRT
<213> ORGANISM: Thlaspi arvense

<400> SEQUENCE: 148

Met Gly Ser Leu Ser Asn Thr Pro Gln Leu Pro Val Ile Tyr Leu Ser
1 5 10 15

Asp Gln Thr Leu Lys Pro Gly Ser Ser Lys Trp Val Glu Val Arg Ser
20 25 30

Asp Val Arg Lys Ala Leu Glu Glu Tyr Gly Gly Phe Glu Val Ser Tyr
35 40 45

Asp Arg Val Ser Glu Glu Leu Lys Lys Ser Val Leu Gln Ala Met Glu
50 55 60

Glu Leu Phe Ala Leu Pro Val Glu Ala Lys Gln Arg Asn Val Ser Pro
65 70 75 80

Lys Pro Phe Ser Gly Tyr Ser Thr His Asn Gly Leu Ser Glu Arg Tyr
85 90 95

Gly Asp Pro Gly Ser Ser Cys Phe Gly Gln Ser Leu Arg Val Tyr Ser
100 105 110

Thr Ser Thr Ser
115

<210> SEQ ID NO 149
<211> LENGTH: 1363
<212> TYPE: DNA
<213> ORGANISM: Thlaspi arvense

<400> SEQUENCE: 149
atgggttcac tttcaaacac tcctcagctt ccagtcatct acctctcgga ccaaacccta 60
aaaccaggaa gctcaaagtg ggttgaagtc aggagtgatg tccgtaaagc tcttgaagag 120
tacggcggtt tcgaggtgtc gtacgataga gtgtcggagg agcttaagaa gtcggttttg 180
caagccatgg aagagctttt cgcgttacca gttgaggcta aacagagaaa cgtctctcct 240
aaacccttca gcggttattc cactcataac ggtctttccg agaatgggga tccaggatcc 300
tcatgttttg gacaaagttt acgagtttac tcaacttcta cgtcctgatc attgtgacgg 360
taacaagagc atcagcgaaa cgatccagac gttttcagag aagttatcag aattggatat 420
aatggtgaga agaatggtaa tggaaagctt cgggatagag aagtaccttg acaaacacct 480
gaactcaacg aattaccgtc tgcggctgat gaagtatata gcaccgcctg atgctgatgc 540
tactaatgtt gcggctgatg ccaaagatgc tgatgataat gctaagacga ttacaaatga 600
taaagttgat gcggctggtg ctaatgatgt agatgctggt gatatcgcta atggtattgc 660
taatcttcat attggtgatg atgctaacgc tggtgctaat ggtgctggtg ttgatgctaa 720
tgatggtggt gaggatgcta agactggtga ggatgctaag actggtgaat gtgctagtgt 780
taagtctaat gccgaagatg gtactgatgt taatgccagt gctgatgctg gtgttactgt 840
tggctctaat gctgatgcta atgctaatgc taatgctaat actagtactg atgctggtgt 900
tggcgatagt gttaaagcta atggtggtgc tgatgatgtt gagaagaaat tgggtctacc 960
ttctcacact gataagaacc ttataacggt gctttatcaa tacgagattg aaggcttgga 1020
ggttctaacc aaagatgaca agtggatcag actcaaacca tctcataatt ctttcgttgt 1080
tatggctgga gattctctat acgcacttat gaatggtaga ctaactcgtc cctttcatcg 1140
agtaagagta acggagaaaa agaagacaag atattcaata gcattgttct cggctccaac 1200
cgcagattac atcatagaca caccaaaaga acttgtggac gagaagcatc cacgtatctt 1260
cgaaccattt aactataacg acttgatgag tttctatcat agtgaagctg gtcgtaaagc 1320
tcgatctact cttgatgctt tctgtgccgt ctctcgagca taa 1363

<210> SEQ ID NO 150
<211> LENGTH: 115
<212> TYPE: PRT
<213> ORGANISM: Thlaspi arvense

<400> SEQUENCE: 150

Met Gly Ser Leu Ser Asn Thr Pro Gln Leu Pro Val Ile Tyr Leu Ser
1 5 10 15

Asp Gln Thr Leu Lys Pro Gly Ser Ser Lys Trp Val Glu Val Arg Ser
20 25 30

Asp Val Arg Lys Ala Leu Glu Glu Tyr Gly Gly Phe Glu Val Ser Tyr
35 40 45

Asp Arg Val Ser Glu Glu Leu Lys Lys Ser Val Leu Gln Ala Met Glu
50 55 60

Glu Leu Phe Ala Leu Pro Val Glu Ala Lys Gln Arg Asn Val Ser Pro
65 70 75 80

Lys Pro Phe Ser Gly Tyr Ser Thr His Asn Gly Leu Ser Glu Asn Gly
85 90 95

Asp Pro Gly Ser Ser Cys Phe Gly Gln Ser Leu Arg Val Tyr Ser Thr
100 105 110

Ser Thr Ser
115

<210> SEQ ID NO 151
<211> LENGTH: 1363
<212> TYPE: DNA
<213> ORGANISM: Thlaspi arvense

<400> SEQUENCE: 151
atgggttcac tttcaaacac tcctcagctt ccagtcatct acctctcgga ccaaacccta 60
aaaccaggaa gctcaaagtg ggttgaagtc aggagtgatg tccgtaaagc tcttgaagag 120
tacggcggtt tcgaggtgtc gtacgataga gtgtcggagg agcttaagaa gtcggttttg 180
caagccatgg aagagctttt cgcgttacca gttgaggcta aacagagaaa cgtctctcct 240
aaacccttca gcggttattc cactcataac ggtctttccg agagtgggga tccaggatcc 300
tcatgttttg gacaaagttt acgagtttac tcaacttcta cgtcctgatc attgtgacgg 360
taacaagagc atcagcgaaa cgatccagac gttttcagag aagttatcag aattggatat 420
aatggtgaga agaatggtaa tggaaagctt cgggatagag aagtaccttg acaaacacct 480
gaactcaacg aattaccgtc tgcggctgat gaagtatata gcaccgcctg atgctgatgc 540
tactaatgtt gcggctgatg ccaaagatgc tgatgataat gctaagacga ttacaaatga 600
taaagttgat gcggctggtg ctaatgatgt agatgctggt gatatcgcta atggtattgc 660
taatcttcat attggtgatg atgctaacgc tggtgctaat ggtgctggtg ttgatgctaa 720
tgatggtggt gaggatgcta agactggtga ggatgctaag actggtgaat gtgctagtgt 780
taagtctaat gccgaagatg gtactgatgt taatgccagt gctgatgctg gtgttactgt 840
tggctctaat gctgatgcta atgctaatgc taatgctaat actagtactg atgctggtgt 900
tggcgatagt gttaaagcta atggtggtgc tgatgatgtt gagaagaaat tgggtctacc 960
ttctcacact gataagaacc ttataacggt gctttatcaa tacgagattg aaggcttgga 1020
ggttctaacc aaagatgaca agtggatcag actcaaacca tctcataatt ctttcgttgt 1080
tatggctgga gattctctat acgcacttat gaatggtaga ctaactcgtc cctttcatcg 1140
agtaagagta acggagaaaa agaagacaag atattcaata gcattgttct cggctccaac 1200
cgcagattac atcatagaca caccaaaaga acttgtggac gagaagcatc cacgtatctt 1260
cgaaccattt aactataacg acttgatgag tttctatcat agtgaagctg gtcgtaaagc 1320
tcgatctact cttgatgctt tctgtgccgt ctctcgagca taa 1363

<210> SEQ ID NO 152
<211> LENGTH: 115
<212> TYPE: PRT
<213> ORGANISM: Thlaspi arvense

<400> SEQUENCE: 152

Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Gly
                85                  90                  95

Asp Pro Gly Ser Ser Cys Phe Gly Gln Ser Leu Arg Val Tyr Ser Thr
            100                 105                 110

Ser Thr Ser
        115

<210> SEQ ID NO 153
<211> LENGTH: 1360
<212> TYPE: DNA
<213> ORGANISM: Thlaspi arvense

<400> SEQUENCE: 153
atgggttcac tttcaaacac tcctcagctt ccagtcatct acctctcgga ccaaacccta 60
aaaccaggaa gctcaaagtg ggttgaagtc aggagtgatg tccgtaaagc tcttgaagag 120
tacggcggtt tcgaggtgtc gtacgataga gtgtcggagg agcttaagaa gtcggttttg 180
caagccatgg aagagctttt cgcgttacca gttgaggcta aacagagaaa cgtctctcct 240
aaacccttca gcggttattc cactcataac ggtctttccg agagggatcc aggatcctca 300
tgttttggac aaagtttacg agtttactca acttctacgt cctgatcatt gtgacggtaa 360
caagagcatc agcgaaacga tccagacgtt ttcagagaag ttatcagaat tggatataat 420
ggtgagaaga atggtaatgg aaagcttcgg gatagagaag taccttgaca aacacctgaa 480

```
ctcaacgaat taccgtctgc ggctgatgaa gtatatagca ccgcctgatg ctgatgctac    540

taatgttgcg gctgatgcca aagatgctga tgataatgct aagacgatta caaatgataa    600

agttgatgcg gctggtgcta atgatgtaga tgctggtgat atcgctaatg gtattgctaa    660

tcttcatatt ggtgatgatg ctaacgctgg tgctaatggt gctggtgttg atgctaatga    720

tggtggtgag gatgctaaga ctggtgagga tgctaagact ggtgaatgtg ctagtgttaa    780

gtctaatgcc gaagatggta ctgatgttaa tgccagtgct gatgctggtg ttactgttgg    840

ctctaatgct gatgctaatg ctaatgctaa tgctaatact agtactgatg ctggtgttgg    900

cgatagtgtt aaagctaatg gtggtgctga tgatgttgag aagaaattgg gtctaccttc    960

tcacactgat aagaacctta taacggtgct ttatcaatac gagattgaag gcttggaggt   1020

tctaaccaaa gatgacaagt ggatcagact caaaccatct cataattctt tcgttgttat   1080

ggctggagat tctctatacg cacttatgaa tggtagacta actcgtccct ttcatcgagt   1140

aagagtaacg gagaaaaaga agacaagata ttcaatagca ttgttctcgg ctccaaccgc   1200

agattacatc atagacacac caaaagaact tgtggacgag aagcatccac gtatcttcga   1260

accatttaac tataacgact tgatgagttt ctatcatagt gaagctggtc gtaaagctcg   1320

atctactctt gatgctttct gtgccgtctc tcgagcataa                         1360
```

<210> SEQ ID NO 154
<211> LENGTH: 114
<212> TYPE: PRT
<213> ORGANISM: Thlaspi arvense

<400> SEQUENCE: 154

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Arg Asp
                85                  90                  95

Pro Gly Ser Ser Cys Phe Gly Gln Ser Leu Arg Val Tyr Ser Thr Ser
            100                 105                 110

Thr Ser
```

<210> SEQ ID NO 155
<211> LENGTH: 1366
<212> TYPE: DNA
<213> ORGANISM: Thlaspi arvense

<400> SEQUENCE: 155

```
atgggttcac tttcaaacac tcctcagctt ccagtcatct acctctcgga ccaaacccta     60

aaaccaggaa gctcaaagtg ggttgaagtc aggagtgatg tccgtaaagc tcttgaagag    120

tacggcggtt tcgaggtgtc gtacgataga gtgtcggagg agcttaagaa gtcggttttg    180

caagccatgg aagagctttt cgcgttacca gttgaggcta aacagagaaa cgtctctcct    240

aaacccttca gcggttattc cactcataac ggtctttccg agagttatgg ggatccagga    300
```

```
tcctcatgtt ttggacaaag tttacgagtt tactcaactt ctacgtcctg atcattgtga    360

cggtaacaag agcatcagcg aaacgatcca gacgttttca gagaagttat cagaattgga    420

tataatggtg agaagaatgg taatggaaag cttcgggata gagaagtacc ttgacaaaca    480

cctgaactca acgaattacc gtctgcggct gatgaagtat atagcaccgc ctgatgctga    540

tgctactaat gttgcggctg atgccaaaga tgctgatgat aatgctaaga cgattacaaa    600

tgataaagtt gatgcggctg gtgctaatga tgtagatgct ggtgatatcg ctaatggtat    660

tgctaatctt catattggtg atgatgctaa cgctggtgct aatggtgctg gtgttgatgc    720

taatgatggt ggtgaggatg ctaagactgg tgaggatgct aagactggtg aatgtgctag    780

tgttaagtct aatgccgaag atggtactga tgttaatgcc agtgctgatg ctggtgttac    840

tgttggctct aatgctgatg ctaatgctaa tgctaatgct aatactagta ctgatgctgg    900

tgttggcgat agtgttaaag ctaatggtgg tgctgatgat gttgagaaga aattgggtct    960

accttctcac actgataaga accttataac ggtgctttat caatacgaga ttgaaggctt   1020

ggaggttcta accaaagatg acaagtggat cagactcaaa ccatctcata attctttcgt   1080

tgttatggct ggagattctc tatacgcact tatgaatggt agactaactc gtccctttca   1140

tcgagtaaga gtaacggaga aaaagaagac aagatattca atagcattgt tctcggctcc   1200

aaccgcagat tacatcatag acacaccaaa agaacttgtg gacgagaagc atccacgtat   1260

cttcgaacca tttaactata acgacttgat gagtttctat catagtgaag ctggtcgtaa   1320

agctcgatct actcttgatg ctttctgtgc cgtctctcga gcataa                  1366
```

<210> SEQ ID NO 156
<211> LENGTH: 116
<212> TYPE: PRT
<213> ORGANISM: Thlaspi arvense

<400> SEQUENCE: 156

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Tyr
                85                  90                  95

Gly Asp Pro Gly Ser Ser Cys Phe Gly Gln Ser Leu Arg Val Tyr Ser
            100                 105                 110

Thr Ser Thr Ser
        115
```

<210> SEQ ID NO 157
<211> LENGTH: 1357
<212> TYPE: DNA
<213> ORGANISM: Thlaspi arvense

<400> SEQUENCE: 157

```
atgggttcac tttcaaacac tcctcagctt ccagtcatct acctctcgga ccaaacccta     60

aaaccaggaa gctcaaagtg ggttgaagtc aggagtgatg tccgtaaagc tcttgaagag    120
```

```
tacggcggtt tcgaggtgtc gtacgataga gtgtcggagg agcttaagaa gtcggttttg    180

caagccatgg aagagctttt cgcgttacca gttgaggcta aacagagaaa cgtctctcct    240

aaacccttca gcggttattc cactcataac ggtctttctg gggatccagg atcctcatgt    300

tttggacaaa gtttacgagt ttactcaact tctacgtcct gatcattgtg acggtaacaa    360

gagcatcagc gaaacgatcc agacgttttc agagaagtta tcagaattgg atataatggt    420

gagaagaatg gtaatggaaa gcttcgggat agagaagtac cttgacaaac acctgaactc    480

aacgaattac cgtctgcggc tgatgaagta tatagcaccg cctgatgctg atgctactaa    540

tgttgcggct gatgccaaag atgctgatga taatgctaag acgattacaa atgataaagt    600

tgatgcggct ggtgctaatg atgtagatgc tggtgatatc gctaatggta ttgctaatct    660

tcatattggt gatgatgcta acgctggtgc taatggtgct ggtgttgatg ctaatgatgg    720

tggtgaggat gctaagactg gtgaggatgc taagactggt gaatgtgcta gtgttaagtc    780

taatgccgaa gatggtactg atgttaatgc cagtgctgat gctggtgtta ctgttggctc    840

taatgctgat gctaatgcta atgctaatgc taatactagt actgatgctg gtgttggcga    900

tagtgttaaa gctaatggtg gtgctgatga tgttgagaag aaattgggtc taccttctca    960

cactgataag aaccttataa cggtgcttta tcaatacgag attgaaggct tggaggttct   1020

aaccaaagat gacaagtgga tcagactcaa accatctcat aattctttcg ttgttatggc   1080

tggagattct ctatacgcac ttatgaatgg tagactaact cgtccctttc atcgagtaag   1140

agtaacggag aaaaagaaga caagatattc aatagcattg ttctcggctc caaccgcaga   1200

ttacatcata gacacaccaa aagaacttgt ggacgagaag catccacgta tcttcgaacc   1260

atttaactat aacgacttga tgagtttcta tcatagtgaa gctggtcgta aagctcgatc   1320

tactcttgat gctttctgtg ccgtctctcg agcataa                             1357
```

<210> SEQ ID NO 158
<211> LENGTH: 39
<212> TYPE: PRT
<213> ORGANISM: Thlaspi arvense

<400> SEQUENCE: 158

```
Met Phe Trp Thr Lys Phe Thr Ser Leu Leu Asn Phe Tyr Val Leu Ile
1               5                   10                  15

Ile Val Thr Val Thr Arg Ala Ser Ala Lys Arg Ser Arg Arg Phe Gln
            20                  25                  30

Arg Ser Tyr Gln Asn Trp Ile
        35
```

<210> SEQ ID NO 159
<211> LENGTH: 1818
<212> TYPE: DNA
<213> ORGANISM: Thlaspi arvense

<400> SEQUENCE: 159

```
atgaacgact acttcctcaa ccagtcaaca gccaccgacg ataacgcgtc ggcggcgatg     60

gaagctttca tcggaacaaa tcactcaact ctctggcccc aaccatctct tcctcctcct    120

cctccactat ctcaattcaa cgaagacact cttcaacaac gtctccaagc tttgatcgaa    180

tcagcaggag aaggctggac ctacgcgatt ttctggcaga tctcacacga tttcgattct    240

tccaccggag acaacacagt gattctcgga tggggagatg ggtactacaa aggggaggaa    300

gataaagaga agaagaagaa tagctcaagt tcgaattcgg cggagcaaga gcatcggaaa    360
```

agagtaatcc gtgagctgaa ttcgttgatc tccggcggaa ccggagtttc cgatgaatcg 420
aacgacgaag aagtcaccga tactgagtgg ttcttcttgg tctcgatgac acagagcttc 480
atgaacggcg ttgggcttcc cggggagtcg tacttgaact ctcgcgtgat ttggttatcc 540
gggccgggtg ctttaatcgg gtcgggttgc gaacgagcgg gtcaaggtca gatatacggg 600
ttacagacga tggtgtgtat cgcggcggag aacggcgtcg ttgagcttgg ttcatcggag 660
gtgttaagcc atagctcaga tctgatggat aaagtcaaca gtctgttcaa ttccaacaac 720
ggtaatggag aagcttcttc ttgggggttt aatctgaatc cggatcaagg agagaacgat 780
ccggctttgt ggataagcga accgaccacc accggaatcg aatcgggtca ggtaatcccg 840
gcgataaaca acagtaattc caattcaaat tcaaaatccg attctcatca aatctccaag 900
ctcgagaaga acgagagctc gattgaaaac cctagacaac aacaaaatcc gtcgcttgta 960
gagcgagatt tgaatttctc gagttctggg ttgaatcaaa acgggaactt tcaagatggg 1020
tcgtcgcgga tgatgaaatc gaacgaaaca ctgagcttta cggcggagga gagcaacaag 1080
aggaggtctc cggtttcgaa agggagtaac aacgacgaag ggatgctttc tttcagcacc 1140
gtggttcgtt ccgcggcgaa atccgtcgat tcggatcatt ccgatctcga agcgtcggtg 1200
gttaaggaag caattgtcgt tgaaccggag aagaaaccga ggaaacgggg aagaaaaccg 1260
gcgaacggaa gagaggagcc gttgaatcac gtggaagcag agagacagag aagggagaag 1320
ctaaaccaga gattctactc tttgagagct gtggttccca acgtttcgaa aatggacaaa 1380
gcgtctcttc tcggagacgc catttcgtat atcaacgagc ttaaatcgaa gctgcagcaa 1440
gcggaatccg ataaggaaga gattcagaag cagctcgacg ggatgagcaa ggaaggaaac 1500
agggaaggcg gcggcggaac gaaggcgaaa gaacgaaaat gctcgaatca agattcggct 1560
agctcgatag aaatggagat cgacgtgaag atcataggtt gggatgtgat gatacgtgta 1620
caatgcagca agaagaatca tcccggggca agattcatgg aagcgctcaa ggaattggat 1680
ctggaagtga atcacgcaag tttgtcagtg gtgaatgatt tgatgattca acaagccact 1740
gtgaagatgg gaagccagtt tttcaatcat gaccagctca aggttgcttt gatgtcgaaa 1800
gtcggagaag acaattga 1818

<210> SEQ ID NO 160
<211> LENGTH: 1818
<212> TYPE: DNA
<213> ORGANISM: Thlaspi arvense

<400> SEQUENCE: 160
atgaacgact acttcctcaa ccagtcaaca gccaccgacg ataacgcgtc ggcggcgatg 60
gaagctttca tcggaacaaa tcactcaact ctctggcccc aaccatctct tcctcctcct 120
cctccactat ctcaattcaa cgaagacact cttcaacaac gtctccaagc tttgatcgaa 180
tcagcaggag aaggctggac ctacgcgatt ttctggcaga tctcacacga tttcgattct 240
tccaccggag acaacacagt gattctcgga tggggagatg ggtactacaa aggggaggaa 300
gataaagaga agaagaagaa tagctcaagt tcgaattcgg cggagcaaga gcatcggaaa 360
agagtaatcc gtgagctgaa ttcgttgatc tccggcggaa ccggagtttc cgatgaatcg 420
aacgacgaag aagtcaccga tactgagtgg ttcttcttgg tctcgatgac acagagcttc 480
atgaacggcg ttgggcttcc cggggagtcg tacttgaact ctcgcgtgat ttggttatcc 540
gggccgggtg ctttaatcgg gtcgggttgc gaacgagcgg gtcaaggtca gatatacggg 600

-continued

```
ttacagacga tggtgtgtat cgcggcggag aacggcgtcg ttgagcttgg ttcatcggag    660

gtgttaagcc atagctcaga tctgatggat aaagtcaaca gtctgttcaa ttccaacaac    720

ggtaatggag aagcttcttc ttgggggttt aatctgaatc cggatcaagg agagaacgat    780

ccggctttgt ggataagcga accgaccacc accggaatcg aatcgggtca ggtaatcccg    840

gcgataaaca acagtaattc caattcaaat tcaaaatccg attctcatca aatctccaag    900

ctcgagaaga acgagagctc gattgaaaac cctagacaac aacaaaatcc gtcgcttgta    960

gagcgagatt tgaatttctc gagttctggg ttgaatcaaa acgggaactt tcaagatggg   1020

tcgtcgcgga tgatgaaatc gaacgaaaca ctgagcttta cggcggagga gagcaacaag   1080

aggaggtctc cggtttcgaa agggagtaac aacgacgaag ggatgctttc tttcagcacc   1140

gtggttcgtt ccgcggcgaa atccgtcgat tcggatcatt ccgatctcga agcgtcggtg   1200

gttaaggaag caattgtcgt tgaaccggag aagaaaccga ggaaacgggg aagaaaaccg   1260

gcgaacggaa gagaggagcc gttgaatcac gtggaagcag agagacagag aagggagaag   1320

ctaaaccaga gattctactc tttgagagct gtggttccca acgtttcgaa aatggacaaa   1380

gcgtctcttc tcggagacgc catttcgtat atcaacgagc ttaaatcgaa gctgcagcaa   1440

gcggaatccg ataaggaaga gattcagaag cagctcgacg ggatgagcaa ggaaggaaac   1500

agggaaggcg gcggcggaac gaaggcgaaa gaacgaaaat gctcgaatca agattcggct   1560

agctcgatag aaatggagat cgacgtgaag atcataggtt gggatgtgat gatacgtgta   1620

caatgcagca agaagaatca tcccggggca agattcatgg aagcgctcaa ggaattggat   1680

ctggaagtga atcacgcaag tttgtcagtg gtgaatgatt tgatgattca acaagccact   1740

gtgaagatgg gaagccagtt tttcaatcat gaccagctca aggttgcttt gatgtcgaaa   1800

gtcggagaag acaattga                                                 1818
```

<210> SEQ ID NO 161
<211> LENGTH: 605
<212> TYPE: PRT
<213> ORGANISM: Thlaspi arvense

<400> SEQUENCE: 161

```
Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile Ser His Asp Phe Asp Ser
65                  70                  75                  80

Ser Thr Gly Asp Asn Thr Val Ile Leu Gly Trp Gly Asp Gly Tyr Tyr
                85                  90                  95

Lys Gly Glu Glu Asp Lys Glu Lys Lys Lys Asn Ser Ser Ser Ser Asn
            100                 105                 110

Ser Ala Glu Gln Glu His Arg Lys Arg Val Ile Arg Glu Leu Asn Ser
        115                 120                 125

Leu Ile Ser Gly Gly Thr Gly Val Ser Asp Glu Ser Asn Asp Glu Glu
    130                 135                 140

Val Thr Asp Thr Glu Trp Phe Phe Leu Val Ser Met Thr Gln Ser Phe
145                 150                 155                 160
```

```
Met Asn Gly Val Gly Leu Pro Gly Glu Ser Tyr Leu Asn Ser Arg Val
                165                 170                 175

Ile Trp Leu Ser Gly Pro Gly Ala Leu Ile Gly Ser Gly Cys Glu Arg
            180                 185                 190

Ala Gly Gln Gly Gln Ile Tyr Gly Leu Gln Thr Met Val Cys Ile Ala
        195                 200                 205

Ala Glu Asn Gly Val Val Glu Leu Gly Ser Ser Glu Val Leu Ser His
    210                 215                 220

Ser Ser Asp Leu Met Asp Lys Val Asn Ser Leu Phe Asn Ser Asn Asn
225                 230                 235                 240

Gly Asn Gly Glu Ala Ser Ser Trp Gly Phe Asn Leu Asn Pro Asp Gln
                245                 250                 255

Gly Glu Asn Asp Pro Ala Leu Trp Ile Ser Glu Pro Thr Thr Thr Gly
            260                 265                 270

Ile Glu Ser Gly Gln Val Ile Pro Ala Ile Asn Asn Ser Asn Ser Asn
        275                 280                 285

Ser Asn Ser Lys Ser Asp Ser His Gln Ile Ser Lys Leu Glu Lys Asn
    290                 295                 300

Glu Ser Ser Ile Glu Asn Pro Arg Gln Gln Gln Asn Pro Ser Leu Val
305                 310                 315                 320

Glu Arg Asp Leu Asn Phe Ser Ser Ser Gly Leu Asn Gln Asn Gly Asn
                325                 330                 335

Phe Gln Asp Gly Ser Ser Arg Met Met Lys Ser Asn Glu Thr Leu Ser
            340                 345                 350

Phe Thr Ala Glu Glu Ser Asn Lys Arg Arg Ser Pro Val Ser Lys Gly
        355                 360                 365

Ser Asn Asn Asp Glu Gly Met Leu Ser Phe Ser Thr Val Val Arg Ser
    370                 375                 380

Ala Ala Lys Ser Val Asp Ser Asp His Ser Asp Leu Glu Ala Ser Val
385                 390                 395                 400

Val Lys Glu Ala Ile Val Val Glu Pro Glu Lys Lys Pro Arg Lys Arg
                405                 410                 415

Gly Arg Lys Pro Ala Asn Gly Arg Glu Glu Pro Leu Asn His Val Glu
            420                 425                 430

Ala Glu Arg Gln Arg Arg Glu Lys Leu Asn Gln Arg Phe Tyr Ser Leu
        435                 440                 445

Arg Ala Val Val Pro Asn Val Ser Lys Met Asp Lys Ala Ser Leu Leu
    450                 455                 460

Gly Asp Ala Ile Ser Tyr Ile Asn Glu Leu Lys Ser Lys Leu Gln Gln
465                 470                 475                 480

Ala Glu Ser Asp Lys Glu Glu Ile Gln Lys Gln Leu Asp Gly Met Ser
                485                 490                 495

Lys Glu Gly Asn Arg Glu Gly Gly Gly Gly Thr Lys Ala Lys Glu Arg
            500                 505                 510

Lys Cys Ser Asn Gln Asp Ser Ala Ser Ser Ile Glu Met Glu Ile Asp
        515                 520                 525

Val Lys Ile Ile Gly Trp Asp Val Met Ile Arg Val Gln Cys Ser Lys
    530                 535                 540

Lys Asn His Pro Gly Ala Arg Phe Met Glu Ala Leu Lys Glu Leu Asp
545                 550                 555                 560

Leu Glu Val Asn His Ala Ser Leu Ser Val Val Asn Asp Leu Met Ile
                565                 570                 575
```

Gln Gln Ala Thr Val Lys Met Gly Ser Gln Phe Phe Asn His Asp Gln
580 585 590

Leu Lys Val Ala Leu Met Ser Lys Val Gly Glu Asp Asn
595 600 605

<210> SEQ ID NO 162
<211> LENGTH: 1332
<212> TYPE: DNA
<213> ORGANISM: Thlaspi arvense

<400> SEQUENCE: 162
atggcggcgt gtttacaatc gaacatccgg ctgaatctga acaatatcgt cggaggaaaa 60
tgcagatccc tcaccgatca gtctcgcacg ccgtgtcgaa taaggtgcgc cgccgcttca 120
cctgggaaaa aacggttcaa catcgctctc cttcctggcg acggtatcgg tcctgaagtc 180
atctccgttg ccaagaatgt gcttcagcaa gctggatctc tcgaaggttc ttctatctct 240
cgctcagttt atttactaat tttgacaaaa ttagtaatca gcgaatgtgt tgcttaccca 300
gaagagtgtg cgtatttgat gtgtatcaca ggactggagt tcaatttcca ggagatgccc 360
atcggaggag cagccttgga tttggtcgga gtggccttgc cggaggaaac cttatcggct 420
gcaaaacagt ctgatgccat acttcttgga gctatcggag ggtacaaatg ggacaacaat 480
gagaaacatc tgagacctga gatggctctg atttaccttc ggagagatct caaagtcttt 540
gctaatctga gacctgcttc agttttgcca cagctagttg atgcatccac cttgaagaga 600
gaagtagcag aaggtgttga tatgatgatt gtaagggagc ttacaggagg aatttacttt 660
ggagagccca gaggcattaa gaccaacgaa aacggagaag aagtcggttt taatacagag 720
ttttacgctg ctcacgagat tgacagaatt gctcgtgttg catttgagac tgctaggaaa 780
cggcgtggca agctgtgttc tgtcgacaaa gccaatgtgt tggatgcatc agtattgtgg 840
aggagaagag taacagcgtt agcctctgag tatccagatg ttgagctctc acatatgtat 900
gtagacaacg ctgcaatgca gcttattcgt gacccgaaac agtttgacac aatcgtcacc 960
aataacattt tcggtgacat attatccgat gaggcctcaa tgatcactgg aagcattggg 1020
atgcttccat ctgctagtct cggtgtatcg ggacctggac tctttgagcc gatacatggt 1080
tctgcgccag atatagctgg tcaggacaag gcaaacccat tggccaccat tctcagcgca 1140
gcgatgcttc tgaaatatgg acttggagaa gagaaggccg caaagaggat cgaggacgcg 1200
gtcttggatg ctctcaacaa agggtttaga accggagaca tctactcccc cggaaataaa 1260
ctggtgggat gcaaggagat gggtgaggag gtgcttaaat cagtggactc cagagttaca 1320
gctactgttt aa 1332

<210> SEQ ID NO 163
<211> LENGTH: 1936
<212> TYPE: DNA
<213> ORGANISM: Thlaspi arvense

<400> SEQUENCE: 163
atggcggcgt gtttacaatc gaacatccgg ctgaatctga acaatatcgt cggaggaaaa 60
tgcagatccc tcaccgatca gtctcgcacg ccgtgtcgaa taaggtgcgc cgccgcttca 120
cctgggaaaa aacggttcaa catcgctctc cttcctggcg acggtatcgg tcctgaagtc 180
atctccgttg ccaagaatgt gcttcagcaa gctggatctc tcgaaggttc ttctatctct 240
cgctcagttt atttactaat tttgacaaaa ttagtaatca gcgaatgtgt tgcttaccca 300
gaagagtgtg cgtatttgat gtgtatcaca ggactggagt tcaatttcca ggagatgccc 360

```
atcggaggag cagccttgga tttggtcgga gtggccttgc cggaggaaac cttatcggct    420
gcaaaacagt ctgatgccat acttcttgga gctatcggag ggtgtgtgtt tgtgtgtctt    480
gtttcttttt ttaattggtc tcttggttca gaaatctgtc tgcttcgagt cttcttctca    540
gcttgagttt tttggatgat tcatggttgg ttggattata ttcaggtaca aatgggacaa    600
caatgagaaa catctgagac ctgagatggc tctgatttac cttcggagag atctcaaagt    660
ctttgctaat ctgagacctg cttcagtttt gccacaggta tatatatata tatatatata    720
tataaacgtt tatctaattc ggtttgatct gcttaccact tgcaattttt acaatcactt    780
gcttgttgtt ctcagctagt tgatgcatcc accttgaaga gagaagtagc agaaggtgtt    840
gatatgatga ttgtaaggga gcttacagga ggaatttact ttggagagcc cagaggcatt    900
aagaccaacg aaaacggaga agaagtcggt tttaatacag agttttacgc tgctcacgag    960
gtcacatact cttcacagtg tggtctatga tatgatgggt ctaaggctat atatgtataa   1020
tataatgcat taattgctca tgttacttcc agattgacag aattgctcgt gttgcatttg   1080
agactgctag gaaacggcgt ggcaagctgt gttctgtcga caaagccaat gtgttggatg   1140
tacgtttgat caacaatttt ttccatttct gtgtgtgtgt gttttttttt ctcgtaatgc   1200
agaattattt ttttcatata ggcatcagta ttgtggagga gaagagtaac agcgttagcc   1260
tctgagtatc cagatgttga gctctcacat atgtatgtag acaacgctgc aatgcagctt   1320
attcgtgacc cgaaacagtt tgacacaatc gtcaccaata acatttttcgg tgacatatta   1380
tccgatgagg cctcaatgat cactggaagc attgggatgc ttccatctgc tagtctcggt   1440
gtatcggtaa ccaacaaatt taaactgaaa atctttcaag gttcctccct gtttattacc   1500
atatatacac atggaatgtt gaaacttgtg tttggatcag ggacctggac tctttgagcc   1560
gatacatggt tctgcgccag atatagctgg tcaggacaag gcaaacccat tggccaccat   1620
tctcagcgca gcgatgcttc tgaaatatgg acttggagaa gagaaggccg caaagaggat   1680
cgaggacgcg gtcttggatg ctctcaacaa agggtttaga accggagaca tctactcccc   1740
cggaaatgta tgttttgatg gtatttttat catttgctta tataataagt taaacaacaa   1800
acagttagta gtatattata tacttttgtg ttattttaat gaaatttgga atgtgaagca   1860
gaaactggtg ggatgcaagg agatgggtga ggaggtgctt aaatcagtgg actccagagt   1920
tacagctact gtttaa                                                   1936
```

<210> SEQ ID NO 164
<211> LENGTH: 443
<212> TYPE: PRT
<213> ORGANISM: Thlaspi arvense

<400> SEQUENCE: 164

```
Met Ala Ala Cys Leu Gln Ser Asn Ile Arg Leu Asn Leu Asn Asn Ile
1               5                   10                  15

Val Gly Gly Lys Cys Arg Ser Leu Thr Asp Gln Ser Arg Thr Pro Cys
            20                  25                  30

Arg Ile Arg Cys Ala Ala Ala Ser Pro Gly Lys Lys Arg Phe Asn Ile
        35                  40                  45

Ala Leu Leu Pro Gly Asp Gly Ile Gly Pro Glu Val Ile Ser Val Ala
    50                  55                  60

Lys Asn Val Leu Gln Gln Ala Gly Ser Leu Glu Gly Ser Ser Ile Ser
65                  70                  75                  80

Arg Ser Val Tyr Leu Leu Ile Leu Thr Lys Leu Val Ile Ser Glu Cys
```

-continued

```
                85                  90                  95

Val Ala Tyr Pro Glu Glu Cys Ala Tyr Leu Met Cys Ile Thr Gly Leu
            100                 105                 110

Glu Phe Asn Phe Gln Glu Met Pro Ile Gly Gly Ala Ala Leu Asp Leu
        115                 120                 125

Val Gly Val Ala Leu Pro Glu Glu Thr Leu Ser Ala Ala Lys Gln Ser
    130                 135                 140

Asp Ala Ile Leu Leu Gly Ala Ile Gly Gly Tyr Lys Trp Asp Asn Asn
145                 150                 155                 160

Glu Lys His Leu Arg Pro Glu Met Ala Leu Ile Tyr Leu Arg Arg Asp
                165                 170                 175

Leu Lys Val Phe Ala Asn Leu Arg Pro Ala Ser Val Leu Pro Gln Leu
            180                 185                 190

Val Asp Ala Ser Thr Leu Lys Arg Glu Val Ala Glu Gly Val Asp Met
        195                 200                 205

Met Ile Val Arg Glu Leu Thr Gly Gly Ile Tyr Phe Gly Glu Pro Arg
    210                 215                 220

Gly Ile Lys Thr Asn Glu Asn Gly Glu Glu Val Gly Phe Asn Thr Glu
225                 230                 235                 240

Phe Tyr Ala Ala His Glu Ile Asp Arg Ile Ala Arg Val Ala Phe Glu
                245                 250                 255

Thr Ala Arg Lys Arg Arg Gly Lys Leu Cys Ser Val Asp Lys Ala Asn
            260                 265                 270

Val Leu Asp Ala Ser Val Leu Trp Arg Arg Arg Val Thr Ala Leu Ala
        275                 280                 285

Ser Glu Tyr Pro Asp Val Glu Leu Ser His Met Tyr Val Asp Asn Ala
    290                 295                 300

Ala Met Gln Leu Ile Arg Asp Pro Lys Gln Phe Asp Thr Ile Val Thr
305                 310                 315                 320

Asn Asn Ile Phe Gly Asp Ile Leu Ser Asp Glu Ala Ser Met Ile Thr
                325                 330                 335

Gly Ser Ile Gly Met Leu Pro Ser Ala Ser Leu Gly Val Ser Gly Pro
            340                 345                 350

Gly Leu Phe Glu Pro Ile His Gly Ser Ala Pro Asp Ile Ala Gly Gln
        355                 360                 365

Asp Lys Ala Asn Pro Leu Ala Thr Ile Leu Ser Ala Ala Met Leu Leu
    370                 375                 380

Lys Tyr Gly Leu Gly Glu Glu Lys Ala Ala Lys Arg Ile Glu Asp Ala
385                 390                 395                 400

Val Leu Asp Ala Leu Asn Lys Gly Phe Arg Thr Gly Asp Ile Tyr Ser
                405                 410                 415

Pro Gly Asn Lys Leu Val Gly Cys Lys Glu Met Gly Glu Glu Val Leu
            420                 425                 430

Lys Ser Val Asp Ser Arg Val Thr Ala Thr Val
        435                 440


<210> SEQ ID NO 165
<211> LENGTH: 1635
<212> TYPE: DNA
<213> ORGANISM: Thlaspi arvense

<400> SEQUENCE: 165

atggatactt tagcttcaaa ctcttcgggt ctcaggacca agtcgagtcc cgagacgtcg      60

ccgtttagca acatgtatct cctcacaaca cttcaagccc ttgcggttat ttctctcttg     120
```

-continued atgatattca agaaaataaa gtattcctct tcacaaaaaa aaaagtttca tcctctcccg 180
ccgggcccca gcgggtttcc agtcgtcgga atgattccgg cgatgcttaa aaaccgtccg 240
gttttccggt ggcttcacag cctcatgaaa gagcttaaca cggagatagc ttgtgttcgt 300
ctaggaaaga ctcacgtgat ccccgtcaca tgtcctaaga tcgcacgtga gattttcaag 360
caacaagacg cactcttcgc gtcgagacca ctcacttatg ctcaaaagat actttccaac 420
ggctacaaaa cctgcgtgat cacaccgttc ggagaacaat tcaagaagat gaggaaagta 480
atcatgacgg agattgtttg tccagcaaga caccgatggt tacacgacaa cagagccgag 540
gaaaccgatc atttaactgc ttggctttac aacatggtta agaaatccga accggtcgat 600
ctccggtttg ttacaaggca ctactgcgga aatgcgatta agaggcttat gttcggaacg 660
aggacgttct cggcgaaaac cgaaaccgac ggtggaccaa ccgtggaaga tatcgagcat 720
atggatgcta tgtttgaagg gttagggttt acgtttgcgt tctgtgtatc ggattatcta 780
ccgatgctta cgggattgga tctaaacgga catgagaaga tcatgagaga agctagtgcg 840
attatggaca aatatcacga tcccattatt gatgagagga ttaagatgtg gagagaagga 900
aagagaactc agattgaaga ttttctagac attttcatct ctatcaagga cgaagctggc 960
cagcctttgc ttaccgctga tgaaatcaaa ccaaccatta aggaacttgt aatggcggcg 1020
ccggacaacc catcaaacgc cgtggaatgg gccatggcgg agatgataaa caaacctgag 1080
attctccaca aagcaatgga agagattgaa agagtcgttg gcaaagaaag actcgtccaa 1140
gaatccgata tcccaaaact taactatctc aaagctatta tccgagaagc tttccgtctg 1200
catcccgtcg ccgccttcaa cctcccacac gtggcacttt ccgacacaac cgtcgctggt 1260
tatcacatcc ctaaggggag tcaagtttta cttagccgtt acggtcttgg tcgtaaccca 1320
aaggtttggt ctgatccact tagctttaaa ccggagagac acctcaatga gtgcttggaa 1380
gtaacgttga ctgagaatga tctccggttt atctcgttta gtaccggaaa aagaggatgt 1440
gctgctccgg cgttaggtac ggcgataacc gtcatgatgc tcgccaggct tttgcaaggg 1500
tttaagtgga agttagctgg aggtgagaca cgtgttgagt tgatggaatc gagtcatgat 1560
atgtttcttg cgacgccttt ggttatggtc ggagaattga gattgtcgga ggatctttac 1620
cccacggtga agtga 1635

<210> SEQ ID NO 166
<211> LENGTH: 2050
<212> TYPE: DNA
<213> ORGANISM: Thlaspi arvense

<400> SEQUENCE: 166
atggatactt tagcttcaaa ctcttcgggt ctcaggacca agtcgagtcc cgagacgtcg 60
ccgtttagca acatgtatct cctcacaaca cttcaagccc ttgcggttat ttctctcttg 120
atgatattca agaaaataaa gtattcctct tcacaaaaaa aaaagtttca tcctctcccg 180
ccgggcccca gcgggtttcc agtcgtcgga atgattccgg cgatgcttaa aaaccgtccg 240
gttttccggt ggcttcacag cctcatgaaa gagcttaaca cggagatagc ttgtgttcgt 300
ctaggaaaga ctcacgtgat ccccgtcaca tgtcctaaga tcgcacgtga gattttcaag 360
caacaagacg cactcttcgc gtcgagacca ctcacttatg ctcaaaagat actttccaac 420
ggctacaaaa cctgcgtgat cacaccgttc ggagaacaat tcaagaagat gaggaaagta 480
atcatgacgg agattgtttg tccagcaaga caccgatggt tacacgacaa cagagccgag 540

```
gaaaccgatc atttaactgc ttggctttac aacatggtta agaaatccga accggtcgat    600
ctccggtttg ttacaaggca ctactgcgga aatgcgatta agaggcttat gttcggaacg    660
aggacgttct cggcgaaaac cgaaaccgac ggtggaccaa ccgtggaaga tatcgagcat    720
atggatgcta tgtttgaagg gttagggttt acgtttgcgt tctgtgtatc ggattatcta    780
ccgatgctta cgggattgga tctaaacgga catgagaaga tcatgagaga agctagtgcg    840
attatggaca aatatcacga tcccattatt gatgagagga ttaagatgtg gagagaagga    900
aagagaactc agattgaaga ttttctagac attttcatct ctatcaagga cgaagctggc    960
cagcctttgc ttaccgctga tgaaatcaaa ccaaccatta aggtaactaa ttagatatat   1020
tgaattatat ttattagatt tcttgtcgac taattacgca tattacttat atgtttggat   1080
ttaatatagc agaactaagt ttattattag tattagcaat ttttaagatt aagtggtaaa   1140
aaagtggata caaatgtttt tggggggggg ttctagcgac aacctaagat tttaagttgt   1200
cgttaaaact tttttttttt ctgatttttt aaaaagggta aaacgccaaa acatccatag   1260
tcagaaactt tatgctaatc catagtcaga aactttatgc taatccatag tcagaaactt   1320
tatgtatagc ataaagttta tatttatgtt gacccgtgag tccatgcata gaatagtaaa   1380
acaataatta atcatttata tattttatat tgaataggaa cttgtaatgg cggcgccgga   1440
caacccatca aacgccgtgg aatgggccat ggcggagatg ataaacaaac ctgagattct   1500
ccacaaagca atggaagaga ttgaaagagt cgttggcaaa gaaagactcg tccaagaatc   1560
cgatatccca aaacttaact atctcaaagc tattatccga gaagctttcc gtctgcatcc   1620
cgtcgccgcc ttcaacctcc cacacgtggc actttccgac acaaccgtcg ctggttatca   1680
catccctaag ggagtcaag ttttacttag ccgttacggt cttggtcgta acccaaaggt   1740
ttggtctgat ccacttagct ttaaaccgga gagacacctc aatgagtgct tggaagtaac   1800
gttgactgag aatgatctcc ggtttatctc gtttagtacc ggaaaaagag gatgtgctgc   1860
tccggcgtta ggtacggcga taaccgtcat gatgctcgcc aggcttttgc aagggtttaa   1920
gtggaagtta gctggaggtg agacacgtgt tgagttgatg gaatcgagtc atgatatgtt   1980
tcttgcgacg cctttggtta tggtcggaga attgagattg tcggaggatc tttaccccac   2040
ggtgaagtga                                                          2050
```

```
<210> SEQ ID NO 167
<211> LENGTH: 544
<212> TYPE: PRT
<213> ORGANISM: Thlaspi arvense

<400> SEQUENCE: 167

Met Asp Thr Leu Ala Ser Asn Ser Ser Gly Leu Arg Thr Lys Ser Ser
1               5                   10                  15

Pro Glu Thr Ser Pro Phe Ser Asn Met Tyr Leu Leu Thr Thr Leu Gln
            20                  25                  30

Ala Leu Ala Val Ile Ser Leu Leu Met Ile Phe Lys Lys Ile Lys Tyr
        35                  40                  45

Ser Ser Ser Gln Lys Lys Lys Phe His Pro Leu Pro Pro Gly Pro Ser
    50                  55                  60

Gly Phe Pro Val Val Gly Met Ile Pro Ala Met Leu Lys Asn Arg Pro
65                  70                  75                  80

Val Phe Arg Trp Leu His Ser Leu Met Lys Glu Leu Asn Thr Glu Ile
                85                  90                  95

Ala Cys Val Arg Leu Gly Lys Thr His Val Ile Pro Val Thr Cys Pro
```

```
            100                 105                 110

Lys Ile Ala Arg Glu Ile Phe Lys Gln Gln Asp Ala Leu Phe Ala Ser
        115                 120                 125

Arg Pro Leu Thr Tyr Ala Gln Lys Ile Leu Ser Asn Gly Tyr Lys Thr
    130                 135                 140

Cys Val Ile Thr Pro Phe Gly Glu Gln Phe Lys Lys Met Arg Lys Val
145                 150                 155                 160

Ile Met Thr Glu Ile Val Cys Pro Ala Arg His Arg Trp Leu His Asp
                165                 170                 175

Asn Arg Ala Glu Glu Thr Asp His Leu Thr Ala Trp Leu Tyr Asn Met
            180                 185                 190

Val Lys Lys Ser Glu Pro Val Asp Leu Arg Phe Val Thr Arg His Tyr
        195                 200                 205

Cys Gly Asn Ala Ile Lys Arg Leu Met Phe Gly Thr Arg Thr Phe Ser
    210                 215                 220

Ala Lys Thr Glu Thr Asp Gly Gly Pro Thr Val Glu Asp Ile Glu His
225                 230                 235                 240

Met Asp Ala Met Phe Glu Gly Leu Gly Phe Thr Phe Ala Phe Cys Val
                245                 250                 255

Ser Asp Tyr Leu Pro Met Leu Thr Gly Leu Asp Leu Asn Gly His Glu
            260                 265                 270

Lys Ile Met Arg Glu Ala Ser Ala Ile Met Asp Lys Tyr His Asp Pro
        275                 280                 285

Ile Ile Asp Glu Arg Ile Lys Met Trp Arg Glu Gly Lys Arg Thr Gln
    290                 295                 300

Ile Glu Asp Phe Leu Asp Ile Phe Ile Ser Ile Lys Asp Glu Ala Gly
305                 310                 315                 320

Gln Pro Leu Leu Thr Ala Asp Glu Ile Lys Pro Thr Ile Lys Glu Leu
                325                 330                 335

Val Met Ala Ala Pro Asp Asn Pro Ser Asn Ala Val Glu Trp Ala Met
            340                 345                 350

Ala Glu Met Ile Asn Lys Pro Glu Ile Leu His Lys Ala Met Glu Glu
        355                 360                 365

Ile Glu Arg Val Val Gly Lys Glu Arg Leu Val Gln Glu Ser Asp Ile
    370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                405                 410                 415

Thr Val Ala Gly Tyr His Ile Pro Lys Gly Ser Gln Val Leu Leu Ser
            420                 425                 430

Arg Tyr Gly Leu Gly Arg Asn Pro Lys Val Trp Ser Asp Pro Leu Ser
        435                 440                 445

Phe Lys Pro Glu Arg His Leu Asn Glu Cys Leu Glu Val Thr Leu Thr
    450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
            500                 505                 510

Glu Leu Met Glu Ser Ser His Asp Met Phe Leu Ala Thr Pro Leu Val
        515                 520                 525
```

```
Met Val Gly Glu Leu Arg Leu Ser Glu Asp Leu Tyr Pro Thr Val Lys
    530                 535                 540


<210> SEQ ID NO 168
<211> LENGTH: 1188
<212> TYPE: DNA
<213> ORGANISM: Thlaspi arvense

<400> SEQUENCE: 168

atgatcacca ccacctgttg cactgtggtc gcccagttag gcttgccctt tggatcttcc     60

ttgtcctctc tctgcctgac ccgtccgaac aaaaagccgt ccttgttcac ctcatgttgc    120

tcctctgtgt ccaaaaatgt tggcgctagt gctgctgaca gcaaacacgt cgtggaacgg    180

tggccagagt acattccgaa taagctccct gacaagaact atgtgcgtat tttgacacg     240

acgctccgtg acggcgaaca agctcctggt gcagccctta ctccaccgca gaagctagag    300

attgcccggc agctcgctaa gctccgagta gacatcatgg aagttggttt ccctgggtcc    360

tctgaggaag agttcgaaac cgtcaagacc atcgccaaga ccgtagggaa cgaggtggat    420

gaggaaacag gctacgtccc agtgatatgc gccctcgcac gatgcaaaca tagagacatt    480

gaggcggttt gggaggcggt gaagtacgca aagaggcctt cgatactcat attcatatct    540

actagtgaca ttcatatgaa acataagttg aaaaagacta aagaagaagt catagagatg    600

gcagcaagta gtattaggtt tgctaagaac ttaggcttca atgacatcca attgggttgc    660

gaagatgccg gcaggtcgga taaggagttt ctatgcaaga ttctaggaga agcgatcaaa    720

gcgggtgcaa ccacgatgaa catggcagac acggtaggga tcaacatgcc ggaagaattt    780

ggagaactcg tgagctacct taaagccaac actcctggaa ttgacgatgt tgtcttaagc    840

gttcattgtc acaacgacct tggtgttgct accgccaacg caatcgccgg tgtgtgtgct    900

ggagcaagac aagttgacgt tacggtcaat ggaataggtg aaagatgtgg gaacgcgcca    960

cttgaagagg tcgtgatggc tttgaaatgc cgaggagcat acctgatgaa tggggtttac   1020

acaagaacag acatacgcca aattatggct actagcaaga tggttcagga atatactggc   1080

ttttatgttc aaccacataa gcccatagtt ggagccaaca gttttttca tgagagcagc   1140

gatgaatatg atggttgttc aaacattttg caggatatgg attattga               1188


<210> SEQ ID NO 169
<211> LENGTH: 1820
<212> TYPE: DNA
<213> ORGANISM: Thlaspi arvense

<400> SEQUENCE: 169

atgatcacca ccacctgttg cactgtggtc gcccagttag gcttgccctt tggatcttcc     60

ttgtcctctc tctgcctgac ccgtccgaac aaaaagccgt ccttgttcac ctcatgttgc    120

tcctctgtgt ccaaaaatgt tggcgctagt gctgctgaca gcaaacacgt cgtggaacgg    180

tggccagagt acattccgaa taagctccct gacaagaact atgtgcgtat tttgacacg     240

acgctccgtg acggcgaaca agctcctggt gcagccctta ctccaccgca gaagctagag    300

attgcccggc agctcgctaa gctccgagta gacatcatgg aagttggttt ccctgggtcc    360

tctgaggaag agttcgaaac cgtcaagacc atcgccaaga ccgtagggaa cgaggttgtt    420

tctctgtttc cttcattttc tagtataaaa atttctacgt tcctactgta tattcagtca    480

accttgtcgc tttggggaca tatgataata tttgaacgaa tattaacata gttttgacgc    540

aaatagtaca aacacaaatt gagtaaatct ccaaatttta ccatagttat atagtaaacg    600
```

```
attgatttga ttaggtggat gaggaaacag gctacgtccc agtgatatgc gccctcgcac    660

gatgcaaaca tagagacatt gaggcggttt gggaggcggt gaagtacgca aagaggcctt    720

cgatactcat attcatatct actagtgaca ttcatatgaa acataagttg aaaaagacta    780

aagaagaagt catagagatg gcagcaagta gtattaggtt tgctaagaac ttaggcttca    840

atgacatcca attgggttgc gaagatgccg gcaggtccat atcttaaaac cttaatatac    900

atatatagcc ttttgttaga taatgttaag gatttttgtg aataatgacc atgtcacaaa    960

aattctagcg tgtgattaaa actaagcagg tcggataagg agtttctatg caagattcta   1020

ggagaagcga tcaaagcggg tgcaaccacg atgaacatgg cagacacggt agggatcaac   1080

atgccggaag aatttggaga actcgtgagc taccttaaag ccaacactcc tggaattgac   1140

gatgttgtct taagcgttca ttgtcacaac gaccttggtg ttgctaccgc caacgcaatc   1200

gccgtatttt tctaaccctc tccttcatct catatattta aaatatctat ataaatacat   1260

atagatcatt attgcggtta tattatatac gtagggtgtg tgtgctggag caagacaagt   1320

tgacgttacg gtcaatggaa taggtgaaag atgtgggaac gcgccacttg aagaggtaaa   1380

agatcatgat tatcatcaag accgtcttac actatttgta ggatcggttc catattttta   1440

tatacggccc tgatccatca tcatcaattc atcaacaaca taaatatttt tttggtatgt   1500

ataggtcgtg atggctttga aatgccgagg agcatacctg atgaatgggg tttacacaag   1560

aacagacata cgccaaatta tggctactag caagatggta tttttacat taatttacac    1620

atggaaaaac gatcgtgcta gtttttttt tatatatgtt ggcattatag taatatatgt    1680

aaattcttga gcaggttcag gaatatactg gcttttatgt tcaaccacat aagcccatag   1740

ttggagccaa cagtttttt catgagagca gcgatgaata tgatggttgt tcaaacattt    1800

tgcaggatat ggattattga                                               1820
```

<210> SEQ ID NO 170
<211> LENGTH: 395
<212> TYPE: PRT
<213> ORGANISM: Thlaspi arvense

<400> SEQUENCE: 170

```
Met Ile Thr Thr Thr Cys Cys Thr Val Val Ala Gln Leu Gly Leu Pro
1               5                   10                  15

Phe Gly Ser Ser Leu Ser Ser Leu Cys Leu Thr Arg Pro Asn Lys Lys
            20                  25                  30

Pro Ser Leu Phe Thr Ser Cys Cys Ser Ser Val Ser Lys Asn Val Gly
        35                  40                  45

Ala Ser Ala Ala Asp Ser Lys His Val Val Glu Arg Trp Pro Glu Tyr
    50                  55                  60

Ile Pro Asn Lys Leu Pro Asp Lys Asn Tyr Val Arg Ile Phe Asp Thr
65                  70                  75                  80

Thr Leu Arg Asp Gly Glu Gln Ala Pro Gly Ala Ala Leu Thr Pro Pro
                85                  90                  95

Gln Lys Leu Glu Ile Ala Arg Gln Leu Ala Lys Leu Arg Val Asp Ile
            100                 105                 110

Met Glu Val Gly Phe Pro Gly Ser Ser Glu Glu Glu Phe Glu Thr Val
        115                 120                 125

Lys Thr Ile Ala Lys Thr Val Gly Asn Glu Val Asp Glu Glu Thr Gly
    130                 135                 140

Tyr Val Pro Val Ile Cys Ala Leu Ala Arg Cys Lys His Arg Asp Ile
```

```
145                 150                 155                 160

Glu Ala Val Trp Glu Ala Val Lys Tyr Ala Lys Arg Pro Ser Ile Leu
                165                 170                 175

Ile Phe Ile Ser Thr Ser Asp Ile His Met Lys His Lys Leu Lys Lys
            180                 185                 190

Thr Lys Glu Glu Val Ile Glu Met Ala Ala Ser Ser Ile Arg Phe Ala
        195                 200                 205

Lys Asn Leu Gly Phe Asn Asp Ile Gln Leu Gly Cys Glu Asp Ala Gly
    210                 215                 220

Arg Ser Asp Lys Glu Phe Leu Cys Lys Ile Leu Gly Glu Ala Ile Lys
225                 230                 235                 240

Ala Gly Ala Thr Thr Met Asn Met Ala Asp Thr Val Gly Ile Asn Met
                245                 250                 255

Pro Glu Glu Phe Gly Glu Leu Val Ser Tyr Leu Lys Ala Asn Thr Pro
            260                 265                 270

Gly Ile Asp Asp Val Val Leu Ser Val His Cys His Asn Asp Leu Gly
        275                 280                 285

Val Ala Thr Ala Asn Ala Ile Ala Gly Val Cys Ala Gly Ala Arg Gln
    290                 295                 300

Val Asp Val Thr Val Asn Gly Ile Gly Glu Arg Cys Gly Asn Ala Pro
305                 310                 315                 320

Leu Glu Glu Val Val Met Ala Leu Lys Cys Arg Gly Ala Tyr Leu Met
                325                 330                 335

Asn Gly Val Tyr Thr Arg Thr Asp Ile Arg Gln Ile Met Ala Thr Ser
            340                 345                 350

Lys Met Val Gln Glu Tyr Thr Gly Phe Tyr Val Gln Pro His Lys Pro
        355                 360                 365

Ile Val Gly Ala Asn Ser Phe Phe His Glu Ser Ser Asp Glu Tyr Asp
    370                 375                 380

Gly Cys Ser Asn Ile Leu Gln Asp Met Asp Tyr
385                 390                 395
```

<210> SEQ ID NO 171
<211> LENGTH: 798
<212> TYPE: DNA
<213> ORGANISM: Thlaspi arvense

<400> SEQUENCE: 171

```
atgttgtatc gaaaagagta cttgtggttc atgatgattt tgtgggccag atctttatca      60

gagggcctaa aatattctcc gtctcttagg aatcttgtaa acacgatgac accttcctta     120

tcaccaatta gatctcacca cgtggcagtt atcggagctg gagccgccgg tttagtagcc     180

gcgcgagagc ttcgacggga aggtcactcg gtggtcgttt tcgagaggca gaatcaggtc     240

ggaggaacat ggatctacac cgatcatgtc gagccggatc cgttaagcgt cgacccgacc     300

cgacccgttg ttcactcgag cgtctatggc tctctccgga ccaaccttcc gcgtgagtgt     360

atgggataca gagacttccc gttcgtgatc cgatccggcg tctcggaatc gagagacccg     420

aggaggtttc cgagtcatag tgaagttctg gcgtatctgc aggatttcgc aaaggagttt     480

cggatcgagg agatgatacg gttcgagacg gcggttgagc gtgttgctcc ggcggaggaa     540

agcgacggcg aagcaggaaa aatgaaatgg aggattgaat ctacagagaa agaggagaaa     600

cttcgtcgcg atgagattta cgatgccgtt gtcgtctgta acggacatta cattgagcct     660

cgtctagctg aaattcctgg tgattcccct ttgattctcc tcttgaagtt tcaacatctt     720
```

```
gactttcgat ggattcgtgt gttaataaga ttactctttt gcttcattca agaaaattta    780

gatagaattt ggaaatag                                                  798


<210> SEQ ID NO 172
<211> LENGTH: 798
<212> TYPE: DNA
<213> ORGANISM: Thlaspi arvense

<400> SEQUENCE: 172

atgttgtatc gaaaagagta cttgtggttc atgatgattt tgtgggccag atctttatca     60

gagggcctaa aatattctcc gtctcttagg aatcttgtaa acacgatgac accttcctta    120

tcaccaatta gatctcacca cgtggcagtt atcggagctg gagccgccgg tttagtagcc    180

gcgcgagagc ttcgacggga aggtcactcg gtggtcgttt tcgagaggca gaatcaggtc    240

ggaggaacat ggatctacac cgatcatgtc gagccggatc cgttaagcgt cgacccgacc    300

cgacccgttg ttcactcgag cgtctatggc tctctccgga ccaaccttcc gcgtgagtgt    360

atgggataca gagacttccc gttcgtgatc cgatccggcg tctcggaatc gagagacccg    420

aggaggtttc cgagtcatag tgaagttctg gcgtatctgc aggatttcgc aaaggagttt    480

cggatcgagg agatgatacg gttcgagacg gcggttgagc gtgttgctcc ggcggaggaa    540

agcgacggcg aagcaggaaa aatgaaatgg aggattgaat ctacagagaa agaggagaaa    600

cttcgtcgcg atgagattta cgatgccgtt gtcgtctgta acggacatta cattgagcct    660

cgtctagctg aaattcctgg tgattcccct ttgattctcc tcttgaagtt tcaacatctt    720

gactttcgat ggattcgtgt gttaataaga ttactctttt gcttcattca agaaaattta    780

gatagaattt ggaaatag                                                  798


<210> SEQ ID NO 173
<211> LENGTH: 265
<212> TYPE: PRT
<213> ORGANISM: Thlaspi arvense

<400> SEQUENCE: 173

Met Leu Tyr Arg Lys Glu Tyr Leu Trp Phe Met Met Ile Leu Trp Ala
1               5                   10                  15

Arg Ser Leu Ser Glu Gly Leu Lys Tyr Ser Pro Ser Leu Arg Asn Leu
            20                  25                  30

Val Asn Thr Met Thr Pro Ser Leu Ser Pro Ile Arg Ser His His Val
        35                  40                  45

Ala Val Ile Gly Ala Gly Ala Ala Gly Leu Val Ala Ala Arg Glu Leu
    50                  55                  60

Arg Arg Glu Gly His Ser Val Val Val Phe Glu Arg Gln Asn Gln Val
65                  70                  75                  80

Gly Gly Thr Trp Ile Tyr Thr Asp His Val Glu Pro Asp Pro Leu Ser
                85                  90                  95

Val Asp Pro Thr Arg Pro Val Val His Ser Ser Val Tyr Gly Ser Leu
            100                 105                 110

Arg Thr Asn Leu Pro Arg Glu Cys Met Gly Tyr Arg Asp Phe Pro Phe
        115                 120                 125

Val Ile Arg Ser Gly Val Ser Glu Ser Arg Asp Pro Arg Arg Phe Pro
    130                 135                 140

Ser His Ser Glu Val Leu Ala Tyr Leu Gln Asp Phe Ala Lys Glu Phe
145                 150                 155                 160

Arg Ile Glu Glu Met Ile Arg Phe Glu Thr Ala Val Glu Arg Val Ala
```

-continued

```
                165                 170                 175

Pro Ala Glu Glu Ser Asp Gly Glu Ala Gly Lys Met Lys Trp Arg Ile
            180                 185                 190

Glu Ser Thr Glu Lys Glu Glu Lys Leu Arg Arg Asp Glu Ile Tyr Asp
        195                 200                 205

Ala Val Val Val Cys Asn Gly His Tyr Ile Glu Pro Arg Leu Ala Glu
    210                 215                 220

Ile Pro Gly Asp Ser Pro Leu Ile Leu Leu Leu Lys Phe Gln His Leu
225                 230                 235                 240

Asp Phe Arg Trp Ile Arg Val Leu Ile Arg Leu Leu Phe Cys Phe Ile
                245                 250                 255

Gln Glu Asn Leu Asp Arg Ile Trp Lys
            260                 265


<210> SEQ ID NO 174
<211> LENGTH: 1392
<212> TYPE: DNA
<213> ORGANISM: Thlaspi arvense

<400> SEQUENCE: 174

atggtggaaa tagtcaacaa atgcaaaggc cacgtcatca ttttacctta cccagttcaa      60

ggccacctta accccatggt tcagttcgct aaacgtctcg tctccaaagg cgtcaaagtc     120

accatcgcaa ccactaccta caccgccttc tccatctcca ctccatcagt ctccgtcgag     180

ccaatctccg acggatacga cttcatcccc atagctattc ccggtttcag cgtcgacacc     240

tactcggaat ccttcaagct ccacggctcc gaaaccctaa cccgcgtgat cgagaaattc     300

aaatccaccg attccccgat cgattcttta gtctacgact cctttcttcc ctggggactc     360

gacgtcgcca gatccaactc gatttcagct gccgctttct tcaccaacaa cctcacggtt     420

tgttccgtgc tgcgtaattt ctccaccggg gagtttcctc tccccgccga tccagattct     480

gcgccgtacc taatccgtgg cttgccggcg ttgagctacg acgagctgcc ttccttcgtc     540

ggacgccact ggttgagcca cccggagcac gggaaggttc ttctgaatca gttccataac     600

catgaaaacg ccgattggct tttcgtcaat ggattcgaag gcttagaaac acaagattgt     660

gaaactggag aatcagaggc gatgaaggcg acgttgatcg gcccgttgat cccatcggcg     720

tacctcgacg accggataaa agacgataaa gactatggct cgagcctaat gaaaccgctc     780

tcagaggaat gtatggagtg gctcgggact aagccagcaa agtcagtagt tttcgtctcg     840

ttcggttcct ttgggatcct ctttgacaag cagctcgctg aggtagcaaa ggctctgcaa     900

gaatcgaact tgaacttctt gtgggtgatc aaagaagctc atatcgcgaa actgcctgaa     960

gggtttgtgg aatcgaccaa agacagagcc ttgctggttt cttggtgtaa ccagcttgag    1020

gttttagcac acgagtccat cggttgcttt ttgactcact gcggttggaa ctcgacgctt    1080

gaagggttga gtttgggagt gccgatggtg ggtgtgccgc agtggagtga tcagatgaac    1140

gatgctaagt ttgtggagga agtttggaga gttgggtaca gagcgaaaga ggaagctgag    1200

gaaggagtcg tgaagagcga agaagtggtg aggtgtttga aaggagtgat ggaaggagag    1260

agtagtgtga agattagaga gagttcgaag aagtggaaag atttggctgt gaaggcaatg    1320

actgaaggag gaagctctga tcggagcatt gacgagtttg tggagagttt aaggaaggaa    1380

acgttgaggt ag                                                        1392


<210> SEQ ID NO 175
<211> LENGTH: 1477
```

<212> TYPE: DNA
<213> ORGANISM: Thlaspi arvense

<400> SEQUENCE: 175
atggtggaaa tagtcaacaa atgcaaaggc cacgtcatca ttttacctta cccagttcaa 60
ggccacctta accccatggt tcagttcgct aaacgtctcg tctccaaagg cgtcaaagtc 120
accatcgcaa ccactaccta caccgccttc tccatctcca ctccatcagt ctccgtcgag 180
ccaatctccg acggatacga cttcatcccc atagctattc ccggtttcag cgtcgacacc 240
tactcggaat ccttcaagct ccacggctcc gaaaccctaa cccgcgtgat cgagaaattc 300
aaatccaccg attccccgat cgattcttta gtctacgact cctttcttcc ctggggactc 360
gacgtcgcca gatccaactc gatttcagct gccgctttct tcaccaacaa cctcacggtt 420
tgttccgtgc tgcgtaattt ctccaccggg gagtttcctc tccccgccga tccagattct 480
gcgccgtacc taatccgtgg cttgccggcg ttgagctacg acgagctgcc ttccttcgtc 540
ggacgccact ggttgagcca cccggagcac gggaaggttc ttctgaatca gttccataac 600
catgaaaacg ccgattggct tttcgtcaat ggattcgaag gcttagaaac acaagtaaga 660
aagagtccaa gatttacgcg atattgttca attgaaactt ggaattgatg tttttggct 720 tggatttgtg ttcgattagg attgtgaaac tggagaatca gaggcgatga aggcgacgtt 780
gatcggcccg ttgatcccat cggcgtacct cgacgaccgg ataaaagacg ataaagacta 840
tggctcgagc ctaatgaaac cgctctcaga ggaatgtatg gagtggctcg ggactaagcc 900
agcaaagtca gtagttttcg tctcgttcgg ttcctttggg atcctctttg acaagcagct 960
cgctgaggta gcaaaggctc tgcaagaatc gaacttgaac ttcttgtggg tgatcaaaga 1020
agctcatatc gcgaaactgc ctgaagggtt tgtggaatcg accaaagaca gagccttgct 1080
ggtttcttgg tgtaaccagc ttgaggtttt agcacacgag tccatcggtt gctttttgac 1140
tcactgcggt tggaactcga cgcttgaagg gttgagtttg ggagtgccga tggtgggtgt 1200
gccgcagtgg agtgatcaga tgaacgatgc taagtttgtg gaggaagttt ggagagttgg 1260
gtacagagcg aaagaggaag ctgaggaagg agtcgtgaag agcgaagaag tggtgaggtg 1320
tttgaaagga gtgatggaag gagagagtag tgtgaagatt agagagagtt cgaagaagtg 1380
gaaagatttg gctgtgaagg caatgactga aggaggaagc tctgatcgga gcattgacga 1440
gtttgtggag agtttaagga aggaaacgtt gaggtag 1477

<210> SEQ ID NO 176
<211> LENGTH: 463
<212> TYPE: PRT
<213> ORGANISM: Thlaspi arvense

<400> SEQUENCE: 176

Met Val Glu Ile Val Asn Lys Cys Lys Gly His Val Ile Ile Leu Pro
1 5 10 15

Tyr Pro Val Gln Gly His Leu Asn Pro Met Val Gln Phe Ala Lys Arg
20 25 30

Leu Val Ser Lys Gly Val Lys Val Thr Ile Ala Thr Thr Thr Tyr Thr
35 40 45

Ala Phe Ser Ile Ser Thr Pro Ser Val Ser Val Glu Pro Ile Ser Asp
50 55 60

Gly Tyr Asp Phe Ile Pro Ile Ala Ile Pro Gly Phe Ser Val Asp Thr
65 70 75 80

Tyr Ser Glu Ser Phe Lys Leu His Gly Ser Glu Thr Leu Thr Arg Val

```
                85                  90                  95

Ile Glu Lys Phe Lys Ser Thr Asp Ser Pro Ile Asp Ser Leu Val Tyr
            100                 105                 110

Asp Ser Phe Leu Pro Trp Gly Leu Asp Val Ala Arg Ser Asn Ser Ile
        115                 120                 125

Ser Ala Ala Ala Phe Phe Thr Asn Asn Leu Thr Val Cys Ser Val Leu
    130                 135                 140

Arg Asn Phe Ser Thr Gly Glu Phe Pro Leu Pro Ala Asp Pro Asp Ser
145                 150                 155                 160

Ala Pro Tyr Leu Ile Arg Gly Leu Pro Ala Leu Ser Tyr Asp Glu Leu
                165                 170                 175

Pro Ser Phe Val Gly Arg His Trp Leu Ser His Pro Glu His Gly Lys
            180                 185                 190

Val Leu Leu Asn Gln Phe His Asn His Glu Asn Ala Asp Trp Leu Phe
        195                 200                 205

Val Asn Gly Phe Glu Gly Leu Glu Thr Gln Asp Cys Glu Thr Gly Glu
    210                 215                 220

Ser Glu Ala Met Lys Ala Thr Leu Ile Gly Pro Leu Ile Pro Ser Ala
225                 230                 235                 240

Tyr Leu Asp Asp Arg Ile Lys Asp Asp Lys Asp Tyr Gly Ser Ser Leu
                245                 250                 255

Met Lys Pro Leu Ser Glu Glu Cys Met Glu Trp Leu Gly Thr Lys Pro
            260                 265                 270

Ala Lys Ser Val Val Phe Val Ser Phe Gly Ser Phe Gly Ile Leu Phe
        275                 280                 285

Asp Lys Gln Leu Ala Glu Val Ala Lys Ala Leu Gln Glu Ser Asn Leu
    290                 295                 300

Asn Phe Leu Trp Val Ile Lys Glu Ala His Ile Ala Lys Leu Pro Glu
305                 310                 315                 320

Gly Phe Val Glu Ser Thr Lys Asp Arg Ala Leu Leu Val Ser Trp Cys
                325                 330                 335

Asn Gln Leu Glu Val Leu Ala His Glu Ser Ile Gly Cys Phe Leu Thr
            340                 345                 350

His Cys Gly Trp Asn Ser Thr Leu Glu Gly Leu Ser Leu Gly Val Pro
        355                 360                 365

Met Val Gly Val Pro Gln Trp Ser Asp Gln Met Asn Asp Ala Lys Phe
    370                 375                 380

Val Glu Glu Val Trp Arg Val Gly Tyr Arg Ala Lys Glu Glu Ala Glu
385                 390                 395                 400

Glu Gly Val Val Lys Ser Glu Glu Val Val Arg Cys Leu Lys Gly Val
                405                 410                 415

Met Glu Gly Glu Ser Ser Val Lys Ile Arg Glu Ser Ser Lys Lys Trp
            420                 425                 430

Lys Asp Leu Ala Val Lys Ala Met Thr Glu Gly Gly Ser Ser Asp Arg
        435                 440                 445

Ser Ile Asp Glu Phe Val Glu Ser Leu Arg Lys Glu Thr Leu Arg
    450                 455                 460
```

<210> SEQ ID NO 177
<211> LENGTH: 798
<212> TYPE: DNA
<213> ORGANISM: Thlaspi arvense

<400> SEQUENCE: 177

-continued

```
atgttgtatc gaaaagagta cttgtggttc atgatgattt tgtgggccag atctttatca     60

gagggcctaa aatattctcc gtctcttagg aatcttgtaa acacgatgac accttcctta    120

tcaccaatta gatctcacca cgtggcagtt atcggagctg gagccgccgg tttagtagcc    180

gcgcgagagc ttcgacggga aggtcactcg gtggtcgttt tcgagaggca gaatcaggtc    240

ggaggaacat ggatctacac cgatcatgtc gagccggatc cgttaagcgt cgacccgacc    300

cgacccgttg ttcactcgag cgtctatggc tctctccgga ccaaccttcc gcgtgagtgt    360

atgggataca gagacttccc gttcgtgatc cgatccggcg tctcggaatc gagagacccg    420

aggaggtttc cgagtcatag tgaagttctg gcgtatctgc aggatttcgc aaaggagttt    480

cggatcgagg agatgatacg gttcgagacg gcggttgagc gtgttgctcc ggcggaggaa    540

agcgacggcg aagcaggaaa aatgaaatgg aggattgaat ctacagagaa agaggagaaa    600

cttcgtcgcg atgagattta cgatgccgtt gtcgtctgta acggacatta cattgagcct    660

catctagctg aaattcctgg tgattcccct ttgattctcc tcttgaagtt tcaacatctt    720

gactttcgat ggattcgtgt gttaataaga ttactctttt gcttcattca agaaaattta    780

gatagaattt ggaaatag                                                  798
```

<210> SEQ ID NO 178
<211> LENGTH: 265
<212> TYPE: PRT
<213> ORGANISM: Thlaspi arvense

<400> SEQUENCE: 178

```
Met Leu Tyr Arg Lys Glu Tyr Leu Trp Phe Met Met Ile Leu Trp Ala
1               5                   10                  15

Arg Ser Leu Ser Glu Gly Leu Lys Tyr Ser Pro Ser Leu Arg Asn Leu
            20                  25                  30

Val Asn Thr Met Thr Pro Ser Leu Ser Pro Ile Arg Ser His His Val
        35                  40                  45

Ala Val Ile Gly Ala Gly Ala Ala Gly Leu Val Ala Ala Arg Glu Leu
    50                  55                  60

Arg Arg Glu Gly His Ser Val Val Val Phe Glu Arg Gln Asn Gln Val
65                  70                  75                  80

Gly Gly Thr Trp Ile Tyr Thr Asp His Val Glu Pro Asp Pro Leu Ser
                85                  90                  95

Val Asp Pro Thr Arg Pro Val Val His Ser Ser Val Tyr Gly Ser Leu
            100                 105                 110

Arg Thr Asn Leu Pro Arg Glu Cys Met Gly Tyr Arg Asp Phe Pro Phe
        115                 120                 125

Val Ile Arg Ser Gly Val Ser Glu Ser Arg Asp Pro Arg Arg Phe Pro
    130                 135                 140

Ser His Ser Glu Val Leu Ala Tyr Leu Gln Asp Phe Ala Lys Glu Phe
145                 150                 155                 160

Arg Ile Glu Glu Met Ile Arg Phe Glu Thr Ala Val Glu Arg Val Ala
                165                 170                 175

Pro Ala Glu Glu Ser Asp Gly Glu Ala Gly Lys Met Lys Trp Arg Ile
            180                 185                 190

Glu Ser Thr Glu Lys Glu Glu Lys Leu Arg Arg Asp Glu Ile Tyr Asp
        195                 200                 205

Ala Val Val Val Cys Asn Gly His Tyr Ile Glu Pro His Leu Ala Glu
    210                 215                 220

Ile Pro Gly Asp Ser Pro Leu Ile Leu Leu Leu Lys Phe Gln His Leu
```

-continued 225 230 235 240

Asp Phe Arg Trp Ile Arg Val Leu Ile Arg Leu Leu Phe Cys Phe Ile
245 250 255

Gln Glu Asn Leu Asp Arg Ile Trp Lys
260 265

<210> SEQ ID NO 179
<211> LENGTH: 1188
<212> TYPE: DNA
<213> ORGANISM: Thlaspi arvense

<400> SEQUENCE: 179
atgatcacca ccacctgttg cactgtggtc gcccagttag gcttgccctt tggatcttcc 60
ttgtcctctc tctgcctgac ccgtccgaac aaaaagccgt ccttgttcac ctcatgttgc 120
tcctctgtgt ccaaaaatgt tggcgctagt gctgctgaca gcaaacacgt cgtggaacgg 180
tggccagagt acattccgaa taagctccct gacaagaact atgtgcgtat ttttgacacg 240
acgctccgtg acggcgaaca agctcctggt gcagccctta ctccaccgca gaagctagag 300
attgcccggc agctcgctaa gctccgagta gacatcatgg aagttggttt ccctgggtcc 360
tctgaggaag agttcgaaac cgtcaagacc atcgccaaga ccgtagggaa cgaggtggat 420
gaggaaacag gctacgtccc agtgatatgc gccctcgcac gatgcaaaca taaagacatt 480
gaggcggttt gggaggcggt gaagtacgca aagaggcctt cgatactcat attcatatct 540
actagtgaca ttcatatgaa acataagttg aaaaagacta aagaagaagt catagagatg 600
gcagcaagta gtattaggtt tgctaagaac ttaggcttca atgacatcca attgggttgc 660
gaagatgccg gcaggtcgga taaggagttt ctatgcaaga ttctaggaga agcgatcaaa 720
gcgggtgcaa ccacgatgaa catggcagac acggtaggga tcaacatgcc ggaagaattt 780
ggagaactcg tgagctacct taaagccaac actcctggaa ttgacgatgt tgtcttaagc 840
gttcattgtc acaacgacct tggtgttgct accgccaacg caatcgccgg tgtgtgtgct 900
ggagcaagac aagttgacgt tacggtcaat ggaataggtg aaagatgtgg gaacgcgcca 960
cttgaagagg tcgtgatggc tttgaaatgc cgaggagcat acctgatgaa tggggtttac 1020
acaagaacag acatacgcca aattatggct actagcaaga tggttcagga atatactggc 1080
ttttatgttc aaccacataa gcccatagtt ggagccaaca gttttttca tgagagcagc 1140 gatgaatatg atggttgttc aaacattttg caggatatgg attattga 1188

<210> SEQ ID NO 180
<211> LENGTH: 395
<212> TYPE: PRT
<213> ORGANISM: Thlaspi arvense

<400> SEQUENCE: 180

Met Ile Thr Thr Thr Cys Cys Thr Val Val Ala Gln Leu Gly Leu Pro
1 5 10 15

Phe Gly Ser Ser Leu Ser Ser Leu Cys Leu Thr Arg Pro Asn Lys Lys
20 25 30

Pro Ser Leu Phe Thr Ser Cys Cys Ser Ser Val Ser Lys Asn Val Gly
35 40 45

Ala Ser Ala Ala Asp Ser Lys His Val Val Glu Arg Trp Pro Glu Tyr
50 55 60

Ile Pro Asn Lys Leu Pro Asp Lys Asn Tyr Val Arg Ile Phe Asp Thr
65 70 75 80

-continued

```
Thr Leu Arg Asp Gly Glu Gln Ala Pro Gly Ala Ala Leu Thr Pro Pro
                85                  90                  95

Gln Lys Leu Glu Ile Ala Arg Gln Leu Ala Lys Leu Arg Val Asp Ile
            100                 105                 110

Met Glu Val Gly Phe Pro Gly Ser Ser Glu Glu Glu Phe Glu Thr Val
        115                 120                 125

Lys Thr Ile Ala Lys Thr Val Gly Asn Glu Val Asp Glu Glu Thr Gly
    130                 135                 140

Tyr Val Pro Val Ile Cys Ala Leu Ala Arg Cys Lys His Lys Asp Ile
145                 150                 155                 160

Glu Ala Val Trp Glu Ala Val Lys Tyr Ala Lys Arg Pro Ser Ile Leu
                165                 170                 175

Ile Phe Ile Ser Thr Ser Asp Ile His Met Lys His Lys Leu Lys Lys
            180                 185                 190

Thr Lys Glu Glu Val Ile Glu Met Ala Ala Ser Ser Ile Arg Phe Ala
        195                 200                 205

Lys Asn Leu Gly Phe Asn Asp Ile Gln Leu Gly Cys Glu Asp Ala Gly
    210                 215                 220

Arg Ser Asp Lys Glu Phe Leu Cys Lys Ile Leu Gly Glu Ala Ile Lys
225                 230                 235                 240

Ala Gly Ala Thr Thr Met Asn Met Ala Asp Thr Val Gly Ile Asn Met
                245                 250                 255

Pro Glu Glu Phe Gly Glu Leu Val Ser Tyr Leu Lys Ala Asn Thr Pro
            260                 265                 270

Gly Ile Asp Asp Val Val Leu Ser Val His Cys His Asn Asp Leu Gly
        275                 280                 285

Val Ala Thr Ala Asn Ala Ile Ala Gly Val Cys Ala Gly Ala Arg Gln
    290                 295                 300

Val Asp Val Thr Val Asn Gly Ile Gly Glu Arg Cys Gly Asn Ala Pro
305                 310                 315                 320

Leu Glu Glu Val Val Met Ala Leu Lys Cys Arg Gly Ala Tyr Leu Met
                325                 330                 335

Asn Gly Val Tyr Thr Arg Thr Asp Ile Arg Gln Ile Met Ala Thr Ser
            340                 345                 350

Lys Met Val Gln Glu Tyr Thr Gly Phe Tyr Val Gln Pro His Lys Pro
        355                 360                 365

Ile Val Gly Ala Asn Ser Phe Phe His Glu Ser Ser Asp Glu Tyr Asp
    370                 375                 380

Gly Cys Ser Asn Ile Leu Gln Asp Met Asp Tyr
385                 390                 395
```

<210> SEQ ID NO 181
<211> LENGTH: 1188
<212> TYPE: DNA
<213> ORGANISM: Thlaspi arvense

<400> SEQUENCE: 181

```
atgatcacca ccacctgttg cactgtggtc gcccagttag gcttgccctt tggatcttcc      60

ttgtcctctc tctgcctgac ccgtccgaac aaaaagccgt ccttgttcac ctcatgttgc     120

tcctctgtgt ccaaaaatgt tggcgctagt gctgctgaca gcaaacacgt cgtggaacgg     180

tggccagagt acattccgaa taagctccct gacaagaact atgtgcgtat ttttgacacg     240

acgctccgtg acggcgaaca agctcctggt gcagccctta ctccaccgca gaagctagag     300

attgcccggc agctcgctaa gctccgagta gacatcatgg aagttggttt ccctgggtcc     360
```

```
tctgaggaag agttcgaaac cgtcaagacc atcgccaaga ccgtagggaa cgaggtggat    420

gaggaaacag gctacgtccc agtgatatgc gccctcgcac gatgcaaaca tagagacatt    480

gaggcggttt gggaggcggt gaagtacgca aagaggcctt cgatactcat attcatatct    540

actagtgaca ttcatatgaa acataagttg aaaaagacta aagaagaagt catagagatg    600

gcagcaagta gtattaggtt tgctaagaac ttaggcttca atgacatcca attgggttgc    660

gaagatgccg gcaggtcgga taaggagttt ctatgcaaga ttctaggaga agcgatcaaa    720

gcgggtgcaa ccacgatgaa catggcagac acggtaggga tcaacatgcc ggaagaattt    780

ggagaactcg tgagctacct taaagccaac actcctggaa ttgacgatgt tgtcttaagc    840

gttcattgtc acaacgacct tggtgttgct accgccaacg caatcgccgg tgtgtgtgct    900

ggaacaagac aagttgacgt tacggtcaat ggaataggtg aaagatgtgg gaacgcgcca    960

cttgaagagg tcgtgatggc tttgaaatgc cgaggagcat acctgatgaa tggggtttac   1020

acaagaacag acatacgcca aattatggct actagcaaga tggttcagga atatactggc   1080

ttttatgttc aaccacataa gcccatagtt ggagccaaca gtttttttca tgagagcagc   1140

gatgaatatg atggttgttc aaacattttg caggatatgg attattga                1188
```

<210> SEQ ID NO 182
<211> LENGTH: 395
<212> TYPE: PRT
<213> ORGANISM: Thlaspi arvense

<400> SEQUENCE: 182

```
Met Ile Thr Thr Thr Cys Cys Thr Val Val Ala Gln Leu Gly Leu Pro
1               5                   10                  15

Phe Gly Ser Ser Leu Ser Ser Leu Cys Leu Thr Arg Pro Asn Lys Lys
            20                  25                  30

Pro Ser Leu Phe Thr Ser Cys Cys Ser Ser Val Ser Lys Asn Val Gly
        35                  40                  45

Ala Ser Ala Ala Asp Ser Lys His Val Val Glu Arg Trp Pro Glu Tyr
    50                  55                  60

Ile Pro Asn Lys Leu Pro Asp Lys Asn Tyr Val Arg Ile Phe Asp Thr
65                  70                  75                  80

Thr Leu Arg Asp Gly Glu Gln Ala Pro Gly Ala Ala Leu Thr Pro Pro
                85                  90                  95

Gln Lys Leu Glu Ile Ala Arg Gln Leu Ala Lys Leu Arg Val Asp Ile
            100                 105                 110

Met Glu Val Gly Phe Pro Gly Ser Ser Glu Glu Glu Phe Glu Thr Val
        115                 120                 125

Lys Thr Ile Ala Lys Thr Val Gly Asn Glu Val Asp Glu Glu Thr Gly
    130                 135                 140

Tyr Val Pro Val Ile Cys Ala Leu Ala Arg Cys Lys His Arg Asp Ile
145                 150                 155                 160

Glu Ala Val Trp Glu Ala Val Lys Tyr Ala Lys Arg Pro Ser Ile Leu
                165                 170                 175

Ile Phe Ile Ser Thr Ser Asp Ile His Met Lys His Lys Leu Lys Lys
            180                 185                 190

Thr Lys Glu Glu Val Ile Glu Met Ala Ala Ser Ser Ile Arg Phe Ala
        195                 200                 205

Lys Asn Leu Gly Phe Asn Asp Ile Gln Leu Gly Cys Glu Asp Ala Gly
    210                 215                 220
```

-continued

```
Arg Ser Asp Lys Glu Phe Leu Cys Lys Ile Leu Gly Glu Ala Ile Lys
225                 230                 235                 240

Ala Gly Ala Thr Thr Met Asn Met Ala Asp Thr Val Gly Ile Asn Met
                245                 250                 255

Pro Glu Glu Phe Gly Glu Leu Val Ser Tyr Leu Lys Ala Asn Thr Pro
            260                 265                 270

Gly Ile Asp Asp Val Val Leu Ser Val His Cys His Asn Asp Leu Gly
        275                 280                 285

Val Ala Thr Ala Asn Ala Ile Ala Gly Val Cys Ala Gly Thr Arg Gln
    290                 295                 300

Val Asp Val Thr Val Asn Gly Ile Gly Glu Arg Cys Gly Asn Ala Pro
305                 310                 315                 320

Leu Glu Glu Val Val Met Ala Leu Lys Cys Arg Gly Ala Tyr Leu Met
                325                 330                 335

Asn Gly Val Tyr Thr Arg Thr Asp Ile Arg Gln Ile Met Ala Thr Ser
            340                 345                 350

Lys Met Val Gln Glu Tyr Thr Gly Phe Tyr Val Gln Pro His Lys Pro
        355                 360                 365

Ile Val Gly Ala Asn Ser Phe Phe His Glu Ser Ser Asp Glu Tyr Asp
    370                 375                 380

Gly Cys Ser Asn Ile Leu Gln Asp Met Asp Tyr
385                 390                 395


<210> SEQ ID NO 183
<211> LENGTH: 1365
<212> TYPE: DNA
<213> ORGANISM: Thlaspi arvense

<400> SEQUENCE: 183

atgggttcac tttcaaacac tcctcagctt ccagtcatct acctctcgga ccaaacccta      60

aaaccaggaa gctcaaagtg ggttgaagtc aggagtgatg tccgtaaagc tcttgaagag     120

tacggcggtt tcgaggtgtc gtacgataga gtgtcggagg agcttaagaa gtcggttttg     180

caagccatgg aagagctttt cgcgttacca gttgaggcta aacagagaaa cgtctctcct     240

aaacccttca gcggttattc cactcataac ggtctttccg agagtatgag gatccaggat     300

cctcatgttt tggacaaagt ttacgagttt actcaacttc tacgtcctga tcattgtgac     360

ggtaacaaga gcatcagcga aacgatccag acgttttcag agaagttatc agaattggat     420

ataatggtga gaagaatggt aatggaaagc ttcgggatag agaagtacct tgacaaacac     480

ctgaactcaa cgaattaccg tctgcggctg atgaagtata tagcaccgcc tgatgctgat     540

gctactaatg ttgcggctga tgccaaagat gctgatgata atgctaagac gattacaaat     600

gataaagttg atgcggctgg tgctaatgat gtagatgctg gtgatatcgc taatggtatt     660

gctaatcttc atattggtga tgatgctaac gctggtgcta atggtgctgg tgttgatgct     720

aatgatggtg gtgaggatgc taagactggt gaggatgcta agactggtga atgtgctagt     780

gttaagtcta atgccgaaga tggtactgat gttaatgcca gtgctgatgc tggtgttact     840

gttggctcta atgctgatgc taatgctaat gctaatgcta atactagtac tgatgctggt     900

gttggcgata gtgttaaagc taatggtggt gctgatgatg ttgagaagaa attgggtcta     960

ccttctcaca ctgataagaa ccttataacg gtgctttatc aatacgagat tgaaggcttg    1020

gaggttctaa ccaaagatga caagtggatc agactcaaac catctcataa ttctttcgtt    1080

gttatggctg gagattctct atacgcactt atgaatggta gactaactcg tccctttcat    1140
```

-continued cgagtaagag taacggagaa aaagaagaca agatattcaa tagcattgtt ctcggctcca 1200
accgcagatt acatcataga cacaccaaaa gaacttgtgg acgagaagca tccacgtatc 1260
ttcgaaccat ttaactataa cgacttgatg agtttctatc atagtgaagc tggtcgtaaa 1320
gctcgatcta ctcttgatgc tttctgtgcc gtctctcgag cataa 1365

<210> SEQ ID NO 184
<211> LENGTH: 454
<212> TYPE: PRT
<213> ORGANISM: Thlaspi arvense

<400> SEQUENCE: 184

Met Gly Ser Leu Ser Asn Thr Pro Gln Leu Pro Val Ile Tyr Leu Ser
1 5 10 15

Asp Gln Thr Leu Lys Pro Gly Ser Ser Lys Trp Val Glu Val Arg Ser
20 25 30

Asp Val Arg Lys Ala Leu Glu Glu Tyr Gly Gly Phe Glu Val Ser Tyr
35 40 45

Asp Arg Val Ser Glu Glu Leu Lys Lys Ser Val Leu Gln Ala Met Glu
50 55 60

Glu Leu Phe Ala Leu Pro Val Glu Ala Lys Gln Arg Asn Val Ser Pro
65 70 75 80

Lys Pro Phe Ser Gly Tyr Ser Thr His Asn Gly Leu Ser Glu Ser Met
85 90 95

Arg Ile Gln Asp Pro His Val Leu Asp Lys Val Tyr Glu Phe Thr Gln
100 105 110

Leu Leu Arg Pro Asp His Cys Asp Gly Asn Lys Ser Ile Ser Glu Thr
115 120 125

Ile Gln Thr Phe Ser Glu Lys Leu Ser Glu Leu Asp Ile Met Val Arg
130 135 140

Arg Met Val Met Glu Ser Phe Gly Ile Glu Lys Tyr Leu Asp Lys His
145 150 155 160

Leu Asn Ser Thr Asn Tyr Arg Leu Arg Leu Met Lys Tyr Ile Ala Pro
165 170 175

Pro Asp Ala Asp Ala Thr Asn Val Ala Ala Asp Ala Lys Asp Ala Asp
180 185 190

Asp Asn Ala Lys Thr Ile Thr Asn Asp Lys Val Asp Ala Ala Gly Ala
195 200 205

Asn Asp Val Asp Ala Gly Asp Ile Ala Asn Gly Ile Ala Asn Leu His
210 215 220

Ile Gly Asp Asp Ala Asn Ala Gly Ala Asn Gly Ala Gly Val Asp Ala
225 230 235 240

Asn Asp Gly Gly Glu Asp Ala Lys Thr Gly Glu Asp Ala Lys Thr Gly
245 250 255

Glu Cys Ala Ser Val Lys Ser Asn Ala Glu Asp Gly Thr Asp Val Asn
260 265 270

Ala Ser Ala Asp Ala Gly Val Thr Val Gly Ser Asn Ala Asp Ala Asn
275 280 285

Ala Asn Ala Asn Ala Asn Thr Ser Thr Asp Ala Gly Val Gly Asp Ser
290 295 300

Val Lys Ala Asn Gly Gly Ala Asp Asp Val Glu Lys Lys Leu Gly Leu
305 310 315 320

Pro Ser His Thr Asp Lys Asn Leu Ile Thr Val Leu Tyr Gln Tyr Glu
325 330 335

```
Ile Glu Gly Leu Glu Val Leu Thr Lys Asp Asp Lys Trp Ile Arg Leu
            340                 345                 350

Lys Pro Ser His Asn Ser Phe Val Val Met Ala Gly Asp Ser Leu Tyr
        355                 360                 365

Ala Leu Met Asn Gly Arg Leu Thr Arg Pro Phe His Arg Val Arg Val
    370                 375                 380

Thr Glu Lys Lys Lys Thr Arg Tyr Ser Ile Ala Leu Phe Ser Ala Pro
385                 390                 395                 400

Thr Ala Asp Tyr Ile Ile Asp Thr Pro Lys Glu Leu Val Asp Glu Lys
                405                 410                 415

His Pro Arg Ile Phe Glu Pro Phe Asn Tyr Asn Asp Leu Met Ser Phe
            420                 425                 430

Tyr His Ser Glu Ala Gly Arg Lys Ala Arg Ser Thr Leu Asp Ala Phe
        435                 440                 445

Cys Ala Val Ser Arg Ala
    450
```

<210> SEQ ID NO 185
<211> LENGTH: 1818
<212> TYPE: DNA
<213> ORGANISM: Thlaspi arvense

<400> SEQUENCE: 185

```
atgaacgact acttcctcaa ccagtcaaca gccaccgacg ataacgcgtc ggcggcgatg     60

gaagctttca tcggaacaaa tcactcaact ctctggcccc aaccatctct tcctcctcct    120

cctccactat ctcaattcaa cgaagacact cttcaacaac gtctccaagc tttgatcgaa    180

tcagcaggag aaggctgaac ctacgcgatt ttctggcaga tctcacacga tttcgattct    240

tccaccggag acaacacagt gattctcgga tggggagatg ggtactacaa aggggaggaa    300

gataaagaga agaagaagaa tagctcaagt tcgaattcgg cggagcaaga gcatcggaaa    360

agagtaatcc gtgagctgaa ttcgttgatc tccggcggaa ccggagtttc cgatgaatcg    420

aacgacgaag aagtcaccga tactgagtgg ttcttcttgg tctcgatgac acagagcttc    480

atgaacggcg ttgggcttcc cggggagtcg tacttgaact ctcgcgtgat ttggttatcc    540

gggccgggtg ctttaatcgg gtcgggttgc gaacgagcgg gtcaaggtca gatatacggg    600

ttacagacga tggtgtgtat cgcggcggag aacggcgtcg ttgagcttgg ttcatcggag    660

gtgttaagcc atagctcaga tctgatggat aaagtcaaca gtctgttcaa ttccaacaac    720

ggtaatggag aagcttcttc ttgggggttt aatctgaatc cggatcaagg agagaacgat    780

ccggctttgt ggataagcga accgaccacc accggaatcg aatcgggtca ggtaatcccg    840

gcgataaaca acagtaattc caattcaaat tcaaaatccg attctcatca aatctccaag    900

ctcgagaaga acgagagctc gattgaaaac cctagacaac aacaaaatcc gtcgcttgta    960

gagcgagatt tgaatttctc gagttctggg ttgaatcaaa acgggaactt tcaagatggg   1020

tcgtcgcgga tgatgaaatc gaacgaaaca ctgagcttta cggcggagga gagcaacaag   1080

aggaggtctc cggtttcgaa agggagtaac aacgacgaag ggatgctttc tttcagcacc   1140

gtggttcgtt ccgcggcgaa atccgtcgat tcggatcatt ccgatctcga agcgtcggtg   1200

gttaaggaag caattgtcgt tgaaccggag aagaaaccga ggaaacgggg aagaaaaccg   1260

gcgaacggaa gagaggagcc gttgaatcac gtggaagcag agagacagag aagggagaag   1320

ctaaaccaga gattctactc tttgagagct gtggttccca acgtttcgaa aatggacaaa   1380

gcgtctcttc tcggagacgc catttcgtat atcaacgagc ttaaatcgaa gctgcagcaa   1440
```

```
gcggaatccg ataaggaaga gattcagaag cagctcgacg ggatgagcaa ggaaggaaac   1500

agggaaggcg gcggcggaac gaaggcgaaa gaacgaaaat gctcgaatca agattcggct   1560

agctcgatag aaatggagat cgacgtgaag atcataggtt gggatgtgat gatacgtgta   1620

caatgcagca agaagaatca tcccggggca agattcatgg aagcgctcaa ggaattggat   1680

ctggaagtga atcacgcaag tttgtcagtg gtgaatgatt tgatgattca acaagccact   1740

gtgaagatgg gaagccagtt tttcaatcat gaccagctca aggttgcttt gatgtcgaaa   1800

gtcggagaag acaattga                                                 1818
```

<210> SEQ ID NO 186
<211> LENGTH: 65
<212> TYPE: PRT
<213> ORGANISM: Thlaspi arvense

<400> SEQUENCE: 186

```
Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly
65
```

<210> SEQ ID NO 187
<211> LENGTH: 1817
<212> TYPE: DNA
<213> ORGANISM: Thlaspi arvense

<400> SEQUENCE: 187

```
atgaacgact acttcctcaa ccagtcaaca gccaccgacg ataacgcgtc ggcggcgatg     60

gaagctttca tcggaacaaa tcactcaact ctctggcccc aaccatctct tcctcctcct    120

cctccactat ctcaattcaa cgaagacact cttcaacaac gtctccaagc tttgatcgaa    180

tcagcaggag aaggctggac ctacgcgatt ttctggcaga tctcacacga tttcgattct    240

tccaccggag acaaccagtg attctcggat ggggagatgg gtactacaaa ggggaggaag    300

ataaagagaa gaagaagaat agctcaagtt cgaattcggc ggagcaagag catcggaaaa    360

gagtaatccg tgagctgaat tcgttgatct ccggcggaac cggagtttcc gatgaatcga    420

acgacgaaga agtcaccgat actgagtggt tcttcttggt ctcgatgaca cagagcttca    480

tgaacggcgt tgggcttccc ggggagtcgt acttgaactc tcgcgtgatt tggttatccg    540

ggccgggtgc tttaatcggg tcgggttgcg aacgagcggg tcaaggtcag atatacgggt    600

tacagacgat ggtgtgtatc gcggcggaga acggcgtcgt tgagcttggt tcatcggagg    660

tgttaagcca tagctcagat ctgatggata aagtcaacag tctgttcaat tccaacaacg    720

gtaatggaga agcttcttct tgggggttta atctgaatcc ggatcaagga gagaacgatc    780

cggctttgtg gataagcgaa ccgaccacca ccggaatcga atcgggtcag gtaatcccgg    840

cgataaacaa cagtaattcc aattcaaatt caaaatccga ttctcatcaa atctccaagc    900

tcgagaagaa cgagagctcg attgaaaacc ctagacaaca acaaaatccg tcgcttgtag    960

agcgagattt gaatttctcg agttctgggt tgaatcaaaa cgggaacttt caagatgggt   1020
```

```
cgtcgcggat gatgaaatcg aacgaaacac tgagctttac ggcggaggag agcaacaaga   1080

ggaggtctcc ggtttcgaaa gggagtaaca acgacgaagg gatgctttct ttcagcaccg   1140

tggttcgttc cgcggcgaaa tccgtcgatt cggatcattc cgatctcgaa gcgtcggtgg   1200

ttaaggaagc aattgtcgtt gaaccggaga agaaaccgag gaaacgggga agaaaaccgg   1260

cgaacggaag agaggagccg ttgaatcacg tggaagcaga gagacagaga agggagaagc   1320

taaaccagag attctactct ttgagagctg tggttcccaa cgtttcgaaa atggacaaag   1380

cgtctcttct cggagacgcc atttcgtata tcaacgagct taaatcgaag ctgcagcaag   1440

cggaatccga taaggaagag attcagaagc agctcgacgg gatgagcaag gaaggaaaca   1500

gggaaggcgg cggcggaacg aaggcgaaag aacgaaaatg ctcgaatcaa gattcggcta   1560

gctcgataga aatggagatc gacgtgaaga tcataggttg ggatgtgatg atacgtgtac   1620

aatgcagcaa gaagaatcat cccggggcaa gattcatgga agcgctcaag gaattggatc   1680

tggaagtgaa tcacgcaagt ttgtcagtgg tgaatgattt gatgattcaa caagccactg   1740

tgaagatggg aagccagttt ttcaatcatg accagctcaa ggttgctttg atgtcgaaag   1800

tcggagaaga caattga                                                  1817
```

<210> SEQ ID NO 188
<211> LENGTH: 86
<212> TYPE: PRT
<213> ORGANISM: Thlaspi arvense

<400> SEQUENCE: 188

```
Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile Ser His Asp Phe Asp Ser
65                  70                  75                  80

Ser Thr Gly Asp Asn Gln
                85
```

<210> SEQ ID NO 189
<211> LENGTH: 1818
<212> TYPE: DNA
<213> ORGANISM: Thlaspi arvense

<400> SEQUENCE: 189

```
atgaacgact acttcctcaa ccagtcaaca gccaccgacg ataacgcgtc ggcggcgatg     60

gaagctttca tcggaacaaa tcactcaact ctctggcccc aaccatctct tcctcctcct    120

cctccactat ctcaattcaa cgaagacact cttcaacaac gtctccaagc tttgatcgaa    180

tcagcaggag aaggctggac ctacgcgatt ttctggcaga tctcacacga tttcgattct    240

tccaccggag acaacacagt gattctcgga tggggagatg ggtactacaa aggggaggaa    300

gataaagaga agaagaagaa tagctcaagt tcgaattcgg cggagcaaga gcatcggaaa    360

agagtaatcc gtgagctgaa ttcgttgatc tccggcggaa ccgaagtttc cgatgaatcg    420

aacgacgaag aagtcaccga tactgagtgg ttcttcttgg tctcgatgac acagagcttc    480
```

-continued

```
atgaacggcg ttgggcttcc cggggagtcg tacttgaact ctcgcgtgat ttggttatcc    540

gggccgggtg ctttaatcgg gtcgggttgc gaacgagcgg gtcaaggtca gatatacggg    600

ttacagacga tggtgtgtat cgcggcggag aacggcgtcg ttgagcttgg ttcatcggag    660

gtgttaagcc atagctcaga tctgatggat aaagtcaaca gtctgttcaa ttccaacaac    720

ggtaatggag aagcttcttc ttgggggttt aatctgaatc cggatcaagg agagaacgat    780

ccggctttgt ggataagcga accgaccacc accggaatcg aatcgggtca ggtaatcccg    840

gcgataaaca acagtaattc caattcaaat tcaaaatccg attctcatca aatctccaag    900

ctcgagaaga acgagagctc gattgaaaac cctagacaac aacaaaatcc gtcgcttgta    960

gagcgagatt tgaatttctc gagttctggg ttgaatcaaa acgggaactt tcaagatggg   1020

tcgtcgcgga tgatgaaatc gaacgaaaca ctgagcttta cggcggagga gagcaacaag   1080

aggaggtctc cggtttcgaa agggagtaac aacgacgaag ggatgctttc tttcagcacc   1140

gtggttcgtt ccgcggcgaa atccgtcgat tcggatcatt ccgatctcga agcgtcggtg   1200

gttaaggaag caattgtcgt tgaaccggag aagaaaccga ggaaacgggg aagaaaaccg   1260

gcgaacggaa gagaggagcc gttgaatcac gtggaagcag agagacagag aagggagaag   1320

ctaaaccaga gattctactc tttgagagct gtggttccca acgtttcgaa aatggacaaa   1380

gcgtctcttc tcggagacgc catttcgtat atcaacgagc ttaaatcgaa gctgcagcaa   1440

gcggaatccg ataaggaaga gattcagaag cagctcgacg ggatgagcaa ggaaggaaac   1500

agggaaggcg gcggcggaac gaaggcgaaa gaacgaaaat gctcgaatca agattcggct   1560

agctcgatag aaatggagat cgacgtgaag atcataggtt gggatgtgat gatacgtgta   1620

caatgcagca agaagaatca tcccggggca agattcatgg aagcgctcaa ggaattggat   1680

ctggaagtga atcacgcaag tttgtcagtg gtgaatgatt tgatgattca acaagccact   1740

gtgaagatgg gaagccagtt tttcaatcat gaccagctca aggttgcttt gatgtcgaaa   1800

gtcggagaag acaattga                                                 1818
```

<210> SEQ ID NO 190
<211> LENGTH: 605
<212> TYPE: PRT
<213> ORGANISM: Thlaspi arvense

<400> SEQUENCE: 190

```
Met Asn Asp Tyr Phe Leu Asn Gln Ser Thr Ala Thr Asp Asp Asn Ala
1               5                   10                  15

Ser Ala Ala Met Glu Ala Phe Ile Gly Thr Asn His Ser Thr Leu Trp
            20                  25                  30

Pro Gln Pro Ser Leu Pro Pro Pro Pro Pro Leu Ser Gln Phe Asn Glu
        35                  40                  45

Asp Thr Leu Gln Gln Arg Leu Gln Ala Leu Ile Glu Ser Ala Gly Glu
    50                  55                  60

Gly Trp Thr Tyr Ala Ile Phe Trp Gln Ile Ser His Asp Phe Asp Ser
65                  70                  75                  80

Ser Thr Gly Asp Asn Thr Val Ile Leu Gly Trp Gly Asp Gly Tyr Tyr
                85                  90                  95

Lys Gly Glu Glu Asp Lys Glu Lys Lys Lys Asn Ser Ser Ser Ser Asn
            100                 105                 110

Ser Ala Glu Gln Glu His Arg Lys Arg Val Ile Arg Glu Leu Asn Ser
        115                 120                 125

Leu Ile Ser Gly Gly Thr Glu Val Ser Asp Glu Ser Asn Asp Glu Glu
```

-continued

```
    130                 135                 140

Val Thr Asp Thr Glu Trp Phe Phe Leu Val Ser Met Thr Gln Ser Phe
145                 150                 155                 160

Met Asn Gly Val Gly Leu Pro Gly Glu Ser Tyr Leu Asn Ser Arg Val
                165                 170                 175

Ile Trp Leu Ser Gly Pro Gly Ala Leu Ile Gly Ser Gly Cys Glu Arg
            180                 185                 190

Ala Gly Gln Gly Gln Ile Tyr Gly Leu Gln Thr Met Val Cys Ile Ala
        195                 200                 205

Ala Glu Asn Gly Val Val Glu Leu Gly Ser Ser Glu Val Leu Ser His
    210                 215                 220

Ser Ser Asp Leu Met Asp Lys Val Asn Ser Leu Phe Asn Ser Asn Asn
225                 230                 235                 240

Gly Asn Gly Glu Ala Ser Ser Trp Gly Phe Asn Leu Asn Pro Asp Gln
                245                 250                 255

Gly Glu Asn Asp Pro Ala Leu Trp Ile Ser Glu Pro Thr Thr Thr Gly
            260                 265                 270

Ile Glu Ser Gly Gln Val Ile Pro Ala Ile Asn Asn Ser Asn Ser Asn
        275                 280                 285

Ser Asn Ser Lys Ser Asp Ser His Gln Ile Ser Lys Leu Glu Lys Asn
    290                 295                 300

Glu Ser Ser Ile Glu Asn Pro Arg Gln Gln Gln Asn Pro Ser Leu Val
305                 310                 315                 320

Glu Arg Asp Leu Asn Phe Ser Ser Ser Gly Leu Asn Gln Asn Gly Asn
                325                 330                 335

Phe Gln Asp Gly Ser Ser Arg Met Met Lys Ser Asn Glu Thr Leu Ser
            340                 345                 350

Phe Thr Ala Glu Glu Ser Asn Lys Arg Arg Ser Pro Val Ser Lys Gly
        355                 360                 365

Ser Asn Asn Asp Glu Gly Met Leu Ser Phe Ser Thr Val Val Arg Ser
    370                 375                 380

Ala Ala Lys Ser Val Asp Ser Asp His Ser Asp Leu Glu Ala Ser Val
385                 390                 395                 400

Val Lys Glu Ala Ile Val Val Glu Pro Glu Lys Lys Pro Arg Lys Arg
                405                 410                 415

Gly Arg Lys Pro Ala Asn Gly Arg Glu Glu Pro Leu Asn His Val Glu
            420                 425                 430

Ala Glu Arg Gln Arg Arg Glu Lys Leu Asn Gln Arg Phe Tyr Ser Leu
        435                 440                 445

Arg Ala Val Val Pro Asn Val Ser Lys Met Asp Lys Ala Ser Leu Leu
    450                 455                 460

Gly Asp Ala Ile Ser Tyr Ile Asn Glu Leu Lys Ser Lys Leu Gln Gln
465                 470                 475                 480

Ala Glu Ser Asp Lys Glu Glu Ile Gln Lys Gln Leu Asp Gly Met Ser
                485                 490                 495

Lys Glu Gly Asn Arg Glu Gly Gly Gly Gly Thr Lys Ala Lys Glu Arg
            500                 505                 510

Lys Cys Ser Asn Gln Asp Ser Ala Ser Ser Ile Glu Met Glu Ile Asp
        515                 520                 525

Val Lys Ile Ile Gly Trp Asp Val Met Ile Arg Val Gln Cys Ser Lys
    530                 535                 540

Lys Asn His Pro Gly Ala Arg Phe Met Glu Ala Leu Lys Glu Leu Asp
545                 550                 555                 560
```

```
Leu Glu Val Asn His Ala Ser Leu Ser Val Val Asn Asp Leu Met Ile
                565                 570                 575

Gln Gln Ala Thr Val Lys Met Gly Ser Gln Phe Phe Asn His Asp Gln
            580                 585                 590

Leu Lys Val Ala Leu Met Ser Lys Val Gly Glu Asp Asn
        595                 600                 605


<210> SEQ ID NO 191
<211> LENGTH: 1109
<212> TYPE: DNA
<213> ORGANISM: Thlaspi arvense

<400> SEQUENCE: 191

atgtcaagaa agccgtgttg tgtcggagaa gggctgaaga aaggggcatg gaccaccgaa     60

gaagacaaga aactcatctc ttacatccac ggcacggtga aggaggctgg cgcgacattc    120

cccaaaaagc tgggttgaaa cggtgtggaa agagttgtag gctgcgatgg actaactacc    180

taaaacctga gatcaaaaga ggcgagttta gttcagagga ggaacagatt atcattatgc    240

ttcatgcttc tcgtggcaac aagtggtcgg tcatagcgag acatttacct agaagaacag    300

acaacgagat caagaactac tggaacacgc atctcaaaaa acgtttgatc gaacagggtg    360

ttgatcccgt gactcacaag cctctagctt ccaactccgg ccctactgcc accacgccgc    420

ctgagaattt gcatttccta gatgaatcta gctcagacaa gcaatactct cggtcgagct    480

caatgccttc cctgtctcgt cttccttcct ccggattcaa cacggtttcc gagatagcca    540

gcaatgttgg gacaccagtt caggtcggtt ccttgagttg caagaaacgt tttaagaaat    600

cgagttcgac atcaaggctt ctgaacaaat ttgcggctaa ggccacttcc atcaaagata    660

tattgtcggc ttccatggaa ggtagctcga gtgctgctac tacaatatca catgcaagct    720

ttttaaatgg cttttctgag cagagtcgca atgaagagga tagttctaac gcatccctga    780

caaatactct agccgaattt gatcccttct ctcagtcatc gttgtacccg gagcatgaga    840

tcaatgttac ttctgatatc ggcatggacc aggtttacga tttctcacaa tttctcgaaa    900

agctcgggag tgaaggccac aacgaactga atgtcgagta tggtcatgat cttcttatgt    960

ccgatgtttc gcaagaagtc tcatcaccta gcgttgatga tcaagacaat atgattggaa   1020

gcttcgaagg ttggtcaaat tatcttcttg accatgctga ttttatatat gacaccgact   1080

cagattccct cgaaaagcat ttcatgtga                                     1109


<210> SEQ ID NO 192
<211> LENGTH: 45
<212> TYPE: PRT
<213> ORGANISM: Thlaspi arvense

<400> SEQUENCE: 192

Met Ser Arg Lys Pro Cys Cys Val Gly Glu Gly Leu Lys Lys Gly Ala
1               5                   10                  15

Trp Thr Thr Glu Glu Asp Lys Lys Leu Ile Ser Tyr Ile His Gly Thr
            20                  25                  30

Val Lys Glu Ala Gly Ala Thr Phe Pro Lys Lys Leu Gly
        35                  40                  45


<210> SEQ ID NO 193
<211> LENGTH: 1018
<212> TYPE: DNA
<213> ORGANISM: Thlaspi arvense
```

<400> SEQUENCE: 193
atgtcgaaaa gaccatgctg tatcggagaa gggttaaaga aaggagcatg gacgtcaggg 60
gaagacaaaa aactcatctc ttatatccat gaacatggcg aaggaggttg gcgtgacatt 120
cccgaaaaag ctgggctaaa acggttgtgg aaagagttgc agactgcgat gggcgaacta 180
tttgaacccc gatatcaaga gaggaggatt tagctacgag gaagaacaga tcatcatcat 240
gcttcatgct tctcgtggca acaagtggtc agtcatagca agacatttgc cgcaaagaac 300
agacaacgag atcaaaaact attggaacac acatctcaag aaacgcctga tcaataagag 360
cactgattcc gtgacccaca agcctctagc ttcctctaac cctagtccta ccgagcgtaa 420
gaagctcgat tcccaagaag aatccaatcc caaggagcag tcgttacagc cgggttcgaa 480
gtctccagta tctctttccc tttcttcgag tttcaacgac actgtacccg agatcatgac 540
cagtgatgag acgcctctag aaagtggttt cttgagttgc aaaaaaagtg tcgagagatc 600
gagctcaaca tcaaggcttt taaacaaagt tgcagctaga gcttcttcca tcgggagtat 660
cttatcaacc tccatagaag gaactttgag atctcctgca tcgtcctcat gtctcccaaa 720
ctcattgtgt caatcatctg aacacaacaa ggatcaagat ctcggtacga gcattgatct 780
tagcatcccc gattacgatt actcccactt tctcgagcac ttcatcaata gcgaagacga 840
agccgaaaac attggtggct gcaatcaaga tctccttatg tccgatttcc catcaacatt 900
agtggataaa gaaaatatga attttgaaga cataaccggt tggtcaagtt atcttctcga 960
ccatcccagt tttacgtatg aatcggaaca agattccgac gacaacaact tgttatga 1018

<210> SEQ ID NO 194
<211> LENGTH: 70
<212> TYPE: PRT
<213> ORGANISM: Thlaspi arvense

<400> SEQUENCE: 194

Met Ser Lys Arg Pro Cys Cys Ile Gly Glu Gly Leu Lys Lys Gly Ala
1 5 10 15

Trp Thr Ser Gly Glu Asp Lys Lys Leu Ile Ser Tyr Ile His Glu His
20 25 30

Gly Glu Gly Gly Trp Arg Asp Ile Pro Glu Lys Ala Gly Leu Lys Arg
35 40 45

Leu Trp Lys Glu Leu Gln Thr Ala Met Gly Glu Leu Phe Glu Pro Arg
50 55 60

Tyr Gln Glu Arg Arg Ile
65 70

<210> SEQ ID NO 195
<211> LENGTH: 1067
<212> TYPE: DNA
<213> ORGANISM: Thlaspi arvense

<400> SEQUENCE: 195
atgtcaagaa agccatgttg tgtgggagaa gggctgaaga aaggagcatg gaccgccgaa 60
gaagacaaga aactcatctc ttacatccat gaacatggcg aaggaggctg gcgtgacatt 120
ccccaaaaag ctggactaaa acgatgtgga aaaagttgta gattgcgatg ggctaactat 180
ttgaaaccgg atatcaagag aggagaattt agctacgagg aggagcagat tatcatcatg 240
cttcacgctt cccgtggcaa caagtggtcg gtcatagcga gacatttgcc caaaaggaca 300
gacaacgaga tcaagaacta ttggaacaca caccttaaaa aacgccttat cgatcaaggt 360

```
attgatcccg tgacccacaa gccacttgtc cggccacgct caagccttct gatttccaag    420

atgactcatc aaacctggga aactcggatg agcattcaca ttcgggttct atgtctccaa    480

aatctcttcc tccgtcttca agctcctgca atctagcgga gataagcagc agtgatgaga    540

caccgaaaaa tgatggttcc ttgaaatcca agaaacgttc ttttaagaga tcaagttcta    600

catcaaagct gttaaacaaa gttgcatcta gggctgcttc cattggaaat atcttatcag    660

cgtccatgga aggaaccttg gttagctcta ccgcactgtc tccatgtctc aatgatgact    720

tttccgaagc tagccaattc cagatggacg aatatgatcc attccctcag tcgtctgaac    780

acataactga tcatatgaag gaggacaccg gcatgatctt tgatctcaac aactccgaat    840

atgatttctc gcagtttctc gagcaattta gtaacgaagg cgaagaaacc gagaacattg    900

ggggatataa tcaagatctc ctttcgtctg acgtctcatc accaagcgtt gatgaagaca    960

atatgatggg aaacataacc ggttccggtt ggtccagtta tcttgttgac cattccgatt   1020

ttgtttatga caagatccaa gataacgacg acaggaactt catatga                1067


<210> SEQ ID NO 196
<211> LENGTH: 171
<212> TYPE: PRT
<213> ORGANISM: Thlaspi arvense

<400> SEQUENCE: 196

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Val Arg Pro Arg Ser Ser Leu Leu Ile Ser Lys Met Thr His Gln
    130                 135                 140

Thr Trp Glu Thr Arg Met Ser Ile His Ile Arg Val Leu Cys Leu Gln
145                 150                 155                 160

Asn Leu Phe Leu Arg Leu Gln Ala Pro Ala Ile
                165                 170


<210> SEQ ID NO 197
<211> LENGTH: 1074
<212> TYPE: DNA
<213> ORGANISM: Thlaspi arvense

<400> SEQUENCE: 197

atgtcaagaa agccatgttg tgtgggagaa gggctgaaga aaggagcatg gaccgccgaa     60

gaagacaaga aactcatctc ttacatccat gaacatggcg aaggaggctg gcgtgacatt    120

ccccaaaaag ctggactaaa acgatgtgga aaaagttgta gattgcgatg ggctaactat    180
```

-continued

```
ttgaaaccgg atatcaagag aggagaattt agctacgagg aggagcagat tatcatcatg    240

cttcacgctt cccgtggcaa caagtggtcg gtcatagcga gacatttgcc caaaaggaca    300

gacaacgaga tcaagaacta ttggaacaca caccttaaaa aacgccttat cgatcaaggt    360

attgatcccg tgacccacaa gccacttgcc cctagcccta ccacgctcaa gccttctgat    420

ttccaagatg actcatcaaa cctgggaaac tcggatgagc attcacattc gggttctatg    480

tctccaaaat ctcttcctcc gtcttcaagc tcctgcaatc tagcggagat aagcagcagt    540

gatgagacac cgaaaaatga tggttccttg aaatccaaga aacgttcttt taagagatca    600

agttctacat caaagctgtt aaacaaagtt gcatctaggg ctgcttccat tggaaatatc    660

ttatcagcgt ccatggaagg aaccttggtt agctctaccg cactgtctcc atgtctcaat    720

gatgactttt ccgaagctag ccaattccag atggacgaat atgatccatt ccctcagtcg    780

tctgaacaca taactgatca tatgaaggag gacaccggca tgatctttga tctcaacaac    840

tccgaatatg atttctcgca gtttctcgag caatttagta acgaaggcga agaaaccgag    900

aacattgggg gatataatca agatctcctt tcgtctgacg tctcatcacc aagcgttgat    960

gaagacaata tgatgggaaa cataaccggt tccggttggt ccagttatct tgttgaccat   1020

tccgattttg tttatgacaa gatccaagat aacgacgaca ggaacttcat atga         1074


<210> SEQ ID NO 198
<211> LENGTH: 356
<212> TYPE: PRT
<213> ORGANISM: Thlaspi arvense

<400> SEQUENCE: 198

Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Arg Leu Ile Asp Gln Gly Ile Asp Pro Val Thr His Lys Pro
        115                 120                 125

Leu Ala Pro Ser Pro Thr Leu Lys Pro Ser Asp Phe Gln Asp Asp Ser
    130                 135                 140

Ser Asn Leu Gly Asn Ser Asp Glu His Ser His Ser Gly Ser Met Ser
145                 150                 155                 160

Pro Lys Ser Leu Pro Pro Ser Ser Ser Ser Cys Asn Leu Ala Glu Ile
                165                 170                 175

Ser Ser Ser Asp Glu Thr Pro Lys Asn Asp Gly Ser Leu Lys Ser Lys
            180                 185                 190

Lys Arg Ser Phe Lys Arg Ser Ser Ser Thr Ser Lys Leu Leu Asn Lys
        195                 200                 205

Val Ala Ser Arg Ala Ala Ser Ile Gly Asn Ile Leu Ser Ala Ser Met
    210                 215                 220
```

Glu Gly Thr Leu Val Ser Ser Thr Ala Leu Ser Pro Cys Leu Asn Asp
225 230 235 240

Asp Phe Ser Glu Ala Ser Gln Phe Gln Met Asp Glu Tyr Asp Pro Phe
245 250 255

Pro Gln Ser Ser Glu His Ile Thr Asp His Met Lys Glu Asp Thr Gly
260 265 270

Met Ile Phe Asp Leu Asn Asn Ser Glu Tyr Asp Phe Ser Gln Phe Leu
275 280 285

Glu Gln Phe Ser Asn Glu Gly Glu Glu Thr Glu Asn Ile Gly Gly Tyr
290 295 300

Asn Gln Asp Leu Leu Ser Ser Asp Val Ser Ser Pro Ser Val Asp Glu
305 310 315 320

Asp Asn Met Met Gly Asn Ile Thr Gly Ser Gly Trp Ser Ser Tyr Leu
325 330 335

Val Asp His Ser Asp Phe Val Tyr Asp Lys Ile Gln Asp Asn Asp Asp
340 345 350

Arg Asn Phe Ile
355

<210> SEQ ID NO 199
<211> LENGTH: 1332
<212> TYPE: DNA
<213> ORGANISM: Thlaspi arvense

<400> SEQUENCE: 199
atggcggcgt gtttacaatc gaacatccgg ctgaatctga acaatatcgt cggaggaaaa 60
tgcagatccc tcaccgatca gtctcgcacg ccgtgtcgaa taaggtgcgc cgccgcttca 120
cctgggaaaa aacggttcaa catcgctctc cttcctggcg acggtatcgg tcctgaagtc 180
atctccgttg ccaagaatgt gcttcagcaa gctggatctc tcgaaggttc ttctatctct 240
cgctcagttt atttactaat tttgacaaaa ttagtaatca gcgaatgtgt tgcttaccca 300
gaagagtgtg cgtatttgat gtgtatcaca ggactggagt tcaatttcca ggagatgccc 360
atcggaggag cagccttgga tttggtcgga gtggccttgc cggaggaaac cttatcggct 420
gcaaaacagt ctgatgccat acttcttgga gctatcggag ggtacaaatg ggacaacaat 480
gagaaacatc tgagacctga gatggctctg atttaccttc ggagagatct caaagtcttt 540
gctaatctga gacctgcttc agttttgcca cagctagttg atgcatccac cttgaagaga 600
gaagtagcag aaggtgttga tatgatgatt gtaagggagc ttacaggagg aatttacttt 660
ggagagccca aaggcattaa gaccaacgaa aacggagaag aagtcggttt taatacagag 720
ttttacgctg ctcacgagat tgacagaatt gctcgtgttg catttgagac tgctaggaaa 780
cggcgtggca agctgtgttc tgtcgacaaa gccaatgtgt tggatgcatc agtattgtgg 840
aggagaagag taacagcgtt agcctctgag tatccagatg ttgagctctc acatatgtat 900
gtagacaacg ctgcaatgca gcttattcgt gacccgaaac agtttgacac aatcgtcacc 960
aataacattt tcggtgacat attatccgat gaggcctcaa tgatcactgg aagcattggg 1020
atgcttccat ctgctagtct cggtgtatcg ggacctggac tctttgagcc gatacatggt 1080
tctgcgccag atatagctgg tcaggacaag gcaaacccat tggccaccat tctcagcgca 1140
gcgatgcttc tgaaatatgg acttggagaa gagaaggccg caaagaggat cgaggacgcg 1200
gtcttggatg ctctcaacaa agggtttaga accggagaca tctactcccc cggaaataaa 1260
ctggtgggat gcaaggagat gggtgaggag gtgcttaaat cagtggactc cagagttaca 1320
gctactgttt aa 1332

<210> SEQ ID NO 200
<211> LENGTH: 443
<212> TYPE: PRT
<213> ORGANISM: Thlaspi arvense

<400> SEQUENCE: 200

```
Met Ala Ala Cys Leu Gln Ser Asn Ile Arg Leu Asn Leu Asn Asn Ile
1               5                   10                  15

Val Gly Gly Lys Cys Arg Ser Leu Thr Asp Gln Ser Arg Thr Pro Cys
            20                  25                  30

Arg Ile Arg Cys Ala Ala Ala Ser Pro Gly Lys Lys Arg Phe Asn Ile
        35                  40                  45

Ala Leu Leu Pro Gly Asp Gly Ile Gly Pro Glu Val Ile Ser Val Ala
    50                  55                  60

Lys Asn Val Leu Gln Gln Ala Gly Ser Leu Glu Gly Ser Ser Ile Ser
65                  70                  75                  80

Arg Ser Val Tyr Leu Leu Ile Leu Thr Lys Leu Val Ile Ser Glu Cys
                85                  90                  95

Val Ala Tyr Pro Glu Glu Cys Ala Tyr Leu Met Cys Ile Thr Gly Leu
            100                 105                 110

Glu Phe Asn Phe Gln Glu Met Pro Ile Gly Gly Ala Ala Leu Asp Leu
        115                 120                 125

Val Gly Val Ala Leu Pro Glu Glu Thr Leu Ser Ala Ala Lys Gln Ser
    130                 135                 140

Asp Ala Ile Leu Leu Gly Ala Ile Gly Gly Tyr Lys Trp Asp Asn Asn
145                 150                 155                 160

Glu Lys His Leu Arg Pro Glu Met Ala Leu Ile Tyr Leu Arg Arg Asp
                165                 170                 175

Leu Lys Val Phe Ala Asn Leu Arg Pro Ala Ser Val Leu Pro Gln Leu
            180                 185                 190

Val Asp Ala Ser Thr Leu Lys Arg Glu Val Ala Glu Gly Val Asp Met
        195                 200                 205

Met Ile Val Arg Glu Leu Thr Gly Gly Ile Tyr Phe Gly Glu Pro Lys
    210                 215                 220

Gly Ile Lys Thr Asn Glu Asn Gly Glu Glu Val Gly Phe Asn Thr Glu
225                 230                 235                 240

Phe Tyr Ala Ala His Glu Ile Asp Arg Ile Ala Arg Val Ala Phe Glu
                245                 250                 255

Thr Ala Arg Lys Arg Arg Gly Lys Leu Cys Ser Val Asp Lys Ala Asn
            260                 265                 270

Val Leu Asp Ala Ser Val Leu Trp Arg Arg Arg Val Thr Ala Leu Ala
        275                 280                 285

Ser Glu Tyr Pro Asp Val Glu Leu Ser His Met Tyr Val Asp Asn Ala
    290                 295                 300

Ala Met Gln Leu Ile Arg Asp Pro Lys Gln Phe Asp Thr Ile Val Thr
305                 310                 315                 320

Asn Asn Ile Phe Gly Asp Ile Leu Ser Asp Glu Ala Ser Met Ile Thr
                325                 330                 335

Gly Ser Ile Gly Met Leu Pro Ser Ala Ser Leu Gly Val Ser Gly Pro
            340                 345                 350

Gly Leu Phe Glu Pro Ile His Gly Ser Ala Pro Asp Ile Ala Gly Gln
        355                 360                 365
```

Asp Lys Ala Asn Pro Leu Ala Thr Ile Leu Ser Ala Ala Met Leu Leu
370 375 380

Lys Tyr Gly Leu Gly Glu Glu Lys Ala Ala Lys Arg Ile Glu Asp Ala
385 390 395 400

Val Leu Asp Ala Leu Asn Lys Gly Phe Arg Thr Gly Asp Ile Tyr Ser
405 410 415

Pro Gly Asn Lys Leu Val Gly Cys Lys Glu Met Gly Glu Glu Val Leu
420 425 430

Lys Ser Val Asp Ser Arg Val Thr Ala Thr Val
435 440

<210> SEQ ID NO 201
<211> LENGTH: 1332
<212> TYPE: DNA
<213> ORGANISM: Thlaspi arvense

<400> SEQUENCE: 201
atggcggcgt gtttacaatc gaacatccgg ctgaatctga acaatatcgt cggaggaaaa 60
tgcagatccc tcaccgatca gtctcgcacg ccgtgtcgaa taaggtgcgc cgccgcttca 120
cctgggaaaa aacggttcaa catcgctctc cttcctggcg acggtatcgg tcctgaagtc 180
atctccgttg ccaagaatgt gcttcagcaa gctggatctc tcgaaggttc ttctatctct 240
cgctcagttt atttactaat tttgacaaaa ttagtaatca gcgaatgtgt tgcttaccca 300
gaagagtgtg cgtatttgat gtgtatcaca ggactggagt tcaatttcca ggagatgccc 360
atcggaggag cagccttgga tttggtcgga gtggccttgc cggaggaaac cttatcggct 420
gcaaaacagt ctgatgccat acttcttgga gctatcggag ggtacaaatg ggacaacaat 480
gagaaacatc tgagacctga gatggctctg atttaccttc ggagagatct caaagtcttt 540
gctaatctga gacctgcttc agttttgcca cagctagttg atgcatccac cttgaagaga 600
gaagtagcag aaggtgttga tatgatgatt gtaagggagc ttacaggagg aatttacttt 660
ggagagccca gaggcattaa gaccaacgaa aacggagaag aagtcggttt taatacagag 720
ttttacgctg ctcacgagat tgacagaatt gctcgtgttg catttgagac tgctaggaaa 780
cggcgtggca agctgtgttc tgtcgacaaa gccaatgtgt tggatgcatc agtattgtgg 840
aggagaagag taacagcgtt agcctctgag tatccagatg ttgagctctc acatatgtat 900
gtagacaacg ctgcaatgca gcttattcgt gacccgaaac agtttgacac aatcgtcacc 960
aataacattt tcggtgacat attatccgat gaggcctcaa tgatcactgg aagcattggg 1020
atgcttccat ctgctagtct cggtgtattg ggacctggac tctttgagcc gatacatggt 1080
tctgcgccag atatagctgg tcaggacaag gcaaacccat tggccaccat tctcagcgca 1140
gcgatgcttc tgaaatatgg acttggagaa gagaaggccg caaagaggat cgaggacgcg 1200
gtcttggatg ctctcaacaa agggtttaga accggagaca tctactcccc cggaaataaa 1260
ctggtgggat gcaaggagat gggtgaggag gtgcttaaat cagtggactc cagagttaca 1320
gctactgttt aa 1332

<210> SEQ ID NO 202
<211> LENGTH: 443
<212> TYPE: PRT
<213> ORGANISM: Thlaspi arvense

<400> SEQUENCE: 202

Met Ala Ala Cys Leu Gln Ser Asn Ile Arg Leu Asn Leu Asn Asn Ile

-continued

```
1               5                   10                  15

Val Gly Gly Lys Cys Arg Ser Leu Thr Asp Gln Ser Arg Thr Pro Cys
            20                  25                  30

Arg Ile Arg Cys Ala Ala Ala Ser Pro Gly Lys Lys Arg Phe Asn Ile
        35                  40                  45

Ala Leu Leu Pro Gly Asp Gly Ile Gly Pro Glu Val Ile Ser Val Ala
    50                  55                  60

Lys Asn Val Leu Gln Gln Ala Gly Ser Leu Glu Gly Ser Ser Ile Ser
65                  70                  75                  80

Arg Ser Val Tyr Leu Leu Ile Leu Thr Lys Leu Val Ile Ser Glu Cys
                85                  90                  95

Val Ala Tyr Pro Glu Glu Cys Ala Tyr Leu Met Cys Ile Thr Gly Leu
                100                 105                 110

Glu Phe Asn Phe Gln Glu Met Pro Ile Gly Gly Ala Ala Leu Asp Leu
        115                 120                 125

Val Gly Val Ala Leu Pro Glu Glu Thr Leu Ser Ala Ala Lys Gln Ser
    130                 135                 140

Asp Ala Ile Leu Leu Gly Ala Ile Gly Gly Tyr Lys Trp Asp Asn Asn
145                 150                 155                 160

Glu Lys His Leu Arg Pro Glu Met Ala Leu Ile Tyr Leu Arg Arg Asp
                165                 170                 175

Leu Lys Val Phe Ala Asn Leu Arg Pro Ala Ser Val Leu Pro Gln Leu
            180                 185                 190

Val Asp Ala Ser Thr Leu Lys Arg Glu Val Ala Glu Gly Val Asp Met
        195                 200                 205

Met Ile Val Arg Glu Leu Thr Gly Gly Ile Tyr Phe Gly Glu Pro Arg
    210                 215                 220

Gly Ile Lys Thr Asn Glu Asn Gly Glu Glu Val Gly Phe Asn Thr Glu
225                 230                 235                 240

Phe Tyr Ala Ala His Glu Ile Asp Arg Ile Ala Arg Val Ala Phe Glu
                245                 250                 255

Thr Ala Arg Lys Arg Arg Gly Lys Leu Cys Ser Val Asp Lys Ala Asn
            260                 265                 270

Val Leu Asp Ala Ser Val Leu Trp Arg Arg Arg Val Thr Ala Leu Ala
        275                 280                 285

Ser Glu Tyr Pro Asp Val Glu Leu Ser His Met Tyr Val Asp Asn Ala
    290                 295                 300

Ala Met Gln Leu Ile Arg Asp Pro Lys Gln Phe Asp Thr Ile Val Thr
305                 310                 315                 320

Asn Asn Ile Phe Gly Asp Ile Leu Ser Asp Glu Ala Ser Met Ile Thr
                325                 330                 335

Gly Ser Ile Gly Met Leu Pro Ser Ala Ser Leu Gly Val Leu Gly Pro
            340                 345                 350

Gly Leu Phe Glu Pro Ile His Gly Ser Ala Pro Asp Ile Ala Gly Gln
        355                 360                 365

Asp Lys Ala Asn Pro Leu Ala Thr Ile Leu Ser Ala Ala Met Leu Leu
    370                 375                 380

Lys Tyr Gly Leu Gly Glu Glu Lys Ala Ala Lys Arg Ile Glu Asp Ala
385                 390                 395                 400

Val Leu Asp Ala Leu Asn Lys Gly Phe Arg Thr Gly Asp Ile Tyr Ser
                405                 410                 415

Pro Gly Asn Lys Leu Val Gly Cys Lys Glu Met Gly Glu Glu Val Leu
            420                 425                 430
```

```
Lys Ser Val Asp Ser Arg Val Thr Ala Thr Val
        435                 440


<210> SEQ ID NO 203
<211> LENGTH: 1635
<212> TYPE: DNA
<213> ORGANISM: Thlaspi arvense

<400> SEQUENCE: 203

atggatactt tagcttcaaa ctcttcgggt ctcaggacca agtcgagtcc cgagacgtcg     60

ccgtttagca acatgtatct cctcacaaca cttcaagccc ttgcggttat ttctctcttg    120

atgatattca agaaaataaa gtattcctct tcacaaaaaa aaaagtttca tcctctcccg    180

ccgggcccca gcgggtttcc agtcgtcgga atgattccgg cgatgcttaa aaaccgtccg    240

gttttccggt ggcttcacag cctcatgaaa gagcttaaca cggagatagc ttgtgttcgt    300

ctaggaaaga ctcacgtgat ccccgtcaca tgtcctaaga tcgcacgtga gattttcaag    360

caacaagacg cactcttcgc gtcgagacca ctcacttatg ctcaaaagat actttccaac    420

agctacaaaa cctgcgtgat cacaccgttc ggagaacaat tcaagaagat gaggaaagta    480

atcatgacgg agattgtttg tccagcaaga caccgatggt tacacgacaa cagagccgag    540

gaaaccgatc atttaactgc ttggctttac aacatggtta agaaatccga accggtcgat    600

ctccggtttg ttacaaggca ctactgcgga aatgcgatta agaggcttat gttcggaacg    660

aggacgttct cggcgaaaac cgaaaccgac ggtggaccaa ccgtggaaga tatcgagcat    720

atggatgcta tgtttgaagg gttagggttt acgtttgcgt tctgtgtatc ggattatcta    780

ccgatgctta cgggattgga tctaaacgga catgagaaga tcatgagaga agctagtgcg    840

attatggaca aatatcacga tcccattatt gatgagagga ttaagatgtg gagagaagga    900

aagagaactc agattgaaga ttttctagac attttcatct ctatcaagga cgaagctggc    960

cagcctttgc ttaccgctga tgaaatcaaa ccaaccatta aggaacttgt aatggcggcg   1020

ccggacaacc catcaaacgc cgtggaatgg gccatggcgg agatgataaa caaacctgag   1080

attctccaca aagcaatgga agagattgaa agagtcgttg gcaaagaaag actcgtccaa   1140

gaatccgata tcccaaaact taactatctc aaagctatta tccgagaagc tttccgtctg   1200

catcccgtcg ccgccttcaa cctcccacac gtggcacttt ccgacacaac cgtcgctggt   1260

tatcacatcc ctaaggggag tcaagtttta cttagccgtt acggtcttgg tcgtaaccca   1320

aaggtttggt ctgatccact tagctttaaa ccggagagac acctcaatga gtgcttggaa   1380

gtaacgttga ctgagaatga tctccggttt atctcgttta gtaccggaaa aagaggatgt   1440

gctgctccgg cgttaggtac ggcgataacc gtcatgatgc tcgccaggct tttgcaaggg   1500

tttaagtgga agttagctgg aggtgagaca cgtgttgagt tgatggaatc gagtcatgat   1560

atgtttcttg cgacgccttt ggttatggtc ggagaattga gattgtcgga ggatctttac   1620

cccacggtga agtga                                                    1635


<210> SEQ ID NO 204
<211> LENGTH: 544
<212> TYPE: PRT
<213> ORGANISM: Thlaspi arvense

<400> SEQUENCE: 204

Met Asp Thr Leu Ala Ser Asn Ser Ser Gly Leu Arg Thr Lys Ser Ser
1               5                   10                  15
```

-continued

```
Pro Glu Thr Ser Pro Phe Ser Asn Met Tyr Leu Leu Thr Thr Leu Gln
            20                  25                  30

Ala Leu Ala Val Ile Ser Leu Leu Met Ile Phe Lys Lys Ile Lys Tyr
        35                  40                  45

Ser Ser Ser Gln Lys Lys Lys Phe His Pro Leu Pro Pro Gly Pro Ser
    50                  55                  60

Gly Phe Pro Val Val Gly Met Ile Pro Ala Met Leu Lys Asn Arg Pro
65                  70                  75                  80

Val Phe Arg Trp Leu His Ser Leu Met Lys Glu Leu Asn Thr Glu Ile
                85                  90                  95

Ala Cys Val Arg Leu Gly Lys Thr His Val Ile Pro Val Thr Cys Pro
            100                 105                 110

Lys Ile Ala Arg Glu Ile Phe Lys Gln Gln Asp Ala Leu Phe Ala Ser
        115                 120                 125

Arg Pro Leu Thr Tyr Ala Gln Lys Ile Leu Ser Asn Ser Tyr Lys Thr
    130                 135                 140

Cys Val Ile Thr Pro Phe Gly Glu Gln Phe Lys Lys Met Arg Lys Val
145                 150                 155                 160

Ile Met Thr Glu Ile Val Cys Pro Ala Arg His Arg Trp Leu His Asp
                165                 170                 175

Asn Arg Ala Glu Glu Thr Asp His Leu Thr Ala Trp Leu Tyr Asn Met
            180                 185                 190

Val Lys Lys Ser Glu Pro Val Asp Leu Arg Phe Val Thr Arg His Tyr
        195                 200                 205

Cys Gly Asn Ala Ile Lys Arg Leu Met Phe Gly Thr Arg Thr Phe Ser
    210                 215                 220

Ala Lys Thr Glu Thr Asp Gly Gly Pro Thr Val Glu Asp Ile Glu His
225                 230                 235                 240

Met Asp Ala Met Phe Glu Gly Leu Gly Phe Thr Phe Ala Phe Cys Val
                245                 250                 255

Ser Asp Tyr Leu Pro Met Leu Thr Gly Leu Asp Leu Asn Gly His Glu
            260                 265                 270

Lys Ile Met Arg Glu Ala Ser Ala Ile Met Asp Lys Tyr His Asp Pro
        275                 280                 285

Ile Ile Asp Glu Arg Ile Lys Met Trp Arg Glu Gly Lys Arg Thr Gln
    290                 295                 300

Ile Glu Asp Phe Leu Asp Ile Phe Ile Ser Ile Lys Asp Glu Ala Gly
305                 310                 315                 320

Gln Pro Leu Leu Thr Ala Asp Glu Ile Lys Pro Thr Ile Lys Glu Leu
                325                 330                 335

Val Met Ala Ala Pro Asp Asn Pro Ser Asn Ala Val Glu Trp Ala Met
            340                 345                 350

Ala Glu Met Ile Asn Lys Pro Glu Ile Leu His Lys Ala Met Glu Glu
        355                 360                 365

Ile Glu Arg Val Val Gly Lys Glu Arg Leu Val Gln Glu Ser Asp Ile
    370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                405                 410                 415

Thr Val Ala Gly Tyr His Ile Pro Lys Gly Ser Gln Val Leu Leu Ser
            420                 425                 430

Arg Tyr Gly Leu Gly Arg Asn Pro Lys Val Trp Ser Asp Pro Leu Ser
```

```
        435                 440                 445

Phe Lys Pro Glu Arg His Leu Asn Glu Cys Leu Glu Val Thr Leu Thr
    450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
            500                 505                 510

Glu Leu Met Glu Ser Ser His Asp Met Phe Leu Ala Thr Pro Leu Val
        515                 520                 525

Met Val Gly Glu Leu Arg Leu Ser Glu Asp Leu Tyr Pro Thr Val Lys
    530                 535                 540


<210> SEQ ID NO 205
<211> LENGTH: 1635
<212> TYPE: DNA
<213> ORGANISM: Thlaspi arvense

<400> SEQUENCE: 205

atggatactt tagcttcaaa ctcttcgggt ctcaggacca agtcgagtcc cgagacgtcg      60

ccgtttagca acatgtatct cctcacaaca cttcaagccc ttgcggttat ttctctcttg     120

atgatattca agaaaataaa gtattcctct tcacaaaaaa aaaagtttca tcctctcccg     180

ccgggcccca gcgggtttcc agtcgtcgga atgattccgg cgatgcttaa aaaccgtccg     240

gttttccggt ggcttcacag cctcatgaaa gagcttaaca cggagatagc ttgtgttcgt     300

ctaggaaaga ctcacgtgat ccccgtcaca tgtcctaaga tcgcacgtga gattttcaag     360

caacaagacg cactcttcgc gtcgagacca ctcacttatg ctcaaaagat actttccaac     420

ggctacaaaa cctgcgtgat cacaccgttc ggagaacaat tcaagaagat gaggaaagta     480

atcatgacgg agattgtttg tccagcaaga caccgatggt tacacgacaa cagagccgag     540

gaaaccgatc atttaactgc ttggctttac aacatggtta agaaatccga accggtcgat     600

ctccggtttg ttacaaggca ctactgcgga aatgcgatta agaggcttat gttcggaacg     660

aggacgttct cggcgaaaac cgaaaccgac ggtggaccaa ccgtggaaga tatcgagcat     720

atggatgcta tgtttgaagg gttagggttt acgtttgcgt tctgtgtatc ggattatcta     780

ccgatgctta cgggattgga tctaaacgga catgagaaga tcatgagaga agctagtgcg     840

attatggaca aatatcacga tcccattatt gatgagagga ttaagatgtg gagagaagga     900

aagagaactc agattgaaga ttttctagac attttcatct ctatcaagga cgaagctggc     960

cagcctttgc ttaccgctga tgaaatcaaa ccaaccatta aggaacttgt aatggcggcg    1020

ccggacaacc catcaaacgc cgtggaatgg gccatggcgg agatgataaa caaacctgag    1080

attctccaca aagcaatgga agagattgaa agagtcgttg gcaaagaaag actcgtccaa    1140

gaatccgata tcccaaaact taactatctc aaagctatta tccgagaagc tttccgtctg    1200

catcccgtcg ccgccttcaa cctcccacac gtggcacttt ccgacacaac cgtcgctggt    1260

tatcacatcc ctaaggggag tcaagtttta cttagccgtt acggtcttgg tcgtaaccca    1320

aaggtttggt ctgattcact tagctttaaa ccggagagac acctcaatga gtgcttggaa    1380

gtaacgttga ctgagaatga tctccggttt atctcgttta gtaccggaaa aagaggatgt    1440

gctgctccgg cgttaggtac ggcgataacc gtcatgatgc tcgccaggct tttgcaaggg    1500

tttaagtgga agttagctgg aggtgagaca cgtgttgagt tgatggaatc gagtcatgat    1560
```

atgtttcttg cgacgccttt ggttatggtc ggagaattga gattgtcgga ggatctttac 1620
cccacggtga agtga 1635

<210> SEQ ID NO 206
<211> LENGTH: 544
<212> TYPE: PRT
<213> ORGANISM: Thlaspi arvense

<400> SEQUENCE: 206

Met Asp Thr Leu Ala Ser Asn Ser Ser Gly Leu Arg Thr Lys Ser Ser
1 5 10 15

Pro Glu Thr Ser Pro Phe Ser Asn Met Tyr Leu Leu Thr Thr Leu Gln
20 25 30

Ala Leu Ala Val Ile Ser Leu Leu Met Ile Phe Lys Lys Ile Lys Tyr
35 40 45

Ser Ser Ser Gln Lys Lys Lys Phe His Pro Leu Pro Pro Gly Pro Ser
50 55 60

Gly Phe Pro Val Val Gly Met Ile Pro Ala Met Leu Lys Asn Arg Pro
65 70 75 80

Val Phe Arg Trp Leu His Ser Leu Met Lys Glu Leu Asn Thr Glu Ile
85 90 95

Ala Cys Val Arg Leu Gly Lys Thr His Val Ile Pro Val Thr Cys Pro
100 105 110

Lys Ile Ala Arg Glu Ile Phe Lys Gln Gln Asp Ala Leu Phe Ala Ser
115 120 125

Arg Pro Leu Thr Tyr Ala Gln Lys Ile Leu Ser Asn Gly Tyr Lys Thr
130 135 140

Cys Val Ile Thr Pro Phe Gly Glu Gln Phe Lys Lys Met Arg Lys Val
145 150 155 160

Ile Met Thr Glu Ile Val Cys Pro Ala Arg His Arg Trp Leu His Asp
165 170 175

Asn Arg Ala Glu Glu Thr Asp His Leu Thr Ala Trp Leu Tyr Asn Met
180 185 190

Val Lys Lys Ser Glu Pro Val Asp Leu Arg Phe Val Thr Arg His Tyr
195 200 205

Cys Gly Asn Ala Ile Lys Arg Leu Met Phe Gly Thr Arg Thr Phe Ser
210 215 220

Ala Lys Thr Glu Thr Asp Gly Gly Pro Thr Val Glu Asp Ile Glu His
225 230 235 240

Met Asp Ala Met Phe Glu Gly Leu Gly Phe Thr Phe Ala Phe Cys Val
245 250 255

Ser Asp Tyr Leu Pro Met Leu Thr Gly Leu Asp Leu Asn Gly His Glu
260 265 270

Lys Ile Met Arg Glu Ala Ser Ala Ile Met Asp Lys Tyr His Asp Pro
275 280 285

Ile Ile Asp Glu Arg Ile Lys Met Trp Arg Glu Gly Lys Arg Thr Gln
290 295 300

Ile Glu Asp Phe Leu Asp Ile Phe Ile Ser Ile Lys Asp Glu Ala Gly
305 310 315 320

Gln Pro Leu Leu Thr Ala Asp Glu Ile Lys Pro Thr Ile Lys Glu Leu
325 330 335

Val Met Ala Ala Pro Asp Asn Pro Ser Asn Ala Val Glu Trp Ala Met
340 345 350

-continued

```
Ala Glu Met Ile Asn Lys Pro Glu Ile Leu His Lys Ala Met Glu Glu
        355                 360                 365

Ile Glu Arg Val Val Gly Lys Glu Arg Leu Val Gln Glu Ser Asp Ile
    370                 375                 380

Pro Lys Leu Asn Tyr Leu Lys Ala Ile Ile Arg Glu Ala Phe Arg Leu
385                 390                 395                 400

His Pro Val Ala Ala Phe Asn Leu Pro His Val Ala Leu Ser Asp Thr
                405                 410                 415

Thr Val Ala Gly Tyr His Ile Pro Lys Gly Ser Gln Val Leu Leu Ser
            420                 425                 430

Arg Tyr Gly Leu Gly Arg Asn Pro Lys Val Trp Ser Asp Ser Leu Ser
        435                 440                 445

Phe Lys Pro Glu Arg His Leu Asn Glu Cys Leu Glu Val Thr Leu Thr
    450                 455                 460

Glu Asn Asp Leu Arg Phe Ile Ser Phe Ser Thr Gly Lys Arg Gly Cys
465                 470                 475                 480

Ala Ala Pro Ala Leu Gly Thr Ala Ile Thr Val Met Met Leu Ala Arg
                485                 490                 495

Leu Leu Gln Gly Phe Lys Trp Lys Leu Ala Gly Gly Glu Thr Arg Val
            500                 505                 510

Glu Leu Met Glu Ser Ser His Asp Met Phe Leu Ala Thr Pro Leu Val
        515                 520                 525

Met Val Gly Glu Leu Arg Leu Ser Glu Asp Leu Tyr Pro Thr Val Lys
    530                 535                 540


<210> SEQ ID NO 207
<211> LENGTH: 1509
<212> TYPE: DNA
<213> ORGANISM: Thlaspi arvense

<400> SEQUENCE: 207

atggaagata tcatcatcgg cgttgtggct ctcgccgccg ttctcctctt cttcctctac     60

caaagcccaa aaaccaaacg gtataagctg cctcccggcc cacggccgct tccggtgatc    120

ggaaacctcc accagcttag ccaggttaac ccacaacggt tcttctatgg atgggccaaa    180

aaatatggac caatcttatc atacaagata ggaaacaaaa caatgatggt aatttcttcg    240

gctgagctaa ccaaagagct tctcaagacg caagatgtca acttcgccaa ccggcctcct    300

caccgtggtc acgagctcat gacctacggc cgaagtgaca tggcgatgaa ccactacaca    360

ccgttgtacc gggagatgag gaagatgggc atgaaccact tgttctcccc cactcgtgta    420

gccaccttta agcacgtacg ggaggaggag gctaggagga tgatgtttaa gatcgagaag    480

gctgcggaga gatctgaacc ggtcgatata agcgagctta tgttgacctt cacgaactcg    540

gttgtgtgta ggcaagcttt cgggaagaag tacaatgaag atggggaaga gatgaagaga    600

ttcatcagga ttctttatgg gactcagagc gtattgggga agattttttt ctctgatttt    660

ttcccgttta ctcgctacgt tcttgataat tggaccggcc tcacgaaata tatgatggac    720

tgttttgaaa gacaagacac ttacatacaa gagattatcg atgagacact tgatcccaac    780

aaggtaaagc cagaaacgga gagcatgatc gatctcttga tggaggtcta caaagaacaa    840

ccattcgcct ccaagttcac aattgggaat gtcaaaggcg ttatcttgaa tatagtggtt    900

gcgggaaccg acacggcggc tgcggcggtt gtgtggggga tgacgtatct aatgaagtac    960

cctcaagtta tgaagaaagc tcaagcagaa gtgagagagt atgcaaaaga gaaagatcta   1020

acgtttatta ctgaagacga cgtcaagaac cttccttact tcagagcttt agttaaagaa   1080
```

-continued

```
accttaagga tcgaaccagt gattcctctc cttatccctc gttgttgcat tcaagacacc   1140

aagatcgccg gttacgatgt ccccgcgggg accacggtca acgtaaacgc gtgggcggtg   1200

tcacgcgacg agaaggagtg gggcccaaac cctgatgaat tcaggcccaa gaggtttctt   1260

gagaaggacg tggacttcaa aggcacggac tatgagttta taccgtttgg gtcaggccgg   1320

agaatgtgcc ctggaatgcg tcttggcgcg gcgatgatcg aggttccgta tgcgaacctt   1380

ttgctcaact ttgacttcaa acttgctgat ggactgaaac cagaagagat caacatggat   1440

gttatgacag gtcttgctat gcacaaggcg gttcatctca ggcttgttcc cgagaaagtg   1500

aggaagtga                                                            1509


<210> SEQ ID NO 208
<211> LENGTH: 502
<212> TYPE: PRT
<213> ORGANISM: Thlaspi arvense

<400> SEQUENCE: 208

Met Glu Asp Ile Ile Ile Gly Val Val Ala Leu Ala Ala Val Leu Leu
1               5                   10                  15

Phe Phe Leu Tyr Gln Ser Pro Lys Thr Lys Arg Tyr Lys Leu Pro Pro
            20                  25                  30

Gly Pro Arg Pro Leu Pro Val Ile Gly Asn Leu His Gln Leu Ser Gln
        35                  40                  45

Val Asn Pro Gln Arg Phe Phe Tyr Gly Trp Ala Lys Lys Tyr Gly Pro
    50                  55                  60

Ile Leu Ser Tyr Lys Ile Gly Asn Lys Thr Met Met Val Ile Ser Ser
65                  70                  75                  80

Ala Glu Leu Thr Lys Glu Leu Leu Lys Thr Gln Asp Val Asn Phe Ala
                85                  90                  95

Asn Arg Pro Pro His Arg Gly His Glu Leu Met Thr Tyr Gly Arg Ser
            100                 105                 110

Asp Met Ala Met Asn His Tyr Thr Pro Leu Tyr Arg Glu Met Arg Lys
        115                 120                 125

Met Gly Met Asn His Leu Phe Ser Pro Thr Arg Val Ala Thr Phe Lys
    130                 135                 140

His Val Arg Glu Glu Glu Ala Arg Arg Met Met Phe Lys Ile Glu Lys
145                 150                 155                 160

Ala Ala Glu Arg Ser Glu Pro Val Asp Ile Ser Glu Leu Met Leu Thr
                165                 170                 175

Phe Thr Asn Ser Val Val Cys Arg Gln Ala Phe Gly Lys Lys Tyr Asn
            180                 185                 190

Glu Asp Gly Glu Glu Met Lys Arg Phe Ile Arg Ile Leu Tyr Gly Thr
        195                 200                 205

Gln Ser Val Leu Gly Lys Ile Phe Phe Ser Asp Phe Phe Pro Phe Thr
    210                 215                 220

Arg Tyr Val Leu Asp Asn Trp Thr Gly Leu Thr Lys Tyr Met Met Asp
225                 230                 235                 240

Cys Phe Glu Arg Gln Asp Thr Tyr Ile Gln Glu Ile Ile Asp Glu Thr
                245                 250                 255

Leu Asp Pro Asn Lys Val Lys Pro Glu Thr Glu Ser Met Ile Asp Leu
            260                 265                 270

Leu Met Glu Val Tyr Lys Glu Gln Pro Phe Ala Ser Lys Phe Thr Ile
        275                 280                 285
```

```
Gly Asn Val Lys Gly Val Ile Leu Asn Ile Val Val Ala Gly Thr Asp
    290                 295                 300

Thr Ala Ala Ala Ala Val Val Trp Gly Met Thr Tyr Leu Met Lys Tyr
305                 310                 315                 320

Pro Gln Val Met Lys Lys Ala Gln Ala Glu Val Arg Glu Tyr Ala Lys
                325                 330                 335

Glu Lys Asp Leu Thr Phe Ile Thr Glu Asp Asp Val Lys Asn Leu Pro
            340                 345                 350

Tyr Phe Arg Ala Leu Val Lys Glu Thr Leu Arg Ile Glu Pro Val Ile
        355                 360                 365

Pro Leu Leu Ile Pro Arg Cys Cys Ile Gln Asp Thr Lys Ile Ala Gly
    370                 375                 380

Tyr Asp Val Pro Ala Gly Thr Thr Val Asn Val Asn Ala Trp Ala Val
385                 390                 395                 400

Ser Arg Asp Glu Lys Glu Trp Gly Pro Asn Pro Asp Glu Phe Arg Pro
                405                 410                 415

Lys Arg Phe Leu Glu Lys Asp Val Asp Phe Lys Gly Thr Asp Tyr Glu
            420                 425                 430

Phe Ile Pro Phe Gly Ser Gly Arg Arg Met Cys Pro Gly Met Arg Leu
        435                 440                 445

Gly Ala Ala Met Ile Glu Val Pro Tyr Ala Asn Leu Leu Leu Asn Phe
    450                 455                 460

Asp Phe Lys Leu Ala Asp Gly Leu Lys Pro Glu Glu Ile Asn Met Asp
465                 470                 475                 480

Val Met Thr Gly Leu Ala Met His Lys Ala Val His Leu Arg Leu Val
                485                 490                 495

Pro Glu Lys Val Arg Lys
            500


<210> SEQ ID NO 209
<211> LENGTH: 1510
<212> TYPE: DNA
<213> ORGANISM: Thlaspi arvense

<400> SEQUENCE: 209

atggaagata tcatcatcgg cgttgtggct ctcgccgccg ttctcctctt cttcctctac     60

caaagcccaa aaaccaaacg gtataagctg cctcccggcc cacggccgct tccggtgatc    120

ggaaacctcc accagcttag ccaggttaac ccacaacggt tcttctatgg atgggccaaa    180

aaatatggac caatcttatc atacaaagat aggaaacaaa acaatgatgg taatttcttc    240

ggctgagcta accaaagagc ttctcaagac gcaagatgtc aacttcgcca accggcctcc    300

tcaccgtggt cacgagctca tgacctacgg ccgaagtgac atggcgatga accactacac    360

accgttgtac cgggagatga ggaagatggg catgaaccac ttgttctccc ccactcgtgt    420

agccaccttt aagcacgtac gggaggagga ggctaggagg atgatgttta agatcgagaa    480

ggctgcggag agatctgaac cggtcgatat aagcgagctt atgttgacct tcacgaactc    540

ggttgtgtgt aggcaagctt tcgggaagaa gtacaatgaa gatggggaag agatgaagag    600

attcatcagg attctttatg ggactcagag cgtattgggg aagatttttt tctctgattt    660

tttcccgttt actcgctacg ttcttgataa ttggaccggc ctcacgaaat atatgatgga    720

ctgttttgaa agacaagaca cttacataca agagattatc gatgagacac ttgatcccaa    780

caaggtaaag ccagaaacgg agagcatgat cgatctcttg atggaggtct acaaagaaca    840

accattcgcc tccaagttca caattgggaa tgtcaaaggc gttatcttga atatagtggt    900
```

tgcgggaacc gacacggcgg ctgcggcggt tgtgtggggg atgacgtatc taatgaagta 960
ccctcaagtt atgaagaaag ctcaagcaga agtgagagag tatgcaaaag agaaagatct 1020
aacgtttatt actgaagacg acgtcaagaa ccttccttac ttcagagctt tagttaaaga 1080
aaccttaagg atcgaaccag tgattcctct ccttatccct cgttgttgca ttcaagacac 1140
caagatcgcc ggttacgatg tccccgcggg gaccacggtc aacgtaaacg cgtgggcggt 1200
gtcacgcgac gagaaggagt ggggcccaaa ccctgatgaa ttcaggcccg agaggtttct 1260
tgagaaggac gtggacttca aaggcacgga ctatgagttt ataccgtttg ggtcaggccg 1320
gagaatgtgc cctggaatgc gtcttggcgc ggcgatgatc gaggttccgt atgcgaacct 1380
tttgctcaac tttgacttca aacttgctga tggactgaaa ccagaagaga tcaacatgga 1440
tgttatgaca ggtcttgcta tgcacaaggc ggttcatctc aggcttgttc ccgagaaagt 1500
gaggaagtga 1510

<210> SEQ ID NO 210
<211> LENGTH: 81
<212> TYPE: PRT
<213> ORGANISM: Thlaspi arvense

<400> SEQUENCE: 210

Met Glu Asp Ile Ile Ile Gly Val Val Ala Leu Ala Ala Val Leu Leu
1 5 10 15

Phe Phe Leu Tyr Gln Ser Pro Lys Thr Lys Arg Tyr Lys Leu Pro Pro
20 25 30

Gly Pro Arg Pro Leu Pro Val Ile Gly Asn Leu His Gln Leu Ser Gln
35 40 45

Val Asn Pro Gln Arg Phe Phe Tyr Gly Trp Ala Lys Lys Tyr Gly Pro
50 55 60

Ile Leu Ser Tyr Lys Asp Arg Lys Gln Asn Asn Asp Gly Asn Phe Phe
65 70 75 80

Gly

<210> SEQ ID NO 211
<211> LENGTH: 1510
<212> TYPE: DNA
<213> ORGANISM: Thlaspi arvense

<400> SEQUENCE: 211
atggaagata tcatcatcgg cgttgtggct ctcgccgccg ttctcctctt cttcctctac 60
caaagcccaa aaaccaaacg gtataagctg cctcccggcc cacggccgct tccggtgatc 120
ggaaacctcc accagcttag ccaggttaac ccacaacggt tcttctatgg atgggccaaa 180
aaatatggac caatcttatc atacaatgat aggaaacaaa acaatgatgg taatttcttc 240
ggctgagcta accaaagagc ttctcaagac gcaagatgtc aacttcgcca accggcctcc 300
tcaccgtggt cacgagctca tgacctacgg ccgaagtgac atggcgatga accactacac 360
accgttgtac cgggagatga ggaagatggg catgaaccac ttgttctccc ccactcgtgt 420
agccaccttt aagcacgtac gggaggagga ggctaggagg atgatgttta agatcgagaa 480
ggctgcggag agatctgaac cggtcgatat aagcgagctt atgttgacct tcacgaactc 540
ggttgtgtgt aggcaagctt tcgggaagaa gtacaatgaa gatggggaag agatgaagag 600
attcatcagg attctttatg ggactcagag cgtattgggg aagatttttt tctctgattt 660
tttcccgttt actcgctacg ttcttgataa ttggaccggc ctcacgaaat atatgatgga 720
ctgttttgaa agacaagaca cttacataca agagattatc gatgagacac ttgatcccaa 780
caaggtaaag ccagaaacgg agagcatgat cgatctcttg atggaggtct acaaagaaca 840
accattcgcc tccaagttca caattgggaa tgtcaaaggc gttatcttga atatagtggt 900
tgcgggaacc gacacggcgg ctgcggcggt tgtgtggggg atgacgtatc taatgaagta 960
ccctcaagtt atgaagaaag ctcaagcaga agtgagagag tatgcaaaag agaaagatct 1020
aacgtttatt actgaagacg acgtcaagaa ccttccttac ttcagagctt tagttaaaga 1080
aaccttaagg atcgaaccag tgattcctct ccttatccct cgttgttgca ttcaagacac 1140
caagatcgcc ggttacgatg tccccgcggg gaccacggtc aacgtaaacg cgtgggcggt 1200
gtcacgcgac gagaaggagt ggggcccaaa ccctgatgaa ttcaggcccg agaggtttct 1260
tgagaaggac gtggacttca aaggcacgga ctatgagttt ataccgtttg ggtcaggccg 1320
gagaatgtgc cctggaatgc gtcttggcgc ggcgatgatc gaggttccgt atgcgaacct 1380
tttgctcaac tttgacttca aacttgctga tggactgaaa ccagaagaga tcaacatgga 1440
tgttatgaca ggtcttgcta tgcacaaggc ggttcatctc aggcttgttc ccgagaaagt 1500
gaggaagtga 1510

<210> SEQ ID NO 212
<211> LENGTH: 81
<212> TYPE: PRT
<213> ORGANISM: Thlaspi arvense

<400> SEQUENCE: 212

Met Glu Asp Ile Ile Ile Gly Val Val Ala Leu Ala Ala Val Leu Leu
1 5 10 15

Phe Phe Leu Tyr Gln Ser Pro Lys Thr Lys Arg Tyr Lys Leu Pro Pro
20 25 30

Gly Pro Arg Pro Leu Pro Val Ile Gly Asn Leu His Gln Leu Ser Gln
35 40 45

Val Asn Pro Gln Arg Phe Phe Tyr Gly Trp Ala Lys Lys Tyr Gly Pro
50 55 60

Ile Leu Ser Tyr Asn Asp Arg Lys Gln Asn Asn Asp Gly Asn Phe Phe
65 70 75 80

Gly

<210> SEQ ID NO 213
<211> LENGTH: 1332
<212> TYPE: DNA
<213> ORGANISM: Thlaspi arvense

<400> SEQUENCE: 213
atgggttcac tttcaaacac tcctcagctt ccagtcatct acctctcgga ccaaacccta 60
aaaccaggaa gctcaaagtg ggttgaagtc aggagtgatg tccgtaaagc tcttgaagag 120
tacggcggtt tcgaggtgtc gtacgataga gtgtcggagg agcttaagaa gtcggttttg 180
caagccatgg aagagctttt cgcgttacca gttgaggcta aacagagaaa cgtctctcct 240
aaacccttca gcggttattc cactcataac ggtcttttgg acaaagttta cgagtttact 300
caacttctac gtcctgatca ttgtgacggt aacaagagca tcagcgaaac gatccagacg 360
ttttcagaga agttatcaga attggatata atggtgagaa gaatggtaat ggaaagcttc 420
gggatagaga agtaccttga caaacacctg aactcaacga attaccgtct gcggctgatg 480
aagtatatag caccgcctga tgctgatgct actaatgttg cggctgatgc caaagatgct 540

-continued

```
gatgataatg ctaagacgat tacaaatgat aaagttgatg cggctggtgc taatgatgta    600

gatgctggtg atatcgctaa tggtattgct aatcttcata ttggtgatga tgctaacgct    660

ggtgctaatg gtgctggtgt tgatgctaat gatggtggtg aggatgctaa gactggtgag    720

gatgctaaga ctggtgaatg tgctagtgtt aagtctaatg ccgaagatgg tactgatgtt    780

aatgccagtg ctgatgctgg tgttactgtt ggctctaatg ctgatgctaa tgctaatgct    840

aatgctaata ctagtactga tgctggtgtt ggcgatagtg ttaaagctaa tggtggtgct    900

gatgatgttg agaagaaatt gggtctacct tctcacactg ataagaacct tataacggtg    960

ctttatcaat acgagattga aggcttggag gttctaacca aagatgacaa gtggatcaga   1020

ctcaaaccat ctcataattc tttcgttgtt atggctggag attctctata cgcacttatg   1080

aatggtagac taactcgtcc ctttcatcga gtaagagtaa cggagaaaaa gaagacaaga   1140

tattcaatag cattgttctc ggctccaacc gcagattaca tcatagacac accaaaagaa   1200

cttgtggacg agaagcatcc acgtatcttc gaaccattta actataacga cttgatgagt   1260

ttctatcata gtgaagctgg tcgtaaagct cgatctactc ttgatgcttt ctgtgccgtc   1320

tctcgagcat aa                                                       1332
```

<210> SEQ ID NO 214
<211> LENGTH: 443
<212> TYPE: PRT
<213> ORGANISM: Thlaspi arvense

<400> SEQUENCE: 214

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Leu Asp Lys Val
                85                  90                  95

Tyr Glu Phe Thr Gln Leu Leu Arg Pro Asp His Cys Asp Gly Asn Lys
            100                 105                 110

Ser Ile Ser Glu Thr Ile Gln Thr Phe Ser Glu Lys Leu Ser Glu Leu
        115                 120                 125

Asp Ile Met Val Arg Arg Met Val Met Glu Ser Phe Gly Ile Glu Lys
    130                 135                 140

Tyr Leu Asp Lys His Leu Asn Ser Thr Asn Tyr Arg Leu Arg Leu Met
145                 150                 155                 160

Lys Tyr Ile Ala Pro Pro Asp Ala Asp Ala Thr Asn Val Ala Ala Asp
                165                 170                 175

Ala Lys Asp Ala Asp Asp Asn Ala Lys Thr Ile Thr Asn Asp Lys Val
            180                 185                 190

Asp Ala Ala Gly Ala Asn Asp Val Asp Ala Gly Asp Ile Ala Asn Gly
        195                 200                 205

Ile Ala Asn Leu His Ile Gly Asp Asp Ala Asn Ala Gly Ala Asn Gly
    210                 215                 220
```

```
Ala Gly Val Asp Ala Asn Asp Gly Gly Glu Asp Ala Lys Thr Gly Glu
225                 230                 235                 240

Asp Ala Lys Thr Gly Glu Cys Ala Ser Val Lys Ser Asn Ala Glu Asp
                245                 250                 255

Gly Thr Asp Val Asn Ala Ser Ala Asp Ala Gly Val Thr Val Gly Ser
            260                 265                 270

Asn Ala Asp Ala Asn Ala Asn Ala Asn Ala Asn Thr Ser Thr Asp Ala
        275                 280                 285

Gly Val Gly Asp Ser Val Lys Ala Asn Gly Gly Ala Asp Asp Val Glu
    290                 295                 300

Lys Lys Leu Gly Leu Pro Ser His Thr Asp Lys Asn Leu Ile Thr Val
305                 310                 315                 320

Leu Tyr Gln Tyr Glu Ile Glu Gly Leu Glu Val Leu Thr Lys Asp Asp
                325                 330                 335

Lys Trp Ile Arg Leu Lys Pro Ser His Asn Ser Phe Val Val Met Ala
            340                 345                 350

Gly Asp Ser Leu Tyr Ala Leu Met Asn Gly Arg Leu Thr Arg Pro Phe
        355                 360                 365

His Arg Val Arg Val Thr Glu Lys Lys Lys Thr Arg Tyr Ser Ile Ala
    370                 375                 380

Leu Phe Ser Ala Pro Thr Ala Asp Tyr Ile Ile Asp Thr Pro Lys Glu
385                 390                 395                 400

Leu Val Asp Glu Lys His Pro Arg Ile Phe Glu Pro Phe Asn Tyr Asn
                405                 410                 415

Asp Leu Met Ser Phe Tyr His Ser Glu Ala Gly Arg Lys Ala Arg Ser
            420                 425                 430

Thr Leu Asp Ala Phe Cys Ala Val Ser Arg Ala
        435                 440
```

<210> SEQ ID NO 215
<211> LENGTH: 1363
<212> TYPE: DNA
<213> ORGANISM: Thlaspi arvense

<400> SEQUENCE: 215

```
atgggttcac tttcaaacac tcctcagctt ccagtcatct acctctcgga ccaaacccta      60

aaaccaggaa gctcaaagtg ggttgaagtc aggagtgatg tccgtaaagc tcttgaagag     120

tacggcggtt tcgaggtgtc gtacgataga gtgtcggagg agcttaagaa gtcggttttg     180

caagccatgg aagagctttt cgcgttacca gttgaggcta aacagagaaa cgtctctcct     240

aaacccttca gcggttattc cactcataac ggtctttccg agagtatggg gatccaggat     300

cctcattttg gacaaagttt acgagtttac tcaacttcta cgtcctgatc attgtgacgg     360

taacaagagc atcagcgaaa cgatccagac gttttcagag aagttatcag aattggatat     420

aatggtgaga agaatggtaa tggaaagctt cgggatagag aagtaccttg acaaacacct     480

gaactcaacg aattaccgtc tgcggctgat gaagtatata gcaccgcctg atgctgatgc     540

tactaatgtt gcggctgatg ccaaagatgc tgatgataat gctaagacga ttacaaatga     600

taaagttgat gcggctggtg ctaatgatgt agatgctggt gatatcgcta atggtattgc     660

taatcttcat attggtgatg atgctaacgc tggtgctaat ggtgctggtg ttgatgctaa     720

tgatggtggt gaggatgcta agactggtga ggatgctaag actggtgaat gtgctagtgt     780

taagtctaat gccgaagatg gtactgatgt taatgccagt gctgatgctg gtgttactgt     840

tggctctaat gctgatgcta atgctaatgc taatgctaat actagtactg atgctggtgt     900
```

tggcgatagt gttaaagcta atggtggtgc tgatgatgtt gagaagaaat tgggtctacc 960
ttctcacact gataagaacc ttataacggt gctttatcaa tacgagattg aaggcttgga 1020
ggttctaacc aaagatgaca agtggatcag actcaaacca tctcataatt ctttcgttgt 1080
tatggctgga gattctctat acgcacttat gaatggtaga ctaactcgtc cctttcatcg 1140
agtaagagta acggagaaaa agaagacaag atattcaata gcattgttct cggctccaac 1200
cgcagattac atcatagaca caccaaaaga acttgtggac gagaagcatc cacgtatctt 1260
cgaaccattt aactataacg acttgatgag tttctatcat agtgaagctg gtcgtaaagc 1320
tcgatctact cttgatgctt tctgtgccgt ctctcgagca taa 1363

<210> SEQ ID NO 216
<211> LENGTH: 115
<212> TYPE: PRT
<213> ORGANISM: Thlaspi arvense

<400> SEQUENCE: 216

Met Gly Ser Leu Ser Asn Thr Pro Gln Leu Pro Val Ile Tyr Leu Ser
1 5 10 15

Asp Gln Thr Leu Lys Pro Gly Ser Ser Lys Trp Val Glu Val Arg Ser
20 25 30

Asp Val Arg Lys Ala Leu Glu Glu Tyr Gly Gly Phe Glu Val Ser Tyr
35 40 45

Asp Arg Val Ser Glu Glu Leu Lys Lys Ser Val Leu Gln Ala Met Glu
50 55 60

Glu Leu Phe Ala Leu Pro Val Glu Ala Lys Gln Arg Asn Val Ser Pro
65 70 75 80

Lys Pro Phe Ser Gly Tyr Ser Thr His Asn Gly Leu Ser Glu Ser Met
85 90 95

Gly Ile Gln Asp Pro His Phe Gly Gln Ser Leu Arg Val Tyr Ser Thr
100 105 110

Ser Thr Ser
115

<210> SEQ ID NO 217
<211> LENGTH: 1364
<212> TYPE: DNA
<213> ORGANISM: Thlaspi arvense

<400> SEQUENCE: 217
atgggttcac tttcaaacac tcctcagctt ccagtcatct acctctcgga ccaaacccta 60
aaaccaggaa gctcaaagtg ggttgaagtc aggagtgatg tccgtaaagc tcttgaagag 120
tacggcggtt tcgaggtgtc gtacgataga gtgtcggagg agcttaagaa gtcggttttg 180
caagccatgg aagagctttt cgcgttacca gttgaggcta aacagagaaa cgtctctcct 240
aaacccttca gcggttattc cactcataac ggtctttccg agagtatggg gatccaggat 300
cctcatgttt ggacaaagtt tacgagttta ctcaacttct acgtcctgat cattgtgacg 360
gtaacaagag catcagcgaa acgatccaga cgttttcaga gaagttatca gaattggata 420
taatggtgag aagaatggta atggaaagct tcgggataga gaagtacctt gacaaacacc 480
tgaactcaac gaattaccgt ctgcggctga tgaagtatat agcaccgcct gatgctgatg 540
ctactaatgt tgcggctgat gccaaagatg ctgatgataa tgctaagacg attacaaatg 600
ataaagttga tgcggctggt gctaatgatg tagatgctgg tgatatcgct aatggtattg 660

```
ctaatcttca tattggtgat gatgctaacg ctggtgctaa tggtgctggt gttgatgcta    720

atgatggtgg tgaggatgct aagactggtg aggatgctaa gactggtgaa tgtgctagtg    780

ttaagtctaa tgccgaagat ggtactgatg ttaatgccag tgctgatgct ggtgttactg    840

ttggctctaa tgctgatgct aatgctaatg ctaatgctaa tactagtact gatgctggtg    900

ttggcgatag tgttaaagct aatggtggtg ctgatgatgt tgagaagaaa ttgggtctac    960

cttctcacac tgataagaac cttataacgg tgctttatca atacgagatt gaaggcttgg   1020

aggttctaac caaagatgac aagtggatca gactcaaacc atctcataat tctttcgttg   1080

ttatggctgg agattctcta tacgcactta tgaatggtag actaactcgt ccctttcatc   1140

gagtaagagt aacggagaaa aagaagacaa gatattcaat agcattgttc tcggctccaa   1200

ccgcagatta catcatagac acaccaaaag aacttgtgga cgagaagcat ccacgtatct   1260

tcgaaccatt taactataac gacttgatga gtttctatca tagtgaagct ggtcgtaaag   1320

ctcgatctac tcttgatgct ttctgtgccg tctctcgagc ataa                    1364
```

<210> SEQ ID NO 218
<211> LENGTH: 140
<212> TYPE: PRT
<213> ORGANISM: Thlaspi arvense

<400> SEQUENCE: 218

```
Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Gly Ile Gln Asp Pro His Val Trp Thr Lys Phe Thr Ser Leu Leu Asn
            100                 105                 110

Phe Tyr Val Leu Ile Ile Val Thr Val Thr Arg Ala Ser Ala Lys Arg
        115                 120                 125

Ser Arg Arg Phe Gln Arg Ser Tyr Gln Asn Trp Ile
    130                 135                 140
```

<210> SEQ ID NO 219
<211> LENGTH: 1366
<212> TYPE: DNA
<213> ORGANISM: Thlaspi arvense

<400> SEQUENCE: 219

```
atgggttcac tttcaaacac tcctcagctt ccagtcatct acctctcgga ccaaacccta     60

aaaccaggaa gctcaaagtg ggttgaagtc aggagtgatg tccgtaaagc tcttgaagag    120

tacggcggtt tcgaggtgtc gtacgataga gtgtcggagg agcttaagaa gtcggttttg    180

caagccatgg aagagctttt cgcgttacca gttgaggcta aacagagaaa cgtctctcct    240

aaacccttca gcggttattc cactcataac ggtctttccg agagtatggg gatccaggat    300

cctcatgttt ttggacaaag tttacgagtt tactcaactt ctacgtcctg atcattgtga    360
```

cggtaacaag agcatcagcg aaacgatcca gacgttttca gagaagttat cagaattgga 420
tataatggtg agaagaatgg taatggaaag cttcgggata gagaagtacc ttgacaaaca 480
cctgaactca acgaattacc gtctgcggct gatgaagtat atagcaccgc ctgatgctga 540
tgctactaat gttgcggctg atgccaaaga tgctgatgat aatgctaaga cgattacaaa 600
tgataaagtt gatgcggctg gtgctaatga tgtagatgct ggtgatatcg ctaatggtat 660
tgctaatctt catattggtg atgatgctaa cgctggtgct aatggtgctg gtgttgatgc 720
taatgatggt ggtgaggatg ctaagactgg tgaggatgct aagactggtg aatgtgctag 780
tgttaagtct aatgccgaag atggtactga tgttaatgcc agtgctgatg ctggtgttac 840
tgttggctct aatgctgatg ctaatgctaa tgctaatgct aatactagta ctgatgctgg 900
tgttggcgat agtgttaaag ctaatggtgg tgctgatgat gttgagaaga aattgggtct 960
accttctcac actgataaga accttataac ggtgctttat caatacgaga ttgaaggctt 1020
ggaggttcta accaaagatg acaagtggat cagactcaaa ccatctcata attctttcgt 1080
tgttatggct ggagattctc tatacgcact tatgaatggt agactaactc gtccctttca 1140
tcgagtaaga gtaacggaga aaaagaagac aagatattca atagcattgt tctcggctcc 1200
aaccgcagat tacatcatag acacaccaaa agaacttgtg gacgagaagc atccacgtat 1260
cttcgaacca tttaactata acgacttgat gagtttctat catagtgaag ctggtcgtaa 1320
agctcgatct actcttgatg ctttctgtgc cgtctctcga gcataa 1366

<210> SEQ ID NO 220
<211> LENGTH: 116
<212> TYPE: PRT
<213> ORGANISM: Thlaspi arvense

<400> SEQUENCE: 220

Met Gly Ser Leu Ser Asn Thr Pro Gln Leu Pro Val Ile Tyr Leu Ser
1               5                   10                  15

Asp Gln Thr Leu Lys Pro Gly Ser Ser Lys Trp Val Glu Val Arg Ser
            20                  25                  30

Asp Val Arg Lys Ala Leu Glu Glu Tyr Gly Gly Phe Glu Val Ser Tyr
        35                  40                  45

Asp Arg Val Ser Glu Glu Leu Lys Lys Ser Val Leu Gln Ala Met Glu
    50                  55                  60

Glu Leu Phe Ala Leu Pro Val Glu Ala Lys Gln Arg Asn Val Ser Pro
65                  70                  75                  80

Lys Pro Phe Ser Gly Tyr Ser Thr His Asn Gly Leu Ser Glu Ser Met
                85                  90                  95

Gly Ile Gln Asp Pro His Val Phe Gly Gln Ser Leu Arg Val Tyr Ser
            100                 105                 110

Thr Ser Thr Ser
        115

<210> SEQ ID NO 221
<211> LENGTH: 1956
<212> TYPE: DNA
<213> ORGANISM: Thlaspi arvense

<400> SEQUENCE: 221
atgaagagta gagtcatcct cagccataga gagagaagag ataagaagaa taataacatt 60
aacaacaaag acatctcctg taatttcaca cagattgaaa ccatggagag aaagcccttt 120
gaggttgaga cgacggagaa tcacaaaccc tactccaccg tcgatggcgg tggcgttggt 180

```
tctgatttga gatcgccggt cgattcattt gatgacgagc agaaaaagct cgtttacaga    240
ggctggaaag tcatgccttt tatcattggt aatgagacat ttgagaagat tgggatcata    300
gggacattat caaaccttct tttgtaccta actcaagtat tcaaccttaa gaaagttaca    360
gctgcaacaa tcatcaatgc ctttagtggc acaatcaact tcgggacttt catcgctgct    420
ttcctctgcg acacttactt tggtcgctac aagactctca gtgtagctgt catcgcttgt    480
ttcctgggat cgcttgtgat attactgacg gctgcagttc ctgcattgca cccgactcca    540
tgtggaacac atagctggtg ccaagggcca agcccgggcc agatcgcgtt cttgctgctg    600
ggtttagcgt ttcttgtggt cggtgcgggt gggatcaggc cgtgtaactt ggcttttgga    660
gctgatcagt tcaaccccaa atccgaatcc gggaagaaag gaatcaacag cttctttaac    720
tggtatttct tcaccttcac gtttgcgcag atcgtctcgc tcacgctggt cgtgtatatc    780
cagtcgaacg tgagctggac gatcggtttg ctcatccctg tggctctgat gttcttggcc    840
tgcgtcatct tctttgctgg acataaactg tatgtgaaag tgaaagcctc gggtagtccc    900
ttggctagta tcggtcacgt tatcacggca gcgatcaaga aacgagggtt gaagcaagtt    960
aagcagcctt ggctcgatct ttacaaccac attccaacta actatccaaa ctccaccttg   1020
aaatacaccg accagtttag gtttcttgac aaagcagcga ttatgacccc tgaggacaag   1080
ctgaattccg atggagctgc tttcgatcca tggaccctat gtacattgca gaaagtggaa   1140
gaagtgaaat gcattgtgag agtgattccg atctggtttg cttgcgcgat ttactacctc   1200
actgtaacta tacagatgac ttatccggtc ttccaagcgc agcagagcga ccggagattg   1260
ggttctggtg gcttcaagat ccccgcagcc acctatgtgg tgttcttgat gtcgggtatg   1320
actgttttca tcgtgttcta cgaccgtgtc cttgtcccgt tgctcagaag agtgaccggg   1380
ttagaaaccg gtttgaccct cttgcagaga gtcggatcag ggatcttctt tgccatgttg   1440
agtttgttgg tctccgggtt cgtagaggaa cggagaagaa ccttcgccct gacgaaaccg   1500
actctcggga tggagccacg agcgggagag atctcctcca tgtcggccat gtggctgatt   1560
ccgcagctct tgtttgcagg cgtaggagag gcttttacag ccattggaca gatggagttt   1620
tattacaagc agttccctga gaacatgaag agcttcgctg gctctatctt ctatgtcggt   1680
gcaggtgttt cgagctatct tgctagcttc ttgatctcga ctgttcatcg aagaactgaa   1740
cattcaccct ccgggaactg gttagctgag gatctgaaca aagggagact cgattacttc   1800
tacttcatgc tcaccggaat catggtcgtt aacatggttt acttcttgat aatgtctaaa   1860
tggtatagat acaaaggcat taacgatgaa gcgaattctt tggtcgagac caatgaagaa   1920
gagaccaagc agaaacaagt caagaattct gtctga                             1956
```

<210> SEQ ID NO 222
<211> LENGTH: 651
<212> TYPE: PRT
<213> ORGANISM: Thlaspi arvense

<400> SEQUENCE: 222

```
Met Lys Ser Arg Val Ile Leu Ser His Arg Glu Arg Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Gly Val Gly Ser Asp Leu Arg
```

-continued

```
    50                  55                  60

Ser Pro Val Asp Ser Phe Asp Asp Glu Gln Lys Lys Leu Val Tyr Arg
65                  70                  75                  80

Gly Trp Lys Val Met Pro Phe Ile Ile Gly Asn Glu Thr Phe Glu Lys
                85                  90                  95

Ile Gly Ile Ile Gly Thr Leu Ser Asn Leu Leu Leu Tyr Leu Thr Gln
            100                 105                 110

Val Phe Asn Leu Lys Lys Val Thr Ala Ala Thr Ile Ile Asn Ala Phe
        115                 120                 125

Ser Gly Thr Ile Asn Phe Gly Thr Phe Ile Ala Ala Phe Leu Cys Asp
    130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                165                 170                 175

His Pro Thr Pro Cys Gly Thr His Ser Trp Cys Gln Gly Pro Ser Pro
            180                 185                 190

Gly Gln Ile Ala Phe Leu Leu Leu Gly Leu Ala Phe Leu Val Val Gly
        195                 200                 205

Ala Gly Gly Ile Arg Pro Cys Asn Leu Ala Phe Gly Ala Asp Gln Phe
    210                 215                 220

Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
                245                 250                 255

Val Val Tyr Ile Gln Ser Asn Val Ser Trp Thr Ile Gly Leu Leu Ile
            260                 265                 270

Pro Val Ala Leu Met Phe Leu Ala Cys Val Ile Phe Phe Ala Gly His
        275                 280                 285

Lys Leu Tyr Val Lys Val Lys Ala Ser Gly Ser Pro Leu Ala Ser Ile
    290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
                325                 330                 335

Asn Ser Thr Leu Lys Tyr Thr Asp Gln Phe Arg Phe Leu Asp Lys Ala
            340                 345                 350

Ala Ile Met Thr Pro Glu Asp Lys Leu Asn Ser Asp Gly Ala Ala Phe
        355                 360                 365

Asp Pro Trp Thr Leu Cys Thr Leu Gln Lys Val Glu Glu Val Lys Cys
    370                 375                 380

Ile Val Arg Val Ile Pro Ile Trp Phe Ala Cys Ala Ile Tyr Tyr Leu
385                 390                 395                 400

Thr Val Thr Ile Gln Met Thr Tyr Pro Val Phe Gln Ala Gln Gln Ser
                405                 410                 415

Asp Arg Arg Leu Gly Ser Gly Gly Phe Lys Ile Pro Ala Ala Thr Tyr
            420                 425                 430

Val Val Phe Leu Met Ser Gly Met Thr Val Phe Ile Val Phe Tyr Asp
        435                 440                 445

Arg Val Leu Val Pro Leu Leu Arg Arg Val Thr Gly Leu Glu Thr Gly
    450                 455                 460

Leu Thr Leu Leu Gln Arg Val Gly Ser Gly Ile Phe Phe Ala Met Leu
465                 470                 475                 480
```

```
Ser Leu Leu Val Ser Gly Phe Val Glu Glu Arg Arg Arg Thr Phe Ala
                485                 490                 495

Leu Thr Lys Pro Thr Leu Gly Met Glu Pro Arg Ala Gly Glu Ile Ser
            500                 505                 510

Ser Met Ser Ala Met Trp Leu Ile Pro Gln Leu Leu Phe Ala Gly Val
        515                 520                 525

Gly Glu Ala Phe Thr Ala Ile Gly Gln Met Glu Phe Tyr Tyr Lys Gln
    530                 535                 540

Phe Pro Glu Asn Met Lys Ser Phe Ala Gly Ser Ile Phe Tyr Val Gly
545                 550                 555                 560

Ala Gly Val Ser Ser Tyr Leu Ala Ser Phe Leu Ile Ser Thr Val His
                565                 570                 575

Arg Arg Thr Glu His Ser Pro Ser Gly Asn Trp Leu Ala Glu Asp Leu
            580                 585                 590

Asn Lys Gly Arg Leu Asp Tyr Phe Tyr Phe Met Leu Thr Gly Ile Met
        595                 600                 605

Val Val Asn Met Val Tyr Phe Leu Ile Met Ser Lys Trp Tyr Arg Tyr
    610                 615                 620

Lys Gly Ile Asn Asp Glu Ala Asn Ser Leu Val Glu Thr Asn Glu Glu
625                 630                 635                 640

Glu Thr Lys Gln Lys Gln Val Lys Asn Ser Val
                645                 650


<210> SEQ ID NO 223
<211> LENGTH: 1957
<212> TYPE: DNA
<213> ORGANISM: Thlaspi arvense

<400> SEQUENCE: 223

atgaagagta gagtcatcct cagccataga gagagaagag ataagaagaa taataacatt     60

aacaacaaag acatctcctg taatttcaca cagattgaaa ccatggagag aaagcccttt    120

gaggttgaga cgacggagaa tcacaaaccc tactccaccg tcgatggcgg tggcgttggt    180

tctgatttga gatcgccggt cgattcattt gatgacgagc agaaaaagct cgtttacaga    240

ggctggaaag tcatgccttt tatcattggt aatgagacat ttgagaagat tgggatcata    300

gggacattat caaaccttct tttgtaccta actcaagtat tcaaccttaa gaaagttaca    360

gctgcaacaa tcatcaatgc ctttagtggc acaatcaact tcgggacttt catcgctgct    420

ttcctctgcg acacttactt tggtcgctac aagactctca gtgtagctgt catcgcttgt    480

ttcctgggat cgcttgtgat attactgacg gctgcagttc ctgcattgca cccgactcca    540

tgtggaacac atagctggtg ccaagggcca agcccgggcc agatcgcgtt cttgctgctg    600

ggtttagcgt ttcttgtggt cggtgcgggt gggatcaggc cgtgtaactt ggcttttgga    660

gctgatcagt tcaaccccaa atccgaatcc gggaagaaag gaatcaacag cttctttaac    720

tggtatttct tcaccttcac gtttgcgcag atcgtctcgc tcacgctggt cgtgtatatc    780

cagtcgaacg tgagctggac gatcggtttg ctcatccctg tggctctgat gttcttggcc    840

tgcgtcatct tctttgctgg acataaactg tatgtgaaag tgaaagcctc gggtagtccc    900

ttggctagta tcggtcacgt tatcacggca gcgatcaaga aacgagggtt gaagcaagtt    960

aagcagcctt ggctcgatct ttacaaccac attccaacta actatccaaa ctccaccttg   1020

aaatacaccg accagtttag gtttcttgac aaagcagcga ttatgacccc tgaggacaag   1080

ctgaattccg atggagctgc tttcgatcca tggaccctat gtacattgca gaaagtggaa   1140
```

gaagtgaaat gcatgtgtga gagtgattcc gatctggttt gcttgcgcga tttactacct 1200
cactgtaact atacagatga cttatccggt cttccaagcg cagcagagcg accggagatt 1260
gggttctggt ggcttcaaga tccccgcagc cacctatgtg gtgttcttga tgtcgggtat 1320
gactgttttc atcgtgttct acgaccgtgt ccttgtcccg ttgctcagaa gagtgaccgg 1380
gttagaaacc ggtttgaccc tcttgcagag agtcggatca gggatcttct ttgccatgtt 1440
gagtttgttg gtctccgggt tcgtagagga acggagaaga accttcgccc tgacgaaacc 1500
gactctcggg atggagccac gagcgggaga gatctcctcc atgtcggcca tgtggctgat 1560
tccgcagctc ttgcttgcag gcgtaggaga ggcttttaca gccattggac agatggagtt 1620
ttattacaag cagttccctg agaacatgaa gagcttcgct ggctctatct tctatgtcgg 1680
tgcaggtgtt tcgagctatc ttgctagctt cttgatctcg actgttcatc gaagaactga 1740
acattcaccc tccgggaact ggttagctga ggatctgaac aaagggagac tcgattactt 1800
ctacttcatg ctcaccggaa tcatggtcgt taacatggtt tacttcttga taatgtctaa 1860
atggtataga tacaaaggca ttaacgatga agcgaattct ttggtcgaga ccaatgaaga 1920
agagaccaag cagaaacaag tcaagaattc tgtctga 1957

<210> SEQ ID NO 224
<211> LENGTH: 546
<212> TYPE: PRT
<213> ORGANISM: Thlaspi arvense

<400> SEQUENCE: 224

Met Lys Ser Arg Val Ile Leu Ser His Arg Glu Arg Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Gly Val Gly Ser Asp Leu Arg
    50                  55                  60

Ser Pro Val Asp Ser Phe Asp Asp Glu Gln Lys Lys Leu Val Tyr Arg
65                  70                  75                  80

Gly Trp Lys Val Met Pro Phe Ile Ile Gly Asn Glu Thr Phe Glu Lys
                85                  90                  95

Ile Gly Ile Ile Gly Thr Leu Ser Asn Leu Leu Leu Tyr Leu Thr Gln
            100                 105                 110

Val Phe Asn Leu Lys Lys Val Thr Ala Ala Thr Ile Ile Asn Ala Phe
        115                 120                 125

Ser Gly Thr Ile Asn Phe Gly Thr Phe Ile Ala Ala Phe Leu Cys Asp
    130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                165                 170                 175

His Pro Thr Pro Cys Gly Thr His Ser Trp Cys Gln Gly Pro Ser Pro
            180                 185                 190

Gly Gln Ile Ala Phe Leu Leu Leu Gly Leu Ala Phe Leu Val Val Gly
        195                 200                 205

Ala Gly Gly Ile Arg Pro Cys Asn Leu Ala Phe Gly Ala Asp Gln Phe
    210                 215                 220

```
Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
                245                 250                 255

Val Val Tyr Ile Gln Ser Asn Val Ser Trp Thr Ile Gly Leu Leu Ile
            260                 265                 270

Pro Val Ala Leu Met Phe Leu Ala Cys Val Ile Phe Phe Ala Gly His
        275                 280                 285

Lys Leu Tyr Val Lys Val Lys Ala Ser Gly Ser Pro Leu Ala Ser Ile
    290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
                325                 330                 335

Asn Ser Thr Leu Lys Tyr Thr Asp Gln Phe Arg Phe Leu Asp Lys Ala
            340                 345                 350

Ala Ile Met Thr Pro Glu Asp Lys Leu Asn Ser Asp Gly Ala Ala Phe
        355                 360                 365

Asp Pro Trp Thr Leu Cys Thr Leu Gln Lys Val Glu Glu Val Lys Cys
    370                 375                 380

Met Cys Glu Ser Asp Ser Asp Leu Val Cys Leu Arg Asp Leu Leu Pro
385                 390                 395                 400

His Cys Asn Tyr Thr Asp Asp Leu Ser Gly Leu Pro Ser Ala Ala Glu
                405                 410                 415

Arg Pro Glu Ile Gly Phe Trp Trp Leu Gln Asp Pro Arg Ser His Leu
            420                 425                 430

Cys Gly Val Leu Asp Val Gly Tyr Asp Cys Phe His Arg Val Leu Arg
        435                 440                 445

Pro Cys Pro Cys Pro Val Ala Gln Lys Ser Asp Arg Val Arg Asn Arg
    450                 455                 460

Phe Asp Pro Leu Ala Glu Ser Arg Ile Arg Asp Leu Leu Cys His Val
465                 470                 475                 480

Glu Phe Val Gly Leu Arg Val Arg Arg Gly Thr Glu Lys Asn Leu Arg
                485                 490                 495

Pro Asp Glu Thr Asp Ser Arg Asp Gly Ala Thr Ser Gly Arg Asp Leu
            500                 505                 510

Leu His Val Gly His Val Ala Asp Ser Ala Ala Leu Ala Cys Arg Arg
        515                 520                 525

Arg Arg Gly Phe Tyr Ser His Trp Thr Asp Gly Val Leu Leu Gln Ala
    530                 535                 540

Val Pro
545
```

<210> SEQ ID NO 225
<211> LENGTH: 1842
<212> TYPE: DNA
<213> ORGANISM: Thlaspi arvense

<400> SEQUENCE: 225

```
atggagagac agcctctcga actcgagtct acggatcacc aaaaaccttc ccccgccgtc      60

tacggtggct ctgttacgac ggttgattct gttgaggaag aagttcagga gaaaaaagtc     120

gtatatagag gctggaaagt catgcccttt atcattggaa atgagacatt cgagaagctt     180

gggatcattg gaacactatc aaaccttctg gtttttttaa cagctgtctt caacatgaag     240
```

```
agtatcacag ctgcaacaat cattaacgca ttcagtggca caataaattt cggaactttc    300

gttgctgctt tcctctgcga cacttacttc ggtcgataca agacactaac cgtcgcggtc    360

atcgcctgtt ttcttggatc acttgtgata ctattgacag ctgcagtgcc acaactgcac    420

ccagctccat gtggaacagc gagctcgtgc agcggtccaa gcggtgggca aatcgcgttt    480

cttctgatgg gtctcgggtt tcttgtagtt ggagcgggcg ggatcagacc gtgcaatcta    540

gctttcggag ccgatcagtt caacccgaag agcgagtcag ggagaagagg gactgatagt    600

ttcttcaatt ggtacttctt cagcttcact ttcgcgcaga tcttgtcgct gacgctagtg    660

gtctacatcc agtctaacgt cagctggacg atcggtctaa ccataccggt ggttctaatg    720

ttcttggcct ccgtgatctt ctttgcggga gataagctgt atgtgaaagt caaggcctcg    780

ggtagtccat tggctggtat agctcaagtg atcattgttg caatcaagaa acgcggatta    840

aagcccgtga aacagccttg gcttaacctc tacaattact gccctccaaa acacgcaaac    900

tccattctca aatacaccga ccaattcaga tttcttgata aggcggcgat cttggctccc    960

gaggacaagt tggaggcgga tggtaagcct gcggatccat ggaagctgtg tacgatgcaa   1020

caggtggaag aagtgaagtg cattgtgaga gtgcttccta tatggttcgc tgcatcaatc   1080

tactacgtaa ccataaccca gcaaatgaca tatccggtct tccaagccct gcagagcgat   1140

cgtcgcttag gctcgggagg gttcgtgatc cccgcagcca cctacgtggt cttcttgatg   1200

acagggatga cggttttcat catcatctac gaccgtctcc tcgtgcctac cttgagaaga   1260

ataaccggtc tagacaccgg gatcacgctc ctgcagagaa tcggaaccgg gatcttcttc   1320

gcctttgcaa gcttagtagt ctccggtttc gtcgaggagc ggaggagaca cattgcgctg   1380

actaaaccaa ctcttggcat ggcgccaaga aaaggagaaa tctcctcaat gtcagctatg   1440

tggctcatcc cgcagctcac tctctcgggt gtagccgagg cgtttggagc catcggacag   1500

atggagtttt actacaagca gttcccagaa aacatgagga gtttcgcggg ttccatcttt   1560

tatgtaggaa taggggtttc gagttacctc ggcagcttct tgattgcaac ggttcaccgg   1620

acgacgcaga actcggcggg tggtaactgg ttggctgagg atttgaacaa aggcagattg   1680

gattacttct atttcatgat cgctggaatc ttggctgtta atttcgccta cttcttggtc   1740

gtgtcaagat ggtataggta caaagaaagt aatgatgatc aaaagacagc ttctgaaacc   1800

aatggagatg tcatcaaaca acaagacaag aacactgcct ga                      1842
```

<210> SEQ ID NO 226
<211> LENGTH: 613
<212> TYPE: PRT
<213> ORGANISM: Thlaspi arvense

<400> SEQUENCE: 226

```
Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95
```

-continued

```
Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285

Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Val Arg Val Leu
            340                 345                 350

Pro Ile Trp Phe Ala Ala Ser Ile Tyr Tyr Val Thr Ile Thr Gln Gln
        355                 360                 365

Met Thr Tyr Pro Val Phe Gln Ala Leu Gln Ser Asp Arg Arg Leu Gly
    370                 375                 380

Ser Gly Gly Phe Val Ile Pro Ala Ala Thr Tyr Val Val Phe Leu Met
385                 390                 395                 400

Thr Gly Met Thr Val Phe Ile Ile Ile Tyr Asp Arg Leu Leu Val Pro
                405                 410                 415

Thr Leu Arg Arg Ile Thr Gly Leu Asp Thr Gly Ile Thr Leu Leu Gln
            420                 425                 430

Arg Ile Gly Thr Gly Ile Phe Phe Ala Phe Ala Ser Leu Val Val Ser
        435                 440                 445

Gly Phe Val Glu Glu Arg Arg Arg His Ile Ala Leu Thr Lys Pro Thr
    450                 455                 460

Leu Gly Met Ala Pro Arg Lys Gly Glu Ile Ser Ser Met Ser Ala Met
465                 470                 475                 480

Trp Leu Ile Pro Gln Leu Thr Leu Ser Gly Val Ala Glu Ala Phe Gly
                485                 490                 495

Ala Ile Gly Gln Met Glu Phe Tyr Tyr Lys Gln Phe Pro Glu Asn Met
            500                 505                 510
```

-continued

```
Arg Ser Phe Ala Gly Ser Ile Phe Tyr Val Gly Ile Gly Val Ser Ser
        515                 520                 525

Tyr Leu Gly Ser Phe Leu Ile Ala Thr Val His Arg Thr Thr Gln Asn
    530                 535                 540

Ser Ala Gly Gly Asn Trp Leu Ala Glu Asp Leu Asn Lys Gly Arg Leu
545                 550                 555                 560

Asn Tyr Phe Tyr Phe Met Ile Ala Gly Ile Leu Ala Val Asn Phe Ala
                565                 570                 575

Tyr Phe Leu Val Val Ser Arg Trp Tyr Arg Tyr Lys Glu Ser Asp Asp
            580                 585                 590

Asp Gln Lys Thr Ala Ser Glu Thr Asn Gly Asp Val Ile Lys Gln Gln
        595                 600                 605

Asp Lys Asn Thr Ala
    610
```

<210> SEQ ID NO 227
<211> LENGTH: 1843
<212> TYPE: DNA
<213> ORGANISM: Thlaspi arvense

<400> SEQUENCE: 227

```
atggagagac agcctctcga actcgagtct acggatcacc aaaaaccttc ccccgccgtc     60

tacggtggct ctgttacgac ggttgattct gttgaggaag aagttcagga gaaaaaagtc    120

gtatatagag gctggaaagt catgcccttt atcattggaa atgagacatt cgagaagctt    180

gggatcattg gaacactatc aaaccttctg gttttttaa cagctgtctt caacatgaag    240

agtatcacag ctgcaacaat cattaacgca ttcagtggca caataaattt cggaactttc    300

gttgctgctt tcctctgcga cacttacttc ggtcgataca agacactaac cgtcgcggtc    360

atcgcctgtt ttcttggatc acttgtgata ctattgacag ctgcagtgcc acaactgcac    420

ccagctccat gtggaacagc gagctcgtgc agcggtccaa gcggtgggca aatcgcgttt    480

cttctgatgg gtctcgggtt tcttgtagtt ggagcgggcg ggatcagacc gtgcaatcta    540

gctttcggag ccgatcagtt caacccgaag agcgagtcag ggagaagagg gactgatagt    600

ttcttcaatt ggtacttctt cagcttcact ttcgcgcaga tcttgtcgct gacgctagtg    660

gtctacatcc agtctaacgt cagctggacg atcggtctaa ccataccggt ggttctaatg    720

ttcttggcct ccgtgatctt ctttgcggga gataagctgt atgtgaaagt caaggcctcg    780

ggtagtccat tggctggtat agctcaagtg atcattgttg caatcaagaa acgcggatta    840

aagcccgtga aacagccttg gcttaacctc tacaattact gccctccaaa acacgcaaac    900

tccattctca aatacaccga ccaattcaga tttcttgata aggcggcgat cttggctccc    960

gaggacaagt tggaggcgga tggtaagcct gcggatccat ggaagctgtg tacgatgcaa   1020

caggtggaag aagtgaagtg catatgtgag agtgcttcct atatggttcg ctgcatcaat   1080

ctactacgta accataaccc agcaaatgac atatccggtc ttccaagccc tgcagagcga   1140

tcgtcgctta ggctcgggag ggttcgtgat ccccgcagcc acctacgtgg tcttcttgat   1200

gacagggatg acggttttca tcatcatcta cgaccgtctc ctcgtgccta ccttgagaag   1260

aataaccggt ctagacaccg ggatcacgct cctgcagaga atcggaaccg ggatcttctt   1320

cgcctttgca agcttagtag tctccggttt cgtcgaggag cggaggagac acattgcgct   1380

gactaaacca actcttggca tggcgccaag aaaaggagaa atctcctcaa tgtcagctat   1440

gtggctcatc ccgcagctca ctctctcggg tgtagccgag gcgtttggag ccatcggaca   1500
```

```
gatggagttt tactacaagc agttcccaga aaacatgagg agtttcgcgg gttccatctt   1560

ttatgtagga ataggggttt cgagttacct cggcagcttc ttgattgcaa cggttcaccg   1620

gacgacgcag aactcggcgg gtggtaactg gttggctgag gatttgaaca aaggcagatt   1680

ggattacttc tatttcatga tcgctggaat cttggctgtt aatttcgcct acttcttggt   1740

cgtgtcaaga tggtataggt acaaagaaag tgatgatgat caaaagacag cttctgaaac   1800

caatggagat gtcatcaaac aacaagacaa gaacactgcc tga                     1843
```

<210> SEQ ID NO 228
<211> LENGTH: 461
<212> TYPE: PRT
<213> ORGANISM: Thlaspi arvense

<400> SEQUENCE: 228

```
Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
        275                 280                 285

Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320
```

```
Glu Asp Lys Leu Glu Ala Asp Gly Lys Pro Ala Asp Pro Trp Lys Leu
                325                 330                 335

Cys Thr Met Gln Gln Val Glu Glu Val Lys Cys Ile Cys Glu Ser Ala
            340                 345                 350

Ser Tyr Met Val Arg Cys Ile Asn Leu Leu Arg Asn His Asn Pro Ala
        355                 360                 365

Asn Asp Ile Ser Gly Leu Pro Ser Pro Ala Glu Arg Ser Ser Leu Arg
    370                 375                 380

Leu Gly Arg Val Arg Asp Pro Arg Ser His Leu Arg Gly Leu Leu Asp
385                 390                 395                 400

Asp Arg Asp Asp Gly Phe His His His Leu Arg Pro Ser Pro Arg Ala
                405                 410                 415

Tyr Leu Glu Lys Asn Asn Arg Ser Arg His Arg Asp His Ala Pro Ala
            420                 425                 430

Glu Asn Arg Asn Arg Asp Leu Leu Arg Leu Cys Lys Leu Ser Ser Leu
        435                 440                 445

Arg Phe Arg Arg Gly Ala Glu Glu Thr His Cys Ala Asp
    450                 455                 460
```

<210> SEQ ID NO 229
<211> LENGTH: 1843
<212> TYPE: DNA
<213> ORGANISM: Thlaspi arvense

<400> SEQUENCE: 229

```
atggagagac agcctctcga actcgagtct acggatcacc aaaaaccttc ccccgccgtc      60

tacggtggct ctgttacgac ggttgattct gttgaggaag aagttcagga gaaaaaagtc     120

gtatatagag gctggaaagt catgcccttt atcattggaa atgagacatt cgagaagctt     180

gggatcattg gaacactatc aaaccttctg gttttttaa cagctgtctt caacatgaag      240

agtatcacag ctgcaacaat cattaacgca ttcagtggca caataaattt cggaactttc     300

gttgctgctt tcctctgcga cacttacttc ggtcgataca agacactaac cgtcgcggtc     360

atcgcctgtt ttcttggatc acttgtgata ctattgacag ctgcagtgcc acaactgcac     420

ccagctccat gtggaacagc gagctcgtgc agcggtccaa gcggtgggca aatcgcgttt     480

cttctgatgg gtctcgggtt tcttgtagtt ggagcgggcg ggatcagacc gtgcaatcta     540

gctttcggag ccgatcagtt caacccgaag agcgagtcag ggagaagagg gactgatagt     600

ttcttcaatt ggtacttctt cagcttcact ttcgcgcaga tcttgtcgct gacgctagtg     660

gtctacatcc agtctaacgt cagctggacg atcggtctaa ccataccggt ggttctaatg     720

ttcttggcct ccgtgatctt ctttgcggga gataagctgt atgtgaaagt caaggcctcg     780

ggtagtccat tggctggtat agctcaagtg atcattgttg caatcaagaa acgcggatta     840

aagcccgtga aacagccttg gcttaacctc tacaattact gccctccaaa acacgcaaac     900

tccattctca aatacaccga ccaattcaga tttcttgata aggcggcgat cttggctccc     960

gaggacaagt tggaggcgga tggtaagcct gcggatccat ggaagctgtg tacgatgcaa    1020

caggtggaag aagtgaagtg catgtgtgag agtgcttcct atatggttcg ctgcatcaat    1080

ctactacgta accataaccc agcaaatgac atatccggtc ttccaagccc tgcagagcga    1140

tcgtcgctta ggctcgggag ggttcgtgat ccccgcagcc acctacgtgg tcttcttgat    1200

gacagggatg acggttttca tcatcatcta cgaccgtctc ctcgtgccta ccttgagaag    1260

aataaccggt ctagacaccg ggatcacgct cctgcagaga atcggaaccg ggatcttctt    1320
```

```
cgcctttgca agcttagtag tctccggttt cgtcgaggag cggaggagac acattgcgct   1380

gactaaacca actcttggca tggcgccaag aaaaggagaa atctcctcaa tgtcagctat   1440

gtggctcatc ccgcagctca ctctctcggg tgtagccgag gcgtttggag ccatcggaca   1500

gatggagttt tactacaagc agttcccaga aaacatgagg agtttcgcgg gttccatctt   1560

ttatgtagga ataggggttt cgagttacct cggcagcttc ttgattgcaa cggttcaccg   1620

gacgacgcag aactcggcgg gtggtaactg gttggctgag gatttgaaca aaggcagatt   1680

ggattacttc tatttcatga tcgctggaat cttggctgtt aatttcgcct acttcttggt   1740

cgtgtcaaga tggtataggt acaaagaaag tgatgatgat caaaagacag cttctgaaac   1800

caatggagat gtcatcaaac aacaagacaa gaacactgcc tga                      1843


<210> SEQ ID NO 230
<211> LENGTH: 461
<212> TYPE: PRT
<213> ORGANISM: Thlaspi arvense

<400> SEQUENCE: 230

Met Glu Arg Gln Pro Leu Glu Leu Glu Ser Thr Asp His Gln Lys Pro
1               5                   10                  15

Ser Pro Ala Val Tyr Gly Gly Ser Val Thr Thr Val Asp Ser Val Glu
            20                  25                  30

Glu Glu Val Gln Glu Lys Lys Val Val Tyr Arg Gly Trp Lys Val Met
        35                  40                  45

Pro Phe Ile Ile Gly Asn Glu Thr Phe Glu Lys Leu Gly Ile Ile Gly
    50                  55                  60

Thr Leu Ser Asn Leu Leu Val Phe Leu Thr Ala Val Phe Asn Met Lys
65                  70                  75                  80

Ser Ile Thr Ala Ala Thr Ile Ile Asn Ala Phe Ser Gly Thr Ile Asn
                85                  90                  95

Phe Gly Thr Phe Val Ala Ala Phe Leu Cys Asp Thr Tyr Phe Gly Arg
            100                 105                 110

Tyr Lys Thr Leu Thr Val Ala Val Ile Ala Cys Phe Leu Gly Ser Leu
        115                 120                 125

Val Ile Leu Leu Thr Ala Ala Val Pro Gln Leu His Pro Ala Pro Cys
    130                 135                 140

Gly Thr Ala Ser Ser Cys Ser Gly Pro Ser Gly Gly Gln Ile Ala Phe
145                 150                 155                 160

Leu Leu Met Gly Leu Gly Phe Leu Val Val Gly Ala Gly Gly Ile Arg
                165                 170                 175

Pro Cys Asn Leu Ala Phe Gly Ala Asp Gln Phe Asn Pro Lys Ser Glu
            180                 185                 190

Ser Gly Arg Arg Gly Thr Asp Ser Phe Phe Asn Trp Tyr Phe Phe Ser
        195                 200                 205

Phe Thr Phe Ala Gln Ile Leu Ser Leu Thr Leu Val Val Tyr Ile Gln
    210                 215                 220

Ser Asn Val Ser Trp Thr Ile Gly Leu Thr Ile Pro Val Val Leu Met
225                 230                 235                 240

Phe Leu Ala Ser Val Ile Phe Phe Ala Gly Asp Lys Leu Tyr Val Lys
                245                 250                 255

Val Lys Ala Ser Gly Ser Pro Leu Ala Gly Ile Ala Gln Val Ile Ile
            260                 265                 270

Val Ala Ile Lys Lys Arg Gly Leu Lys Pro Val Lys Gln Pro Trp Leu
```

```
        275                 280                 285

Asn Leu Tyr Asn Tyr Cys Pro Pro Lys His Ala Asn Ser Ile Leu Lys
    290                 295                 300

Tyr Thr Asp Gln Phe Arg Phe Leu Asp Lys Ala Ala Ile Leu Ala Pro
305                 310                 315                 320

Glu Asp Lys Leu Glu Ala Asp Gly Lys Pro Ala Asp Pro Trp Lys Leu
                325                 330                 335

Cys Thr Met Gln Gln Val Glu Glu Val Lys Cys Met Cys Glu Ser Ala
            340                 345                 350

Ser Tyr Met Val Arg Cys Ile Asn Leu Leu Arg Asn His Asn Pro Ala
        355                 360                 365

Asn Asp Ile Ser Gly Leu Pro Ser Pro Ala Glu Arg Ser Ser Leu Arg
    370                 375                 380

Leu Gly Arg Val Arg Asp Pro Arg Ser His Leu Arg Gly Leu Leu Asp
385                 390                 395                 400

Asp Arg Asp Asp Gly Phe His His His Leu Arg Pro Ser Pro Arg Ala
                405                 410                 415

Tyr Leu Glu Lys Asn Asn Arg Ser Arg His Arg Asp His Ala Pro Ala
            420                 425                 430

Glu Asn Arg Asn Arg Asp Leu Leu Arg Leu Cys Lys Leu Ser Ser Leu
        435                 440                 445

Arg Phe Arg Arg Gly Ala Glu Glu Thr His Cys Ala Asp
    450                 455                 460


<210> SEQ ID NO 231
<211> LENGTH: 1108
<212> TYPE: DNA
<213> ORGANISM: Thlaspi arvense

<400> SEQUENCE: 231

atgtcaagaa agccgtgttg tcggagaagg gctgaagaaa ggggcatgga ccaccgaaga     60

agacaagaaa ctcatctctt acatccacga gcacggtgaa ggaggctggc gcgacattcc    120

ccaaaaagct gggttgaaac ggtgtggaaa gagttgtagg ctgcgatgga ctaactacct    180

aaaacctgag atcaaaagag gcgagtttag ttcagaggag gaacagatta tcattatgct    240

tcatgcttct cgtggcaaca agtggtcggt catagcgaga catttaccta gaagaacaga    300

caacgagatc aagaactact ggaacacgca tctcaaaaaa cgtttgatcg aacagggtgt    360

tgatcccgtg actcacaagc ctctagcttc caactccggc cctactgcca ccacgccgcc    420

tgagaatttg catttcctag atgaatctag ctcagacaag caatactctc ggtcgagctc    480

aatgccttcc ctgtctcgtc ttccttcctc cggattcaac acggtttccg agatagccag    540

caatgttggg acaccagttc aggtcggttc cttgagttgc aagaaacgtt ttaagaaatc    600

gagttcgaca tcaaggcttc tgaacaaatt tgcggctaag gccacttcca tcaaagatat    660

attgtcggct tccatggaag gtagctcgag tgctgctact acaatatcac atgcaagctt    720

tttaaatggc ttttctgagc agagtcgcaa tgaagaggat agttctaacg catccctgac    780

aaatactcta gccgaatttg atcccttctc tcagtcatcg ttgtacccgg agcatgagat    840

caatgttact tctgatatcg gcatggacca ggtttacgat ttctcacaat ttctcgaaaa    900

gctcgggagt gaaggccaca acgaactgaa tgtcgagtat ggtcatgatc ttcttatgtc    960

cgatgtttcg caagaagtct catcacctag cgttgatgat caagacaata tgattggaag   1020

cttcgaaggt tggtcaaatt atcttcttga ccatgctgat tttatatatg acaccgactc   1080
```

agattccctc gaaaagcatt tcatgtga 1108

<210> SEQ ID NO 232
<211> LENGTH: 32
<212> TYPE: PRT
<213> ORGANISM: Thlaspi arvense

<400> SEQUENCE: 232

Met Ser Arg Lys Pro Cys Cys Arg Arg Arg Ala Glu Glu Arg Gly Met
1 5 10 15

Asp His Arg Arg Arg Gln Glu Thr His Leu Leu His Pro Arg Ala Arg
20 25 30

<210> SEQ ID NO 233
<211> LENGTH: 1108
<212> TYPE: DNA
<213> ORGANISM: Thlaspi arvense

<400> SEQUENCE: 233
atgtcaagaa agccgtgttg tcggagaagg gctgaagaaa ggggcatgga ccaccgaaga 60
agacaagaaa ctcatctctt acatccacga gcacggtgaa ggaggctggc gcgacattcc 120
ccaaaaagct gggttgaaac ggtgtggaaa gagttgtagg ctgcgatgga ctaactacct 180
aaaacctgag atcaaaagag gcgagtttag ttcagaggag gaacagatta tcattatgct 240
tcatgcttct cgtggcaaca agtggtcggt catagcgaga catttaccta gaagaacaga 300
caacgagatc aagaactact ggaacacgca tctcaaaaaa cgtttgatcg aacagggtgt 360
tgatcccgtg actcacaagc ctctagcttc caactccggc cctactgcca ccacgccgcc 420
tgagaatttg catttcctag atgaatctag ctcagacaag caatactctc ggtcgagctc 480
aatgccttcc ctgtctcgtc ttccttcctc cggattcaac acggtttccg agatagccag 540
caatgttggg acaccagttc aggtcggttc cttgagttgc aagaaacgtt ttaagaaatc 600
gagttcgaca tcaaggcttc tgaacaaatt tgcggctaag gccacttcca tcaaagatat 660
attgtcggct tccatggaag gtagctcgag tgctgctact acaatatcac atgcaagctt 720
tttaaatggc ttttctgagc agagtcgcaa tgaagaggat agttctaacg catccctgac 780
aaatactcta gccgaatttg atcccttctc tcagtcatcg ttgtacccgg agcatgagat 840
caatgttact tctgatatcg gcatggacca ggtttacgat ttctcacaat ttctcgaaaa 900
gctcgggagt gaaggccaca acgaactgaa tgtcgagtat ggtcatgatc ttcttatgtc 960
cgatgtttcg caagaagtct catcacctag cgttgatgat caagacaata tgattggaag 1020
cttcgaaggt tggtcaaatt atcttcttga ccatgctgat tttatatatg acaccgactc 1080
agattccctc gaaaagcatt tcatgtga 1108

<210> SEQ ID NO 234
<211> LENGTH: 32
<212> TYPE: PRT
<213> ORGANISM: Thlaspi arvense

<400> SEQUENCE: 234

Met Ser Arg Lys Pro Cys Cys Arg Arg Arg Ala Glu Glu Arg Gly Met
1 5 10 15

Asp His Arg Arg Arg Gln Glu Thr His Leu Leu His Pro Arg Ala Arg
20 25 30

<210> SEQ ID NO 235
<211> LENGTH: 1955

<212> TYPE: DNA
<213> ORGANISM: Thlaspi arvense

<400> SEQUENCE: 235
atgaagagta gagtcatcct cagccataga gagagaagag ataagaagaa taataacatt 60
aacaacaaag acatctcctg taatttcaca cagattgaaa ccatggagag aaagcccttt 120
gaggttgaga cgacggagaa tcacaaaccc tactccaccg tcgatggcgg tggcgttggt 180
tctgatttga gatcgccggt cgattcattt gatgacgagc agaaaaagct cgtttacaga 240
ggctggaaag tcatgccttt tatcattggt aatgagacat ttgagaagat tgggatcata 300
gggacattat caaaccttct tttgtaccta actcaagtat tcaaccttaa gaaagttaca 360
gctgcaacaa tcatcaatgc ctttagtggc acaatcaact tcgggacttt catcgctgct 420
ttcctctgcg acacttactt tggtcgctac aagactctca gtgtagctgt catcgcttgt 480
ttcctgggat cgcttgtgat attactgacg gctgcagttc ctgcattgca cccgactcca 540
tgtggaacac atagctggtg ccaagggcca agcccgggcc agatcgcgtt cttgctgctg 600
ggtttagcgt ttcttgtggt cggtgcgggt gggatcaggc cgtgtaactt ggcttttgga 660
gctgatcagt tcaaccccaa atccgaatcc gggaagaaag gaatcaacag cttctttaac 720
tggtatttct tcaccttcac gtttgcgcag atcgtctcgc tcacgctggt cgtgtatatc 780
cagtcgaacg tgagctggac gatcggtttg ctcatccctg tggctctgat gttcttggcc 840
tgcgtcatct tctttgctgg acataaactg tatgtgaaag tgaaagcctc gggtagtccc 900
ttggctagta tcggtcacgt tatcacggca gcgatcaaga aacgagggtt gaagcaagtt 960
aagcagcctt ggctcgatct ttacaaccac attccaacta actatccaaa ctccaccttg 1020
aaatacaccg accagtttag gtttcttgac aaagcagcga ttatgacccc tgaggacaag 1080
ctgaattccg atggagctgc tttcgatcca tggaccctat gtacattgca gaaagtggaa 1140
gaagtgaaat gcatgtgaga gtgattccga tctggtttgc ttgcgcgatt tactacctca 1200
ctgtaactat acagatgact tatccggtct tccaagcgca gcagagcgac cggagattgg 1260
gttctggtgg cttcaagatc cccgcagcca cctatgtggt gttcttgatg tcgggtatga 1320
ctgttttcat cgtgttctac gaccgtgtcc ttgtcccgtt gctcagaaga gtgaccgggt 1380
tagaaaccgg tttgaccctc ttgcagagag tcggatcagg gatcttcttt gccatgttga 1440
gtttgttggt ctccgggttc gtagaggaac ggagaagaac cttcgccctg acgaaaccga 1500
ctctcgggat ggagccacga gcgggagaga tctcctccat gtcggccatg tggctgattc 1560
cgcagctctt gcttgcaggc gtaggagagg cttttacagc cattggacag atggagtttt 1620
attacaagca gttccctgag aacatgaaga gcttcgctgg ctctatcttc tatgtcggtg 1680
caggtgtttc gagctatctt gctagcttct tgatctcgac tgttcatcga agaactgaac 1740
attcaccctc cgggaactgg ttagctgagg atctgaacaa agggagactc gattacttct 1800
acttcatgct caccggaatc atggtcgtta acatggttta cttcttgata atgtctaaat 1860
ggtatagata caaaggcatt aacgatgaag cgaattcttt ggtcgagacc aatgaagaag 1920
agaccaagca gaaacaagtc aagaattctg tctga 1955

<210> SEQ ID NO 236
<211> LENGTH: 385
<212> TYPE: PRT
<213> ORGANISM: Thlaspi arvense

<400> SEQUENCE: 236

-continued

```
Met Lys Ser Arg Val Ile Leu Ser His Arg Glu Arg Arg Asp Lys Lys
1               5                   10                  15

Asn Asn Asn Ile Asn Asn Lys Asp Ile Ser Cys Asn Phe Thr Gln Ile
            20                  25                  30

Glu Thr Met Glu Arg Lys Pro Phe Glu Val Glu Thr Thr Glu Asn His
        35                  40                  45

Lys Pro Tyr Ser Thr Val Asp Gly Gly Gly Val Gly Ser Asp Leu Arg
    50                  55                  60

Ser Pro Val Asp Ser Phe Asp Asp Glu Gln Lys Lys Leu Val Tyr Arg
65                  70                  75                  80

Gly Trp Lys Val Met Pro Phe Ile Ile Gly Asn Glu Thr Phe Glu Lys
                85                  90                  95

Ile Gly Ile Ile Gly Thr Leu Ser Asn Leu Leu Leu Tyr Leu Thr Gln
            100                 105                 110

Val Phe Asn Leu Lys Lys Val Thr Ala Ala Thr Ile Ile Asn Ala Phe
        115                 120                 125

Ser Gly Thr Ile Asn Phe Gly Thr Phe Ile Ala Ala Phe Leu Cys Asp
    130                 135                 140

Thr Tyr Phe Gly Arg Tyr Lys Thr Leu Ser Val Ala Val Ile Ala Cys
145                 150                 155                 160

Phe Leu Gly Ser Leu Val Ile Leu Leu Thr Ala Ala Val Pro Ala Leu
                165                 170                 175

His Pro Thr Pro Cys Gly Thr His Ser Trp Cys Gln Gly Pro Ser Pro
            180                 185                 190

Gly Gln Ile Ala Phe Leu Leu Leu Gly Leu Ala Phe Leu Val Val Gly
        195                 200                 205

Ala Gly Gly Ile Arg Pro Cys Asn Leu Ala Phe Gly Ala Asp Gln Phe
    210                 215                 220

Asn Pro Lys Ser Glu Ser Gly Lys Lys Gly Ile Asn Ser Phe Phe Asn
225                 230                 235                 240

Trp Tyr Phe Phe Thr Phe Thr Phe Ala Gln Ile Val Ser Leu Thr Leu
                245                 250                 255

Val Val Tyr Ile Gln Ser Asn Val Ser Trp Thr Ile Gly Leu Leu Ile
            260                 265                 270

Pro Val Ala Leu Met Phe Leu Ala Cys Val Ile Phe Phe Ala Gly His
        275                 280                 285

Lys Leu Tyr Val Lys Val Lys Ala Ser Gly Ser Pro Leu Ala Ser Ile
    290                 295                 300

Gly His Val Ile Thr Ala Ala Ile Lys Lys Arg Gly Leu Lys Gln Val
305                 310                 315                 320

Lys Gln Pro Trp Leu Asp Leu Tyr Asn His Ile Pro Thr Asn Tyr Pro
                325                 330                 335

Asn Ser Thr Leu Lys Tyr Thr Asp Gln Phe Arg Phe Leu Asp Lys Ala
            340                 345                 350

Ala Ile Met Thr Pro Glu Asp Lys Leu Asn Ser Asp Gly Ala Ala Phe
        355                 360                 365

Asp Pro Trp Thr Leu Cys Thr Leu Gln Lys Val Glu Glu Val Lys Cys
    370                 375                 380

Met
385
```

<210> SEQ ID NO 237
<211> LENGTH: 100
<212> TYPE: DNA

<213> ORGANISM: Artificial Sequence
<220> FEATURE:
<223> OTHER INFORMATION: Synthetic

<400> SEQUENCE: 237
attgttgcag ctgtaacttt cttagtttta gagctagaaa tagcaagtta aaataaggct 60
agtccgttat caacttgaaa aagtggcacc gagtcggtgc 100

<210> SEQ ID NO 238
<211> LENGTH: 100
<212> TYPE: DNA
<213> ORGANISM: Artificial Sequence
<220> FEATURE:
<223> OTHER INFORMATION: Synthetic

<400> SEQUENCE: 238
attgagccct tctccgacac aacagtttta gagctagaaa tagcaagtta aaataaggct 60
agtccgttat caacttgaaa aagtggcacc gagtcggtgc 100

<210> SEQ ID NO 239
<211> LENGTH: 100
<212> TYPE: DNA
<213> ORGANISM: Artificial Sequence
<220> FEATURE:
<223> OTHER INFORMATION: Synthetic

<400> SEQUENCE: 239
attgagcctc cttcaccgtg ctcggtttta gagctagaaa tagcaagtta aaataaggct 60
agtccgttat caacttgaaa aagtggcacc gagtcggtgc 100

<210> SEQ ID NO 240
<211> LENGTH: 70
<212> TYPE: DNA
<213> ORGANISM: Artificial Sequence
<220> FEATURE:
<223> OTHER INFORMATION: Synthetic

<400> SEQUENCE: 240
agatagagaa gttatcagaa ttggatataa tttctactgt tgtagattca aggtacttct 60
ctatcccgaa 70

<210> SEQ ID NO 241
<211> LENGTH: 70
<212> TYPE: DNA
<213> ORGANISM: Artificial Sequence
<220> FEATURE:
<223> OTHER INFORMATION: Synthetic

<400> SEQUENCE: 241
tagattcggg atagagaagt accttgaatc tacaacagta gaaattatat ccaattctga 60
taacttctct 70

<210> SEQ ID NO 242
<211> LENGTH: 70
<212> TYPE: DNA
<213> ORGANISM: Artificial Sequence
<220> FEATURE:
<223> OTHER INFORMATION: Synthetic

<400> SEQUENCE: 242
agattatgcc gtatccatcg gtcgatctaa tttctactgt tgtagatgtc tggtcggaat 60
atcattatcc 70

<210> SEQ ID NO 243
<211> LENGTH: 70
<212> TYPE: DNA
<213> ORGANISM: Artificial Sequence
<220> FEATURE:
<223> OTHER INFORMATION: Synthetic

<400> SEQUENCE: 243
tagaggataa tgatattccg accagacatc tacaacagta gaaattagat cgaccgatgg 60
atacggcata 70

<210> SEQ ID NO 244
<211> LENGTH: 70
<212> TYPE: DNA
<213> ORGANISM: Artificial Sequence
<220> FEATURE:
<223> OTHER INFORMATION: Synthetic

<400> SEQUENCE: 244
agatagacct tcaaatagtc cctacaataa tttctactgt tgtagatctt ctgaaaaact 60
ctctccttgt 70

<210> SEQ ID NO 245
<211> LENGTH: 70
<212> TYPE: DNA
<213> ORGANISM: Artificial Sequence
<220> FEATURE:
<223> OTHER INFORMATION: Synthetic

<400> SEQUENCE: 245
tagaacaagg agagagtttt tcagaagatc tacaacagta gaaattattg tagggactat 60
ttgaaggtct 70

<210> SEQ ID NO 246
<211> LENGTH: 70
<212> TYPE: DNA
<213> ORGANISM: Artificial Sequence
<220> FEATURE:
<223> OTHER INFORMATION: Synthetic

<400> SEQUENCE: 246
agatacatct ccgcaagtgt ccattcctaa tttctactgt tgtagatcca ctacttcgtc 60
taactccttc 70

<210> SEQ ID NO 247
<211> LENGTH: 70
<212> TYPE: DNA
<213> ORGANISM: Artificial Sequence
<220> FEATURE:
<223> OTHER INFORMATION: Synthetic

<400> SEQUENCE: 247
tagagaagga gttagacgaa gtagtggatc tacaacagta gaaattagga atggacactt 60
gcggagatgt 70

<210> SEQ ID NO 248
<211> LENGTH: 70
<212> TYPE: DNA
<213> ORGANISM: Artificial Sequence
<220> FEATURE:
<223> OTHER INFORMATION: Synthetic

<400> SEQUENCE: 248
agatttaagg ttgaatactt gagttagtaa tttctactgt tgtagatgtg gcacaatcaa 60
cttcgggact 70

<210> SEQ ID NO 249
<211> LENGTH: 70
<212> TYPE: DNA
<213> ORGANISM: Artificial Sequence
<220> FEATURE:
<223> OTHER INFORMATION: Synthetic

<400> SEQUENCE: 249
tagaagtccc gaagttgatt gtgccacatc tacaacagta gaaattacta actcaagtat 60
tcaaccttaa 70

<210> SEQ ID NO 250
<211> LENGTH: 70
<212> TYPE: DNA
<213> ORGANISM: Artificial Sequence
<220> FEATURE:
<223> OTHER INFORMATION: Synthetic

<400> SEQUENCE: 250
agatggagcc gatcagttca acccgaataa tttctactgt tgtagatgcg cagatcttgt 60
cgctgacgct 70

<210> SEQ ID NO 251
<211> LENGTH: 70
<212> TYPE: DNA
<213> ORGANISM: Artificial Sequence
<220> FEATURE:
<223> OTHER INFORMATION: Synthetic

<400> SEQUENCE: 251
tagaagcgtc agcgacaaga tctgcgcatc tacaacagta gaaattattc gggttgaact 60
gatcggctcc 70

<210> SEQ ID NO 252
<211> LENGTH: 70
<212> TYPE: DNA
<213> ORGANISM: Artificial Sequence
<220> FEATURE:
<223> OTHER INFORMATION: Synthetic

<400> SEQUENCE: 252
agatggtagt tagtccatcg cagcctataa tttctactgt tgtagatgtt cagaggagga 60
acagattatc 70

<210> SEQ ID NO 253
<211> LENGTH: 70
<212> TYPE: DNA
<213> ORGANISM: Artificial Sequence
<220> FEATURE:
<223> OTHER INFORMATION: Synthetic

<400> SEQUENCE: 253
tagagataat ctgttcctcc tctgaacatc tacaacagta gaaattatag gctgcgatgg 60
actaactacc 70

<210> SEQ ID NO 254
<211> LENGTH: 70

<212> TYPE: DNA
<213> ORGANISM: Artificial Sequence
<220> FEATURE:
<223> OTHER INFORMATION: Synthetic

<400> SEQUENCE: 254
agatatcgaa cagggtgttg atcccgttaa tttctactgt tgtagataac atagaaacgt 60
acttgttgcc 70

<210> SEQ ID NO 255
<211> LENGTH: 70
<212> TYPE: DNA
<213> ORGANISM: Artificial Sequence
<220> FEATURE:
<223> OTHER INFORMATION: Synthetic

<400> SEQUENCE: 255
tagaggcaac aagtacgttt ctatgttatc tacaacagta gaaattaacg ggatcaacac 60
cctgttcgat 70

<210> SEQ ID NO 256
<211> LENGTH: 70
<212> TYPE: DNA
<213> ORGANISM: Artificial Sequence
<220> FEATURE:
<223> OTHER INFORMATION: Synthetic

<400> SEQUENCE: 256
agatgctacg aggaggagca gattatctaa tttctactgt tgtagataaa tagttagccc 60
atcgcaatct 70

<210> SEQ ID NO 257
<211> LENGTH: 70
<212> TYPE: DNA
<213> ORGANISM: Artificial Sequence
<220> FEATURE:
<223> OTHER INFORMATION: Synthetic

<400> SEQUENCE: 257
tagaagattg cgatgggcta actatttatc tacaacagta gaaattagat aatctgctcc 60
tcctcgtagc 70

<210> SEQ ID NO 258
<211> LENGTH: 70
<212> TYPE: DNA
<213> ORGANISM: Artificial Sequence
<220> FEATURE:
<223> OTHER INFORMATION: Synthetic

<400> SEQUENCE: 258
agataccctt ctccgataca gcatggttaa tttctactgt tgtagattct tcccctgacg 60
tccatgctcc 70

<210> SEQ ID NO 259
<211> LENGTH: 70
<212> TYPE: DNA
<213> ORGANISM: Artificial Sequence
<220> FEATURE:
<223> OTHER INFORMATION: Synthetic

<400> SEQUENCE: 259
tagaggagca tggacgtcag gggaagaatc tacaacagta gaaattaacc atgctgtatc 60

-continued

```
ggagaagggt                                                            70


<210> SEQ ID NO 260
<211> LENGTH: 70
<212> TYPE: DNA
<213> ORGANISM: Artificial Sequence
<220> FEATURE:
<223> OTHER INFORMATION: Synthetic

<400> SEQUENCE: 260

agatgtccag cttcgtcagg aacttcctaa tttctactgt tgtagatgag aaaccttctc     60

gtaggagctg                                                            70


<210> SEQ ID NO 261
<211> LENGTH: 70
<212> TYPE: DNA
<213> ORGANISM: Artificial Sequence
<220> FEATURE:
<223> OTHER INFORMATION: Synthetic

<400> SEQUENCE: 261

tagacagctc ctacgagaag gtttctcatc tacaacagta gaaattagga agttcctgac     60

gaagctggac                                                            70
```

LOW GLUCOSINOLATE PENNYCRESS MEAL AND METHODS OF MAKING

CROSS REFERENCE TO RELATED APPLICATIONS

This application claims the benefit of U.S. Provisional Patent Application No. 62/619,360, filed Jan. 19, 2018, which is incorporated herein by reference in its entirety.

STATEMENT REGARDING FEDERAL FUNDING

This invention was made with government support under Grant Number 2014-67009-22305 awarded by the National Institute of Food and Agriculture, USDA. The government has certain rights in the invention.

INCORPORATION OF SEQUENCE LISTING

The substitute sequence listing contained in the file named "CC-9 Low GSL_ST25_V2.txt", which is 413045 bytes in size (measured in operating system MS-Windows), contains 261 sequences, and which was created on Dec. 2, 2019, was filed on Dec. 2, 2019 by electronic submission (using United States Patent Office EFS-Web filing system) and is incorporated herein by reference in its entirety.

BACKGROUND

Different plants have seed contents that make them desirable for feed compositions. Examples are soybean, canola, rapeseed and sunflower. After crushing the seeds and recovering the oil, the resulting meal has a protein content making the meal useful as a feed ingredient for ruminants and other animals. Nevertheless, there remains a desire for improved plant seeds that can provide additional sources of nutrition to animals.

Field Pennycress *Thlaspi arvense* L. (common names: fanweed, stinkweed, field pennycress), hereafter referred to as Pennycress or pennycress, is a winter cover crop that helps to protect soil from erosion, prevent the loss of farm-field nitrogen into water systems, and retain nutrients and residues to improve soil productivity. While it is well established that cover crops provide agronomic and ecological benefits to agriculture and environment, only 5% of U.S. farmers today are using them. One reason is economics—it requires on average ~$30-50/acre to grow a cover crop on the land that is otherwise idle between two seasons of cash crops such as corn and soy. In the last 5 years, it has been recognized that pennycress could be used as a novel cover crop, because in addition to providing cover crop benefits, it produces harvestable seeds rich in oil and protein having value for feed, food, fuel, and industrial applications. Extensive testing indicates that pennycress can be interseeded over standing corn in early fall and harvested in spring prior to soybean planting (in appropriate climates). As such, its growth and development require minimal incremental inputs (e.g., no/minimum tillage, no/low nitrogen, insecticides or herbicides). Pennycress also does not directly compete with existing crops when intercropped e.g., for energy production, and the recovered oil and meal can provide an additional source of income for farmers.

Pennycress is a winter annual belonging to the Brassicaceae (mustard) family. It's related to cultivated crops, rapeseed and canola, which are also members of the Brassicaceae family. Pennycress seeds are smaller than those of canola, but they are also high in oil and protein content. They typically contain 36% oil, which is roughly twice the level found in soybean, and the oil has a very low saturated fat content (~4%). Pennycress represents a clear opportunity for sustainable optimization of agricultural systems. For example, in the U.S. Midwest, ~35M acres that remain idle could be planted with pennycress near the time of corn crop harvest, with pennycress seeds and/or plants harvested before the next soybean crop is planted. Pennycress can serve as an important winter cover crop working within the no/low-till corn and soybean rotation to guard against soil erosion and improve overall field soil nitrogen and pest management.

Pennycress seeds contain oil that is highly desirable as a feedstock for biofuels and/or chemicals and potentially as a food oil. Once the oil is obtained from pennycress seeds, either from mechanical expeller pressing or hexane extraction, the resulting meal has a high protein level with a favorable amino acid profile that could provide nutritional benefits to animals. However, studies of pennycress processing have consistently demonstrated that the meal produced has a high level of the anti-nutrient compound sinigrin (allyl-glucosinolate or 2-propenyl-glucosinolate), and as a result, without additional treatments, may not be competitive with high-value products like soybean and canola meals, ingredients commonly used in animal feed. Glucosinolates (GSLs) are secondary plant metabolites that are found in all *Brassica* plants such as rapeseed, canola, camelina, carinata and pennycress. Content and composition of GSLs vary due to plant species, agronomic practices and environmental conditions (Tripathi and Mishra, 2007). Glucosinolates and their breakdown products that are a result of hydrolysis during the processing of the seeds into animal feed can result in negative effects on animal nutrition. The toxicity of glucosinolates for animals has been primarily associated with the metabolites thiocyanates, oxazolidinethiones and nitriles. These compounds interfere with iodine uptake (thiocyanates) and the synthesis of the thyroid hormones T3 and T4 (oxazolidinethiones), leading eventually to hypothyroidism and enlargement of the thyroid gland (EFSA, 2008). The major clinical signs of toxicity described in farm animals include growth retardation, reduction in performance (milk and egg production), impaired reproductive activity, and impairment of liver and kidney functions (EFSA, 2008). A comprehensive review of the effects of glucosinolates in animal nutrition has been published by Tripathi and Mishra (2007) and EFSA (2008).

SUMMARY

Compositions comprising non-defatted pennycress seed meal that comprises less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Non-defatted pennycress seed meal that comprise less than 30, 28, 25, 16, or 15 micromoles sinigrin per gram by dry weight are provided herein.

Defatted pennycress seed meal comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Compositions comprising defatted pennycress seed meal that comprise less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed lots comprising pennycress seed with less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

In one embodiment, this disclosure provides methods for producing low glucosinolate pennycress seeds and meal. In certain embodiments, the methods comprise genetically modifying pennycress seed (e.g., using gene editing, mutagenesis, or a transgenic approach) to suppress expression of one or more genes involved in sinigrin biosynthesis, transport, and/or hydrolysis. Genetically altered seed lots with lower sinigrin content in comparison to control seed lots that lack the genetic alteration can be obtained by these methods.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings:

FIG. 1A, B illustrate glucosinolate (GSL) biosynthetic pathways for many *Brassica* plants. Panel A: A schematic diagram of aliphatic GSL pathway which begins with amino acid methionine as the precursor and is relevant for GSL modification in pennycress seed. Panel B: Various GSL forms found in *Brassica* are shown.

FIG. 2 A, B, C, illustrates pARV1 (SS32_GTR1), *Agrobacterium* CRISPR-Cas9 vector and its gene editing sgRNA cassette, for targeting pennycress homolog of Glucosinolate transporter 1 (GTR1 or Glut1) gene. Panel A: Plasmid map of pARV1 (SS32_GTR1). Panel B: sgRNA cluster in pARV1, targeting nucleotides 2503-2522 and 2538-2557 of SEQ ID NO: 14. Panel C: Sequence example of one of gRNA cassettes targeting pennycress homolog of Glucosinolate transporter 1 (GTR1 or Glut1) gene (SEQ ID NO: 237).

FIG. 3A, B illustrates pDe-SpCas9 and pDe-SaCas9, *Agrobacterium* CRISPR-Cas9 base vectors for editing plant genome. gRNA cassette stuffers are inserted at the multiple cloning site between the Cas9 and HygR cassettes, replacing a small fragment of the vector with synthetic gRNA cassette.

FIG. 4A, B, C, illustrates pARV145, *Agrobacterium* CRISPR-Cas9 vector and its gene editing sgRNA cassettes, for targeting pennycress homolog of MYB28 (HAG1) gene. Panel A: Plasmid map of pARV145. Panel B: sgRNA cluster in pARV145, targeting nucleotides 719-738 and 793-812 of SEQ ID NO: 20. Panel C: Sequence examples of gRNA cassettes targeting pennycress homolog of MYB28 (HAG1) gene (SEQ ID NOs: 238 and 239).

FIG. 7 A, B, C, D, E, F, G, H, I, J, K, gRNA cassettes targeting pennycress homologs of multiple genes in glucosinolate biosynthetic/metabolic pathway. FIG. 7A illustrates a gRNA cassette stuffer (SEQ ID NO:240 (top strand) and SEQ ID NO: 241 (bottom strand)), designed for insertion into the Aar I-digested plant genome editing vector (such as pARV187 or pARV190) for targeting pennycress AOP2 gene, nucleotides 2367-2389 and 2419-2441 of SEQ ID NO: 2; FIG. 7B: gRNA cassette stuffer (SEQ ID NO:242 (top strand) and SEQ ID NO: 243 (bottom strand)) for targeting pennycress BCAT4 gene, nucleotides 2984-3006 and 3048-3070 of SEQ ID NO: 5; FIG. 7C: gRNA cassette stuffer (SEQ ID NO:244 (top strand) and SEQ ID NO: 245 (bottom strand)) for targeting pennycress BCAT6 gene, nucleotides 1932-1954 and 2387-2409 of SEQ ID NO: 8; FIG. 7D: gRNA cassette stuffer (SEQ ID NO:246 (top strand) and SEQ ID NO: 247 (bottom strand)) for targeting pennycress CYP79 gene, nucleotides 2914-2936 and 2968-2990 of SEQ ID NO: 11; FIG. 7E: gRNA cassette stuffer (SEQ ID NO:248 (top strand) and SEQ ID NO: 249 (bottom strand)) for targeting pennycress GTR1 gene, nucleotides 2483-2505 and 2541-2563 of SEQ ID NO: 14; FIG. 7F: gRNA cassette stuffer (SEQ ID NO:250 (top strand) and SEQ ID NO: 251 (bottom strand)) for targeting pennycress GTR2 gene, nucleotides 2317-2339 and 2404-2426 of SEQ ID NO: 18; FIGS. 7G and 7H: gRNA cassette stuffers (SEQ ID NO:252 (top strand) and SEQ ID NO: 253 (bottom strand) in 7G; SEQ ID NO:254 (top strand) and SEQ ID NO: 255 (bottom strand) in 7H) for targeting pennycress MYB28 gene, nucleotides 948-970, 1001-1023, 1045-1067 and 1315-1337 of SEQ ID NO: 20; FIG. 7I: gRNA cassette stuffer (SEQ ID NO:256 (top strand) and SEQ ID NO: 257 (bottom strand)) for targeting pennycress MYB29 gene, nucleotides 2573-2595 and 2625-2647 of SEQ ID NO: 23; FIG. 7J: gRNA cassette stuffer (SEQ ID NO:258 (top strand) and SEQ ID NO: 259 (bottom strand)) for targeting pennycress MYB76 gene, nucleotides 1539-1561 and 1570-1592 of SEQ ID NO: 26; FIG. 7K: gRNA cassette stuffer (SEQ ID NO:260 (top strand) and SEQ ID NO: 261 (bottom strand)) for targeting pennycress TFP gene, nucleotides 2170-2192 and 2559-2581 of SEQ ID NO: 29.

DETAILED DESCRIPTION

Figure 5:
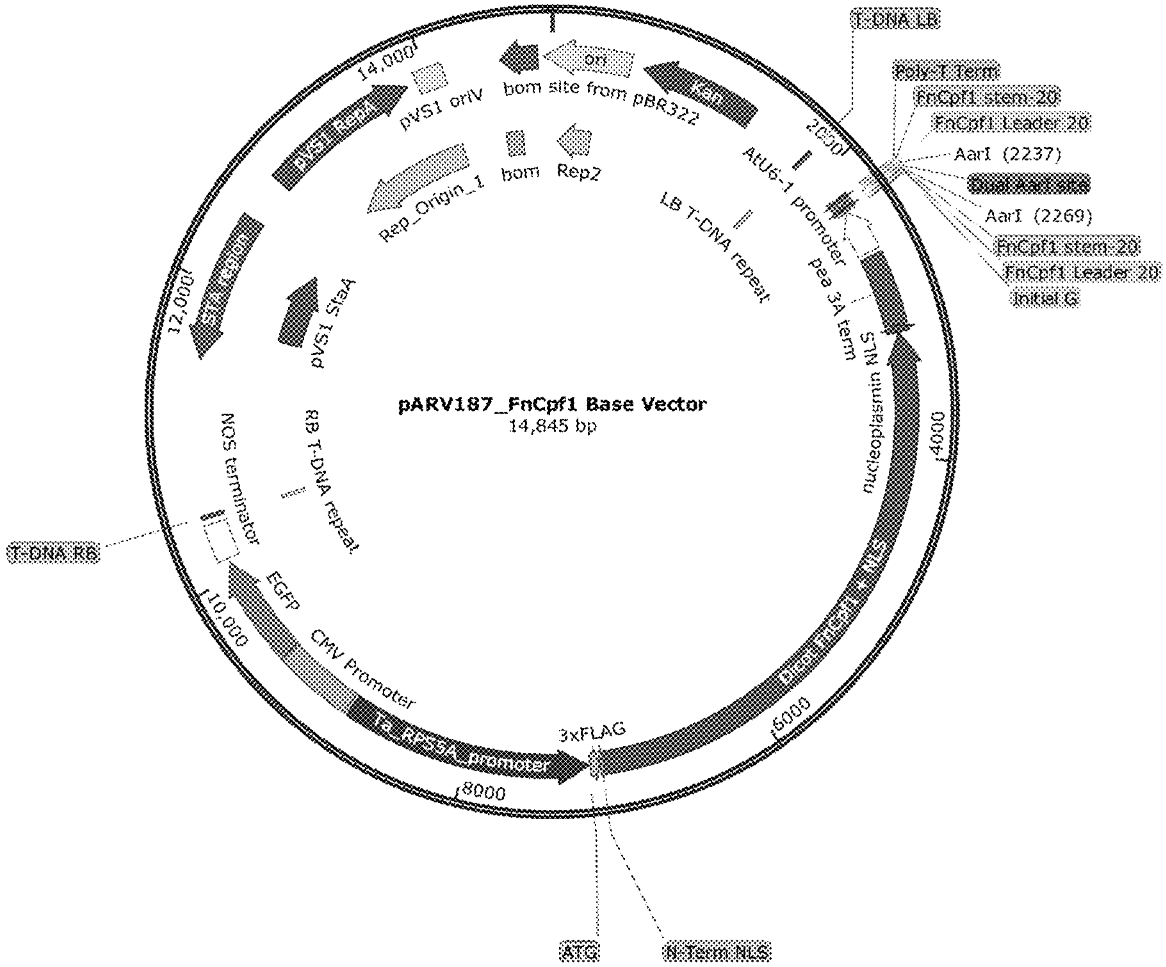
FIG. 5 illustrates pARV187, *Agrobacterium* CRISPR-FnCpf1 base vector for editing plant genome. gRNA cassette stuffers are inserted at the dual AarI site, replacing a small fragment of the vector with synthetic gRNA cassette.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features to which they refer while not excluding any additional unspecified features.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Reductions in sinigrin content of various pennycress plants, seeds, seed lots, seed meals, and compositions obtained therefrom as well as associated methods of obtaining and using such plants, seeds, seed lots, seed meals, and compositions is provided herein by suppression of certain endogenous pennycress genes. The endogenous pennycress genes that can be suppressed to provide such reductions in sinigrin content include, but are not limited to, endogenous pennycress genes set forth in the following Table 1 and allelic variants of those genes.

Suppression of certain endogenous pennycress gene expression to provide for reductions in sinigrin content can be affected by a variety of techniques including, but not limited to, loss-of-function (LOF) mutations in endogenous genes, with transgenes, or by using gene-editing- or mutagenesis-mediated genome rearrangements. In certain embodiments, the pennycress plants, seeds, seed lots, seed meals (which can be defatted or non-defatted), and related compositions can comprise one or more LOF mutations that suppress or otherwise alter expression and/or function of one or more genes, coding sequences, and/or proteins, thus resulting in reduced sinigrin content in comparison to control or wild-type pennycress seed, seed lots, and plant lots. Such LOF mutations include, but are not limited to, INDELS (insertions, deletions, and/or substitutions or any combination thereof), translocations, inversions, duplications, or any combination thereof in a promoter, and/or other regulatory elements including enhancers, a 5' untranslated region, coding region, an intron of a gene, and/or a 3' UTR of a gene. Such INDELS can introduce one or more mutations including, but not limited to, frameshift mutations, missense mutations, pre-mature translation termination codons, splice donor and/or acceptor mutations, regulatory mutations, and the like that result in a LOF mutation. In certain embodiments, the LOF mutation will result in: (a) a reduction in the enzymatic, transport, or other biochemical activity associated with the encoded polypeptide in the plant comprising the LOF mutation in comparison to a wild-type control plant; or (b) both a reduction in the enzymatic, transport or other biochemical activity (e.g., transcription factor) and a reduction in the amount of a transcript (e.g., mRNA) or polypeptide in the plant comprising the LOF mutation in comparison to a wild-type control plant. Such reductions in activity or activity and transcript levels can, in certain embodiments, comprise a reduction of at least 20%, 30%, 40%, 50%, 60%, 70%, 75%, 80%, 85%, 90%, 95%, 98%, 99%, or 100% of activity or activity and transcript levels in the LOF mutant in comparison to the activity or transcript levels in a wild-type control plant. In certain embodiments, the pennycress plants, seeds, seed lots, seed meals (which can be defatted or non-defatted), and related compositions will comprise one or more transgenes or genetic modifications that suppress or otherwise alter expression of one or more genes, coding sequences, and/or proteins, thus resulting in reduced sinigrin content in comparison to control or wild-type pennycress seed lots. Transgenes or genetic modifications that can provide for such suppression or alteration include, but are not limited to, transgenes or genome rearrangements introduced via gene editing or other mutagenesis techniques that produce small interfering RNAs (siRNAs), miRNA, or artificial miRNAs targeting a given gene or gene transcript for suppression. Such genome rearrangements include, but are not limited to, deletions, duplications, insertions, inversions, translocations, and combinations thereof. Useful genome rearrangements include, but are not limited to, rearrangements that place an endogenous promoter and/or transcriptional enhancer in proximity to 3' end of a target gene or coding sequence (e.g., a gene or coding sequence of Table 1) or within the target gene or coding sequence such that the endogenous promoter and/or enhancer drive expression of an siRNA or miRNA that suppresses or otherwise alters expression of the target gene. In certain embodiments, the transgenes or genetic modifications that suppress expression will result in: (a) a reduction in the enzymatic, transport, or other biochemical activity associated with the encoded polypeptide in the plant comprising the transgene or genome rearrangement in comparison to a wild-type control plant; or (b) both a reduction in the enzymatic or other biochemical activity and a reduction in the amount of a transcript (e.g., mRNA) or polypeptide in the plant comprising the transgene or genome rearrangement in comparison to a wild-type control plant. Such reductions in activity and transcript levels can in certain embodiments comprise a reduction of at least 20%, 30%, 40%, 50%, 60%, 70%, 75%, 80%, 85%, 90%, 95%, 98%, 99%, or 100% of activity and/or transcript levels in the transgenic plant in comparison to the activity or transcript levels in a wild-type control plant. In certain embodiments, certain genes, coding sequences, and/or proteins that can be targeted for introduction of LOF mutations or that are targeted for transgene- or genome rearrangement-mediated suppression are provided in the following Table 1 and accompanying Sequence Listing. In certain embodiments, allelic variants of the wild-type genes, coding sequences, and/or proteins provided in Table 1 and the sequence listing are targeted for introduction of LOF mutations or are targeted for transgene- or genome rearrangement-mediated suppression. Allelic variants found in distinct pennycress isolates or varieties that exhibit wild-type seed sinigrin content can be targeted for introduction of LOF mutations or are targeted for transgene- or genome rearrangement-mediated suppression to obtain seed lots having reduced sinigrin content in comparison to sinigrin content of the control seed lots of wild-type pennycress. Such allelic variants can comprise polynucleotide sequences that have at least 80%, 85%, 90%, 95%, 96%, 97%, 98%, or 99% sequence identity across the entire length of the polynucleotide sequences of the wild-type coding regions or wild-type genes of Table 1 and the sequence listing. Such allelic variants can comprise polypeptide sequences that have at least 80%, 85%, 90%, 95%, 96%, 97%, 98%, or 99% sequence identity across the entire length of the polypeptide sequences of the wild-type proteins of Table 1 and the sequence listing. Pennycress seed lots having reduced sinigrin content as described herein can comprise one or more LOF mutations in one or more genes that encode polypeptides involved in GSL biosynthesis, in GSL transport, in GSL hydrolysis, regulating expression of genes encoding GSL biosynthetic and/or transport genes (e.g., transcription factors) or can comprise transgenes or genome rearrangements that suppress expression of those biosynthetic, transporter, hydrolysis, or expression regulator (e.g., transcription factor) encoding genes. Polypeptides affecting these traits include, without limitation, AOP2, BCAT4, BCAT6, CYP79F1, CYP83A1, GTR1, GTR2, MYB28 (HAG1), MYB29, MYB76, TFP, BHLH05, IMD1, CYP79B3, MAM1, FMO-GS-Ox1, and UGT74B-1 polypeptides disclosed in Table 1 and allelic variants thereof. In certain embodiments, pennycress seed lots, plants, seeds, as well as the seed meals and compositions obtained therefrom, all having reduced sinigrin content, can comprise one or more LOF mutations found in the pennycress mutant E3 196, E5 444P1, E5 356P5, I87113, E5 543, or I87207 germplasm. Compositions comprising defatted or non-defatted seed meal obtained from any of the aforementioned seed lots, and seed cakes obtained from any of the aforementioned seed lots are also provided herein. Methods of making any of the aforementioned seed lots, compositions, seed meals, or seed cakes are also provided herein. As used herein, the phrase "seed cake" refers to the material obtained after the seeds are crushed, ground, heated, and expeller pressed or extruded prior to solvent extraction.

In certain embodiments, reductions in sinigrin content of seed lots, seed meal compositions, seed meal, or seed cake are in comparison to sinigrin content of control or wild-type seed lots, seed meal compositions, seed meal, or seed cake. Such controls include, but are not limited to, seed lots, seed meal compositions, seed meal, or seed cake obtained from control plants that lack the LOF mutations or transgene- or genome rearrangement-mediated gene suppression. In certain embodiments, control plants that lack the LOF mutations or transgene or genome rearrangement mediated gene suppression will be otherwise isogenic to the plants that contain the LOF mutations or transgene- or genome rearrangement-mediated gene suppression. In certain embodiments, the controls will comprise seed lots, seed meal compositions, seed meal, or seed cake obtained from plants that lack the LOF mutations or transgene or genome rearrangement mediated gene suppression and that were grown in parallel with the plants having the LOF mutations or transgene or genome rearrangement-mediated gene suppression. In certain embodiments, the pennycress seed lots, plants, seeds, as well as the defatted or non-defatted seed meals and compositions obtained therefrom, can comprise a less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight.

In certain embodiments, pennycress seed lots, plants, seeds, as well as the seed meals and compositions obtained therefrom, all having reduced sinigrin content, can include at least one loss-of-function mutation in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof) and/or at least one loss-of-function mutation in a GSL transport (SEQ ID NO: 13, 14, 16, 18, or allelic variant thereof), in a GSL hydrolysis (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL transport coding sequence or gene (e.g., SEQ ID NO: 13, 14, 16, 18, or allelic variant thereof) and at least one loss-of-function mutation in a GSL hydrolysis (SEQ ID NO: 28, 29, or allelic variant thereof), and/or in a expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL hydrolysis (SEQ ID NO: 28, 29, or allelic variant thereof) coding sequence or gene and/or at least one loss-of-function mutation in an expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can be obtained from pennycress plants comprising the mutant E3 196, E5 444P1, E5 356P5, I87113, E5 543, or I87207 germplasm.

TABLE 1

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 1 | AOP2-CDS | WT Coding region | Plays a role in the secondary modification of aliphatic (methionine-derived) GSLs, namely the conversion of methylsulfinylalkyl GSLs to form alkenyl GSLs, and also influences aliphatic GSL accumulation | ALKENYL HYDROXALKYL PRODUCING 2-CAPE VERDE ISLANDS, AOP2-CVI, GSL ALK enzyme, AOP (2-oxoglutarate-dependent dioxygenase) |
| 2 | AOP2-Genomic locus | WT Gene | | |
| 3 | AOP2-PRT | WT Protein | | |
| 4 | BCAT4-CDS | WT Coding region | Involved in the methionine chain elongation pathway that leads to the ultimate biosynthesis of methionine-derived glucosinolates | BCAT4 (BRANCHED-CHAIN AMINOTRANSFERASE 4) |
| 5 | BCA T4-Genomic locus | WT Gene | | |
| 6 | BCAT4-PRT | WT Protein | | |
| 7 | BCAT6-CDS | WT Coding region | Encodes a cytosolic branched-chain aminotransferase that acts on Leu, Ile, Val and also on Met. Together with | BCAT6 (BRANCHED-CHAIN AMINOTRANSFERASE 6) |
| 8 | BCAT6-Genomic locus | WT Gene | | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 9 | BCAT6-PRT | WT Protein | BCAT4 and BCAT3, it is involved in methionine salvage and glucosinolate biosynthesis | |
| 10 | CYP79F1-CDS | WT Coding region | Catalyzes the first committed step in biosynthesis of the core structure of GSLs, Modulates the level of short chain methionine derived aliphatic GSLs | CYP79F1 (CYTOCHROME P450 79F1), BUS1, BUSHY 1, SPS1, SUPERSHOOT 1 |
| 11 | CYP79F1-Genomic locus | WT Gene | | |
| 12 | CYP79F1-PRT | WT Protein | | |
| 13 | GTR1-CDS | WT Coding region | GTR1 encodes high-affinity, proton-dependent GSL-specific transporter essential for the accumulation of GSLs in seeds | GTR1 (Glucosinolate Transporter 1), NPF2.10, NRT1/PTR FAMILY 2.10 |
| 14 | GTR1-Genomic locus | WT Gene | | |
| 15 | GTR1-PRT | WT Protein | | |
| 16 | GTR2-CDS | WT Coding region | GTR2 encodes high-affinity, proton-dependent GSL-specific transporter essential for the accumulation of GSLs in seeds | GTR2 (Glucosinolate Transporter 2), NPF2.11, NRT1/PTR FAMILY 2.11 |
| 17 | GTR2-PRT | WT Protein | | |
| 18 | GTR2-Genomic locus | WT Gene | | |
| 19 | MYB28-CDS | WT Coding region | Principal regulator of aliphatic glucosinolate biosynthesis and affects the production of both short- and long-chain aliphatic glucosinolates | HAG1 (High Aliphatic Glucosinolate 1), MYB DOMAIN PROTEIN 28, PMG1 (Production of Methionine-derived Glucosinolate 1) |
| 20 | MYB28-Genomic locus | WT Gene | | |
| 21 | MYB28-PRT | WT Protein | | |
| 22 | MYB29-CDS | WT Coding region | MYB DOMAIN PROTEIN 29, a Myb transcription factor affects biosynthesis of short-chain aliphatic glucosinolates | HAG3 (High Aliphatic Glucosinolate 3), PMG2 (Production of Methionine-derived Glucosinolate 2), RAO7, (Regulator of Alternative Oxidase 1A 7) |
| 23 | MYB29-Genomic locus | WT Gene | | |
| 24 | MYB29-PRT | WT Protein | | |
| 25 | MYB76-CDS | WT Coding region | MYB DOMAIN PROTEIN 76, a Myb transcription factor affects biosynthesis of short-chain aliphatic glucosinolates. | HAG2 (High Aliphatic Glucosinolate 2), PMG2, (Production of Methionine-derived Glucosinolate 2), RAO7 (Regulator of Alternative Oxidase 1A 7) |
| 26 | MYB76-Genomic locus | WT Gene | | |
| 27 | MYB76-PRT | WT Protein | | |
| 28 | TFP-CDS | WT Coding region | Promotes the formation of allylthiocyanate as well as the epithionitrile upon myrosinase-catalyzed hydrolysis of allylglucosinolate, the major glucosinolate | Thiocyanate-forming protein (TFP) |
| 29 | TFP-Genomic locus | WT Gene | | |
| 30 | TFP-PRT | WT Protein | | |
| 31 | AOP2_scaffold_16_117170_125481_-_CRISPR_64 | Oligonucleotide | AOP2 CDS targeted for cleavage by Cpf1 enzyme; part of gRNA cassette | |
| 32 | AOP2_scaffold_16_117170_125481_-_Cfp1_226 | Oligonucleotide | AOP2 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 33 | AOP2_scaffold_16_117170_125481_-_Cfp1_627 | Oligonucleotide | AOP2 CDS targeted for cleavage by Cpf1 enzyme; part of gRNA cassette | |
| 34 | AOP2_scaffold_16_117170_125481_-_CRISPR_66 | Oligonucleotide | AOP2 CDS targeted for cleavage by Cpf1 enzyme; part of gRNA cassette | |
| 35 | BCAT4_scaffold_7_1484532_1492822_+_Cfp1_566 | Oligonucleotide | BCAT4 CDS targeted for cleavage by Cpf1 enzyme; part of gRNA cassette | |
| 36 | BCAT4_scaffold_7_1484532_1492822_+_CRISPR_184 | Oligonucleotide | BCAT4 CDS targeted for cleavage by Cpf1 enzyme; part of gRNA cassette | |
| 37 | BCAT4_scaffold_7_1484532_1492822_+_CRISPR_185 | Oligonucleotide | BCAT4 CDS targeted for cleavage by Cpf1 enzyme; part of gRNA cassette | |
| 38 | BCAT4_scaffold_7_1484532_1492822_+_Cfp1_172 | Oligonucleotide | BCAT4 CDS targeted for cleavage by Cpf1 enzyme; part of gRNA cassette | |
| 39 | BCAT6_scaffold_18_731862_739845_+_CRISPR_63 | Oligonucleotide | BCAT6 CDS targeted for cleavage by Cpf1 enzyme; part of gRNA cassette | |
| 40 | BCAT6_scaffold_18_731862_739845_+_CRISPR_64 | Oligonucleotide | CAT6 CDS targeted for cleavage by Cpf1 enzyme; part of gRNA cassette | |
| 41 | BCAT6_scaffold_18_731862_739845_+_Cfp1_558 | Oligonucleotide | BCAT6 CDS targeted for cleavage by Cpf1 enzyme; part of gRNA cassette | |
| 42 | BCAT6_scaffold_18_731862_739845_+_Cfp1_577 | Oligonucleotide | BCAT6 CDS targeted for cleavage by Cpf1 enzyme; part of gRNA cassette | |
| 43 | CYP79F1_scaffold_1_3018995_3027106_+_CRISPR_86 | Oligonucleotide | CYP79F1 CDS targeted for cleavage by Cpf1 enzyme; part of gRNA cassette | |
| 44 | CYP79F1_scaffold_1_3018995_3027106_+ Cfp1_493 | Oligonucleotide | CYP79F1 CDS targeted for cleavage by Cpf1 enzyme; part of gRNA cassette | |
| 45 | CYP79F1_scaffold_1_3018995_3027106_+_CRISPR_87 | Oligonucleotide | CYP79F1 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 46 | CYP79F1_ scaffold_1_ 3018995_ 3027106_+_ Cfp1_495 | Oligonucleotide | CYP79F1 CDS targeted for cleavage by Cpf1 enzyme; part of gRNA cassette | |
| 47 | GTR1_scaffold_ 63_146888_ 155577_-_ Cfp1_88 | Oligonucleotide | GTR1 CDS targeted for cleavage by Cpf1 enzyme; part of gRNA cassette | |
| 48 | GTR1_scaffold_ 63_146888_ 155577_-_ Cfp1_92 | Oligonucleotide | GTR1 CDS targeted for cleavage by Cpf1 enzyme; part of gRNA cassette | |
| 49 | GTR1_scaffold_ 63_146888_ 155577_-_ Cfp1_506 | Oligonucleotide | GTR1 CDS targeted for cleavage by Cpf1 enzyme; part of gRNA cassette | |
| 50 | GTR1_scaffold_ 63_146888_ 155577_-_ Cfp1_525 | Oligonucleotide | GTR1 CDS targeted for cleavage by Cpf1 enzyme; part of gRNA cassette | |
| 51 | GTR1_scaffold_ 63_146888_ 155577_-_ Cfp1_574 | Oligonucleotide | GTR1 CDS targeted for cleavage by Cpf1 enzyme; part of gRNA cassette | |
| 52 | GTR1_scaffold_ 63_146888_ 155577_-_ Cfp1_214 | Oligonucleotide | GTR1 CDS targeted for cleavage by Cpf1 enzyme; part of gRNA cassette | |
| 53 | GTR2_scaffold_ 0_1964427_ 1972843_+_ Cfp1_513 | Oligonucleotide | GTR2 CDS targeted for cleavage by Cpf1 enzyme; part of gRNA cassette | |
| 54 | GTR2_scaffold_ 0_1964427_ 1972843_+_ Cfp1_537 | Oligonucleotide | GTR2 CDS targeted for cleavage by Cpf1 enzyme; part of gRNA cassette | |
| 55 | GTR2_scaffold_ 0_1964427_ 1972843_+_ Cfp1_174 | Oligonucleotide | GTR2 CDS targeted for cleavage by Cpf1 enzyme; part of gRNA cassette | |
| 56 | GTR2_scaffold_ 0_1964427_ 1972843_+_ Cfp1_265 | Oligonucleotide | GTR2 CDS targeted for cleavage by Cpf1 enzyme; part of gRNA cassette | |
| 57 | GTR2_scaffold_ 0_1964427_ 1972843_+ Cfp1_267 | Oligonucleotide | GTR2 CDS targeted for cleavage by Cpf1 enzyme; part of gRNA cassette | |
| 58 | MYB28_scaffold_ 0_2473389_ 2480758_+_ CRISPR_170 | Oligonucleotide | MYB28 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 59 | MYB28_scaffold_0_2473389_2480758_+_CRISPR_172 | Oligonucleotide | MYB28 CDS targeted for cleavage by Cpf1 enzyme; part of gRNA cassette | |
| 60 | MYB28_scaffold_0_2473389_2480758_+_Cfp1_569 | Oligonucleotide | MYB28 CDS targeted for cleavage by Cpf1 enzyme; part of gRNA cassette | |
| 61 | MYB28_scaffold_0_2473389_2480758_+_Cfp1_147 | Oligonucleotide | MYB28 CDS targeted for cleavage by Cpf1 enzyme; part of gRNA cassette | |
| 62 | MYB28_scaffold_0_2473389_2480758_+_Cfp1_573 | Oligonucleotide | MYB28 CDS targeted for cleavage by Cpf1 enzyme; part of gRNA cassette | |
| 63 | MYB28_scaffold_0_2473389_2480758_+_Cfp1_157 | Oligonucleotide | MYB28 CDS targeted for cleavage by Cpf1 enzyme; part of gRNA cassette | |
| 64 | MYB29_scaffold_3_2545596_2553101_-_CRISPR_156 | Oligonucleotide | MYB29 CDS targeted for cleavage by Cpf1 enzyme; part of gRNA cassette | |
| 65 | MYB29_scaffold_3_2545596_2553101_-_Cfp1_606 | Oligonucleotide | MYB29 CDS targeted for cleavage by Cpf1 enzyme; part of gRNA cassette | |
| 66 | MYB29_scaffold_3_2545596_2553101_-_CRISPR_161 | Oligonucleotide | MYB29 CDS targeted for cleavage by Cpf1 enzyme; part of gRNA cassette | |
| 67 | MYB29_scaffold_3_2545596_2553101_-_Cfp1_247 | Oligonucleotide | MYB29 CDS targeted for cleavage by Cpf1 enzyme; part of gRNA cassette | |
| 68 | MYB76_scaffold_3_2536681_2543895_-_CRISPR_55 | Oligonucleotide | MYB76 CDS targeted for cleavage by Cpf1 enzyme; part of gRNA cassette | |
| 69 | MYB76_scaffold_3_2536681_2543895_-_Cfp1_493 | Oligonucleotide | MYB76 CDS targeted for cleavage by Cpf1 enzyme; part of gRNA cassette | |
| 70 | MYB76_scaffold_3_2536681_2543895_-_CRISPR_56 | Oligonucleotide | MYB76 CDS targeted for cleavage by Cpf1 enzyme; part of gRNA cassette | |
| 71 | MYB76_scaffold_3_2536681_2543895_-_Cfp1_495 | Oligonucleotide | MYB76 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 72 | Ta_TFP_ scaffold_1_ 4920343_ 4927356_+_ CRISPR_164 | Oligonucleotide | TFP CDS targeted for cleavage by Cpf1 enzyme; part of gRNA cassette | |
| 73 | Ta_TFP_ scaffold_1_ 4920343_ 4927356_+_ Cfp1_482 | Oligonucleotide | TFP CDS targeted for cleavage by Cpf1 enzyme; part of gRNA cassette | |
| 74 | Ta_TFP_ scaffold_1_ 4920343_ 4927356_+_ CRISPR_167 | Oligonucleotide | TFP CDS targeted for cleavage by Cpf1 enzyme; part of gRNA cassette | |
| 75 | Ta_TFP_ scaffold_1_ 4920343_ 4927356_+_ Cfp1_198 | Oligonucleotide | TFP CDS targeted for cleavage by Cpf1 enzyme; part of gRNA cassette | |
| 76 | GTR1_115 | Oligonucleotide | GTR1 CDS targeted for cleavage by SpCAS9 enzyme; part of gRNA cassette | |
| 77 | GTR1_116 | Oligonucleotide | GTR1 CDS targeted for cleavage by SpCAS9 enzyme; part of gRNA cassette | |
| 78 | GTR2_scaffold_ 0_1966458_ 1970958_+_ CRISPR_43 | Oligonucleotide | GTR2 CDS targeted for cleavage by SpCAS9 enzyme; part of gRNA cassette | |
| 79 | GTR2_scaffold_ 0_1966458_ 1970958_+_ CRISPR_46 | Oligonucleotide | GTR2 CDS targeted for cleavage by SpCAS9 enzyme; part of gRNA cassette | |
| 80 | MYB28-m1- CDS | Mutant Coding region | Mutant hag1-1 allele (-G deletion) | hag1-1 |
| 81 | MYB28-m1- PRT | Mutant Protein | Mutant hag1-1 protein (-G deletion) | |
| 82 | MYB28-m2- CDS | Mutant Coding region | Mutant hag1-2 allele (+A insertion) | hag1-2, 2172A |
| 83 | MYB28-m2- PRT | Mutant Protein | Mutant hag1-2 protein (+A insertion) | |
| 84 | MYB28-m3- CDS | Mutant Coding region | Mutant hag1 allele (+G insertion) | |
| 85 | MYB28-m3- PRT | Mutant Protein | Mutant hag1 protein (+G insertion) | |
| 86 | MYB28-m4- CDS | Mutant Coding region | Mutant hag1 allele (A→ G mutation) | |
| 87 | MYB28-m4- PRT | Mutant Protein | Mutant hag1 allele (A→ G mutation) | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 88 | MYB28-m5-CDS | Mutant Coding region | Mutant hag1 allele (+A insertion) | |
| 89 | MYB28-m5-PRT | Mutant Protein | Mutant hag1 protein (+A insertion) | |
| 90 | MYB28-m6-CDS | Mutant Coding region | Mutant hag1 allele (-AG deletion) | |
| 91 | MYB28-m6-PRT | Mutant Protein | Mutant hag1 protein (-AG deletion) | |
| 92 | CYP83A1-CDS | WT Coding region | Biosynthetic enzyme and a member of cytochrome P450 family. Catalyzes conversion of aliphatic aldoximes to nitrile oxides or aci-nitro compounds | REF2 |
| 93 | CYP83A1-Genomic locus | WT Gene | | |
| 94 | CYP83A1-PRT | WT Protein | | |
| 95 | CYP83A1-m1-CDS | Mutant Coding region | Mutant cyp83a1 allele (G insertion) | |
| 96 | CYP83A1-m1-PRT | Mutant Protein | Mutant cyp83a1 allele (G insertion) | |
| 97 | CYP83A1-m2-CDS | Mutant Coding region | Mutant cyp83a1 allele (T→G mutation) | |
| 98 | CYP83A1-m2-PRT | Mutant Protein | Mutant cyp83a1 allele (T→G mutation) | |
| 99 | AOP2_sp_PS3 | Oligonucleotide | AOP2 CDS targeted for cleavage by SpCas9 enzyme; part of gRNA cassette | |
| 100 | AOP2_sp_PS1 | Oligonucleotide | AOP2 CDS targeted for cleavage by SpCas9 enzyme; part of gRNA cassette | |
| 101 | AOP2_sp_PS4 | Oligonucleotide | AOP2 CDS targeted for cleavage by SpCas9 enzyme; part of gRNA cassette | |
| 102 | AOP2_sp_PS2 | Oligonucleotide | AOP2 CDS targeted for cleavage by SpCas9 enzyme; part of gRNA cassette | |
| 103 | AOP2_sp_PS6 | Oligonucleotide | AOP2 CDS targeted for cleavage by SpCas9 enzyme; part of gRNA cassette | |
| 104 | AOP2_sa_PS1 | Oligonucleotide | AOP2 CDS targeted for cleavage by SaCas9 enzyme; part of gRNA cassette | |
| 105 | AOP2_sa_PS2 | Oligonucleotide | AOP2 CDS targeted for cleavage by SaCas9 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 106 | HAG1_513 | Oligonucleotide | HAG1 CDS targeted for cleavage by SpCas9 enzyme; part of gRNA cassette | |
| 107 | HAG1_sp_PS1_F | Oligonucleotide | HAG1 CDS targeted for cleavage by SpCas9 enzyme; part of gRNA cassette | |
| 108 | HAG1/3_sp_R | Oligonucleotide | HAG1/HAG3 CDS targeted for cleavage by SpCas9 enzyme; part of gRNA cassette | |
| 109 | HAG1/2_sa_PS1_F | Oligonucleotide | HAG1/HAG2 CDS targeted for cleavage by SaCas9 enzyme; part of gRNA cassette | |
| 110 | HAG2_sp_PS1_F | Oligonucleotide | HAG2 CDS targeted for cleavage by SpCas9 enzyme; part of gRNA cassette | |
| 111 | HAG2_sp_PS2_F | Oligonucleotide | HAG2 CDS targeted for cleavage by SpCas9 enzyme; part of gRNA cassette | |
| 112 | HAG2_sp_PS3_F | Oligonucleotide | HAG2 CDS targeted for cleavage by SpCas9 enzyme; part of gRNA cassette | |
| 113 | HAG3_sp_PS2_F | Oligonucleotide | HAG3 CDS targeted for cleavage by SpCas9 enzyme; part of gRNA cassette | |
| 114 | HAG3_431 | Oligonucleotide | HAG3 CDS targeted for cleavage by SaCas9 enzyme; part of gRNA cassette | |
| 115 | HAG3_sp_knockout_1 | Oligonucleotide | HAG3 CDS targeted for cleavage by SpCas9 enzyme; part of gRNA cassette | |
| 116 | HAG3_sp_knockout_2 | Oligonucleotide | HAG3 CDS targeted for cleavage by SpCas9 enzyme; part of gRNA cassette | |
| 117 | CYP83A1_sp_PS3_F | Oligonucleotide | CYP83A1 CDS targeted for cleavage by SpCas9 enzyme; part of gRNA cassette | |
| 118 | GTR1_sp_PS1 | Oligonucleotide | GTR1 CDS targeted for cleavage by SpCas9 enzyme; part of gRNA cassette | |
| 119 | GTR1/2_sp_PS1 | Oligonucleotide | GTR1/GTR2 CDS targeted for cleavage by SpCas9 enzyme; part of gRNA cassette | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 120 | GTR1/2_sp_ PS2 | Oligonucleotide | GTR1/GTR2 CDS targeted for cleavage by SpCas9 enzyme; part of gRNA cassette | |
| 121 | GTR1/2_sa_ PS1 | Oligonucleotide | GTR1/GTR2 CDS targeted for cleavage by SaCas9 enzyme; part of gRNA cassette | |
| 122 | GTR1/2_sa_ PS2 | Oligonucleotide | GTR1/GTR2 CDS targeted for cleavage by SaCas9 enzyme; part of gRNA cassette | |
| 123 | GTR1_sp_ PS2_F | Oligonucleotide | GTR1 CDS targeted for cleavage by SpCas9 enzyme; part of gRNA cassette | |
| 124 | GTR1_sp_ PS3_F | Oligonucleotide | GTR1 CDS targeted for cleavage by SpCas9 enzyme; part of gRNA cassette | |
| 125 | GTR1_sp_ knockout_1 | Oligonucleotide | GTR1 CDS targeted for cleavage by SpCas9 enzyme; part of gRNA cassette | |
| 126 | GTR1_sp_ knockout_2 | Oligonucleotide | GTR1 CDS targeted for cleavage by SpCas9 enzyme; part of gRNA cassette | |
| 127 | MYB76-m1ARV-CDS | Mutant Coding Region | TAAAGAAAGGAGCAT GGACGT (nt 35-55 of SEQ ID NO: 25)→ TAAAGAAAGG-GCATGGACGT (nt 35-54 of SEQ ID NO: 127) | A427A |
| 128 | MYB76-m1ARV-PRT | Mutant Protein | Frameshift caused by 1 bp deletion | |
| 129 | MYB76-m2ARV-CDS | Mutant Coding Region | CTGTATCGGAGAAGG GTTAAAGAAAGGAGC AT (nt 18-50 of SEQ ID NO: 25)→CT--------------------------AT (nt 18-21 of SEQ ID NO: 129) | A430B |
| 130 | MYB76-m2ARV-PRT | Mutant Protein | Presumed loss of function caused by 27 bp deletion | |
| 131 | MYB29-m1ARV-CDS | Mutant Coding Region | (nt 86-690 of SEQ ID NO:22) TCCATGAA---598 bp deletion---AAGGAACC (nt 72-82 of SEQ ID NO: 131) | A264A, A296A, A316B, A329B |
| 132 | MYB29-m1ARV-PRT | Mutant Protein | Truncated protein caused by large deletion | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 133 | MYB29-m2ARV-CDS | Mutant Coding Region | (nt 72-709 of SEQ ID NO: 22) ACTCATCT---603 bp deletion---ACCGCACTG (nt 72-87 of SEQ ID NO: 133) | A361B |
| 134 | MYB29-m2ARV-PRT | Mutant Protein | Truncated protein caused by large deletion | |
| 135 | MYB29-m3ARV-CDS | Mutant Coding Region | ATCCATGAACATGGCGAAG (nt 85-103 of SEQ ID NO: 22)→ATCCATGAA(A)CATGGCGAAG (nt 85-104 of SEQ ID NO: 135), and TCAGCGTCCATGGAAGGAACCTT (nt 670-692 of SEQ ID NO: 22)→TCAGCGTCCATGGAA(A)GGAACCTT (nt 670-693 of SEQ ID NO: 135) | A262A, A275A |
| 136 | MYB29-m3ARV-PRT | Mutant Protein | Frameshift caused by 1 bp insertion (second edit also 1 bp insertion) | |
| 137 | MYB29-m4ARV-CDS | Mutant Coding Region | TCAGCGTCCATGGAAGGAACCTT (nt 670-692 of SEQ ID NO: 22)→TCAGCGTCCA---AAGGAACCTT (nt 670-689 of SEQ ID NO: 137) | A261C |
| 138 | MYB29-m4ARV-PRT | Mutant Protein | Missing M227, E228→K | |
| 139 | MYB29-m5ARV-CDS | Mutant Coding Region | TCAGCGTCCATGGAAGGAACCTT (nt 670-692 of SEQ ID NO: 22)→TCAGCGTCC----AAGGAACCTT (nt 670-689 of SEQ ID NO: 139) | A268A |
| 140 | MYB29-m5ARV-PRT | Mutant Protein | Frameshift caused by 4 bp deletion | |
| 141 | MYB29-m6ARV-CDS | Mutant Coding Region | TCAGCGTCCATGGAAGGAACCTT (nt 670-692 of SEQ ID NO: 22)→TCAGCGTCCATGGA-GGAACCTT (nt 670-691 of SEQ ID NO: 141) | A263A, A347D |
| 142 | MYB29-m6ARV-PRT | Mutant Protein | Frameshift caused by 1 bp deletion | |
| 143 | GTR1-m1ARV-CDS | Mutant Coding Region | CCTCTGCGACACTTACTTTG (nt 321-340 of SEQ ID NO: 13)→CCT-------------TTTG (nt 321-327 of SEQ ID NO: 143) | A382A |
| 144 | GTR1-m1ARV-PRT | Mutant Protein | Frameshift caused by 13 bp deletion | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 145 | GTR2-m1ARV-CDS | Mutant Coding Region | AGTGCATTGTGAGAG TGCT (nt 1037-1055 of SEQ ID NO: 16)→ AGTGCATT(T)GTGAG AGTGCT (nt 1037-1056 of SEQ ID NO: 145) | A412A |
| 146 | GTR2-m1ARV-PRT | Mutant Protein | Frameshift caused by 1 bp insertion | |
| 147 | A0P2-m1ARV-CDS | Mutant Coding Region | TTTCCGAGAGTATGG GGATC (nt 275-294 of SEQ ID NO: 1)→ TTTCCGAGAG(A)TAT GGGGATC (nt 275-295 of SEQ ID NO: 147) | A368A |
| 148 | AOP2-m1ARV-PRT | Mutant Protein | Frameshift caused by 1 bp insertion | |
| 149 | AOP2-m2ARV-CDS | Mutant Coding Region | TTTCCGAGAGTATGG GGATC (nt 275-294 of SEQ ID NO: 1) TTTCCGAGA-- ATGGGGATC (nt 275-292 of SEQ ID NO: 149) | A377A |
| 150 | AOP2-m2ARV-PRT | Mutant Protein | Frameshift caused by 2 bp deletion | |
| 151 | AOP2-m3ARV-CDS | Mutant Coding Region | TTTCCGAGAGTATGG GGATC (nt 275-294 of SEQ ID NO: 1)→ TTTCCGAGAGT-- GGGGATC (nt 275-292 of SEQ ID NO: 151) | A390A |
| 152 | AOP2-m3ARV-PRT | Mutant Protein | Frameshift caused by 2 bp deletion | |
| 153 | AOP2-m4ARV-CDS | Mutant Coding Region | TTTCCGAGAGTATGG GGATC (nt 275-294 of SEQ ID NO: 1)→ TTTCCGAGAGT---- GGATC (nt 275-290 of SEQ ID NO: 153) | A402A |
| 154 | AOP2-m4ARV-PRT | Mutant Protein | Frameshift caused by 4 bp deletion | |
| 155 | AOP2-m5ARV-CDS | Mutant Coding Region | TTTCCGAGAGTATGG GGATC (nt 275-294 of SEQ ID NO: 1)→ TTTCCGAGAGT(T)ATG GGGATC (nt 275-295 of SEQ ID NO: 155) | A378A, A379A, A385A, A394A, A403B |
| 156 | AOP2-m5ARV-PRT | Mutant Protein | Frameshift caused by 1 bp insertion | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 157 | AOP2-m6ARV-CDS | Mutant Coding Region | TTTCCGAGAGTATGG GGATC (nt 275-294 of SEQ ID NO: 1)→TTTC-- ------TGGGGATC (nt 275-286 of SEQ ID NO: 157) | A375A |
| 158 | AOP2-m6ARV-PRT | Mutant Protein | Frameshift caused by 8 bp deletion | |
| 159 | BHLH05-WT-CDS | WT Coding region | basic helix-loop-helix transcription factor05 | BHLH05, MYC3, bHLH05 |
| 160 | BHLH05-WT-Genomic Locus | WT Gene | (bHLH05) transcription factor affects the biosynthesis of glucosinolates | |
| 161 | BHLH05-WT-PRT | WT Protein | | |
| 162 | IMD1-WT-CDS | WT Coding region | ISOPROPYLMALATE DEHYDROGENASE 1 (IMD1) is involved in leucine biosynthesis and methionine chain elongation required for glucosinolate biosynthesis | IMD1, ISOPROPYLMALATE DEHYDROGENASE 1 |
| 163 | IMD1-WT-Genomic Locus | WT Gene | | |
| 164 | IMD1-WT-PRT | WT Protein | | |
| 165 | CYP79B3-region WT-CDS | WT Coding | Encodes cytochrome P450 family 79 and is involved in biosynthesis of glucosinolates | CYP79B3, CYTOCHROME P450, FAMILY 79, SUBFAMILY B, POLYPEPTIDE 3 |
| 166 | CYP79B3-WT-Genomic Locus | WT Gene | | |
| 167 | CYP79B3-WT-PRT | WT Protein | | |
| 168 | MAM1-WT-CDS | WT Coding region | Encodes METHYLTHIOALKYL MALATE SYNTHASE 1 is involved in biosynthesis of glucosinolates | MAM1, METHYLTHIOALKYL MALATE SYNTHASE 1, gsm1 |
| 169 | MAM1-WT-Genomic Locus | WT Gene | | |
| 170 | MAM1-WT-PRT | WT Protein | | |
| 171 | Ta_FMO-GS-Ox1-WT-CDS | WT Coding region | FLAVIN-MONOOXYGENASE GLUCOSINOLATE S-OXYGENASE 1 catalyzes the conversion of methylthioalkyl glucosinolates to methylsulfinylalkyl glucosinolates | FMO GS-Ox1, FLAVIN-MONOOXYGENASE GLUCOSINOLATE 5-OXYGENASE 1, |
| 172 | Ta_FMO-GS-Ox1-WT-Gemonic Locus | WT Gene | | |
| 173 | Ta FMO-GS-Ox1-WT-PRT | WT Protein | | |
| 174 | Ta_UGT74B1-WT-CDS | WT Coding region | UDP-glucose:thiohydroximate S-glucosyltransferase involved in glucosinolate biosynthesis | UGT74B1, UDP-GLUCOSYL TRANSFERASE 74B1 |
| 175 | Ta_UGT74B1-WT-Gemonic Locus | WT Gene | | |
| 176 | Ta_UGT74B1-WT-PRT | WT Protein | | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 177 | Ta_FMO-GS-Ox1-1-CDS | Mutant Coding Region | TTGAGCCTCGTCTAGC TGAA (nt 653-672 of SEQ ID NO: 171)→ TTGAGCCTC<A>TC TAGCTGAA (nt 653-672 of SEQ ID NO: 177) | |
| 178 | Ta_FMO-GS-Px1-1-PRT | Mutant Protein | Amino acid change | |
| 179 | Ta_MAM1-1-CDS | Mutant Coding Region | GCAAACATAGAGACA TTGAG (nt 464-483 of SEQ ID NO: 168)→ GCAAACATA<A>AG ACATTGAG (nt 464-483 of SEQ ID NO: 179) | E5 543 |
| 180 | Ta_MAM1-1-PRT | Mutant Protein | Amino acid change | |
| 181 | Ta_MAM1-2-CDS | Mutant Coding Region | TGTGTGTGCTGGAGC AAGAC (nt 891-910 of SEQ ID NO: 168)→ TGTGTGTGCTGGA <A>CAAGAC (nt 891-910 of SEQ ID NO: 181) | D0956 |
| 182 | Ta_MAM1-2-PRT | Mutant Protein | Amino acid change | |
| 183 | Ta_AOP2-like-1MAR-CDS | Mutant Coding Region | CCGAGAGTATGGGGA TCCAG (nt 278-297 of SEQ ID NO: 1)→ CCGAGAGTATG<A> GGATCCAG (nt 278-297 of SEQ ID NO: 183) | E3196, Nutty, aop2-1 |
| 184 | Ta_AOP2-like-1MAR-PRT | Mutant Protein | Amino acid change | |
| 185 | Ta_bhlh05-1-CDS | Mutant Coding Region | AGAAGGCTGGACCTA CGCGA (nt 189-208 of SEQ ID NO: 159)→ AGAAGGCTG<A+>CCT ACGCGA (nt 189-208 of SEQ ID NO: 185) | D3 N13P3 |
| 186 | Ta_bhlh05-1-PRT | Mutant Protein | Truncated protein caused by premature stop codon | |
| 187 | Ta_bhlh05-2-CDS | Mutant Coding Region | CGGAGACAACACAGT GATTCT (nt 246-266 of SEQ ID NO: 159)→ CGGAGACAAC-CAGTGATTCT (nt 246-265 of SEQ ID NO: 187) | E5 202P2 |
| 188 | Ta_bhlh05-2-PRT | Mutant Protein | Frameshift caused by 1 bp deletion | |
| 189 | Ta_bhlh05-3-CDS | Mutant Coding Region | GGCGGAACCGGAGTT TCCGA (nt 394-413 of SEQ ID NO: 159) GGCGGAACCG<A>AG→ TTTCCGA (nt 394-413 of SEQ ID NO: 189) | E5 133P2, fad2-2 |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 190 | Ta_bhlh05-3-PRT | Mutant Protein | Amino acid change | |
| 191 | Ta_myb28-5SED-CDS | Mutant Coding Region | CATCCACGAGCACGGTGAA (nt 84-103 of SEQ ID NO: 22)→ CATCCACG-GCACGGTGAA (nt 84-102 of SEQ ID NO: 191) | |
| 192 | Ta_myb28-5SED-PRT | Mutant Protein | Frameshift due to 1 bp deletion | |
| 193 | myb76-1SED-CDS | Mutant Coding Region | TAAAACGGTGTGGAAAGAG (nt 137-157 of SEQ ID NO: 25)→ TAAAACGGT(T)GTGGAAAGAG (nt 137-156 of SEQ ID NO: 193) | |
| 194 | myb76-1SED-PRT | Mutant Protein | Frameshift due to 1 bp insertion | |
| 195 | myb29-1SED-CDS | Mutant Coding Region | GCCACTTGCCCCTAGCCCTAGTCCGGCCACGCTA (nt 381-413 of SEQ ID NO: 22)→ GCCACTTG-------------TCCGGCCACGCT (nt 381-400 of SEQ ID NO: 195) | 2172A |
| 196 | myb29-1SED-PRT | Mutant Protein | Frameshift due to 13 bp deletion | |
| 197 | myb29-2SED-CDS | Mutant Coding Region | TAGCCCTAGTCCGGCCACGCTC (nt 393-414 of SEQ ID NO: 22)→ TAGCCCTA------CCACGCTC (nt 393-408 of SEQ ID NO: 197) | 2180A |
| 198 | myb29-2SED-PRT | Mutant Protein | Presumed loss of function due to 6 bp deletion | |
| 199 | Ta_imd1-1-CDS | Mutant Coding Region | AGAGCCCAGAGGCATTAAGA (nt 663-682 of SEQ ID NO: 162)→ AGAGCCCA<A>AGGCATTAAGA (nt 663-682 of SEQ ID NO: 199) | A7 95, tt4-1 |
| 200 | Ta_imd1-1-PRT | Mutant Protein | Amino acid change | |
| 201 | Ta_imd1-2-CDS | Mutant Coding Region | TCGGTGTATCGGGACCTGGA (nt 1040-1059 of SEQ ID NO: 162)→ TCGGTGTAT<T>GGGACCTGGA(nt 1040-1059 of SEQ ID NO: 201) | D3 22 |
| 202 | Ta_imd1-2-PRT | Mutant Protein | Amino acid change | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 203 | Ta_cyp79b3-1-CDS | Mutant Coding Region | CTTTCCAACGGCTAC AAAAC (nt 412-431 of SEQ ID NO: 165)→ CTTTCCAAC<A>GCTA CAAAAC (nt 412-431 of SEQ ID NO: 203) | I87207 |
| 204 | Ta_cyp79b3-1-PRT | Mutant Protein | Amino acid change | |
| 205 | Ta_cyp79b3-2-CDS | Mutant Coding Region | GGTCTGATCCACTTA GCTTT (nt 1328-1347 of SEQ ID NO: 165)→ GGTCTGAT<T>CACTT AGCTTT (nt 1328-1347 of SEQ ID NO: 205) | E5 519 |
| 206 | Ta_cyp79b3-2-PRT | Mutant Protein | Amino acid change | |
| 207 | Ta_cyp83a1-1-CDS | Mutant Coding Region | TTCAGGCCCGAGAGG TTTC (nt 1240-1258 of SEQ ID NO: 97)→ TTCAGGCCC<A>AGA GGTTTC (nt 1240-1258 of SEQ ID NO: 207) | A7 66 |
| 208 | Ta_cyp83a1-1-PRT | Mutant Protein | Amino acid change | |
| 209 | Ta_cyp83a1-2-CDS | Mutant Coding Region | TTATCATACAAGATA GGAAA (nt 196-215 of SEQ ID NO: 97)→ TTATCATACAA(A)G ATAGGAAA (nt 196-216 of SEQ ID NO: 209) | |
| 210 | Ta_cyp83a1-2-PRT | Mutant Protein insertion | Frameshift caused by 1 bp | |
| 211 | Ta_cyp83a1-3-CDS | Mutant Coding Region | TTATCATACAAGATA GGAAA (nt 196-215 of SEQ ID NO: 97)→ TTATCATACAA(T)G ATAGGAAA (nt 196-216 of SEQ ID NO: 211) | |
| 212 | Ta_cyp83a1-3-PRT | Mutant Protein insertion | Frameshift caused by 1 bp | |
| 213 | Ta_APP2-like aop2-2SED-CDS | Mutant Coding Region | (nt 270-318 of SEQ ID NO: 1)→CGGTCTTT-- 35 bp deletion-- TGGACAAA (nt 270-285 of SEQ ID NO: 213) | |
| 214 | Ta_AOP2-like aop2-2SED-PRT | Mutant Protein | Presumed loss of function due to 33 bp deletion | |
| 215 | Ta_AOP2-like aop2-3SED-CDS | Mutant Coding Region | TCCTCATGTTTTGGAC AAAGTTTA (nt 300-323 of SEQ ID NO: 1)→ TCCTCAT-- TTTGGACAAAGTTA (nt 300-319 of SEQ ID NO: 215) | |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 216 | Ta_AOP2-like aop2-3 SED-PRT | Mutant Protein | Frameshift caused by 2 bp deletion | |
| 217 | Ta_AOP2-like aop2-4SED-CDS | Mutant Coding Region | TCCTCATGTTTTGGAC AAAGTTTA (nt 300-323 of SEQ ID NO: 1)→ TCCTCATGTTT-GACAAAGTTTA (nt 300-322 of SEQ ID NO: 217) | |
| 218 | Ta_AOP2-like aop2-4SED-PRT | Mutant Protein | Frameshift caused by 1 bp deletion | |
| 219 | Ta_AOP2-like aop2-5SED-CDS | Mutant Coding Region | TCCTCATGTTTTGGAC AAAGTTTA (nt 300-323 of SEQ ID NO: 1)→ TCCTCATGTTTT(T)G GACAAAGTTTA (nt 300-324 of SEQ ID NO: 219) | |
| 220 | Ta_AOP2-like aop2-5SED-PRT | Mutant Protein | Frameshift caused by 1 bp insertion | |
| 221 | Ta_gtr1-1-CDS | Mutant Coding Region | CCGCAGCTCTTGCTTG CAGG (nt 1561-1580 of SEQ ID NO: 13)→ CCGCAGCTCTTGTT<T> GCAGG (nt 1561-1580 of SEQ ID NO: 221) | I87113, gtr1-1 |
| 222 | Ta_gtr1-1-PRT | Mutant Protein | Amino acid change | |
| 223 | Ta_gtr1-2-CDS | Mutant Coding Region | TGAAATGCATTGTGA GAGT (nt 1145-1163 of SEQ ID NO: 13)→ TGAAATGCATGTGTG AGAGT (nt 1145-1164 of SEQ ID NO: 223) | 3A5K, gtr1-2 |
| 224 | Ta_gtr1-2-PRT | Mutant Protein | Frameshift caused by 1 bp insertion | |
| 225 | Ta_gtr2-1-CDS | Mutant Coding Region | AAAGAAAGTGATGAT GATCA (nt 1762-1781 of SEQ ID NO: 16)→ AAAGAAAGT<A>ATG ATGATCA (nt 1762-1781 of SEQ ID NO: 225) | AX17D |
| 226 | Ta_gtr2-1-PRT | Mutant Protein | Amino acid change | |
| 227 | Ta_gtr2-2-CDS | Mutant Coding Region | AGTGCATTGTGAGAG TGCT (nt 1037-1055 of SEQ ID NO: 16)→ AGTGCAT(A)TGTGAG AGTGCT (nt 1037-1056 of SEQ ID NO: 227) | 3A5C, 3A5K, gtr2-2, A427A |
| 228 | Ta_gtr2-2-PRT | Mutant Protein | Frameshift caused by 1 bp insertion | A427A |

TABLE 1-continued

Wild-type (WT) coding regions, encoded proteins, and genes that can be targeted for introduction of LOF mutations or transgene- or genome rearrangement- mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 229 | Ta_gtr2-3-CDS | Mutant Coding Region | AGTGCATTGTGAGAG TGCT (nt 1037-1055 of SEQ ID NO: 16)→ AGTGCAT(G)TGTGAG AGTGCT (nt 1037-1056 of SEQ ID NO: 229) | 3A5K, gtr2-3 |
| 230 | Ta_gtr2-3-PRT | Mutant Protein | Frameshift caused by 1 bp insertion | 3A5K |
| 231 | MYB28-2180A-CDS | Mutant Coding region | Mutant hag1 allele (-GT deletion) | 2180A |
| 232 | MYB28-2180A-PRT | Mutant Protein | Mutant hag1 protein (-GT deletion) | 2180A |
| 233 | MYB28-2172A-CDS | Mutant Coding region | Mutant hag1 allele (-TG deletion) | 2172A |
| 234 | MYB28-2172A-PRT | Mutant Protein | Mutant hag1 protein (-TG deletion) | 2172A |
| 235 | Ta_gtr1-3-CDS | Mutant Coding Region | TGAAATGCATTGTGA GAGT (nt 1145-1163 of SEQ ID NO: 13)→ TGAAATGCAT-GTGAGAGT (nt 1145-1164 of SEQ ID NO: 235) | 3A5C, gtr1-3 |
| 236 | Ta_gtr1-3-PRT | Mutant Protein | Frameshift caused by 1 bp deletion | 3A5C |

In certain embodiments, pennycress plant seeds, seed lots, seed meal, and compositions having reduced sinigrin content as described herein can be obtained from the E3 196, E5 444P1, E5 356P5, I87113, E5 543, or I87207 pennycress mutant lines provided herein, from progeny derived from those mutant lines, from hybrids derived from those mutant lines, or from germplasm from the mutants that provide seed or seed meal comprising less than 30, 28, 25, 16, or 15 micromoles sinigrin per gram by dry weight. In certain embodiments, germplasm from the mutants that provides seed or seed meal comprising less than 30, 28, 25, 16, or 15 micromoles sinigrin per gram by dry weight can be obtained by outcrossing the E3 196, E5 444P1, E5 356P5, I87113, E5 543, or I87207 pennycress mutant lines to other pennycress lines with wild-type sinigrin levels, selfing progeny of the cross, and selecting for progeny of the self that provide seed or seed meal having less than 30, 28, 25, 16, or 15 micromoles sinigrin per gram by dry weight. In certain embodiments, germplasm from the mutants that provides seed meal comprising less than 30, 28, 25, 16, or 15 micromoles sinigrin per gram can be introgressed into the genetic background of a second pennycress line with wild-type sinigrin levels by using the second pennycress line as a recurrent parent in a series of backcrosses followed by selfs, where progeny of the selfs that seed or seed meal comprising less than 30, 28, 25, 16, or 15 micromoles sinigrin per gram by dry weight are selected and carried forward into additional crosses to the recurrent parent. In certain embodiments, the pennycress mutant E3 196, E5 444P1, E5 356P5, I87113, E5 543, and/or I87207 germplasm that provides seed meal comprising less than 30, 28, 25, 16, or 15 micromoles sinigrin per gram by dry weight can be combined in a pennycress plant to provide pennycress plant seeds, seed lots, seed meal, and compositions having reduced sinigrin content as described herein. In certain embodiments, the pennycress mutant E3 196, E5 444P1, E5 356P5, I87113, E5 543, and/or I87207 germplasm can provide pennycress plant seeds, seed lots, seed meal, and compositions comprising 1, 2.5, 5, or 10 to about 15, 16, 18, 20, 25, 28, or 30 μmol sinigrin/gm dw (gram dry weight). Germplasm combinations comprising any of: (i) E3 196 and E5 444P1 germplasm; (ii) E3 196 and I87113 or E5 444P1 germplasm; (iii) E3 196 and I87207 or E5 444P1 germplasm; (iv) I87113 and I87207 or E5 444P germplasm; (iv) E3 196, I87113, E5 444P1, and I87207 germplasm; (v) E5 356P5 and E5 543 germplasm; or (vi) any combination of E3 196, E5 444P1, E5 356P5, I87113, E5 543, and/or I87207 germplasm that provide seed or seed meal comprising less than 30, 28, 25, 16, or 15 micromoles sinigrin per gram by dry weight are provided herein. Also provided herein is the combination of any of the germplasms of the E3 196, E5 444P1, E5 356P5, I87113, E5 543, and/or I87207 pennycress mutant lines that provides for reduced sinigrin content or any of the aforementioned germplasm combinations of (i), (ii), (iii), (iv), or (v) with germplasm comprising loss-of function mutations in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof), at least one loss-of-function mutation in a GSL transport coding sequence or gene (SEQ ID NO: 13, 14, 16, 18, or allelic variant thereof), in a GSL hydrolysis coding sequence or gene (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene.

A representative wild-type (WT) pennycress MYB28 (HAG1) coding sequence is as shown in sequence listing (SEQ ID NO: 19). The terms "MYB28" and "HAG1" are used interchangeably herein. In certain embodiments, a WT pennycress MYB28 coding sequence can have a sequence that deviates from the coding sequence set forth above (e.g., SEQ ID NO: 19), and is referred to as an allelic variant sequence. In certain embodiments, a MYB28 coding sequence allelic variant can have at least 80, at least 85, at least 90, at least 95, at least 98, or at least 99 percent sequence identity to SEQ ID NO: 19. A representative wild-type pennycress MYB28 polypeptide is shown in sequence listing (SEQ ID NO: 21). In certain embodiments, a WT pennycress MYB28 polypeptide can have a sequence that deviates from the polypeptide sequence set forth above (SEQ ID NO: 21), and is referred to as an allelic variant sequence. In certain embodiments, a WT pennycress MYB28 polypeptide can have a sequence that deviates from the polypeptide sequence set forth above (SEQ ID NO: 21), referred to herein as an allelic variant sequence, provided the polypeptide maintains its wild-type function. For example, a MYB28 polypeptide can have at least 80, at least 85, at least 90, at least 95, at least 98, or at least 99) percent sequence identity to SEQ ID NO: 21. A MYB28 polypeptide of an allelic variant can have one or more (e.g., 2, 3, 4, 5, 6, 7, 8, 9, or 10) amino acid modifications (e.g., substitutions) relative to SEQ ID NO: 21.

In certain embodiments, pennycress seed lots, plants, seeds, as well as the seed meals and compositions obtained therefrom, all having reduced sinigrin content, can include at least one loss-of-function modification in a MYB28 gene (e.g., in a MYB28 coding sequence, in a MYB28 regulatory sequence including the promoter, 5' UTR, intron, 3' UTR, or in any combination thereof) or a transgene or genome rearrangement that suppresses expression of the MYB28 gene. As used herein, a loss-of-function mutation in a MYB28 gene can be any modification that is effective to suppress MYB28 polypeptide expression or MYB28 polypeptide function. In certain embodiments, suppressed MYB28 polypeptide expression and/or MYB28 polypeptide function can comprise elimination or a reduction in such expression or function in comparison to a wild-type plant (i.e., can be complete or partial). Examples of genetic modifications that can provide for a loss-of-function mutation include, without limitation, deletions, insertions, substitutions, translocations, inversions, duplications, or any combination thereof. In certain embodiments, any of the aforementioned loss-of-function (LOF) modifications in the MYB28 gene can be combined with a loss-of-function modification in a MYB29 gene or allelic variant thereof, and/or a loss-of-function modification in a MYB76 gene or allelic variant thereof to obtain pennycress plant seeds, seed lots, seed meal, and compositions having reduced sinigrin content described herein. Plants, germplasm, seed, seed lots, seed meal, and compositions comprising: (i) MYB28 and MYB29 LOF modifications; (ii) MYB28 and MYB76 LOF modifications; (iii) MYB29 and MYB76 LOF modifications; and (iii) MYB28, MYB29 and MYB76 LOF modifications are also provided herein.

In certain embodiments, pennycress seed lots, plants, seeds, as well as the seed meals and compositions obtained therefrom, all having reduced sinigrin content, can include a deletion (e.g., a single base-pair deletion) relative to the WT pennycress MYB28 coding sequence. In certain embodiments, a modified MYB28 coding sequence can include a single base-pair deletion of the guanine (G) at nucleotide residue 20 in a WT pennycress MYB28 coding sequence (e.g., SEQ ID NO: 19 or an allelic variant thereof). For example, a single base-pair deletion of the guanine (G) at nucleotide residue at nucleotide residue 20 in a WT pennycress MYB28 coding sequence thereby producing a premature stop codon. A representative modified pennycress MYB28 coding sequence having a loss-of-function single base pair deletion is presented in SEQ ID NO: 80.

A modified or mutated pennycress MYB28 coding sequence having a loss-of-function single base pair deletion mutation (e.g., SEQ ID NO: 80) can encode a modified MYB28 polypeptide (e.g., a modified MYB28 polypeptide having suppressed MYB28 polypeptide expression and/or reduced MYB28 polypeptide function). For example, a modified pennycress MYB28 coding sequence having a single base-pair deletion (e.g., SEQ ID NO:80) can encode a modified MYB28 polypeptide. In certain embodiments, a modified MYB28 polypeptide can include a truncation resulting from the introduction of a stop codon at codon position 20 within the MYB28 open reading frame (e.g., SEQ ID NO:19). A representative truncated pennycress MYB28 polypeptide is presented in SEQ ID NO:81. The aforementioned loss-of-function modifications in a MYB28 encoding gene or a transgene or genome rearrangement that suppresses expression of the MYB28 gene thus include loss-of-function modifications in a gene encoding an MYB28 allelic variant gene, or a transgene or genome rearrangement that suppresses expression of a MYB28 allelic variant gene.

A representative WT pennycress CYP83A1 coding region is presented in SEQ ID NO:92. Two protospacer locations and adjacent protospacer-adjacent motif (PAM) sites that can be targeted by, for example, CRISPR-SpCAS9, correspond to nucleotides 190-209 (protospacer) and 210-212 (PAM site).

In certain embodiments, a WT pennycress CYP83A1 coding sequence can have a sequence that deviates from the coding sequence set forth above (e.g., SEQ ID NO:92), and is referred to as an allelic variant sequence. In certain embodiments, a CYP83A1 coding sequence allelic variant can have at least 80, at least 85, at least 90, at least 95, at least 98, or at least 99 percent sequence identity to SEQ ID NO:92. A representative WT pennycress CYP83A1 polypeptide is presented in SEQ ID NO:94.

In certain embodiments, a WT pennycress CYP83A1 polypeptide can have a sequence that deviates from the polypeptide sequence set forth above (SEQ ID NO:94), and is referred to as an allelic variant sequence, provided the polypeptide maintains its wild-type function. For example, a CYP83A1 polypeptide can have at least 80, at least 85, at least 90, at least 95, at least 98, or at least 99 percent sequence identity to SEQ ID NO:94. A CYP83A1 polypeptide can have one or more (e.g., 2, 3, 4, 5, 6, 7, 8, 9, or 10) amino acid modifications (e.g., substitutions) relative to SEQ ID NO:94.

In certain embodiments, pennycress seed lots, plants, seeds, as well as the seed meals and compositions obtained therefrom, all having reduced sinigrin content, can include a loss-of-function modification in a CYP83A1 gene (e.g., in a CYP83A1 coding sequence) or a transgene or genome rearrangement that suppresses expression of the CYP83A1 gene. As used herein, a loss-of-function mutation in a CYP83A1 gene can be any modification that is effective to suppress CYP83A1 polypeptide expression or CYP83A1 polypeptide function. In certain embodiments, suppressed CYP83A1 polypeptide expression and/or CYP83A1 polypeptide function can comprise elimination or a reduction in such expression (i.e., can be complete or partial). Examples of genetic modifications include, without limitation, deletions, insertions, substitutions, translocations, inversions, duplications, and any combination thereof. The aforementioned loss-of-function modifications in a CYP83A1 encoding gene or a transgene or genome rearrangement that suppresses expression of the CYP83A1 gene thus include loss-of-function modifications in a gene encoding an CYP83A1 allelic variant gene, or a transgene or genome rearrangement that suppresses expression of an CYP83A1 allelic variant gene.

In certain embodiments, a WT pennycress AOP2 coding sequence can have a sequence that deviates from the coding sequence set forth above (e.g., SEQ ID NO:1 or 2), and is referred to as an allelic variant sequence. In certain embodiments, a AOP2 coding sequence allelic variant can have at least 80, at least 85, at least 90, at least 95, at least 98, or at least 99 percent sequence identity to SEQ ID NO:1 or 2. In certain embodiments, a WT pennycress AOP2 polypeptide can have a sequence that deviates from the polypeptide sequence set forth above (SEQ ID NO:3), and is referred to as an allelic variant sequence provided the polypeptide maintains its wild-type function. For example, a AOP2 polypeptide allelic variant can have at least 80, at least 85, at least 90, at least 95, at least 98, or at least 99 percent sequence identity to SEQ ID NO:3. An AOP2 polypeptide allelic variant can have one or more (e.g., 2, 3, 4, 5, 6, 7, 8, 9, or 10) amino acid modifications (e.g., substitutions) relative to SEQ ID NO:3.

In certain embodiments, pennycress seed lots, plants, seeds, as well as the seed meals and compositions obtained therefrom, all having reduced sinigrin content, can include a loss-of-function modification in a AOP2 encoding gene or a transgene or genome rearrangement that suppresses expression of the AOP2 gene. As used herein, a loss-of-function mutation in a AOP2 gene can be any modification that is effective to reduce AOP2 polypeptide expression or AOP2 polypeptide function. In certain embodiments, suppressed AOP2 polypeptide expression and/or AOP2 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in an AOP2 encoding gene or a transgene or genome rearrangement that suppresses expression of the AOP2 gene thus include loss-of-function modifications in a gene encoding an AOP2 allelic variant gene, or a transgene or genome rearrangement that suppresses expression of an AOP2 allelic variant gene.

In certain embodiments, a WT pennycress BCAT4 coding sequence can have a sequence that deviates from the coding sequence set forth above (e.g., SEQ ID NO:4), and is referred to as an allelic variant sequence. In certain embodiments, a BCAT4 coding sequence allelic variant can have at least 80, at least 85, at least 90, at least 95, at least 98, or at least 99 percent sequence identity to SEQ ID NO:4. In certain embodiments, a WT pennycress BCAT4 polypeptide can have a sequence that deviates from the polypeptide sequence set forth above (SEQ ID NO:6), and is referred to as an allelic variant sequence provided the polypeptide maintains its wild-type function. For example, a BCAT4 polypeptide allelic variant can have at least 80, at least 85, at least 90, at least 95, at least 98, or at least 99 percent sequence identity to SEQ ID NO:6. A BCAT4 polypeptide allelic variant can have one or more (e.g., 2, 3, 4, 5, 6, 7, 8, 9, or 10) amino acid modifications (e.g., substitutions) relative to SEQ ID NO:76.

In certain embodiments, pennycress seed lots, plants, seeds, as well as the seed meals and compositions obtained therefrom, all having reduced sinigrin content, can include a loss-of-function modification in a BCAT4 encoding gene or a transgene or genome rearrangement that suppresses expression of the BCAT4 gene. As used herein, a loss-of-function mutation in a BCAT4 gene can be any modification that is effective to reduce BCAT4 polypeptide expression or BCAT4 polypeptide function. In certain embodiments, suppressed BCAT4 polypeptide expression and/or BCAT4 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT4 encoding gene or a transgene or genome rearrangement that suppresses expression of the BCAT4 gene thus include loss-of-function modifications in a gene encoding a BCAT4 allelic variant gene, or a transgene or genome rearrangement that suppresses expression of a BCAT4 allelic variant gene.

In certain embodiments, a WT pennycress BCAT6 coding sequence can have a sequence that deviates from the coding sequence set forth above (e.g., SEQ ID NO:7), and is referred to as an allelic variant sequence. In certain embodiments, a BCAT6 coding sequence allelic variant can have at least 80, at least 85, at least 90, at least 95, at least 98, or at least 99 percent sequence identity to SEQ ID NO:7. In certain embodiments, a WT pennycress BCAT6 polypeptide can have a sequence that deviates from the polypeptide sequence set forth above (SEQ ID NO:9), and is referred to as an allelic variant sequence provided the polypeptide maintains its wild-type function. For example, a BCAT6 polypeptide allelic variant can have at least 80, at least 85, at least 90, at least 95, at least 98, or at least 99 percent sequence identity to SEQ ID NO:9. A BCAT6 polypeptide allelic variant can have one or more (e.g., 2, 3, 4, 5, 6, 7, 8, 9, or 10) amino acid modifications (e.g., substitutions) relative to SEQ ID NO:9.

In certain embodiments, pennycress seed lots, plants, seeds, as well as the seed meals and compositions obtained therefrom, all having reduced sinigrin content, can include a loss-of-function modification in a BCAT6 encoding gene or a transgene or genome rearrangement that suppresses expression of the BCAT6 gene. As used herein, a loss-of-function mutation in a BCAT6 gene can be any modification that is effective to reduce BCAT6 polypeptide expression or BCAT6 polypeptide function. In certain embodiments, suppressed BCAT6 polypeptide expression and/or BCAT6 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT6 encoding gene or a transgene or genome rearrangement that suppresses expression of the BCAT6 gene thus include loss-of-function modifications in a gene encoding a BCAT6 allelic variant gene, or a transgene or genome rearrangement that suppresses expression of a BCAT6 allelic variant gene.

In certain embodiments, pennycress seed lots, plants, seeds, as well as the seed meals and compositions obtained therefrom, all having reduced sinigrin content, can include a loss-of-function modification in a CYP79F1 encoding gene or a transgene or genome rearrangement that suppresses expression of the CYP79F1 gene. As used herein, a loss-of-function mutation in a CYP79F1 gene can be any modification that is effective to reduce CYP79F1 polypeptide expression or CYP79F1 polypeptide function. In certain embodiments, suppressed CYP79F1 polypeptide expression and/or CYP79F1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79F1 coding sequence can have a sequence that deviates from the coding sequence set forth above (e.g., SEQ ID NO:10), and is referred to as an allelic variant sequence. In certain embodiments, a CYP79F1 coding sequence allelic variant can have at least 80, at least 85, at least 90, at least 95, at least 98, or at least 99 percent sequence identity to SEQ ID NO:10. In certain embodiments, a WT pennycress CYP79F1 polypeptide can have a sequence that deviates from the polypeptide sequence set forth above (SEQ ID NO:46), and is referred to as an allelic variant sequence provided the polypeptide maintains its wild-type function. In certain embodiments, a CYP79F1 polypeptide allelic variant can have at least 80, at least 85, at least 90, at least 95, at least 98, or at least 99 percent sequence identity to SEQ ID NO:12. A CYP79F1 polypeptide allelic variant can have one or more (e.g., 2, 3, 4, 5, 6, 7, 8, 9, or 10) amino acid modifications (e.g., substitutions) relative to SEQ ID NO:12. Loss-of-function modifications in a CYP79F1 encoding gene or a transgene or genome rearrangement that suppresses expression of the CYP79F1 gene thus include loss-of-function modifications in a gene encoding a CYP79F1 allelic variant gene, or a transgene or genome rearrangement that suppresses expression of a CYP79F1 allelic variant gene.

In certain embodiments, pennycress seed lots, plants, seeds, as well as the seed meals and compositions obtained therefrom, all having reduced sinigrin content, can include a loss-of-function modification in a GTR1 encoding gene or a transgene or genome rearrangement that suppresses expression of the GTR1 gene. As used herein, a loss-of-function mutation in a GTR1 gene can be any modification that is effective to reduce GTR1 polypeptide expression or GTR1 polypeptide function. In certain embodiments, suppressed GTR1 polypeptide expression and/or GTR1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR1 coding sequence can have a sequence that deviates from the coding sequence set forth above (e.g., SEQ ID NO:13), and is referred to as an allelic variant sequence. In certain embodiments, a GTR1 coding sequence allelic variant can have at least 80, at least 85, at least 90, at least 95, at least 98, or at least 99 percent sequence identity to SEQ ID NO:13. In certain embodiments, a WT pennycress GTR1 polypeptide can have a sequence that deviates from the polypeptide sequence set forth above (SEQ ID NO:15), and is referred to as an allelic variant sequence provided the polypeptide maintains its wild-type function. In certain embodiments, a GTR1 polypeptide allelic variant can have at least 80, at least 85, at least 90, at least 95, at least 98, or at least 99 percent sequence identity to SEQ ID NO:15. A GTR1 polypeptide allelic variant can have one or more (e.g., 2, 3, 4, 5, 6, 7, 8, 9, or 10) amino acid modifications (e.g., substitutions) relative to SEQ ID NO:15. The aforementioned loss-of-function modifications in a GTR1 encoding gene or a transgene or genome rearrangement that suppresses expression of the GTR1 gene thus include loss-of-function modifications in a gene encoding a GTR1 allelic variant gene, or a transgene or genome rearrangement that suppresses expression of a GTR1 allelic variant gene.

In certain embodiments, pennycress seed lots, pennycress seed lots, plants, seeds, as well as the seed meals and compositions obtained therefrom, all having reduced sinigrin content can include a complete or partial loss-of-function modification in a GTR2 encoding gene or a transgene or genome rearrangement that suppresses expression of the GTR2 gene. As used herein, a loss-of-function mutation in a GTR2 gene can be any modification that is effective to reduce GTR2 polypeptide expression or GTR2 polypeptide function. In certain embodiments, suppressed GTR2 polypeptide expression and/or GTR2 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR2 coding sequence can have a sequence that deviates from the coding sequence set forth above (e.g., SEQ ID NO:16), and is referred to as an allelic variant sequence. In certain embodiments, a GTR2 coding sequence allelic variant can have at least 80, at least 85, at least 90, at least 95, at least 98, or at least 99 percent sequence identity to SEQ ID NO:16. In certain embodiments, a WT pennycress GTR2 polypeptide can have a sequence that deviates from the polypeptide sequence set forth above (SEQ ID NO:17), and is referred to as an allelic variant sequence provided the polypeptide maintains its wild-type function. In certain embodiments, a GTR2 polypeptide allelic variant can have at least 80, at least 85, at least 90, at least 95, at least 98, or at least 99 percent sequence identity to SEQ ID NO:17. A GTR2 polypeptide allelic variant can have one or more (e.g., 2, 3, 4, 5, 6, 7, 8, 9, or 10) amino acid modifications (e.g., substitutions) relative to SEQ ID NO:17. The aforementioned loss-of-function modifications in a GTR2 encoding gene or a transgene or genome rearrangement that suppresses expression of the GTR2 gene thus include loss-of-function modifications in a gene encoding a GTR2 allelic variant gene, or a transgene or genome rearrangement that suppresses expression of a GTR2 allelic variant gene.

In certain embodiments, pennycress seed lots, plants, seeds, as well as the seed meals and compositions obtained therefrom, all having reduced sinigrin content can include a complete or partial loss-of-function modification in a TFP encoding gene or a transgene or genome rearrangement that suppresses expression of the TFP gene. As used herein, a loss-of-function mutation in a TFP gene can be any modification that is effective to reduce TFP polypeptide expression or TFP polypeptide function. In certain embodiments, suppressed TFP polypeptide expression and/or TFP polypeptide function can comprise elimination or a reduction in such expression or function (i.e., can be complete or partial).

Examples of genetic modifications include, without limitation, deletions, insertions, substitutions, translocations, inversions, duplications, and any combination thereof.

In certain embodiments, a WT pennycress TFP coding sequence can have a sequence that deviates from the coding sequence set forth above (e.g., SEQ ID NO:28), and is referred to as an allelic variant sequence. In certain embodiments, a TFP coding sequence allelic variant can have at least 80, at least 85, at least 90, at least 95, at least 98, or at least 99 percent sequence identity to SEQ ID NO:28. In certain embodiments, a WT pennycress TFP polypeptide can have a sequence that deviates from the polypeptide sequence set forth above (SEQ ID NO:30), and is referred to as an allelic variant sequence provided the polypeptide maintains its wild-type function. In certain embodiments, a TFP polypeptide allelic variant can have at least 80, at least 85, at least 90, at least 95, at least 98, or at least 99 percent sequence identity to SEQ ID NO:30. A TFP polypeptide allelic variant can have one or more (e.g., 2, 3, 4, 5, 6, 7, 8, 9, or 10) amino acid modifications (e.g., substitutions) relative to SEQ ID NO:30. The aforementioned loss-of-function modifications in a TFP encoding gene or a transgene or genome rearrangement that suppresses expression of the TFP gene thus include loss-of-function modifications in a gene encoding a TFP allelic variant gene, or a transgene or genome rearrangement that suppresses expression of a TFP allelic variant gene.

In certain embodiments, pennycress seed lots, plants, seeds, as well as the seed meals and compositions obtained therefrom, all having reduced sinigrin content, can include a loss-of-function modification in a BHLH05 encoding gene or a transgene or genome rearrangement that suppresses expression of the BHLH05 gene. As used herein, a loss-of-function mutation in a BHLH05 gene can be any modification that is effective to reduce BHLH05 polypeptide expression or BHLH05 polypeptide function. In certain embodiments, suppressed BHLH05 polypeptide expression and/or BHLH05 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress BHLH05 coding sequence can have a sequence that deviates from the coding sequence set forth above (e.g., SEQ ID NO:159 or 160), and is referred to as an allelic variant sequence. In certain embodiments, a BHLH05 coding sequence allelic variant can have at least 80, at least 85, at least 90, at least 95, at least 98, or at least 99 percent sequence identity to SEQ ID NO:159 or 160. In certain embodiments, a WT pennycress BHLH05 polypeptide can have a sequence that deviates from the polypeptide sequence set forth above (SEQ ID NO:161), and is referred to as an allelic variant sequence provided the polypeptide maintains its wild-type function. For example, a BHLH05 polypeptide allelic variant can have at least 80, at least 85, at least 90, at least 95, at least 98, or at least 99 percent sequence identity to SEQ ID NO: 161. An BHLH05 polypeptide allelic variant can have one or more (e.g., 2, 3, 4, 5, 6, 7, 8, 9, or 10) amino acid modifications (e.g., substitutions) relative to SEQ ID NO:161. The aforementioned loss-of-function modifications in a BHLH05 encoding gene or a transgene or genome rearrangement that suppresses expression of the BHLH05 gene thus include loss-of-function modifications in a gene encoding a BHLH05 allelic variant gene, or a transgene or genome rearrangement that suppresses expression of a BHLH05 allelic variant gene.

In certain embodiments, pennycress seed lots, plants, seeds, as well as the seed meals and compositions obtained therefrom, all having reduced sinigrin content, can include a loss-of-function modification in a IMD1 encoding gene or a transgene or genome rearrangement that suppresses expression of the IMD1 gene. As used herein, a loss-of-function mutation in a IMD1 gene can be any modification that is effective to reduce IMD1 polypeptide expression or IMD1 polypeptide function. In certain embodiments, suppressed IMD1 polypeptide expression and/or IMD1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress IMD1 coding sequence can have a sequence that deviates from the coding sequence set forth above (e.g., SEQ ID NO: 162 or 163), and is referred to as an allelic variant sequence. In certain embodiments, a IMD1 coding sequence allelic variant can have at least 80, at least 85, at least 90, at least 95, at least 98, or at least 99 percent sequence identity to SEQ ID NO: 162 or 163. In certain embodiments, a WT pennycress IMD1 polypeptide can have a sequence that deviates from the polypeptide sequence set forth above (SEQ ID NO:164), and is referred to as an allelic variant sequence provided the polypeptide maintains its wild-type function. For example, a IMD1 polypeptide allelic variant can have at least 80, at least 85, at least 90, at least 95, at least 98, or at least 99 percent sequence identity to SEQ ID NO: 164. An IMD1 polypeptide allelic variant can have one or more (e.g., 2, 3, 4, 5, 6, 7, 8, 9, or 10) amino acid modifications (e.g., substitutions) relative to SEQ ID NO:164. The aforementioned loss-of-function modifications in a IMD1 encoding gene or a transgene or genome rearrangement that suppresses expression of the IMD1 gene thus include loss-of-function modifications in a gene encoding a IMD1 allelic variant gene, or a transgene or genome rearrangement that suppresses expression of a IMD1 allelic variant gene.

In certain embodiments, pennycress seed lots, plants, seeds, as well as the seed meals and compositions obtained therefrom, all having reduced sinigrin content, can include a loss-of-function modification in a CYP79B3 encoding gene or a transgene or genome rearrangement that suppresses expression of the CYP79B3 gene. As used herein, a loss-of-function mutation in a CYP79B3 gene can be any modification that is effective to reduce CYP79B3 polypeptide expression or CYP79B3 polypeptide function. In certain embodiments, suppressed CYP79B3 polypeptide expression and/or CYP79B3 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79B3 coding sequence can have a sequence that deviates from the coding sequence set forth above (e.g., SEQ ID NO: 165 or 166), and is referred to as an allelic variant sequence. In certain embodiments, a CYP79B3 coding sequence allelic variant can have at least 80, at least 85, at least 90, at least 95, at least 98, or at least 99 percent sequence identity to SEQ ID NO: 165 or 166. In certain embodiments, a WT pennycress CYP79B3 polypeptide can have a sequence that deviates from the polypeptide sequence set forth above (SEQ ID NO:167), and is referred to as an allelic variant sequence provided the polypeptide maintains its wild-type function. For example, a CYP79B3 polypeptide allelic variant can have at least 80, at least 85, at least 90, at least 95, at least 98, or at least 99 percent sequence identity to SEQ ID NO: 167. A CYP79B3 polypeptide allelic variant can have one or more (e.g., 2, 3, 4, 5, 6, 7, 8, 9, or 10) amino acid modifications (e.g., substitutions) relative to SEQ ID NO:167. The aforementioned loss-of-function modifications in a CYP79B3 encoding gene or a transgene or genome rearrangement that suppresses expression of the CYP79B3 gene thus include loss-of-function modifications in a gene encoding a CYP79B3 allelic variant gene, or a transgene or genome rearrangement that suppresses expression of a CYP79B3 allelic variant gene.

In certain embodiments, pennycress seed lots, plants, seeds, as well as the seed meals and compositions obtained therefrom, all having reduced sinigrin content, can include a loss-of-function modification in a MAM1 encoding gene or a transgene or genome rearrangement that suppresses expression of the MAM1 gene. As used herein, a loss-of-function mutation in a MAM1 gene can be any modification that is effective to reduce MAM1 polypeptide expression or MAM1 polypeptide function. In certain embodiments, suppressed MAM1 polypeptide expression and/or MAM1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress MAM1 coding sequence can have a sequence that deviates from the coding sequence set forth above (e.g., SEQ ID NO:168 or 169), and is referred to as an allelic variant sequence. In certain embodiments, a MAM1 coding sequence allelic variant can have at least 80, at least 85, at least 90, at least 95, at least 98, or at least 99 percent sequence identity to SEQ ID NO: 168 or 169. In certain embodiments, a WT pennycress MAM1 polypeptide can have a sequence that deviates from the polypeptide sequence set forth above (SEQ ID NO:170), and is referred to as an allelic variant sequence provided the polypeptide maintains its wild-type function. For example, a MAM1 polypeptide allelic variant can have at least 80, at least 85, at least 90, at least 95, at least 98, or at least 99 percent sequence identity to SEQ ID NO: 170. A MAM1 polypeptide allelic variant can have one or more (e.g., 2, 3, 4, 5, 6, 7, 8, 9, or 10) amino acid modifications (e.g., substitutions) relative to SEQ ID NO:170. The aforementioned loss-of-function modifications in a MAM1 encoding gene or a transgene or genome rearrangement that suppresses expression of the MAM1 gene thus include loss-of-function modifications in a gene encoding a MAM1 allelic variant gene, or a transgene or genome rearrangement that suppresses expression of a MAM1 allelic variant gene.

In certain embodiments, pennycress seed lots, plants, seeds, as well as the seed meals and compositions obtained therefrom, all having reduced sinigrin content, can include a loss-of-function modification in a FMO-GS-Ox1 encoding gene or a transgene or genome rearrangement that suppresses expression of the FMO-GS-Ox1 gene. As used herein, a loss-of-function mutation in a FMO-GS-Ox1 gene can be any modification that is effective to reduce FMO-GS-Ox1 polypeptide expression or FMO-GS-Ox1 polypeptide function. In certain embodiments, suppressed FMO-GS-Ox1 polypeptide expression and/or FMO-GS-Ox1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress FMO-GS-Ox1 coding sequence can have a sequence that deviates from the coding sequence set forth above (e.g., SEQ ID NO: 171 or 172), and is referred to as an allelic variant sequence. In certain embodiments, a FMO-GS-Ox1 coding sequence allelic variant can have at least 80, at least 85, at least 90, at least 95, at least 98, or at least 99 percent sequence identity to SEQ ID NO: 171 or 172. In certain embodiments, a WT pennycress FMO-GS-Ox1 polypeptide can have a sequence that deviates from the polypeptide sequence set forth above (SEQ ID NO:173), and is referred to as an allelic variant sequence provided the polypeptide maintains its wild-type function. For example, a FMO-GS-Ox1 polypeptide allelic variant can have at least 80, at least 85, at least 90, at least 95, at least 98, or at least 99 percent sequence identity to SEQ ID NO: 173. An FMO-GS-Ox1 polypeptide allelic variant can have one or more (e.g., 2, 3, 4, 5, 6, 7, 8, 9, or 10) amino acid modifications (e.g., substitutions) relative to SEQ ID NO:173. The aforementioned loss-of-function modifications in a FMO-GS-Ox1 encoding gene or a transgene or genome rearrangement that suppresses expression of the FMO-GS-Ox1 gene thus include loss-of-function modifications in a gene encoding a FMO-GS-Ox1 allelic variant gene, or a transgene or genome rearrangement that suppresses expression of a FMO-GS-Ox1 allelic variant gene.

In certain embodiments, pennycress seed lots, plants, seeds, as well as the seed meals and compositions obtained therefrom, all having reduced sinigrin content, can include a loss-of-function modification in a UGT74B1 encoding gene or a transgene or genome rearrangement that suppresses expression of the UGT74B1 gene. As used herein, a loss-of-function mutation in a UGT74B1 gene can be any modification that is effective to reduce UGT74B1 polypeptide expression or UGT74B1 polypeptide function. In certain embodiments, suppressed UGT74B1 polypeptide expression and/or UGT74B1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress UGT74B1 coding sequence can have a sequence that deviates from the coding sequence set forth above (e.g., SEQ ID NO: 174 or 175), and is referred to as an allelic variant sequence. In certain embodiments, a UGT74B1 coding sequence allelic variant can have at least 80, at least 85, at least 90, at least 95, at least 98, or at least 99 percent sequence identity to SEQ ID NO: 174 or 175. In certain embodiments, a WT pennycress UGT74B1 polypeptide can have a sequence that deviates from the polypeptide sequence set forth above (SEQ ID NO:176), and is referred to as an allelic variant sequence provided the polypeptide maintains its wild-type function. For example, a UGT74B1 polypeptide allelic variant can have at least 80, at least 85, at least 90, at least 95, at least 98, or at least 99 percent sequence identity to SEQ ID NO: 176. An UGT74B1 polypeptide allelic variant can have one or more (e.g., 2, 3, 4, 5, 6, 7, 8, 9, or 10) amino acid modifications (e.g., substitutions) relative to SEQ ID NO:176. The aforementioned loss-of-function modifications in a UGT74B1 encoding gene or a transgene or genome rearrangement that suppresses expression of the UGT74B1 gene thus include loss-of-function modifications in a gene encoding a UGT74B1 allelic variant gene, or a transgene or genome rearrangement that suppresses expression of a UGT74B1 allelic variant gene.

In certain embodiments, the pennycress seeds, seed lots, seed meals (defatted and non-defatted), compositions comprising those seed meals, and pennycress plants provided herein can comprise loss-of-function mutation(s), transgene (s), and/or genomic rearrangement(s) that suppress expression and/or activity of at least two of any of the aforementioned endogenous pennycress genes or allelic variants thereof (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) or encoded polypeptides). In one embodiment, the loss-of-function mutation(s), genomic rearrangement(s), and/or transgene(s) can suppress expression of both a GTR1 gene (e.g., of SEQ ID NO:15 or an allelic variant thereof) and a GTR2 gene (e.g., of SEQ ID NO:17 or an allelic variant thereof). In one embodiment, the loss-of-function mutation(s), genomic rearrangement(s), and/or transgene(s) can suppress expression and/or activity of both a MYB28 gene (e.g., of SEQ ID NO:21 or an allelic variant thereof) and a MYB29 gene (e.g., of SEQ ID NO:24 or an allelic variant thereof). In one embodiment, the loss-of-function mutation(s), transgene(s), and/or genomic rearrangement(s) can suppress expression and/or activity of both a GTR1 gene (e.g., of SEQ ID NO:15 or an allelic variant thereof) and a MYB29 gene (e.g., of SEQ ID NO:24 or an allelic variant thereof). In certain embodiments, suppression of gene expression and/or activity provided by the loss-of-function mutation(s), transgene(s), and/or genomic rearrangement(s) is partial. In certain embodiments, such partial suppression in the any of the aforementioned embodiments can comprise a reduction of at least 20%, 30%, 40%, 50%, 60%, 70%, 75%, 80%, 85%, 90%, or 95% of activity and/or transcript levels of the endogenous pennycress gene (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) in the plant or a part of the plant (e.g., seed) comprising the loss-of-function mutation(s), transgene(s), and/or genomic rearrangement(s) in comparison to the activity and/or transcript levels in a wild-type control plant lacking the loss-of-function mutation (s), transgene(s), and/or genomic rearrangement(s).

In certain embodiments, a genome editing system such as a CRISPR-Cas9 system can be used to introduce one or more loss-of-function mutations into genes such as the glucosinolate biosynthesis, transporters and related regulatory genes (i.e., transcription factors) provided herewith in Table 1 and the sequence listing to obtain pennycress plants, seeds, seed lots, and compositions with reduced seed sinigrin content. For example, a CRISPR-Cas9 vector can include at least one guide sequence specific to a pennycress GTR2 sequence (see, e.g., SEQ ID NO:16) and/or at least one guide sequence specific to a pennycress GTR2 sequence (see, e.g., SEQ ID NO:17). A Cas9 enzyme will bind to and cleave within the gene when the target site is followed by a PAM sequence. For example, the canonical SpCAS9 PAM site is the sequence 5'-NGG-3', where N is any nucleotide followed by two guanine (G) nucleotides. The Cas9 component of a CRISPR-Cas9 system designed to introduce one or more loss-of-function modifications described herein can be any appropriate Cas9. In certain embodiments, the Cas9 of a CRISPR-Cas9 system described herein can be a *Streptococcus pyogenes* Cas9 (SpCas9). One example of a SpCas9 is described in Fauser et al., 2014.

The LOF mutations in any of the genes of coding sequences of Table 1 can be introduced by a variety of methods. Methods for introduction of the LOF mutations include, but are not limited to, traditional mutagenesis (e.g., Ethyl Methane Sulfonate (EMS), fast neutrons (FN), or gamma rays), TILLING, meganucleases, zinc finger nucleases, transcription activator-like effector nucleases, clustered regularly interspaced short palindromic repeat (CRISPR)-associated nuclease (e.g., Cas9, Cpf1, Cms1, *S. aureus* Cas9 variants, eSpCas9), targetrons, and the like. Various tools that can be used to introduce mutations into genes have been disclosed in Guha et al., 2017. Methods for modifying genomes by use of Cpf1 or Csm1 nucleases are disclosed in US Patent Application Publication 20180148735, which is incorporated herein by reference in its entirety, can be adapted for introduction of the LOF mutations disclosed herein. Methods for modifying genomes by use of CRISPR-CAS systems are disclosed in US Patent Application Publication 20180179547, which is incorporated herein by reference in its entirety, can be adapted for introduction of the LOF mutations disclosed herein. The genome editing reagents described herein can be introduced into a pennycress plant by any appropriate method. In certain embodiments, nucleic acids encoding the genome editing reagents can be introduced into a plant cell using *Agrobacterium*- or *Ensifer* mediated transformation, particle bombardment, liposome delivery, nanoparticle delivery, electroporation, polyethylene glycol (PEG) transformation, or any other method suitable for introducing a nucleic acid into a plant cell. In certain embodiments, the Site-Specific Nuclease (SSN) or other expressed gene editing reagents can be delivered as RNAs or as proteins to a plant cell and the RT, if one is used, can be delivered as DNA.

Also provided herein are defatted pennycress seed meal with reduced sinigrin content in comparison to defatted pennycress seed meal obtained from wild-type pennycress seed lots. Defatted-pennycress seed meal is a product obtained from high-pressure crushing of seed, or from a pre-press solvent extraction process, which removes oil from the whole seed. Solvents used in such extractions include, but are not limited to, hexane or mixed hexanes. The meal is the material that remains after most of the oil has been removed. The typical range of sinigrin in meal made from wild-type pennycress seed is greater than 190 micromoles sinigrin per gram meal by dry weight (μmol/gm dw). To be useful as a high protein animal feed, and competitive with other protein feedstuffs, the level of sinigrin level in meal should be less than 30 micromoles sinigrin per gram by dry weight of the meal. In certain embodiments, defatted pennycress seed meal having a sinigrin content of less than 30, 28, 25, or 15 μmol sinigrin/gm dw are provided. In certain embodiments, defatted pennycress seed meal having a sinigrin content of about 1, 2.5, 5, or 10 to about 15, 16, 18, 20, 25, 28, or 30 μmol sinigrin/gm dw is provided herein. Compositions comprising such defatted pennycress seed meal are also provided herein. Such seed meal or compositions can comprise polynucleotides encoding any of the aforementioned LOF mutations. Such seed meal or compositions can also comprise any marker that is characteristic of the pennycress mutant E3 196, E5 444P1, E5 356P5, I87113, E5 543, or I87207 germplasm. In certain embodiments, such biomarkers include a polynucleotide comprising at least one loss-of-function mutation in pennycress mutant E3 196, E5 444P1 E5 356P5, I87113, E5 543, or I87207. Mutations in the pennycress mutant E3 196, E5 444P1, E5 356P5, I87113, E5 543, or I87207 can be identified by sequencing the genomic DNA or pertinent genes (e.g., genes of Table 1) and comparing those sequences to the corresponding sequences of the parent pennycress lines from which they were obtained.

Non-defatted pennycress seed meal having less sinigrin than non-defatted control pennycress seed meal obtained from wild-type pennycress seed is provided herein. In certain embodiments, the sinigrin content of non-defatted pennycress seed meal and compositions comprising the same that are provided herein is reduced from about 1.25-, 1.5-, 2-, or 3-fold to about 4-, 5-, 6-, 7-, 10-, 20-, 40-, 50-, 60-, 70-, 80-, 100-, 120-, 140-, 160-, 180-, or 200- fold in comparison to control non-defatted pennycress seed meal and compositions comprising the same obtained from control wild-type pennycress seeds. In certain embodiments, the non-defatted pennycress seed meal is obtained from pennycress seeds that have been crushed, ground, macerated, expelled, extruded, or any combination thereof. Typically, the level of sinigrin in wild-type pennycress seed and non-defatted seed meal obtained therefrom varies from about 70 to about 150 μmol sinigrin/gm dw. To be useful as a high protein animal feed, and competitive with other protein feedstuffs, the sinigrin level in non-defatted meal should be less than 30 μmol sinigrin/gm dw of the meal. In certain embodiments, non-defatted pennycress seed meal having a sinigrin content of less than 30, 28, 25, 16, or 15 μmol sinigrin/gm dw are provided herein. In certain embodiments, non-defatted pennycress seed meal having a sinigrin content of about less than 15, 14, or 12 μmol sinigrin/gm dw is provided herein. In certain embodiments, non-defatted pennycress seed meal having a sinigrin content of 1, 2.5, 5, or 10 to about 15, 16, 18, 20, 25, 28, or 30 μmol sinigrin/gm dw are provided herein. Compositions comprising such non-defatted pennycress seed meal are also provided herein. Such seed meal or compositions can comprise polynucleotides encoding any of the aforementioned LOF mutations.

The disclosure will be further described in the following examples, which do not limit the scope of the disclosure described in the claims.

EXAMPLES

Example 1: Generation of Transgenic Pennycress Lines Harboring the CRISPR-Cas9 or CRISPR-Cpf1 or CRISPR-Cms1 Constructs Materials and Methods Construction of the *Thlaspi arvense* (Pennycress) AOP2, BCAT4, BCAT6, CYP79F1, CYP83A1, GTR1, GTR2, MYB28 (HAG1), HAG3 (MYB29), MYB76 and TFP Gene-Specific CRISPR Genome-Editing Vectors The constructs and cloning procedures for generation of the *Thlaspi arvense* (pennycress) AOP2, BCAT4, BCAT6, CYP79F1, CYP83A1, GTR1, GTR2, MYB28 (HAG1), HAG3 (MYB29), MYB76 and TFP-specific CRISPR-SpCas9 and CRISPR-SaCas9 constructs were adapted in part from the following two publications that describe general procedures for use of SaCas9 in plants: Steinert J, et. al. (2015) and Fauser F, et. al. (2014).

The plant selectable markers (formerly NPT) in the original pDe-SpCas9 and pDe-SaCas9 binary vectors were swapped for hygromycin resistance (Hygromycin phosphotransferase, or HPT) or fluorescent protein marker (FP) gene.

Vector Transformation into *Agrobacterium*

Figure 6:
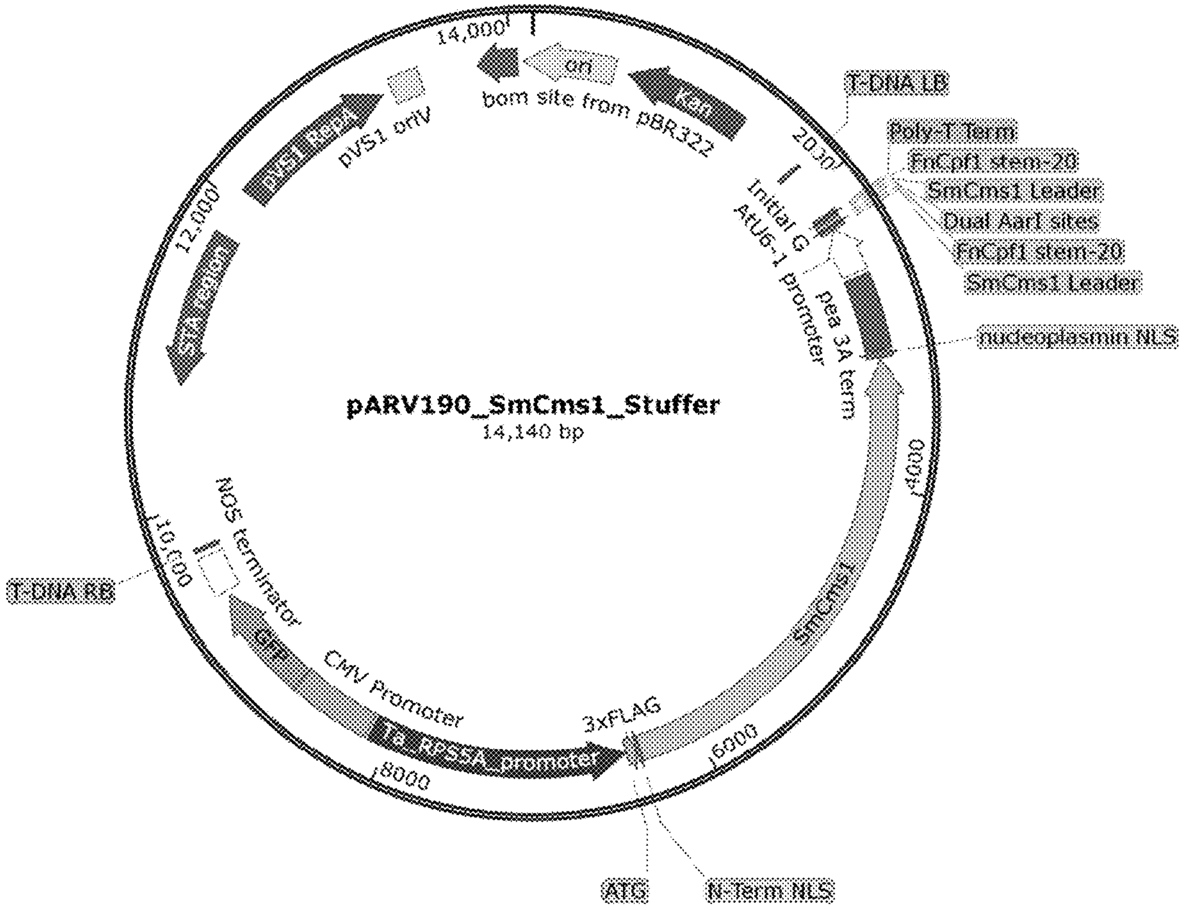
FIG. 6 illustrates pARV190, *Agrobacterium* CRISPR-SmCms1 base vector for editing plant genome. gRNA cassette stuffers are inserted at the dual AarI site, replacing a small fragment of the vector with synthetic gRNA cassette.

The pDe-SpCas9_Hyg, pDe-SaCas9_Hyg, pARV145, containing the *Streptococcus pyogenes* Cas9 (SpCas9) and the *Staphylococcus aureus* Cas9 (SaCas9) cassettes, or related vectors represented in FIGS. 1-7, with the corresponding sequence-specific protospacers were transformed into *Agrobacterium tumefaciens* strain GV3101 using the freeze/thaw method (Holsters et al, 1978).

The transformation product was plated on 1% agar Luria Broth (LB) plates with gentamycin (50 μg/ml) rifampicin (50 μg/ml) and spectinomycin (75 μgimp. Single colonies were selected after two days of growth at 28° C.

Plant Transformation—Pennycress Floral Dip

Day One:

5 mL of LB+5 uL with appropriate antibiotics (Rifampin (50), Spectinomycin (75), and/or Gentamycin (50)) were inoculated with *Agrobacterium*. The cultures were allowed to grow, with shaking, overnight at 28° C.

Day Two (Early Morning):

25 mL of Luria Broth+25 uL appropriate antibiotics (Rifampin (50), Spectinomycin (75), and/or Gentamycin (50)) were inoculated with the initial culture from day one. The cultures were allowed to grow, with shaking, overnight at 28° C.

Day Two (Late Afternoon):

250 mL of Luria Broth+250 uL appropriate antibiotic (Rifampin (50), Spectinomycin (75), and/or Gentamycin (50)) were inoculated with 25 mL culture. The cultures were allowed to grow, with shaking, overnight at 28° C.

Day Three:

When the culture had grown to an $OD_{600}$ of ~1 (or looks thick and silky), the culture was decanted into large centrifuge tubes (all evenly weighted with analytical balance), and spun at 3,500 RPM at room temperature for 10 minutes to pellet cells. The supernatant was decanted off. The pelleted cells were resuspended in a solution of 5% sucrose and 0.02% Silwet L-77. The suspension was poured into clean beakers and placed in a vacuum chamber.

Newly flowering inflorescences of pennycress were fully submerged into the beakers, and subjected to a vacuum pressure of ~30 inches mercury (~14.7 psi) for 5 to 10 minutes.

After racemes of pennycress plants (W0011 variety; these plants were 5 generations removed from seeds) were dipped, they were covered loosely with Saran wrap to maintain humidity and kept in the dark overnight before being uncovered and placed back in the environmental growth chamber.

Screening Transgenic Plants and Growth Condition

Pennycress seeds were surface sterilized by first rinsing in 70% ethanol then incubating 10 minutes in a 30% bleach, 0.05% SDS solution before being rinsed two times with sterile water and plated on selective plates (0.8% agar/one half-strength Murashige and Skoog salts with hygromycin B selection (40 U/ml) or glufosinate (18 μg/ml). Plates were wrapped in parafilm and kept in an environmental growth chamber at 21° C., 16:8 day/night for 8 days until antibiotic or herbicide selection was apparent.

Surviving hygromycin or glufosinate-resistant $T_1$-generation seedlings were transplanted into autoclaved Redi-Earth soil mix and grown in an environmental growth chamber set to 16-hour days/8-hour nights at 21° C. and 50% humidity. $T_2$-generation seeds were planted, and ~1.5 mg of leaf tissue from each $T_2$-generation plant was harvested with a 3-mm hole punch, then processed using the Thermo Scientific™ Phire™ Plant Direct PCR Kit (Catalog #F130WH) as per manufacturer's instructions. PCR (20 μl volume) was performed.

Example 2: Generation and Characterization of EMS-Mutagenized Low Sinigrin Mutant Lines E3 196, E5 444P1, I87113 and I87207

Mutants carrying domestication enabling low glucosinolate trait were isolated from two mutant populations independently created using chemical mutagenesis (ethyl methanesulfonate, EMS) protocol essentially as described in the Materials and Methods section below.

In other embodiments, pennycress plants exhibiting domestication enabling traits such as reduced seed glucosinolate content and loss-of-function mutations in domestication genes can be identified in mutant populations created using fast neutrons (FN), gamma rays (γ rays) or other methods of introducing genetic diversity into genomic DNA.

Materials and Methods

Solutions:

| | | |
|---|---|---|
| A) | 0.2M sodium phosphate monobasic ($NaH_2PO_4*H_2O$) | 6.9 g/250 mL |
| B) | 0.2M sodium phosphate dibasic ($NaH_2PO_4$ anhydrous) | 7.1 g/250 mL |

For 50 mL of 0.1 M sodium phosphate buffer at pH 7:

| | |
|---|---|
| 9.75 mL | A |
| 15.25 mL | B |
| 25.0 mL | $dH_2O$ |

0.2% EMS in buffer:

20 mL 0.1M Sodium Phosphate Buffer, pH 7

40 μL EMS liquid (Sigma #M0880-5G)

0.1 M sodium thiosulfate at pH 7.3:

12.4 g sodium thiosulfate in 500 mL

Primary Seed Surface Sterilization

In the Set #1 experiments, wild-type pennycress (*Thlaspi arvense*) seeds (W0011 ecotype) were surface sterilized for 10 minutes in a 30% bleach, 0.05% SDS solution before being rinsed 3× with sterile water. Sterilized seeds were immediately subjected to EMS treatment.

Ethyl Methane Sulfonate (EMS) Treatment of Pennycress Seeds

In the Set #1 experiments, sterilized pennycress seeds (41 g) were agitated in distilled water overnight. Four 250 mL Erlenmeyer flasks with 10 g seed each, and 1 g in a separate small flask as a control, were agitated. The water was decanted.

25 mLs of 0.2% EMS in 0.1M sodium phosphate buffer (pH 7) was added. The control received only phosphate buffer with no EMS. The flasks were shaken in fume hood for 18 hours. The EMS solution was decanted off into an EMS waste bottle.

To rinse the seeds, 25 ml of $dH_2O$ was added to each flask, and the flasks were shaken for 20 minutes. The rinse water was decanted into the EMS waste bottle.

To deactivate the EMS, seeds were washed for 20 minutes in 0.1M sodium thiosulfate (pH 7.3). The sodium thiosulfate solution was decanted into the EMS waste bottle.

The seeds were rinsed 4 times with $dH_2O$ for 15 minutes.

The seeds were suspended in 0.1% agarose, and germinated directly in autoclaved Redi-Earth soil mix at a density of approximately 10 seeds per 4-inch pot.

In the Set #2 experiments, 42 grams of seeds derived from pennycress accession MN106 were collected as described elsewhere (Dorn et al., 2013), and were treated with 180 ml 0.2% ethyl methanesulfonate (EMS) in a chemical flow hood. The solution and seeds were kept mixed on a rotating platform for 14 hours at room temperature. The seeds were thereafter extensively rinsed with distilled water to remove all traces of the EMS. The seeds were then dried for 24 hours on filter paper in a chemical flow hood. These seeds were considered to be the progenitors of the M1-generation of plants.

Plant Growth Conditions

In the Set #1 experiments, EMS-treated pennycress seeds were germinated and grown in an environmental growth chamber at 21° C., 16:8 6400K fluorescent light/dark, 50% humidity. Approximately 14 days after planting, plants were thinned and transplanted to a density of 4 plants per 4-inch pot. These M1-generation plants showed telltale chlorotic leaf sectors that are indicative of a successful mutagenesis.

After dry-down, these M1-generation W0011 plants were catalogued and harvested. The M2- and M3-generation seeds were surface sterilized, planted and grown according to the protocols previously described.

In the Set #2 experiments, the MN106 mutagenized seeds were sowed into two small field plots. These plots were allowed to grow over the winter. The following spring abundant albino sectors were noted on the flowering plants as an indication of a successful mutagenesis.

Identification and Characterization of Low Seed Sinigrin Mutant Lines

In the Set #1 experiments, seeds (M3-generation) from putative M2-generation mutants were planted and grown in potting soil-containing 4-inch pots in a growth chamber, harvested and the sinigrin content in the seed was assessed upon its desiccation to a moisture level of 7-9%. EMS mutagenesis typically introduces single-nucleotide transition mutations (e.g., G to A, or C to T) into plant genomes.

In the Set #2 experiments, seeds were collected from mature M1-generation MN106 plants. M2-generation seeds from batches of 10 M1-generation plants were pooled together. In all, 500 pools representing 5000 mutagenized M1-generation plants were collected. In August, each pool was sowed in a field into an individual row. Robust growth was noted in October. During the following June, M3-generation seeds were collected from approximately 8,000 mature M2-generation individual plants and stored in individual packets.

In both Sets #1 and #2 experiments, NIR spectral analysis was used to make preliminary identification of lines with reduced glucosinolate in M3-generation seeds from each packet. These seeds were scanned using a Metrohm NIRS XDS Multi Vial Analyzer or a Perten DA7250 NIR Spectroscopy Analyzer to assess the amount of sinigrin as described elsewhere (Sidhu et. al., 2014; Golebiowski et. al, 2005; Riu et. al., 2006; Xin et. al., 2014). These analyses captured information related to the approximate levels of total glucosinolate and were used to identify low sinigrin candidates. Seeds showing a significant predicted reduction were used in a wet lab analysis to confirm or determine the sinigrin amount with better accuracy.

Near infrared (NIR) spectroscopic analysis was used to determine the sinigrin content of selected seed lines E3 196, E5 444P1, I87113 and I87207 and to compare the obtained values to the range of sinigrin in corresponding wild type seeds. These mutant lines showed sinigrin content significantly below population average and along with some other representative lines and controls were further analyzed using a method adapted from (Kliebenstein et. al., 2001). Results presented in Table 2 indicate that sinigrin levels in the seeds of these mutant lines are significantly lower and are outside of the corresponding ranges found in control parental seeds.

TABLE 2

Sinigrin content in seeds from selected pennycress lines with low glucosinolates content was measured using high throughput ion-exchange chromatography-based method. A minimum of three biological replicates each consisting of 20 mg (~20 seeds) per replicate was used. Each biological replicate was split into two technical replicates that were loaded on the mini-column and treated independently after seed extraction process. Last column represents standard error of the mean for glucosinolates (primarily sinigrin) content in each line.

| | Line ID | Origin | Biological Reps | Technical Reps | Sinigrin, Mean μmoles/g seed | Std Error, Mean μmoles/g |
|---|---|---|---|---|---|---|
| 1 | E3 196 | MN106-derived | 6 | 2 | 15 | 1.6 |
| 2 | E5 444P1 | MN106-derived | 6 | 2 | 23 | 3.5 |
| 3 | I87207 | W0011-derived | 3 | 2 | 25 | 4.1 |
| 4 | I87113 | W0011-derived | 6 | 2 | 30 | 4.5 |
| 5 | I87102 | W0011-derived | 3 | 2 | 94 | 8.0 |
| 6 | I87383 | W0011-derived | 3 | 2 | 96 | 10.7 |
| 7 | E5 051 P1 | MN106-derived | 3 | 2 | 99 | 8.9 |
| 8 | I87256 | W0011 wild type | 3 | 2 | 110 | 9.2 |
| 9 | E5 101 P1 | MN106-derived | 3 | 2 | 102 | 10.1 |
| 10 | E5 484P6 | MN106-derived | 3 | 2 | 106 | 10.4 |
| 11 | 1120/1062 1-13 | ARV breeding | 3 | 2 | 101 | 12.1 |
| 12 | 1082/1008 3-12-1 | ARV breeding | 3 | 2 | 106 | 12.2 |
| 13 | 1053/1023 2-5-1 | ARV breeding | 3 | 2 | 112 | 5.9 |
| 14 | Y1067 | ARV low fiber | 3 | 2 | 129 | 9.4 |
| 15 | Y1126 | ARV low fiber | 3 | 2 | 128 | 10.2 |
| 16 | Beecher (WT parent) | USDA | 120 | 2 | 103 | 2.5 |
| 17 | W0011 (WT parent) | WIU/ISU | 6 | 2 | 102 | 6.4 |
| 18 | MN106 (WT parent) | UMN | 6 | 2 | 116 | 8.5 |

Example 3. Identification of Underlying Gene Mutations in EMS-Generated Low Seed Sinigrin Mutant Lines Genomic DNA was extracted from each mutant, and each sample was subjected to whole-genome sequencing (adapted from Zhang, X., et al., 2018) and extensive bioinformatic analysis to identify induced mutations resulting in amino acid substitutions. For every gene target described in Table 1, a sequence from the mutant line was compared to a WT sequence from the parental line. If the EMS-induced change resulted in a non-silent mutation (amino acid change or a stop codon), the mutation was considered to be a candidate for the low sinigrin phenotype. Once the mutation was identified, a co-segregation analysis in the F2 single seeds or F3 families derived from each of these mutants was performed. This whole-genome sequencing (WGS) revealed that E3 196 (Nutty) line contains a mutation in a predicted pennycress ALKNYL HYDROXALKYL PRODUCING (AOP) polypeptide involved in the last step of sinigrin biosynthesis, while the I87113 line carries a homozygous mutation in the GTR1 gene which encodes a glucosinolate transporter.

Mutation in the AOP2-Like Gene Co-Segregates with Low Glucosinolate Phenotype in Seeds and Vegetative Tissues of Mutant E3 196 (Nutty) Pennycress Line.

In order to demonstrate that the mutation in the AOP2 gene discovered in the E3 196 (Nutty) mutant is responsible for the low sinigrin phenotype, a segregating F2 population from the cross of homozygous Nutty mutant with WT MN106 parental line was performed. The results are presented in Table 3.

TABLE 3

Glucosinolates content in seeds and vegetative tissues from the segregating population created using mutant pennycress line E3 196 (Nutty). Each line was genotyped for the presence of G97R mutation found in AOP2 gene variant in E3 196 (Nutty) using standard sequencing. Moisture and sinigrin content in seeds were measured using NIRS, whereas total glucosinolates content in fresh tissue was determined using a wet-lab method described in Chopra et al. (2019).

| | NIR sample # | Genotype, G97R | Moisture, % | Sinigrin, μmoles/g seed | Glucosinolates μmoles/g tissue |
|---|---|---|---|---|---|
| 1 | 15 | wt | 7.3 | 115.4 | 26.1 |
| 2 | 23 | wt | 7.6 | 98.3 | 23.9 |
| 3 | 29 | wt | 7.1 | 101.1 | 20.7 |
| 4 | 34 | wt | 7.1 | 108.1 | 9.7 |
| 5 | 35 | wt | 7.3 | 111.3 | 24.6 |
| 6 | 37 | wt | 7.4 | 115.1 | 13.8 |
| 7 | 38 | wt | 7.3 | 106.0 | 7.8 |
| 8 | 8 | homo | 7.5 | 4.9 | 0.7 |
| 9 | 12 | homo | 7.5 | 9.2 | 0.5 |
| 10 | 17 | homo | 7.0 | 6.9 | 1.4 |
| 11 | 24 | homo | 7.7 | 13.7 | 0.4 |
| 12 | 28 | homo | 7.4 | 7.4 | 0.3 |
| 13 | 41 | homo | 6.9 | 2.1 | 2.1 |
| 14 | 1 | het | 6.9 | 107.7 | 19.0 |
| 15 | 6 | het | 7.1 | 106.3 | 21.5 |
| 16 | 7 | het | 7.1 | 102.0 | 23.9 |
| 17 | 10 | het | 7.7 | 110.0 | 25.6 |
| 18 | 13 | het | 7.3 | 95.4 | 28.6 |
| 19 | 14 | het | 7.5 | 100.4 | 17.2 |
| 20 | 19 | het | 7.4 | 89.8 | 17.7 |
| 21 | 22 | het | 7.4 | 108.1 | 24.4 |
| 22 | 26 | het | 7.4 | 103.5 | 23.3 |
| 23 | 27 | het | 7.6 | 99.6 | 23.7 |
| 24 | 32 | het | 7.0 | 114.3 | n/a |
| 25 | 33 | het | 7.2 | 103.6 | 23.6 |

TABLE 3-continued

Glucosinolates content in seeds and vegetative tissues from the segregating population created using mutant pennycress line E3 196 (Nutty). Each line was genotyped for the presence of G97R mutation found in AOP2 gene variant in E3 196 (Nutty) using standard sequencing. Moisture and sinigrin content in seeds were measured using NIRS, whereas total glucosinolates content in fresh tissue was determined using a wet-lab method described in Chopra et al. (2019).

| NIR sample # | Genotype, G97R | Moisture, % | Sinigrin, µmoles/g seed | Glucosinolates µmoles/g tissue |
|---|---|---|---|---|
| Average | WT | | 107.9 | 18.1 |
| Average | HET | | 103.4 | 22.6 |
| Average | HOMO | | 7.4 | 0.9 |

The results presented in Table 3 strongly indicate that the G97R mutation present in the AOP2 gene variant in mutant line E3 196 (Nutty) mutant line results in ~20-fold reduction of total glucosinolates content in dry seeds and vegetative tissues of the mutant plant.

Mutation in the Homolog of GTR1 Gene Results in Low Glucosinolate Phenotype in Seeds and Vegetative Tissues of Mutant I87113 Pennycress Line.

Using a WGS approach, the I87113 line was found to carry a homozygous mutation believed to confer a L491F amino acid change in GTR1, a glucosinolate transporter and a member of a major facilitator superfamily. In 98 Embryophyta sequences this position is in a conserved transmembrane helical region and is populated exclusively with small hydrophobic AAs, suggesting that the L491F-causing mutation results in at least a partial loss of function. Indeed, in a separate set of NIRS and wet-lab experiments, the progeny of the I87113 mutant has consistently demonstrated a significant reduction in glucosinolates levels in dry seeds (~30% of the WT level).

TABLE 4

Sinigrin content in seeds of gtr1-1 mutant I87113 as determined using a wet-lab method described in Chopra et. al. (2019).

| Line ID | Generation/Type | Sinigrin, Mean µmoles/g seed | Std Error, Mean µmoles/g |
|---|---|---|---|
| I87113 | M3 | 25 | 4 |
| I87113 | M3 | 30 | 4 |
| I87113 | M4 | 33 | 2 |
| W0011 | Control | 98 | 4 |
| Beecher | Control | 101.4 | 7 |

Example 4: Discovery and Characterization of Other Mutant Lines with Low Sinigrin Content in Seeds In the process of whole genome sequencing (WGS) of multiple EMS-mutagenized lines segregating for useful traits (flowering, pod-shattering, oil, protein and fiber content, etc.) mutations in other genes described as potential targets for suppression in Table 1 were identified. In these cases, mutations were present almost exclusively in a heterozygous form, consistent with the fact that they were not selected based on a low glucosinolate phenotype which typically requires a homozygous LOF mutation. Instead, they were identified using this opportunistic approach because the original seed stock was very heavily mutagenized (with an estimated 1,000-2,000 mutations per haploid genome), which makes the presence of more than one potentially useful mutation in the same line relatively likely. Because these lines were selected exclusively based on presence of non-silent mutations, most are expected to be in non-conserved regions and have little or no impact on corresponding gene functions. Nevertheless, these lines were subjected to NIRS and wet-lab assays in order to determine the effects of the identified mutations on glucosinolate content in seeds. The results are summarized in Table 5.

TABLE 5

Sinigrin content in seeds of the segregating populations created using mutant pennycress lines identified via WGS. The genotypes of each mother line were determined using standard sequencing. Moisture and sinigrin content in seeds were measured using NIRS whereas, total glucosinolates content in dry seeds was determined using a wet-lab procedure described in (Chopra et.al., 2019).

| | Line Name | Gene Affected | Moisture % | NIRS Sinigrin, µmoles/g seed | Wet-Lab Glucosinolate µmoles/g seed | Genotype of the mother line |
|---|---|---|---|---|---|---|
| 1 | A7 11 | FMO_GS-OX1 | 7.6 | 103.3 | 113.5 | HET |
| 2 | A7 66-CYP83A1 Mut | CYP83A1 | 7.3 | 101.0 | 123.5 | HOM |
| 3 | A7 66-CYP83A1 WT | CYP83A1 | 8.1 | 85.3 | 119.2 | WT |
| 4 | A7 95 | IMD1 | 4.9 | 115.5 | 115.1 | HOM |
| 5 | D3 22 | IMD1 | 8.3 | 96.6 | 120.0 | HET |
| 6 | D3 N13P3-F2 (Mut)-16 | bHLH05 (MYC3) | 17.1 | 81.1 | 66.0 | HOM |
| 7 | D3 N13P3-F2 (Mut)-22 | bHLH05 (MYC3) | 12.3 | 80.2 | 91.4 | HOM |
| 8 | D3 N13P3-F2 (Wt)-11 | bHLH05 (MYC3) | 13.7 | 119.1 | 125.1 | WT |
| 9 | D3 N13P3-F2 (Wt)-12 | bHLH05 (MYC3) | 16.8 | 122.8 | 118.8 | WT |
| 10 | E5 133P2-1 | bHLH05 (MYC3) | 7.5 | 63.6 | 86.0 | unknown |

TABLE 5-continued

Sinigrin content in seeds of the segregating populations created using mutant pennycress lines identified via WGS. The genotypes of each mother line were determined using standard sequencing. Moisture and sinigrin content in seeds were measured using NIRS whereas, total glucosinolates content in dry seeds was determined using a wet-lab procedure described in (Chopra et.al., 2019).

| | Line Name | Gene Affected | Moisture % | NIRS Sinigrin, μmoles/g seed | Wet-Lab Glucosinolate μmoles/g seed | Genotype of the mother line |
|---|---|---|---|---|---|---|
| 11 | E5 133P2-2 | bHLH05 (MYC3) | 8.1 | 90.3 | 107.9 | unknown |
| 12 | E5 133P2-3 | bHLH05 (MYC3) | 7.9 | 57.9 | 94.9 | unknown |
| 13 | E5 356P5 | FMO_GS-OX1 | 7.5 | 92.5 | 96.7 | HET |
| 14 | E5 519-CYP79B3 Mut 309 | CYP79B3 | 7.9 | 91.8 | 110.2 | HOM |
| 15 | E5 519-CYP79B3 Mut 311 | CYP79B3 | 8.1 | 80.9 | 108.4 | HOM |
| 16 | E5 543 | MAM1 | 6.3 | 57.9 | 89.7 | HET |
| 17 | MN106 #33 | Wt | 8.2 | 91.2 | 106.6 | WT |
| 18 | A7 137 | Wt | 7.7 | 99.8 | 104.0 | WT |
| 19 | E5 301P1 | Wt | 8.3 | 94.5 | 99.0 | WT |

This analysis suggested that some of the mutations (such as in FMO-GS-Ox1 and MAM1 genes) may have at least a partial impact on corresponding protein function. To test this hypothesis, the seeds from the progeny of the original heterozygous lines (segregating in a typical 1:2:1 Mendelian ratio) were subjected to a single-seed wet-lab assay and PCR-based genotyping. The results summarized in Table 6 suggest that mutations in FMO-GS-Ox1 and MAM1 may result in reduction of glucosinolates in dry seeds of homozygous mutant lines (40-60% of WT level).

TABLE 6

Glucosinolates content in seeds of the segregating populations created using mutant pennycress lines. Total glucosinolates content (μmoles/g) in single seeds was determined using a wet-lab method described in Chopra et al. (2019).

| | Gene | WT | Mutant |
|---|---|---|---|
| 1 | CYP83A1 | 138 (±12.22) | 113 (±19.72) |
| 2 | FMO-GS-Ox1 | 106 (±10.4) | 64 (±3.98) |
| 3 | MAM1 | 127 (±8.82) | 51 (±4.67) |

Example 5. Identification and Characterization of CRISPR-Induced Mutations in Target Genes Related to Glucosinolate Pathway and Seed Accumulation Gene editing using Cas9, Cpf1 and Cms1 nucleases typically introduces a double-stranded break into a targeted genome area in close proximity to the nuclease's PAM site. During non-homologous end-joining process (NHEJ) double-stranded breaks are repaired, at times resulting in the introduction of INDELS-type mutations at the repair location in targeted genomes. To identify plants with small INDELS in targeted genes of interest, standard Sanger sequencing and/or T7 endonuclease assays (Guschin et. al., 2010) were employed. Standard PCR protocols followed by Sanger sequencing were used to identify and characterize larger (several hundred base pairs) deletions. Sequence analyses revealed that multiple guide RNAs/CRISPR nuclease combinations were effective in generating loss-of-function (LOF) mutations in gene targets described in Table 1. Plants carrying LOF mutations were grown to the next generation and the phenotypes in seeds or vegetative tissues were confirmed using analytical methods.

Multiple mutations in the MYB28 (HAG1) gene were identified, including frameshift mutations likely conferring complete loss of gene function, but no reduction in sinigrin was observed in any of the corresponding homozygous mutant lines (Table 7). On the other hand, mutations in another MYB family member, MYB29 (HAG3), did result in sinigrin reduction, on average, by 35-50% (Tables 7-9). However, in vegetative tissues of myb28/myb29 (hag1/hag3) mutations stack, a dramatic reductions in glucosinolate content relative to WT controls were observed, suggesting a redundancy in the MYB28 and MYB29 gene functions.

TABLE 7

Sinigrin levels as determined using a wet-lab method described in Chopra et at. (2019), in homozygous lines generated using CRISPR-induced mutagenesis in selected gene targets described in Table 1.

| | Gene Name(s) | Line Name Genotype | Generation | Sinigrin, μmoles/g seed | Glucosinolates μmoles/g fresh tissue | % Control |
|---|---|---|---|---|---|---|
| 1 | WT Control (Beecher) | WT-Beecher | | 105 | 46.1 | n/a |
| 2 | WT Control (W0011) | WT-W0011 | | 94.3 | 40.1 ± 5.7 | n/a |

TABLE 7-continued

Sinigrin levels as determined using a wet-lab method described in Chopra et at. (2019), in homozygous lines generated using CRISPR-induced mutagenesis in selected gene targets described in Table 1.

| | Gene Name(s) | Line Name Genotype | Generation | Sinigrin, μmoles/g seed | Glucosinolates μmoles/g fresh tissue | % Control |
|---|---|---|---|---|---|---|
| 3 | MYB28 (HAG1) | hag1-1 (homozygous−G deletion) | T2 | 98.1 | | 98% |
| 4 | MYB28 (HAG1) | hag1-2 (homozygous+ A insertion) | T3 | 100.7 | | 101% |
| 5 | MYB28 (HAG1) MYB29 (HAG3) Stack | 2180A (hag1 het −2bp; hag3-2 homo −6 bp) | T1 | | 26.0 ± 3.1 | 65% |
| 6 | MYB28 (HAG1)/ MYB29 (HAG3) stack | 2172A (hag1 biallelic −2bp, +A; hag3-1 homo −13 bp) | T1 | | 1.1 ± 0.3 | 3% |
| 7 | GTR1/GTR2 stack | 3A5K (gtr1-2 homo +G, gtr2-3 chimeric +G, +A, WT) | T2 | 20.6 | | 21% |
| 8 | GTR1/GTR2 stack | 3A5C (gtr1-3 het −T, gtr2-2 homo +A) | T2 | 48.9 | | 49% |

TABLE 8

Sinigrin levels in single T2-generation seeds obtained from selected biallelic/homozygous MYB29 (HAG3)-edited lines (wet-lab method, normalized to μmoles/g seed).

| Seed # | WT Control | Line A263A | Line A264A | Line A269A |
|---|---|---|---|---|
| 1 | 117.9 | 70.8 | 121.5 | 77.4 |
| 2 | 106.7 | 58.8 | 103.5 | 84.1 |
| 3 | 119.6 | 46.5 | 94.5 | 60.6 |
| 4 | 124.6 | 42.1 | 70.5 | 56.3 |
| 5 | 130.3 | 64.5 | 84.7 | 56.2 |
| 6 | 123.9 | 51.3 | 86.1 | 54.6 |
| 7 | 111.7 | 56.4 | 94.1 | 62.1 |
| 8 | 126.5 | 45.4 | 89.6 | 41.9 |
| 9 | 127.5 | 52.1 | 114.0 | 57.1 |
| 10 | 125.1 | 45.9 | 83.5 | 51.5 |
| 11 | 124.5 | 44.0 | 71.3 | 63.3 |
| 12 | 116.1 | 49.8 | 68.7 | 57.2 |
| 13 | 126.1 | 75.7 | 113.4 | 85.7 |
| 14 | 128.1 | 53.0 | 73.2 | 61.5 |

TABLE 8-continued

Sinigrin levels in single T2-generation seeds obtained from selected biallelic/homozygous MYB29 (HAG3)-edited lines (wet-lab method, normalized to μmoles/g seed).

| Seed # | WT Control | Line A263A | Line A264A | Line A269A |
|---|---|---|---|---|
| 15 | 115.9 | 46.7 | 84.9 | 87.3 |
| 16 | 114.4 | 46.2 | 74.6 | 69.2 |
| 17 | 103.2 | 55.3 | 101.6 | 86.8 |
| 18 | 114.5 | 54.3 | 99.6 | 81.5 |
| 19 | 101.4 | 47.6 | 116.8 | 56.2 |
| 20 | 150.0 | 98.4 | 62.6 | 41.5 |
| 21 | 127.1 | 48.1 | 71.1 | 63.7 |
| 22 | 135.0 | 58.6 | 101.3 | 60.8 |
| 23 | 133.7 | 70.3 | 78.3 | 48.1 |
| 24 | 126.9 | 51.5 | 83.3 | 65.7 |
| AVE, μmoles/g | 122.1 | 55.5 | 89.3 | 63.8 |
| STDEV | 10.8 | 12.8 | 16.8 | 13.6 |
| % Control | 100% | 45% | 73% | 52% |

TABLE 9

Sinigrin levels in vegetative tissues from selected 4-weeks old T2-generation plants grown from biallelically modified MYB29 (HAG3) CRISPR-mutated line A269A (wet-lab method, normalized to μmoles/g fresh tissue punch).

| | WT | A269A, line # | | | | | | | |
|---|---|---|---|---|---|---|---|---|---|
| BioRep # | Control | 13 | 16 | 21 | 22 | 11 | 14 | 19 | 24 |
| 1 | 19.8 | 4.0 | 7.5 | 3.0 | 3.4 | 3.9 | 8.3 | 7.9 | 8.2 |
| 2 | 19.9 | 4.1 | 5.6 | 3.1 | 5.7 | 2.7 | 6.9 | 5.6 | 8.4 |
| 3 | 16.4 | 3.4 | 5.0 | 3.6 | 5.8 | 2.8 | 7.0 | 6.4 | 7.8 |
| AVERAGE | 18.7 | 3.8 | 6.0 | 3.2 | 5.0 | 3.1 | 7.4 | 6.6 | 8.1 |
| STDEV | 2.0 | 0.4 | 1.3 | 0.3 | 1.4 | 0.7 | 0.8 | 1.2 | 0.3 |
| % Control | 100% | 20% | 32% | 17% | 27% | 17% | 40% | 35% | 43% |

TABLE 10

Sinigrin levels in vegetative tissues from selected T1-generation seedlings grown from biallelically modified AOP2 lines (wet-lab method, normalized to μmoles/4.3 mg fresh tissue punch). Tissue samples were harvested from cauline leaves when plants were setting pods (wet-lab method, normalized to μmoles/g fresh tissue punch). T1 plants are generally chimeric for the edits, resulting in overestimated sinigrin numbers and increased variability.

| BioRep # | 2032 WT control | A370A | A379A | A381A | A380A |
|---|---|---|---|---|---|
| 1 | 7.9 | 0.2 | 1.4 | −0.3 | 0.3 |
| 2 | 4.6 | 2.1 | 0.6 | 0.1 | 0.3 |
| 3 | 4.1 | 0.4 | 0.1 | 6.9 | 0.4 |
| 4 | 4.0 | −0.4 | 2.9 | 7.2 | −0.6 |
| 5 | 4.2 | 3.5 | 0.5 | 0.1 | −0.4 |
| 6 | 1.6 | 4.1 | 0.9 | 0.1 | −0.4 |
| AVERAGE | 4.4 | 1.7 | 1.1 | 2.3 | −0.1 |
| STDEV | 2.0 | 1.9 | 1.0 | 3.6 | 0.4 |
| % Control | 100% | 38% | 24% | 53% | −1% |

REFERENCES

Tripathi, M. K., & Mishra, A. S. (2007). Glucosinolates in animal nutrition: A review. *Animal Feed Science and Technology,* 132 (1-2), 1-27.

EFSA Panel on Contaminants in the Food Chain. (2008). Glucosinolates as undesirable substances in animal feed—scientific opinion of the panel on contaminants in the food chain. *EFSA Journal,* 590, 1-76.

Fauser F., Schiml S., & Puchta H. (2014). Both CRISPR/Cas-based nucleases and nickases can be used efficiently for genome engineering in *Arabidopsis thaliana. Plant J* 79: 348-359.

Guha T. K., Wai A, & Hausner G. (2017). Programmable Genome Editing Tools and their Regulation for Efficient Genome Engineering, *Computational and Structural Biotechnology Journal,* 15, 146-160.

Guschin D Y, Waite A J, Katibah G E, Miller J C, Holmes M C, & Rebar E J. (2010) A rapid and general assay for monitoring endogenous gene modification. In: *Engineered zinc finger proteins:* 247-256. Humana Press, Totowa, N.J.

Holsters, M., De Waele, D., Depicker, A., Messens, E., Van Montagu, M., & Schell, J. (1978). Transfection and transformation of *Agrobacterium tumefaciens. Molecular and General Genetics* 163(2), 181-187.

Steinert J., Schiml S., Fauser F., & Puchta H. (2015). Highly efficient heritable plant genome engineering using Cas9 orthologues from *Streptococcus thermophilus* and *Staphylococcus aureus. The Plant Journal* 84:1295-305.

Kliebenstein, D. J., Lambrix, V. M., Reichelt, M., Gershenzon, J., & Mitchell-Olds, T. (2001). Gene duplication in the diversification of secondary metabolism: tandem 2-oxoglutarate-dependent dioxygenases control glucosinolate biosynthesis in *Arabidopsis. The Plant Cell,* 13(3), 681-693.

Chopra, R., Folstad, N., Lyons, J., Ulmasov, T., Gallaher, C., Sullivan, L., McGovern, A., Mitacek, R., Frels, K., Altendorf, K. Killam, A. Ismail, B., Anderson, J. A., Wyse, D. L. & Marks, M. D. (2019). The adaptable use of *Brassica* NIRS calibration equations to identify pennycress variants to facilitate the rapid domestication of a new winter oilseed crop. *Industrial Crops and Products,* 128, 55-61.

Sidhu, H. K., Haagenson, D. M., Rahman, M., & Wiesenborn, D. P. (2014). Diode Array Near Infrared Spectrometer Calibrations for Composition Analysis of Single Plant Canola (*Brassica napus*) Seed. *Applied Engineering in Agriculture,* 30(1), 69-76.

Golebiowski, T., Leong, A. S., & Panozzo, J. F. (2005). Near infrared reflectance spectroscopy of oil in intact canola seed (*Brassica napus* L.). II. Association between principal components and oil content. *Journal of Near Infrared Spectroscopy,* 13(5), 255-264.

Riu, Y. K., Huang, K. L., Wang, W. M., Guo, J., Jin, Y. H., & Luo, Y. B. (2006). Detection of erucic acid and glucosinolate in intact rapeseed by near-infrared diffuse reflectance spectroscopy. *Guang pu xue yu guang pu fen xi= Guang pu,* 26(12), 2190-2192.

Xin, H., Khan, N. A., Falk, K. C., & Yu, P. (2014). Mid-infrared spectral characteristics of lipid molecular structures in *Brassica carinata* seeds: relationship to oil content, fatty acid and glucosinolate profiles, polyphenols, and condensed tannins. *Journal of Agricultural and Food Chemistry,* 62(32), 7977-7988.

Dorn, K. M., Fankhauser, J. D., Wyse, D. L., & Marks, M. D. (2013). De novo assembly of the pennycress (*Thlaspi arvense*) transcriptome provides tools for the development of a winter cover crop and biodiesel feedstock. *The Plant Journal,* 75(6), 1028-1038.

Zhang, X., Li, R., Chen, L., Niu, S., Chen, L., Gao, J., Wen, J., Yi, B., Ma, C., Tu, J. and Fu, T., (2018). Fine-mapping and candidate gene analysis of the *Brassica juncea* white-flowered mutant Bjpc2 using the whole-genome resequencing. *Molecular Genetics and Genomics,* 293(2), pp. 359-370.

OTHER EMBODIMENTS

It is to be understood that while certain embodiments have been described in conjunction with the detailed description thereof and examples, the foregoing description is intended to illustrate and not limit the scope of the disclosure. Other aspects, advantages, and modifications are within the scope of the following embodiments and claims.

Embodiment 1. A composition comprising non-defatted pennycress seed meal that comprises less than 30, 28, 25, 16, or 15 micromoles sinigrin per gram by dry weight.

Embodiment 2. The composition of embodiment 1, wherein said seed meal comprises about 1, 2.5, 5, or 10 to about 15, 16, 18, 20, or 25 micromoles sinigrin per gram by dry weight.

Embodiment 3. The composition of any one of embodiments 1 or 2, wherein said composition has an oil content of about 30% or 35% to about 40% or 50% by dry weight.

Embodiment 4. The composition of any one of embodiments 1 to 3, wherein said composition further comprises a preservative, a dust preventing agent, a bulking agent, a flowing agent, or any combination thereof.

Embodiment 5. The composition of any one of embodiments 1 to 4, wherein said pennycress seed meal is obtained from pennycress seeds that have been crushed, ground, macerated, expelled, extruded, or any combination thereof.

Embodiment 6. The composition of any one of embodiments 1 to 5, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 7. A non-defatted pennycress seed meal that comprises less than 30, 28, 25, 16, or 15 micromoles sinigrin per gram by dry weight.

Embodiment 8. The seed meal of embodiment 7, wherein said seed meal comprises about 1, 2.5, 5, or 10 to about 15, 16, 18, 20, or 25 micromoles sinigrin per gram by dry weight.

Embodiment 9. The seed meal of embodiment 7 or 8, wherein said composition has an oil content of 30% or 35% to 40% or 50% by dry weight.

Embodiment 10. The seed meal of any one of embodiments 7 to 9, wherein said seed meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 356P5, I87113, or E5 543; or (ii) crushed, ground, and/or macerated seed of pennycress mutant lines E3 196, E5 356P5, I87113, E5 543, or germplasm therefrom.

Embodiment 11. A pennycress seed comprising less than 30, 28, 25, 16, or 15 micromoles sinigrin per gram by dry weight.

Embodiment 12. The pennycress seed of embodiment 11, wherein the seed comprises about 1, 2.5, 5, or 10 to about 15, 16, 18, 20, or 25 micromoles sinigrin per gram by dry weight.

Embodiment 13. The pennycress seed of embodiment 11 or 12, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (iii) seed of pennycress mutant lines E3 196, E5 444P1, E5 356P5, I87113, E5 543, 187207, or germplasm therefrom.

Embodiment 14. The pennycress seed of any one of embodiments 11 to 13, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 15. The pennycress seed of any one of embodiments 11 to 14, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 16. The pennycress seed of embodiment 15, wherein: (i) the sinigrin biosynthetic enzyme comprises a polypeptide selected from the group consisting of SEQ ID NO: 3, 6, 9, 12, 21, 24, 27, 94 162, 163, 165, 166, 168, 169, 171, 172, 174, 175, and allelic variants thereof or (ii) the pennycress seed comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 17. The pennycress seed of embodiment 15 or 16, wherein: (i) the sinigrin transporter comprises a polypeptide selected from the group consisting of SEQ ID NO: 15, 17 and allelic variants thereof; (ii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 18. A seed lot comprising a population of pennycress seeds comprising less than 30, 28, 25, 16, or 15 micromoles sinigrin per gram by dry weight.

Embodiment 19. The seed lot of embodiment 18, wherein the pennycress seeds comprise 1, 2.5, 5, or 10 to 15, 16, 18, 20, or 25 micromoles sinigrin per gram by dry weight.

Embodiment 20. The seed lot of embodiment 18 or 19, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof or (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (ii) seed of pennycress mutant lines E3 196, E5 356P5, I87113, E5 543, or germplasm therefrom.

Embodiment 21. The seed lot of any one of embodiments 18 to 20, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 22. The seed lot of any one of embodiments 18 to 20, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 23. The seed lot of embodiment 22, wherein: (i) the sinigrin biosynthetic enzyme comprises a polypeptide selected from the group consisting of SEQ ID NO: 3, 6, 9, 12, 21, 24, 27, 94, 164, 167, 170, 173, 176, and allelic variants thereof; or (ii) the pennycress seed lot comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 24. The seed lot of embodiment 22 or 23, wherein: (i) the sinigrin transporter comprises a polypeptide selected from the group consisting of SEQ ID NO: 15, 17 and allelic variants thereof; (ii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 25. The seed lot of any one of embodiments 18 to 24, wherein said population of pennycress seeds comprise seeds having at least one loss-of-function mutation in an endogenous pennycress gene that encodes SEQ ID NO:2 or an allelic variant thereof.

Embodiment 26. The seed lot of any one of embodiments 18 to 25, wherein the loss-of-function mutation in the gene encoding SEQ ID NO:2 or the allelic variant thereof comprises an insertion, deletion, or substitution of one or more nucleotides.

Embodiment 27. The seed lot of embodiment 26, wherein the loss-of-function mutation in the gene encoding SEQ ID NO:2 or the allelic variant thereof comprises a mutation that introduces a pre-mature stop codon or frameshift mutation at codon positions 1-108 of SEQ ID NO:1 or an allelic variant thereof.

Embodiment 28. The seed lot of embodiment 26, wherein the loss-of-function mutation is in a polynucleotide encoding MYB28, MYB29, MYB76, or any combination thereof.

Embodiment 29. The seed lot of any one of embodiments 18 to 28, wherein the population comprises at least 10 seeds comprising less than 25 micromoles sinigrin per gram by dry weight or 1, 2.5, 5, or 10 to 15, 16, 18, 20, or 25 micromoles sinigrin per gram by dry weight.

Embodiment 30. The seed lot of any one of embodiments 18 to 29, wherein at least 95% of the pennycress seeds in the seed lot are seeds comprising less than 30, 28, 25, 16, or 15 micromoles sinigrin per gram by dry weight or 1, 2.5, 5, or 10 to 15, 16, 18, 20, or 25 micromoles sinigrin per gram by dry weight.

Embodiment 31. The seed lot of any one of embodiments 18 to 30, wherein less than 5% of the seeds in said seed lot have greater than 25 or 30 micromoles sinigrin per gram by dry weight.

Embodiment 32. The seed lot of any one of embodiments 18 to 31, wherein said seeds further comprise an agriculturally acceptable excipient or adjuvant.

Embodiment 33. The seed lot of any one of embodiments 18 to 32, wherein said seeds further comprise a fungicide, a safener, or any combination thereof.

Embodiment 34. A method of making non-defatted pennycress seed meal comprising less than 30, 28, 25, 16, or 15 micromoles sinigrin per gram by dry weight or 1, 2.5, 5, or 10 to 15, 16, 18, 20, or 25 micromoles sinigrin per gram by dry weight, comprising the step of grinding, macerating, extruding, and/or crushing the seed lot of any one of embodiments 18 to 32 thereby obtaining the non-defatted seed meal.

Embodiment 35. A method of making defatted pennycress seed meal comprising less than 30 micromoles sinigrin per gram by dry weight or about 1, 2.5, 5, or 10 to about 15, 16, 18, 20, 25, 28, or 30 micromoles sinigrin per gram by dry weight, comprising the steps of solvent extracting the seed lot of any one of embodiments 18 to 32, and separating the extracted seed meal from the solvent, thereby obtaining the defatted seed meal.

Embodiment 36. Pennycress seed meal comprising less than 30, 28, or micromoles sinigrin per gram by dry weight or about 1, 2.5, 5, or 10 to about 15, 16, 18, 20, 25, 28, or 30 micromoles sinigrin per gram by dry weight, wherein the seed meal is defatted.

Embodiment 37. The seed meal of embodiment 36, wherein said seed meal has an oil content of about 0% or 0.5% to about 12% or 15% by dry weight.

Embodiment 38. The pennycress seed meal of embodiments 36 or 37, wherein said meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P 5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 39. The pennycress seed meal of any one of embodiments 36 to 38, wherein said meal comprises ground and/or macerated seed of a population of pennycress seeds comprising seeds having at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 40. The pennycress seed meal of any one of embodiments 36 to 39, wherein said meal comprises ground and/or macerated seed of a population of pennycress seeds comprising seeds having at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 41. The pennycress seed meal of any one of embodiments 36 to 40, wherein said meal comprises ground and/or macerated seed of a population of pennycress seeds comprising seeds having at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 42. A composition comprising defatted pennycress seed meal that comprises less than 30, 28, 25, 16, or 15 micromoles sinigrin per gram by dry weight.

Embodiment 43. The composition of embodiment 42, wherein said seed meal comprises about 1, 2.5, 5, or 10 to about 15, 16, 18, 20, 25, 28, or 30 micromoles sinigrin per gram by dry weight.

Embodiment 44. The composition of embodiments 42 or 43, wherein said composition has an oil content of about 0% or 0.5% to about 12% or 15% by dry weight.

Embodiment 45. The composition of any one of embodiments 42 to 44, wherein said composition further comprises a preservative, a dust preventing agent, a bulking agent, a flowing agent, or any combination thereof.

Embodiment 46. The composition of any one of embodiments 42 to 45, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P 5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 47. Pennycress seed cake comprising 30 micromoles sinigrin per gram by dry weight or about 1, 2.5, 5, or 10 to about 15, 16, 18, 20, 25, 28, or 30 micromoles sinigrin per gram by dry weight.

Embodiment 48. The seed cake of embodiment 47, wherein said seed cake has an oil content of about 0% or 0.5% to about 12% or 15% by dry weight.

Embodiment 49. The pennycress seed cake of embodiment 47, wherein the cake comprises crushed or expelled seed of the seed lot of any one of embodiments 18 to 33.

Embodiment 50. The pennycress seed cake of any one of embodiments 47 to 49, wherein the cake comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P5, I87113, E5 543, or I87207; or (iii) seed cake obtained from seed of pennycress mutant lines E3 196, E5 444P1, E5 356P5, I87113, I87207, E5 543, or germplasm therefrom.

Embodiment 51. A method of making a pennycress seed lot comprising the steps of:
(a) introducing at least one loss-of-function mutation in at least one endogenous pennycress gene encoding a polypeptide selected from the group consisting of SEQ ID NO: 3, 6, 9, 12, 15, 17, 21, 24, 27, 30, 92, 93, 159, 160, 162, 163, 165, 166, 168, 169, 171, 172, 174, 175, and allelic variants thereof;
(b) selecting germplasm that is homozygous for said loss-of-function mutation; and,
(c) harvesting seed from the homozygous germplasm, thereby obtaining a seed lot, wherein said seed lot comprises a population of pennycress seed having less than 30, 28, 25, 16, or 15 micromoles sinigrin per gram by dry weight.

Embodiment 52. The method of embodiment 51, wherein the harvested seed of the seed lot comprise 1, 2.5, 5, or 10 to 15, 16, 18, 20, or 25 micromoles sinigrin per gram by dry weight.

Embodiment 53. The method of embodiment 51 or 52, wherein said harvested seed of the seed lot comprises the seed lot of any one of embodiments 18 to 33.

Embodiment 54. A method of making a pennycress seed lot comprising the steps of:
(a) introducing at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof into a pennycress plant genome;
(b) selecting a transgenic plant line that comprises said transgene or genome rearrangement; and,
(c) harvesting seed from the transgenic plant line, thereby obtaining a seed lot, wherein said seed lot comprises a population of pennycress seed having less than 30, 28, 25, 16, or 15 micromoles sinigrin per gram by dry weight.

Embodiment 55. The method of embodiment 54, wherein the harvested seed of the seed lot comprise 1, 2.5, 5, or 10 to 15, 16, 18, 20, or 25 micromoles sinigrin per gram by dry weight.

Embodiment 56. The method of embodiment 54 or 55, wherein said harvested seed comprise a seed lot of any one of embodiments 18 to 33.

What is claimed is:

1. A pennycress seed comprising less than 30 micromoles sinigrin per gram by dry weight, wherein the seed comprises: (i) at least one loss-of-function mutation in an endogenous pennycress gene encoding the polypeptide of SEQ ID NO: 3 or an allelic variant thereof and said loss-of-function mutation reduces expression of said polypeptide or reduces 2-oxoglutarate-dependent dioxygenase activity of said polypeptide; or (ii) at least one transgene or genome rearrangement that suppresses expression of at least one endogenous pennycress gene that encodes the polypeptide of SEQ ID NO: 3 or an allelic variant thereof; and wherein said allelic variants of SEQ ID NO: 3 have at least 95% sequence identity to SEQ ID NO: 3.

2. The pennycress seed of claim 1, wherein the seed comprises 1 to 15 micromoles sinigrin per gram by dry weight.

3. The pennycress seed of claim 1, wherein the seed comprises at least one loss-of-function mutation in an endogenous pennycress gene encoding the polypeptide of SEQ ID NO: 3 or the allelic variant thereof, wherein said loss-of-function mutation reduces expression of said polypeptide or reduces 2-oxoglutarate-dependent dioxygenase activity of said polypeptide.

4. The pennycress seed of claim 1, wherein the seed comprises at least one loss-of-function mutation in at least one endogenous pennycress coding sequence or gene comprising a polynucleotide sequence of SEQ ID NO: 1 or SEQ ID NO: 2, respectively, or an allelic variant thereof having at least 95% sequence identity to SEQ ID NO: 1 or SEQ ID NO: 2, respectively.

5. The pennycress seed of claim 1, wherein the seed comprises less than 15 micromoles sinigrin per gram by dry weight.

6. A method of making defatted pennycress seed meal comprising less than 30 micromoles sinigrin per gram by dry weight sinigrin per gram by dry weight, comprising the steps of solvent extracting a seed lot comprising a population of the pennycress seed of claim 1, and separating the extracted seed meal from the solvent, thereby obtaining the defatted seed meal comprising less than 30 micromoles sinigrin per gram by dry weight.

7. The method of claim 6, wherein the defatted seed meal comprises less than 15 micromoles sinigrin per gram by dry weight.

* * * * *